(12) United States Patent
Nuttall et al.

(10) Patent No.: US 8,524,863 B2
(45) Date of Patent: Sep. 3, 2013

(54) AMYLOID-BETA PEPTIDE CRYSTAL STRUCTURE

(75) Inventors: Stewart Douglas Nuttall, Victoria (AU); Victor Anatolievich Streltsov, Victoria (AU); Joseph Noozhumurry Varghese, Victoria (AU); Vidanagamage Chandana Epa, Victoria (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 13/122,934

(22) PCT Filed: Oct. 6, 2009

(86) PCT No.: PCT/AU2009/001327
§ 371 (c)(1),
(2), (4) Date: Jun. 29, 2011

(87) PCT Pub. No.: WO2010/040175
PCT Pub. Date: Apr. 15, 2010

(65) Prior Publication Data
US 2011/0269938 A1    Nov. 3, 2011

(30) Foreign Application Priority Data

Oct. 6, 2008 (AU) ................................ 2008905174
Oct. 6, 2008 (AU) ................................ 2008905176

(51) Int. Cl.
*C07K 14/00* (2006.01)
(52) U.S. Cl.
USPC .......................................... 530/350; 530/412
(58) Field of Classification Search
None
See application file for complete search history.

(56) References Cited

FOREIGN PATENT DOCUMENTS

WO   WO 2004/056318 A2   7/2004
WO   WO 2005/118629 A1   12/2005
WO   WO 2006/066089 A1   6/2006

OTHER PUBLICATIONS

Wiencek, J. M. Ann. Rev. Biomed. Eng. 1999, 1, 505-534.*
Notification Concerning Transmittal of International Preliminary Report on Patentability (Chapter I of the Patent Cooperation Treaty), including an International Preliminary Report on Patentability and Written Opinion of the International Searching Authority, mailed Apr. 21, 2011 in connection with PCT International Application No. PCT/AU2009/001327, filed Oct. 6, 2009.
International Search Report mailed by the International Searching Authority (ISA/AU) on Jan. 21, 2010 in connection with PCT International Application No. PCT/AU2009/001327, filed Oct. 6, 2009.
Lührs, T., Ritter, C., Adrian, M., Riek-Loher, D., Bohrmann, B., Dübeli, H., . . . Riek, R. (Nov. 29, 2005). 3D Structure of Alzheimer's amyloid-β(1-42) fibrils. PNAS, 102(48), 17342-17347.

* cited by examiner

*Primary Examiner* — Nashaat Nashed
(74) *Attorney, Agent, or Firm* — John P. White; Gary J. Gershik; Cooper & Dunham LLP

(57) ABSTRACT

The invention relates provides a novel crystal structure of the fibrillogenic part of amyloid β-peptide (Aβ). More specifically the crystal structure is Aβ-IgNAR, and accordingly the present invention also relates to selecting and/or designing compounds that modulate amyloid β-peptide (Aβ) activity using techniques such as in silico screening and crystal soaking experiments. The invention further relates to compounds and methods for inhibiting interaction between amyloid β-peptide (Aβ) monomers, more particularly, inhibiting or disrupting amyloid β-peptide (Aβ) oligomer formation and toxic activity.

23 Claims, 13 Drawing Sheets

SEQUENCE LISTING

<160> NUMBER OF SEQ ID NOS: 25

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 145
<212> TYPE: PRT
<213> ORGANISM: Artificial Sequence
<220> FEATURE:
<223> OTHER INFORMATION: Synthetic

<400> SEQUENCE: 2

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Val Phe Phe Ala Glu Asp Val Gly Ser
                85                  90                  95

Asn Lys Gly Ala Ile Ile Gly Leu Met Val Gly Val Val Ile Gly
            100                 105                 110

Gly Glu Lys Gly Ala Gly Thr Ala Leu Thr Val Lys Ala Ala Asp
        115                 120                 125

Tyr Lys Asp Asp Asp Asp Lys Ala Ala Asp Tyr Lys Asp Asp Asp Asp
    130                 135                 140

Lys
145

<210> SEQ ID NO 3
<211> LENGTH: 134
<212> TYPE: PRT
<213> ORGANISM: Artificial Sequence
<220> FEATURE:
<223> OTHER INFORMATION: Synthetic

<400> SEQUENCE: 3

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Ser Leu Pro Leu Gly Asp Tyr Asn Tyr
                85                  90                  95

Ser Leu Leu Phe Arg Gly Glu Lys Gly Ala Gly Thr Ala Leu Thr Val
            100                 105                 110

Lys Ala Ala Ala Asp Tyr Lys Asp Asp Asp Lys Ala Ala Asp Tyr
        115                 120                 125

Lys Asp Asp Asp Asp Lys
    130

<210> SEQ ID NO 4
<211> LENGTH: 149
<212> TYPE: PRT
<213> ORGANISM: Artificial Sequence
<220> FEATURE:
<223> OTHER INFORMATION: Synthetic

<400> SEQUENCE: 4

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

```
Tyr Lys Cys Gln Ala Phe Tyr Gly Leu Val Phe Phe Ala Glu Asp Val
                85                  90                  95

Gly Ser Asn Lys Gly Ala Ile Ile Gly Leu Met Val Gly Gly Val Val
            100                 105                 110

Ile Ala Gly Gly Gly Glu Lys Gly Ala Gly Thr Ala Leu Thr Val Lys
        115                 120                 125

Ala Ala Ala Asp Tyr Lys Asp Asp Asp Lys Ala Ala Asp Tyr Lys
    130                 135                 140

Asp Asp Asp Asp Lys
145

<210> SEQ ID NO 5
<211> LENGTH: 152
<212> TYPE: PRT
<213> ORGANISM: Artificial Sequence
<220> FEATURE:
<223> OTHER INFORMATION: Synthetic

<400> SEQUENCE: 5

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Gly Gly Leu Val Phe Phe Ala Glu
                85                  90                  95

Asp Val Gly Ser Asn Lys Gly Ala Ile Ile Gly Leu Met Val Gly Gly
                100                 105                 110

Val Val Ile Ala Gly Gly Gly Glu Lys Gly Ala Gly Thr Ala Leu
        115                 120                 125

Thr Val Lys Ala Ala Ala Asp Tyr Lys Asp Asp Asp Lys Ala Ala
    130                 135                 140

Asp Tyr Lys Asp Asp Asp Asp Lys
145                 150

<210> SEQ ID NO 6
<211> LENGTH: 147
<212> TYPE: PRT
<213> ORGANISM: Artificial Sequence
<220> FEATURE:
<223> OTHER INFORMATION: Synthetic

<400> SEQUENCE: 6

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80
```

```
Tyr Lys Cys Gln Ala Phe Tyr Gly Gly Val Phe Phe Ala Glu Asp Val
                85                  90                  95

Gly Ser Asn Lys Gly Ala Ile Ile Gly Leu Met Val Gly Val Val
            100                 105                 110

Ile Gly Gly Glu Lys Gly Ala Gly Thr Ala Leu Thr Val Lys Ala Ala
            115                 120                 125

Ala Asp Tyr Lys Asp Asp Asp Lys Ala Ala Asp Tyr Lys Asp Asp
    130                 135                 140

Asp Asp Lys
145

<210> SEQ ID NO 7
<211> LENGTH: 145
<212> TYPE: PRT
<213> ORGANISM: Artificial Sequence
<220> FEATURE:
<223> OTHER INFORMATION: Synthetic

<400> SEQUENCE: 7

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Val Phe Phe Ala Glu Asp Val Gly Ser
                85                  90                  95

Asn Lys Gly Ala Ile Ile Gly Pro Met Val Gly Val Val Ile Gly
            100                 105                 110

Gly Glu Lys Gly Ala Gly Thr Ala Leu Thr Val Lys Ala Ala Ala Asp
            115                 120                 125

Tyr Lys Asp Asp Asp Lys Ala Ala Asp Tyr Lys Asp Asp Asp Asp
    130                 135                 140

Lys
145

<210> SEQ ID NO 8
<211> LENGTH: 145
<212> TYPE: PRT
<213> ORGANISM: Artificial Sequence
<220> FEATURE:
<223> OTHER INFORMATION: Synthetic

<400> SEQUENCE: 8

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80
```

Tyr Lys Cys Gln Ala Phe Tyr Val Phe Ala Glu Asn Val Gly Ser
                85                  90                  95

Asn Lys Gly Ala Ile Ile Gly Leu Met Val Gly Val Val Ile Gly
            100                 105                 110

Gly Glu Lys Gly Ala Gly Thr Ala Leu Thr Val Lys Ala Ala Asp
        115                 120                 125

Tyr Lys Asp Asp Asp Asp Lys Ala Ala Asp Tyr Lys Asp Asp Asp Asp
130                 135                 140

Lys
145

<210> SEQ ID NO 9
<211> LENGTH: 145
<212> TYPE: PRT
<213> ORGANISM: Artificial Sequence
<220> FEATURE:
<223> OTHER INFORMATION: Synthetic

<400> SEQUENCE: 9

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
                20                  25                  30

Asp Thr Gly Trp Tyr Arg Thr Lys Leu Gly Ser Thr Asn Glu Gln Ser
            35                  40                  45

Ile Ser Ile Gly Gly Arg Tyr Val Glu Thr Val Asn Lys Gly Ser Lys
        50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Val Phe Phe Ala Gln Asp Val Gly Ser
                85                  90                  95

Asn Lys Gly Ala Ile Ile Gly Leu Met Val Gly Val Val Ile Gly
            100                 105                 110

Gly Glu Lys Gly Ala Gly Thr Ala Leu Thr Val Lys Ala Ala Asp
        115                 120                 125

Tyr Lys Asp Asp Asp Asp Lys Ala Ala Asp Tyr Lys Asp Asp Asp Asp
130                 135                 140

Lys
145

<210> SEQ ID NO 10
<211> LENGTH: 145
<212> TYPE: PRT
<213> ORGANISM: Artificial Sequence
<220> FEATURE:
<223> OTHER INFORMATION: Synthetic

<400> SEQUENCE: 10

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
                20                  25                  30

Asp Thr Gly Trp Tyr Arg Thr Lys Leu Gly Ser Thr Asn Glu Gln Ser
            35                  40                  45

Ile Ser Ile Gly Gly Arg Tyr Val Glu Thr Val Asn Lys Gly Ser Lys
        50                  55                  60

Ser Phe Ser Leu Arg Ile Ser Asp Leu Arg Val Glu Asp Ser Gly Thr
65                  70                  75                  80

```
Tyr Lys Cys Gln Ala Phe Tyr Val Phe Gly Glu Asp Val Gly Ser
                85                  90                  95

Asn Lys Gly Ala Ile Ile Gly Leu Met Val Gly Val Val Ile Gly
            100                 105                 110

Gly Glu Lys Gly Ala Gly Thr Ala Leu Thr Val Lys Ala Ala Asp
        115                 120                 125

Tyr Lys Asp Asp Asp Asp Lys Ala Ala Asp Tyr Lys Asp Asp Asp
    130                 135                 140

Lys
145

<210> SEQ ID NO 11
<211> LENGTH: 144
<212> TYPE: PRT
<213> ORGANISM: Artificial Sequence
<220> FEATURE:
<223> OTHER INFORMATION: Synthetic

<400> SEQUENCE: 11

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Val Phe Phe Ala Asp Val Gly Ser Asn
                85                  90                  95

Lys Gly Ala Ile Ile Gly Leu Met Val Gly Val Val Ile Gly Gly
            100                 105                 110

Glu Lys Gly Ala Gly Thr Ala Leu Thr Val Lys Ala Ala Asp Tyr
        115                 120                 125

Lys Asp Asp Asp Asp Lys Ala Ala Asp Tyr Lys Asp Asp Asp Lys
    130                 135                 140

<210> SEQ ID NO 12
<211> LENGTH: 145
<212> TYPE: PRT
<213> ORGANISM: Artificial Sequence
<220> FEATURE:
<223> OTHER INFORMATION: Synthetic

<400> SEQUENCE: 12

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Val Phe Phe Ala Glu Asp Val Gly Cys
                85                  90                  95
```

```
Asn Lys Gly Ala Ile Ile Gly Leu Met Val Gly Gly Val Ile Gly
            100                 105                 110

Gly Glu Lys Gly Ala Gly Thr Ala Leu Thr Val Lys Ala Ala Ala Asp
        115                 120                 125

Tyr Lys Asp Asp Asp Asp Lys Ala Ala Asp Tyr Lys Asp Asp Asp Asp
    130                 135                 140

Lys
145

<210> SEQ ID NO 13
<211> LENGTH: 133
<212> TYPE: PRT
<213> ORGANISM: Artificial Sequence
<220> FEATURE:
<223> OTHER INFORMATION: Synthetic

<400> SEQUENCE: 13

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Val Phe Phe Ala Glu Asp Val Gly Ser
                85                  90                  95

Asn Lys Gly Ala Ile Ile Gly Leu Met Val Gly Gly Val Ile Gly
            100                 105                 110

Gly Glu Lys Gly Ala Gly Thr Ala Leu Thr Val Lys Ala Ala Ala His
        115                 120                 125

His His His His His
    130

<210> SEQ ID NO 14
<211> LENGTH: 122
<212> TYPE: PRT
<213> ORGANISM: Artificial Sequence
<220> FEATURE:
<223> OTHER INFORMATION: Synthetic

<400> SEQUENCE: 14

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Ser Leu Pro Leu Gly Asp Tyr Asn Tyr
                85                  90                  95

Ser Leu Leu Phe Arg Gly Glu Lys Gly Ala Gly Thr Ala Leu Thr Val
            100                 105                 110
```

Lys Ala Ala Ala His His His His His His
        115                 120

<210> SEQ ID NO 15
<211> LENGTH: 124
<212> TYPE: PRT
<213> ORGANISM: Artificial Sequence
<220> FEATURE:
<223> OTHER INFORMATION: Synthetic

<400> SEQUENCE: 15

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Val Phe Phe Ala Glu Asp Val Gly Ser
                85                  90                  95

Asn Lys Gly Ala Ile Ile Gly Leu Met Val Gly Gly Val Val Ile Gly
            100                 105                 110

Gly Glu Lys Gly Ala Gly Thr Ala Leu Thr Val Lys
        115                 120

<210> SEQ ID NO 16
<211> LENGTH: 128
<212> TYPE: PRT
<213> ORGANISM: Artificial Sequence
<220> FEATURE:
<223> OTHER INFORMATION: Synthetic

<400> SEQUENCE: 16

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Gly Leu Val Phe Phe Ala Glu Asp Val
                85                  90                  95

Gly Ser Asn Lys Gly Ala Ile Ile Gly Leu Met Val Gly Gly Val Val
            100                 105                 110

Ile Ala Gly Gly Gly Glu Lys Gly Ala Gly Thr Ala Leu Thr Val Lys
        115                 120                 125

<210> SEQ ID NO 17
<211> LENGTH: 131
<212> TYPE: PRT
<213> ORGANISM: Artificial Sequence
<220> FEATURE:
<223> OTHER INFORMATION: Synthetic

```
<400> SEQUENCE: 17

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Gly Gly Leu Val Phe Phe Ala Glu
                85                  90                  95

Asp Val Gly Ser Asn Lys Gly Ala Ile Ile Gly Leu Met Val Gly Gly
                100                 105                 110

Val Val Ile Ala Gly Gly Gly Glu Lys Gly Ala Gly Thr Ala Leu
            115                 120                 125

Thr Val Lys
    130

<210> SEQ ID NO 18
<211> LENGTH: 126
<212> TYPE: PRT
<213> ORGANISM: Artificial Sequence
<220> FEATURE:
<223> OTHER INFORMATION: Synthetic

<400> SEQUENCE: 18

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Gly Gly Val Phe Phe Ala Glu Asp Val
                85                  90                  95

Gly Ser Asn Lys Gly Ala Ile Ile Gly Leu Met Val Gly Gly Val Val
                100                 105                 110

Ile Gly Gly Glu Lys Gly Ala Gly Thr Ala Leu Thr Val Lys
            115                 120                 125

<210> SEQ ID NO 19
<211> LENGTH: 124
<212> TYPE: PRT
<213> ORGANISM: Artificial Sequence
<220> FEATURE:
<223> OTHER INFORMATION: Synthetic

<400> SEQUENCE: 19

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
```

```
                35                  40                  45
Ile Ser Ile Gly Gly Arg Tyr Val Glu Thr Val Asn Lys Gly Ser Lys
 50                  55                  60
Ser Phe Ser Leu Arg Ile Ser Asp Leu Arg Val Glu Asp Ser Gly Thr
 65                  70                  75                  80
Tyr Lys Cys Gln Ala Phe Tyr Val Phe Phe Ala Glu Asp Val Gly Ser
                 85                  90                  95
Asn Lys Gly Ala Ile Ile Gly Pro Met Val Gly Gly Val Val Ile Gly
                100                 105                 110
Gly Glu Lys Gly Ala Gly Thr Ala Leu Thr Val Lys
            115                 120

<210> SEQ ID NO 20
<211> LENGTH: 124
<212> TYPE: PRT
<213> ORGANISM: Artificial Sequence
<220> FEATURE:
<223> OTHER INFORMATION: Synthetic

<400> SEQUENCE: 20

Ala Trp Val Asp Gln Thr Pro Arg Thr Ala Thr Lys Glu Thr Gly Glu
  1               5                  10                  15
Ser Leu Thr Ile Asn Cys Val Leu Arg Asp Ala Ser Phe Glu Leu Lys
                 20                  25                  30
Asp Thr Gly Trp Tyr Arg Thr Lys Leu Gly Ser Thr Asn Glu Gln Ser
             35                  40                  45
Ile Ser Ile Gly Gly Arg Tyr Val Glu Thr Val Asn Lys Gly Ser Lys
 50                  55                  60
Ser Phe Ser Leu Arg Ile Ser Asp Leu Arg Val Glu Asp Ser Gly Thr
 65                  70                  75                  80
Tyr Lys Cys Gln Ala Phe Tyr Val Phe Phe Ala Glu Asn Val Gly Ser
                 85                  90                  95
Asn Lys Gly Ala Ile Ile Gly Leu Met Val Gly Gly Val Val Ile Gly
                100                 105                 110
Gly Glu Lys Gly Ala Gly Thr Ala Leu Thr Val Lys
            115                 120

<210> SEQ ID NO 21
<211> LENGTH: 124
<212> TYPE: PRT
<213> ORGANISM: Artificial Sequence
<220> FEATURE:
<223> OTHER INFORMATION: Synthetic

<400> SEQUENCE: 21

Ala Trp Val Asp Gln Thr Pro Arg Thr Ala Thr Lys Glu Thr Gly Glu
  1               5                  10                  15
Ser Leu Thr Ile Asn Cys Val Leu Arg Asp Ala Ser Phe Glu Leu Lys
                 20                  25                  30
Asp Thr Gly Trp Tyr Arg Thr Lys Leu Gly Ser Thr Asn Glu Gln Ser
             35                  40                  45
Ile Ser Ile Gly Gly Arg Tyr Val Glu Thr Val Asn Lys Gly Ser Lys
 50                  55                  60
Ser Phe Ser Leu Arg Ile Ser Asp Leu Arg Val Glu Asp Ser Gly Thr
 65                  70                  75                  80
Tyr Lys Cys Gln Ala Phe Tyr Val Phe Phe Ala Gln Asp Val Gly Ser
                 85                  90                  95
Asn Lys Gly Ala Ile Ile Gly Leu Met Val Gly Gly Val Val Ile Gly
```

```
                100               105               110
Gly Glu Lys Gly Ala Gly Thr Ala Leu Thr Val Lys
        115                 120
```

<210> SEQ ID NO 22
<211> LENGTH: 124
<212> TYPE: PRT
<213> ORGANISM: Artificial Sequence
<220> FEATURE:
<223> OTHER INFORMATION: Synthetic

<400> SEQUENCE: 22

```
Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Val Phe Phe Gly Glu Asp Val Gly Ser
                85                  90                  95

Asn Lys Gly Ala Ile Ile Gly Leu Met Val Gly Gly Val Val Ile Gly
            100                 105                 110

Gly Glu Lys Gly Ala Gly Thr Ala Leu Thr Val Lys
        115                 120
```

<210> SEQ ID NO 23
<211> LENGTH: 123
<212> TYPE: PRT
<213> ORGANISM: Artificial Sequence
<220> FEATURE:
<223> OTHER INFORMATION: Synthetic

<400> SEQUENCE: 23

```
Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Val Phe Phe Ala Asp Val Gly Ser Asn
                85                  90                  95

Lys Gly Ala Ile Ile Gly Leu Met Val Gly Gly Val Val Ile Gly Gly
            100                 105                 110

Glu Lys Gly Ala Gly Thr Ala Leu Thr Val Lys
        115                 120
```

<210> SEQ ID NO 24
<211> LENGTH: 124
<212> TYPE: PRT
<213> ORGANISM: Artificial Sequence
<220> FEATURE:
<223> OTHER INFORMATION: Synthetic

```
<400> SEQUENCE: 24

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Val Phe Phe Ala Glu Asp Val Gly Cys
                85                  90                  95

Asn Lys Gly Ala Ile Ile Gly Leu Met Val Gly Gly Val Val Ile Gly
            100                 105                 110

Gly Glu Lys Gly Ala Gly Thr Ala Leu Thr Val Lys
            115                 120

<210> SEQ ID NO 25
<211> LENGTH: 9
<212> TYPE: PRT
<213> ORGANISM: Homo sapiens

<400> SEQUENCE: 25

Glu Asp Val Gly Ser Asn Lys Gly Ala
1               5
```

AMYLOID-BETA PEPTIDE CRYSTAL STRUCTURE

FILING DATA

This application is a §371 national stage of PCT International Application No. PCT/AU2009/001327, filed Oct. 6, 2009, claiming priority of Australian Patent Application Nos. 2008905174, filed Oct. 6, 2008 and 2008905176, filed Oct. 6, 2008, the contents of all of which are hereby incorporated by reference into this application.

REFERENCE TO SEQUENCE LISTING

This application incorporates-by-reference nucleotide and/or amino acid sequences which are present in the file named "130306_0687_82750_SEQUENCELISTING_REB.TXT", which is 29.0 kilobytes in size, and which was created Mar. 6, 2013 in the IBM-PC machine format, having an operating system compatibility with MS-Windows, which is contained in the text file filed Mar. 6, 2013 as part of this application.

FIELD

The invention relates generally to a novel crystal structure of the fibrillogenic part of amyloid β-peptide (Aβ). More specifically the crystal structure is Aβ-IgNAR and, accordingly the present invention also relates to selecting and/or designing compounds that modulate amyloid β-peptide (Aβ) activity using techniques such as in silico screening and crystal soaking experiments. The invention further relates to compounds and methods for inhibiting interaction between amyloid β-peptide (Aβ) monomers, more particularly, inhibiting or disrupting amyloid β-peptide (Aβ) oligomer formation and toxic activity

BACKGROUND

Bibliographic details of the publications referred to by author in this specification are collected alphabetically at the end of the description. The disclosure of each reference referred to in this application is incorporated herein by reference.

Reference to any prior art in this specification is not, and should not be taken as, an acknowledgment or any form of suggestion that this prior art forms part of the common general knowledge in any country.

Alzheimer's disease (AD) is a progressive neurodegenerative disorder characterized by the presence of misfolded protein depositions or amyloid plaques Crouch, P. J., S.-M. E. Harding, et al. (2008). "Mechanisms of Aβ mediated neurodegeneration in Alzheimer's disease." Int J Biochem Cell Biol 40(2): 181-198. Plaques consist predominantly of amyloid β-peptide (Aβ), which is produced by cleavage from the membrane-bound amyloid precursor protein (APP) via the β/γ secretase pathway. (The sequence of Aβ is set out in SEQ ID NO 1). However, the current view suggests that soluble Aβ oligomer intermediates, and not the plaque burden, may be the major drivers of Aβ-mediated neuronal dysfunction Walsh, D. M. and D. J. Selkoe (2007). "Aβ oligomers—a decade of discovery." J. Neurochem. 101(5): 1172-1184. Shankar, G. M., S. Li, et al. (2008). "Amyloid-beta protein dimers isolated directly from Alzheimer's brains impair synaptic plasticity and memory." Nat. Med. Frustratingly, obtaining atomic resolution information for Aβ and such oligomers has been a major challenge Kajava, A. V., J. M. Squire, et al. (2006). "β-structures in fibrous proteins." Adv Protein Chem 73: 1-15. Nelson, R. and D. Eisenberg (2006). "Recent atomic models of amyloid fibril structure." Curr Opin Struct Biol 16(2): 260-265. Nelson, R. and D. Eisenberg (2006). "Structural models of amyloid-like fibrils." Adv Protein Chem 73: 235-282, due in part to the propensity of the peptide to form amyloidal fibrils and aggregates rather than form crystallographic lattices.

The present inventors have obtained a 2.2 Å resolution crystal structure of residues 18-41 of Aβ peptide constrained within the CDR3 loop region of a shark immunoglobulin new antigen receptor (IgNAR) single variable domain antibody Henderson, K. A., V. A. Streltsov, et al. (2007). "Structure of an IgNAR-AMA1 complex: targeting a conserved hydrophobic cleft broadens malarial strain recognition." Structure 15(11): 1452-66. The predominant oligomeric species is a tightly associated Aβ dimer, with paired dimers forming a tetramer which is caged within four IgNAR domains, preventing further uncontrolled amyloid formation. The results reveal unusual Aβ loop topologies and inter-peptide interactions, strikingly different from fibrillar models based on solid state NMR spectroscopy data Petkova, A. T., Y. Ishii, et al. (2002). "A structural model for Alzheimer's b-amyloid fibrils based on experimental constraints from solid state NMR." Proc Natl Acad Sci USA 99(26): 16742-16747. Luhrs, T., C. Ritter, et al. (2005). "3D structure of Alzheimer's amyloid-β (1-42) fibrils." Proc Natl Acad Sci USA 102(48): 17342-17347. Petkova, A. T., W. M. Yau, et al. (2006). "Experimental constraints on quaternary structure in Alzheimer's β-amyloid fibrils." Biochemistry 45(2): 498-512. Sato, T., P. Kienlen-Campard, et al. (2006). "Inhibitors of amyloid toxicity based on β-sheet packing of Aβ40 and Aβ42." Biochemistry 45(17): 5503-5516, that describe Aβ residues 18-42 as forming parallel, in-register β-sheets. Notwithstanding, conserved elements can be identified within the structure consistent with residues and motifs previously identified as critical in Ap peptide folding and neurotoxicity. This crystallographic model suggests a novel paradigm for Aβ oligomer formation, and potentially provides a system for the testing of Aβ oligomer imaging reagents and Alzheimer's disease drug candidates.

SUMMARY OF THE INVENTION

In a first aspect the present invention provides a crystal of amyloid β-peptide (Aβ(18-41) as a fusion with IgNAR (Aβ-IgNAR). In a preferred embodiment the Aβ-IgNAR crystal substantially conforms to the atomic co-ordinates of Appendix I. Preferably at least 75% of the structure has the recited RMSD value, more preferably at least 90% of the structure has the recited RMSD value and most preferably about 100% of the structure has the recited RMSD value.

In a second aspect the present invention provides an Aβ-IgNAR molecule having the amino acid sequence of SEQ ID Nos 15 to 24.

In a third aspect the present invention provides a method of assessing the interaction of a compound with Aβ, the method comprising contacting the crystal of the present invention with the compound and measuring the level of binding of the compound to the Aβ crystal.

In a fourth aspect the present invention provides a method of selecting or designing a compound that interacts with Aβ protein, the method comprising (a) assessing the stereochemical complementarity between a compound and a topographic region of Aβ protein, wherein the protein comprises: (i) amino acids 18-41 of the Aβ protein positioned at atomic coordinates as shown in Appendix I, or structural coordinates having a root mean square deviation from the backbone atoms of said amino acids of not more than 1.5 Å; or (ii) one or more subsets of said amino acids related to the coordinates shown in Appendix I by whole body translations and/or rotations; (b) obtaining a compound which possesses stereochemical complementarity to a topographic region of the Aβ protein; and (c) testing the compound for its ability to modulate an activity associated with the Aβ protein.

In a fifth aspect the present invention provides a method for identifying a potential modulator compound for Aβ protein which method comprises: (a) providing a three-dimensional structure of amino acids 18-41 of Aβ protein as defined by the atomic coordinates shown in Appendix I, or atomic coordinates having a root mean square deviation from the backbone atoms of said amino acids of not more than 1.5 Å, or one or more subsets of said amino acids, or one or more subsets of said amino acids related to the coordinates shown in Appendix I by whole body translations and/or rotations; (b) providing the three-dimensional structure of a candidate compound; and (c) assessing the stereochemical complementarity between the three-dimensional structure of step (b) and a topographic region of the three-dimensional structure of step (a).

In a sixth aspect the present invention provides a computer-assisted method for identifying potential compounds able to interact with Aβ protein and thereby modulate an activity mediated by Aβ protein, using a programmed computer comprising a processor, an input device, and an output device, comprising the steps of: (a) inputting into the programmed computer, through the input device, data comprising the atomic coordinates of amino acids 18-41 of Aβ protein as shown in Appendix I, or structural coordinates having a root mean square deviation from the backbone atoms of said amino acids of not more than 1.5 Å, or one or more subsets of said amino acids, or one or more subsets of said amino acids related to the coordinates shown in Appendix I by whole body translations and/or rotations; (b) generating, using computer methods, a set of atomic coordinates of a structure that possesses stereochemical complementarity to the atomic coordinates of amino acids 18-41 of the Aβ protein as shown in Appendix I, or structural coordinates having a root mean square deviation from the backbone atoms of said amino acids of not more than 1.5 Å, or one or more subsets of said amino acids, or one or more subsets of said amino acids related to the coordinates shown in Appendix I by whole body translations and/or rotations, thereby generating a criteria data set; (c) comparing, using the processor, the criteria data set to a computer database of chemical structures; (d) selecting from the database, using computer methods, chemical structures which are similar to a portion of said criteria data set; and (e) outputting, to the output device, the selected chemical structures which are complementary to or similar to a portion of the criteria data set.

In a seventh aspect the present invention provides a method for evaluating the ability of a chemical entity to interact with Aβ protein, said method comprising the steps of: (a) creating a computer model of amino acids 18-41 of Aβ protein using structure coordinates wherein the root mean square deviation between said structure coordinates and the structure coordinates of amino acids 18-41 of Aβ protein as set forth in Appendix I is not more than about 1.5 Å; (b) employing computational means to perform a fitting operation between the chemical entity and said computer model of the binding surface; and (c) analysing the results of said fitting operation to quantify the association between the chemical entity and the Aβ protein model.

In an eighth aspect the present invention provides a computer for producing a three-dimensional representation of a molecule or molecular complex, wherein the computer comprises: (a) a machine-readable data storage medium comprising a data storage material encoded with machine-readable data, wherein the machine readable data comprise the atomic coordinates of amino acids 18-41 of Aβ protein as shown in Appendix I, or structural coordinates having a root mean square deviation from the backbone atoms of said amino acids of not more than 1.5 Å, or one or more subsets of said amino acids, or one or more subsets of said amino acids related to the coordinates shown in Appendix I by whole body translations and/or rotations; (b) a working memory for storing instructions for processing the machine-readable data; (c) a central-processing unit coupled to the working memory and to the machine-readable data storage medium, for processing the machine-readable data into the three dimensional representation; and (d) an output hardware coupled to the central processing unit, for receiving the three-dimensional representation.

In a ninth aspect the present invention provides a method of assessing the ability of a compound to affect the ability of Aβ to form dimers or tetramers, the method comprising assessing the level Aβ-IgNAR dimerisation or tetramerisation in the presence or absence of the compound.

In an embodiment of this aspect of the invention the Aβ-IgNAR has the amino acid sequence of any one of SEQ ID NOs: 2, 4-13, 15-24. In another embodiment the assessment of dimerisation or tetramerisation is made by SDS-PAGE or western blot.

In a tenth aspect the present invention provides a method of assessing the affect of a mutation in Aβ to affect the ability of Aβ to form dimers or tetramers, the method comprising assessing the level of dimerisation or tetramerisation of Aβ-IgNAR including the mutation, assessing the level of dimerisation or tetramerisation of Aβ-IgNAR without the mutation and comparing the two levels.

In an embodiment of this aspect of the invention the Aβ-IgNAR not including the mutation has the amino acid sequence of any one of SEQ ID NOs: 2, 4-6, 15-18. In another embodiment the assessment of dimerisation or tetramerisation is made by SDS-PAGE or western blot.

In a eleventh aspect the present invention provides a compound for inhibiting or disrupting amyloid β-peptide oligomer formation or toxic activity, wherein the compound interacts with the region of Aβ-peptide defined by N27, K28, I31 and L34 of Aβ-peptide wherein amino acids 18-41 of the Aβ protein are positioned at atomic coordinates as shown in Appendix I, or structural coordinates having a root mean square deviation from the backbone atoms of said amino acids of not more than 1.5 Å.

In an twelfth aspect the present invention provides a compound for inhibiting or disrupting amyloid β-peptide oligomer formation or toxic activity, wherein the compound interacts with the region of Aβ-peptide defined by G33, L34, M35 and V36 of Aβ-peptide wherein amino acids 18-41 of the Aβ protein are positioned at atomic coordinates as shown in Appendix I, or structural coordinates having a root mean square deviation from the backbone atoms of said amino acids of not more than 1.5 Å.

In a thirteenth aspect the present invention provides a compound for inhibiting or disrupting amyloid β-peptide oligomer formation or toxic activity, wherein the compound interacts with the region of Aβ-peptide defined by V18, F20, S26, K28, G29, I32, M35, V39 and I41 of Aβ-peptide wherein amino acids 18-41 of the Aβ protein are positioned at atomic coordinates as shown in Appendix I, or structural coordinates having a root mean square deviation from the backbone atoms of said amino acids of not more than 1.5 Å.

In a fourteenth aspect the present invention provides a compound for decreasing metal binding by amyloid β-peptide oligomers, wherein the compound interacts with the aligned E22 of the Aβ monomers in the Aβ oligomer.

In a fifteenth aspect the present invention provides the use of an Aβ-IgNAR molecule of any one SEQ ID NOs 2, 4, 5, 6, 13, 15, 16, 17 or 18 to raise antibodies against Aβ wherein the antibodies bind to residues 18 to 41 of SEQ ID NO 1 when presented in the Aβ-IgNAR molecule of any one of SEQ ID NOs 2, 4, 5, 6, 13, 15, 16, 17 or 18 but not to an isolated linear peptide having a sequence of residues 18 to 41 of SEQ ID NO 1.

In a sixteenth aspect the present invention provides an antibody which specifically binds to residues 18 to 41 of SEQ ID NO 1 when presented in the Aβ-IgNAR molecule of any one of SEQ ID NOs 2, 4, 5, 6, 13, 15, 16, 17 or 18 but not to an isolated linear peptide having the sequence of residues 18 to 41 of SEQ ID NO 1.

DETAILED DESCRIPTION OF THE INVENTION

Definitions

Figure 1:
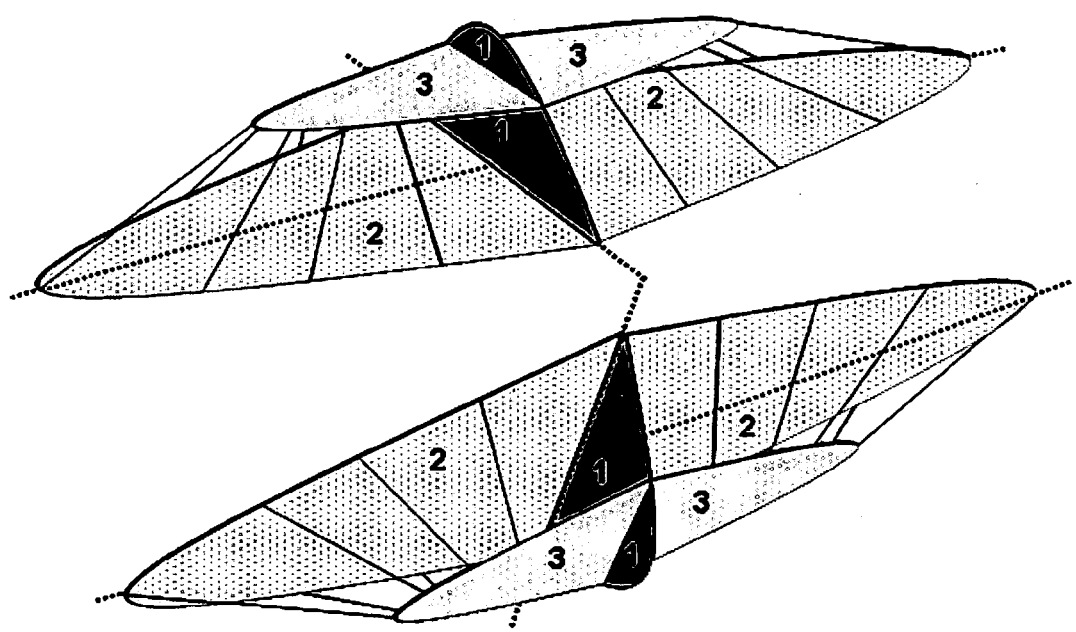
FIG. 1 shows a schematic representation Aβ-IgNAR dimer, illustrating dimer (1), tetramer (2), and amyloid (3) interfaces.

The reference to residue numbers in respect of Aβ is to number residue as in the sequence of Aβ as provided in SEQ ID NO: 1. The residue number is not the number of the residue as it appears in the Aβ-IgNAR molecule.

As used herein, the term "atomic coordinates" refer to a set of values which define the position of one or more atoms with reference to a system of axes.

A structure that "substantially conforms" to a given set of atomic coordinates is a structure wherein at least about 50% of such structure has an RMSD of less than about 1.5 Å for the backbone atoms in secondary structure elements in each domain, and more preferably, less than about 1.3 Å for the backbone atoms in secondary structure elements in each domain, and, in increasing preference, less than about 1.0 Å, less than about 0.7 Å, less than about 0.5 Å, and most preferably, less than about 0.3 Å for the backbone atoms in secondary structure elements in each domain.

Preferably a structure that substantially conforms to a given set of atomic co-ordinates is a structure wherein at least about 75% of such structure has the recited RMSD value, more preferably at least about 90% of such structure has the recited RMSD value, and most preferably, about 100% of such structure has the recited RMSD value.

The above definition of "substantially conforms" can be extended to include atoms of amino acid side chains. As used herein, the phrase "common amino acid side chains" refers to amino acid side chains that are common to both the structure which substantially conforms to a given set of atomic coordinates and the structure that is actually represented by such atomic coordinates.

By the terms "modulate" or "modulating" it is meant that the compound changes an Aβ monomer, dimer, or tetramer by at least 10%. Suitably, a compound modulates Aβ monomer, dimer, or tetramer by decreasing oligomerization or toxicity.

By using the terms "inhibition"/"inhibiting" and/or "disruption"/"disrupting" it is intended to include the concept of "modulate" or "modulating."

The phrase "decrease oligomerization or toxicity" is intended to encompass partial or complete inhibition of oligomerization or toxicity. The ability of a compound to increase or decrease activity can be assessed by any one of the Aβ oligomerization or toxicity assays described herein.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG 3, IgG4, IgA1 and IgA2) or subclass.

The term "antigen binding domain" or "antigen binding portion" of an antibody, as used herein, refers to one or more fragments of an antibody or protein that retain the ability to specifically bind to an antigen (e.g., IL-12). It has been shown that the antigen-binding function of an antibody can be performed by fragments of a full-length antibody. Such antibody embodiments may also be bispecific, dual specific, or multispecific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. 1989 Nature 341 544-6, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); (see e.g., Bird et al. 1988 Science 242 423-6; Huston et al. 1988 Proc Natl Acad Sci USA 85 5879-83). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad. Sci. USA 90:6444-6448; Poljak, R. J., et al., 1994, Structure 2:1121-1123). Such antibody binding portions are known in the art (Kontermann and Dubel eds., Antibody Engineering 2001 Springer-Verlag. New York. 790 pp., ISBN 3-540-41354-5).

In a first aspect the present invention provides a crystal of amyloid β-peptide Aβ(18-41) as a fusion with IgNAR (Aβ-IgNAR). In a preferred embodiment the Aβ3-IgNAR crystal substantially conforms to the atomic co-ordinates of Appendix I. Preferably at least 75% of the structure has the recited RMSD value, more preferably at least 90% of the structure has the recited RMSD value and most preferably about 100% of the structure has the recited RMSD value.

In a second aspect the present invention provides an Aβ-IgNAR molecule having the amino acid sequence of SEQ ID Nos 15 to 24. SEQ ID Nos 15 to 24 set forth the amino acid sequences of the Aβ-IgNAR molecules described in Table 4, but without the 2× FLAG tag present in those molecules listed in Table 4. Thus, SEQ ID No:15 sets forth the amino acid sequence of a fusion of amyloid β-peptide Aβ(18-41) with IgNAR (Aβ-IgNAR); SEQ ID No.16 sets forth the amino acid sequence of a variant Aβ-IgNAR molecule containing the Gly3 mutation; SEQ ID No.17 sets forth the amino acid sequence of a variant Aβ-IgNAR molecule containing the Gly6 mutation; SEQ ID No.18 sets forth the amino acid sequence of a variant Aβ-IgNAR molecule containing the Gly2 mutation; SEQ ID No.19 sets forth the amino acid sequence of a variant Aβ-IgNAR molecule containing the Leu34Pro mutation; SEQ ID No.20 sets forth the amino acid sequence of a variant Aβ-IgNAR molecule containing the Asp23Asn mutation; SEQ ID No.21 sets forth the amino acid sequence of a variant Aβ-IgNAR molecule containing the Glu22Gln mutation; SEQ ID No.22 sets forth the amino acid sequence of a variant Aβ-IgNAR molecule containing the Ala21Gly mutation; SEQ ID No.23 sets forth the amino acid sequence of a variant Aβ-IgNAR molecule containing the ΔGlu22 mutation; and SEQ ID No.24 sets forth the amino acid sequence of a variant Aβ-IgNAR molecule containing the Ser26Cys mutation.

In a third aspect the present invention provides a method of assessing the interaction of a compound with Aβ, the method comprising contacting the crystal of the present invention with the compound and measuring the level of binding of the compound to the Aβ crystal.

In a fourth aspect the present invention provides a method of selecting or designing a compound that interacts with Aβ protein, the method comprising (a) assessing the stereochemical complementarity between a compound and a topographic region of Aβ protein, wherein the protein comprises: (i) amino acids 18-41 of the Aβ protein positioned at atomic coordinates as shown in Appendix I, or structural coordinates having a root mean square deviation from the backbone atoms of said amino acids of not more than 1.5 Å; or (ii) one or more subsets of said amino acids related to the coordinates shown in Appendix I by whole body translations and/or rotations; (b) obtaining a compound which possesses stereochemical complementarity to a topographic region of the Aβ protein; and (c) testing the compound for its ability to modulate an activity associated with the Aβ protein.

In a fifth aspect the present invention provides a method for identifying a potential modulator compound for Aβ protein which method comprises: (a) providing a three-dimensional structure of amino acids 18-41 of Aβ protein as defined by the atomic coordinates shown in Appendix I, or atomic coordinates having a root mean square deviation from the backbone atoms of said amino acids of not more than 1.5 Å, or one or more subsets of said amino acids, or one or more subsets of said amino acids related to the coordinates shown in Appendix I by whole body translations and/or rotations; (b) providing the three-dimensional structure of a candidate compound; and (c) assessing the stereochemical complementarity between the three-dimensional structure of step (b) and a topographical region of the three-dimensional structure of step (a).

In a sixth aspect the present invention provides a computer-assisted method for identifying potential compounds able to interact with Aβ protein and thereby modulate an activity mediated by Aβ protein, using a programmed computer comprising a processor, an input device, and an output device, comprising the steps of: (a) inputting into the programmed computer, through the input device, data comprising the atomic coordinates of amino acids 18-41 of Aβ protein as shown in Appendix I, or structural coordinates having a root mean square deviation from the backbone atoms of said amino acids of not more than 1.5 Å, or one or more subsets of said amino acids, or one or more subsets of said amino acids related to the coordinates shown in Appendix I by whole body translations and/or rotations; (b) generating, using computer methods, a set of atomic coordinates of a structure that possesses stereochemical complementarity to the atomic coordinates of amino acids 18-41 of the Aβ protein as shown in Appendix I, or structural coordinates having a root mean square deviation from the backbone atoms of said amino acids of not more than 1.5 Å, or one or more subsets of said amino acids, or one or more subsets of said amino acids related to the coordinates shown in Appendix I by whole body translations and/or rotations, thereby generating a criteria data set; (c) comparing, using the processor, the criteria data set to a computer database of chemical structures; (d) selecting from the database, using computer methods, chemical structures which are similar to a portion of said criteria data set; and (e) outputting, to the output device, the selected chemical structures which are complementary to or similar to a portion of the criteria data set.

In a seventh aspect the present invention provides a method for evaluating the ability of a chemical entity to interact with Aβ protein, said method comprising the steps of: (a) creating a computer model of amino acids 18-41 of Aβ protein using structure coordinates wherein the root mean square deviation between said structure coordinates and the structure coordinates of amino acids 18-41 of Aβ protein as set forth in Appendix I is not more than about 1.5 Å; (b) employing computational means to perform a fitting operation between the chemical entity and said computer model of the binding surface; and (c) analysing the results of said fitting operation to quantify the association between the chemical entity and the Aβ protein model.

In an eighth aspect the present invention provides a computer for producing a three-dimensional representation of a molecule or molecular complex, wherein the computer comprises: (a) a machine-readable data storage medium comprising a data storage material encoded with machine-readable data, wherein the machine readable data comprise the atomic coordinates of amino acids 18-41 of Aβ protein as shown in Appendix I, or structural coordinates having a root mean square deviation from the backbone atoms of said amino acids of not more than 1.5 Å, or one or more subsets of said amino acids, or one or more subsets of said amino acids related to the coordinates shown in Appendix I by whole body translations and/or rotations; (b) a working memory for storing instructions for processing the machine-readable data; (c) a central-processing unit coupled to the working memory and to the machine-readable data storage medium, for processing the machine-readable data into the three dimensional representation; and (d) an output hardware coupled to the central processing unit, for receiving the three-dimensional representation.

The Aβ-IgNAR crystal may comprises an Aβ-IgNAR monomer, dimer or tetramer as described in more detail below.

In a preferred embodiment, an Aβ-IgNAR crystal of the invention has the atomic coordinates set forth in Appendix I. It will be understood by those skilled in the art that atomic coordinates may be varied, without affecting significantly the accuracy of models derived therefrom; thus, although the invention provides a very precise definition of a preferred atomic structure, it will be understood that minor variations are envisaged and the claims are intended to encompass such variations. Preferred are variants in which the root mean square deviation (RMSD) of the x, y and z co-ordinates for all backbone atoms other than hydrogen is less than 1.5 Å (preferably less than 1 Å, 0.7 Å or less than 0.3 Å) compared with the coordinates given in Appendix I. It will be readily appreciated by those skilled in the art that a 3D rigid body rotation and/or translation of the atomic coordinates does not alter the structure of the molecule concerned.

In a highly preferred embodiment, the crystal has the atomic coordinates as shown in Appendix I.

As used herein, the term "atomic coordinates" refer to a set of values which define the position of one or more atoms with reference to a system of axes.

The present invention also provides a crystal structure of an Aβ(18-41) polypeptide (monomer, dimer and tetramer), or a region thereof.

The atomic coordinates obtained experimentally for amino acids 18 to 41 of Aβ-IgNAR are shown in Appendix I. However, a person skilled in the art will appreciate that a set of atomic coordinates determined by X-ray crystallography is not without standard error. Accordingly, any set of structure coordinates for an Aβ-IgNAR polypeptide that has a root mean square deviation of protein backbone atoms of less than 1.5 Å when superimposed (using backbone atoms) on the atomic coordinates listed in Appendix I shall be considered identical.

The present invention also comprises the atomic coordinates of Aβ(18-41) polypeptide (monomer, dimer and tetramer) that substantially conform to the atomic coordinates listed in Appendix I.

A structure that "substantially conforms" to a given set of atomic coordinates is a structure wherein at least about 50% of such structure has an RMSD of less than about 1.5 Å for the backbone atoms in secondary structure elements in each domain, and more preferably, less than about 1.3 Å for the backbone atoms in secondary structure elements in each domain, and, in increasing preference, less than about 1.0 Å, less than about 0.7 Å, less than about 0.5 Å, and most preferably, less than about 0.3 Å for the backbone atoms in secondary structure elements in each domain.

In a more preferred embodiment, a structure that substantially conforms to a given set of atomic coordinates is a structure wherein at least about 75% of such structure has the recited RMSD value, and more preferably, at least about 90% of such structure has the recited RMSD value, and most preferably, about 100% of such structure has the recited RMSD value.

In an even more preferred embodiment, the above definition of "substantially conforms" can be extended to include atoms of amino acid side chains. As used herein, the phrase "common amino acid side chains" refers to amino acid side chains that are common to both the structure which substantially conforms to a given set of atomic coordinates and the structure that is actually represented by such atomic coordinates.

The variations in coordinates may be generated due to mathematical manipulations of the structure coordinates. For example, the structure coordinates set forth in Appendix I could be manipulated by crystallographic permutations of the structure coordinates, fractionalisation of the structure coordinates, integer additions or subtractions to sets of the structure coordinates, inversion of the structure coordinates, or any combination thereof.

Alternatively, modification in the crystal structure due to mutations, additions, substitutions, and/or deletions of amino acids, or other changes in any of the components that make up the crystal could also account for variations in structure coordinates.

Various computational analyses are used to determine whether a molecular complex or a portion thereof is sufficiently similar to all or parts of the structure of Aβ-IgNAR and Aβ monomer, dimer and tetramer described above. Such analyses may be carried out in current software applications, such as the Molecular Similarity program of QUANTA (Molecular Simulations Inc., San Diego, Calif.) version 4.1.

The Molecular Similarity program permits comparisons between different structures, different conformations of the same structure, and different parts of the same structure.

Comparisons typically involve calculation of the optimum translations and rotations required such that the root mean square difference of the fit over the specified pairs of equivalent atoms is an absolute minimum. This number is given in angstroms.

Accordingly, structural coordinates of Aβ-IgNAR or Aβ monomer, dimer or tetramer within the scope of the present invention include structural coordinates related to the atomic coordinates listed in Appendix I by whole body translations and/or rotations. Accordingly, RMSD values listed above assume that at least the backbone atoms of the structures are optimally superimposed which may require translation and/or rotation to achieve the required optimal fit from which to calculate the RMSD value.

A three dimensional structure of Aβ-IgNAR or Aβ monomer, dimer or tetramer or region thereof which substantially conforms to a specified set of atomic coordinates can be modelled by a suitable modeling computer program such as MODELER (Sali & Blundell, 1993), as implemented in the Insight II Homology software package (Insight II (97.0), MSI, San Diego), using information, for example, derived from the following data: (1) the amino acid sequence of the Aβ-IgNAR or Aβ monomer, dimer or tetramer polypeptide; (2) the amino acid sequence of the related portion(s) of the protein represented by the specified set of atomic coordinates having a three dimensional configuration; and, (3) the atomic coordinates of the specified three dimensional configuration. A three dimensional structure of Aβ-IgNAR or Aβ monomer, dimer or tetramer polypeptide which substantially conforms to a specified set of atomic coordinates can also be calculated by a method such as molecular replacement, which is described in detail below.

Structure coordinates/atomic coordinates are typically loaded onto a machine readable-medium for subsequent computational manipulation. Thus models and/or atomic coordinates are advantageously stored on machine-readable media, such as magnetic or optical media and random-access or read-only memory, including tapes, diskettes, hard disks, CD-ROMs and DVDs, flash memory cards or chips, servers and the internet. The machine is typically a computer.

The structure coordinates/atomic coordinates may be used in a computer to generate a representation, e.g. an image, of the three-dimensional structure of the Aβ-IgNAR or Aβ monomer, dimer or tetramer crystal which can be displayed by the computer and/or represented in an electronic file.

The structure coordinates/atomic coordinates and models derived therefrom may also be used for a variety of purposes such as drug discovery, biological reagent (binding protein) selection and X-ray crystallographic analysis of other protein crystals.

The three-dimensional structure of Aβ-IgNAR or Aβ monomer, dimer or tetramer provided by the present invention can be used to identify potential target binding sites on Aβ monomer, dimer or tetramers, or derived higher order multimers (i.e. to identify those regions of Aβ involved in oligomerization and/or toxicity and/or disease) as well as in methods for identifying or designing compounds which interact with potential target binding sites of Aβ, e.g. potential modulators/inhibitors of Aβ.

In one embodiment, the target binding site is a region of Aβ involved in oligermisation. Preferred target binding sites comprise one or more of the following domains: the dimerisation domain, the tetramerisation domain, the amyloid formation domain.

In a ninth aspect the present invention provides a method of assessing the ability of a compound to affect the ability of Aβ to form dimers or tetramers, the method comprising assessing the level Aβ-IgNAR dimerisation or tetramerisation in the presence or absence of the compound.

In an embodiment of this aspect of the invention the Aβ-IgNAR has the amino acid sequence of any one of SEQ ID NOs: 2, 4-13, 15-24. In another embodiment the assessment of dimerisation or tetramerisation is made by SDS-PAGE or western blot.

In a tenth aspect the present invention provides a method of assessing the affect of a mutation in Aβ to affect the ability of Aβ to form dimers or tetramers, the method comprising assessing the level of dimerisation or tetramerisation of Aβ-IgNAR including the mutation, assessing the level of dimerisation or tetramerisation of Aβ-IgNAR without the mutation and comparing the two levels.

In a eleventh aspect the present invention provides a compound for inhibiting or disrupting amyloid β-peptide oligomer formation or toxic activity, wherein the compound interacts with the region of Aβ-peptide defined by N27, K28, I31 and L34 of Aβ-peptide wherein amino acids 18-41 of the Aβ protein are positioned at atomic coordinates as shown in Appendix I, or structural coordinates having a root mean square deviation from the backbone atoms of said amino acids of not more than 1.5 Å.

In an embodiment of this aspect the region of Aβ-peptide is defined by F19, A21, G25, N27, K28, I31 and L34.

In an embodiment of this aspect of the invention the compound is the peptide 27-NKGAI-31 to compete with formation of the dimer.

In another embodiment of this aspect of the invention the compound is the peptide 27-NKxxIxxL-34 (wherein x is any amino acid) to compete with formation of the dimer with or with out flanking residues.

In another embodiment the compound is an antibody or an antigen binding region thereof which binds Aβ-peptide in the region defined by N27, K28, I31 and L34. The antibody or antigen binding region may bind the Aβ-peptide in the region defined by F19, A21, G25, N27, K28, I31 and L34.

In an twelfth aspect the present invention provides a compound for inhibiting or disrupting amyloid β-peptide oligomer formation or toxic activity, wherein the compound interacts with the region of Aβ-peptide defined by G33, L34, M35 and V36 of Aβ-peptide wherein amino acids 18-41 of the Aβ protein are positioned at atomic coordinates as shown in Appendix I, or structural coordinates having a root mean square deviation from the backbone atoms of said amino acids of not more than 1.5 Å.

In an embodiment of this aspect the region of Aβ-peptide is defined by I32, G33, L34, M35 and V36.

In an embodiment of this aspect of the invention the compound is the peptide 33-GLMV-36 to compete for tetramer with or without flanking residues In another embodiment of this aspect of the invention the compound is the peptide 31-IIGLxV-36 (wherein x is any amino acid) to compete with the formation of the tetramer.

In another embodiment the compound is an antibody or an antigen binding region thereof which binds Aβ-peptide in the region defined by G33, L34, M35 and V36. The antibody or antigen binding region may bind the Aβ-peptide in the region defined by I32, G33, L34, M35 and V36.

In a thirteenth aspect the present invention provides a compound for inhibiting or disrupting amyloid β-peptide oligomer formation or toxic activity, wherein the compound interacts with the region of Aβ-peptide defined by V18, F20, S26, K28, G29, I32, M35, V39 and I41 of Aβ-peptide wherein amino acids 18-41 of the Aβ protein are positioned at atomic coordinates as shown in Appendix I, or structural coordinates having a root mean square deviation from the backbone atoms of said amino acids of not more than 1.5 Å.

In an embodiment of this aspect the region of Aβ-peptide is defined by V18, F20, D23, S26, K28, G29, A30, I32, M35, G37, V39 and I41.

In an embodiment of this aspect of the invention the compound is the peptide selected from the group consisting of the peptides 26-SxKG-29, 18-VxF-20, 32-IxxM-35, and 39-VxI-41 each with or without flanking sequences; wherein the peptide competes for formation of amyloid.

In another embodiment the compound is an antibody or an antigen binding region thereof which binds Aβ-peptide in the region defined by V18, F20, S26, K28, G29, I32, M35, V39 and I41. The antibody or antigen binding region may bind the Aβ-peptide in the region defined by V18, F20, D23, S26, K28, G29, A30, I32, M35, G37, V39 and I41.

In a fourteenth aspect the present invention provides a compound for decreasing metal binding by amyloid β-peptide oligomers, wherein the compound interacts with the aligned E22 of the Aβ monomers in the Aβ oligomer.

The compounds of the present invention may also be foldamers or peptidomimetics including peptidomimetics based on β-peptides. More information these classes of compounds can be found in the following references, the disclosure of which is incorporated herein by reference.

Ripka, Amy Sa; Rich, Daniel Ha. Peptidomimetic design. Current Opinion in Chemical Biology. Vol: 2, Issue: 4, 1998 441-452.

Robinson J A, Demarco S, Gombert F, Moehle K, Obrecht D. The design, structures and therapeutic potential of protein epitope mimetics. Drug Discov Today. 2008 Sep. 10.

Robinson J A. beta-Hairpin Peptidomimetics: Design, Structures and Biological Activities. Acc Chem. Res. 2008 Apr. 16.

Appella, D. H.; Christianson, L. A.; Karle, I. L.; Powell, D. R.; Gellman, S. H. β-Peptide Foldamers: Robust Helix Formation in a New Family of -Amino Acid Oligomers J. Am. Chem. Soc.; (Communication); 1996; 118(51); 13071-13072.

Gellman, S. H., "Foldamers: a manifesto", Acc. Chem. Res 1998, 31(4): 173-180.

Hill D J, Mio M J, Prince R B, Hughes T S, Moore J S, "A field guide to foldamers", Chem. Rev. 2001, 101(12): 3893-4012.

In another aspect the present invention provides a method of inhibiting or disrupting amyloid β-peptide oligomer formation or toxic activity, the method comprising contacting the Aβ-peptide with a compound according to the present invention.

In another embodiment of the present invention the peptides have the same or a similar conformation as they do in the Aβ-peptide. This confirmation is provided by the coordinates amino acids 18-41 of the Aβ protein as shown in Appendix I, or structural coordinates having a root mean square deviation from the backbone atoms of said amino acids of not more than 1.5 Å.

The target or binding site is a region of Aβ involved in oligermisation. Preferred target or binding sites comprise one or more of the following domains: the dimerisation domain, the tetramerisation domain, the amyloid formation domain.

A schematic representation of Aβ-IgNAR dimer is shown in FIG. 1. The interfaces which may be targeted include:
The dimer interface (1)
The tetramer interface (2) and
The amyloid interface (3)

Alternatively, the target binding site may comprise one or more amino acids from one or more of the following amino acid sequences:
(i) amino acids V18-I41;
(ii) amino acids F19, A21, G25, N27, K28, G29, I31, L34 (dimer interface)
(iii) amino acids I32, G33, L34, M35, V36 (tetramer interface)
(iv) amino acids V18, F20, D23, S26, K28, G29, A30, I32, M35, G37, V39, I41 (amyloid interface)

A compound may interact with a specified region of Aβ-IgNAR and Aβ monomer, dimer, or tetramer (e.g. an interface) by binding either directly or indirectly to that region. A compound which binds directly, binds to the specified region. A compound which binds indirectly, binds to a region in close proximity to or adjacent to the specified region with the result that it interferes with the ability of the specified region to oligomerise, either antagonistically or agonistically. Such interference may be steric, electrostatic, or allosteric. Preferably, a compound interacts with a specified region of the Aβ-IgNAR and Aβ monomer, dimer, or tetramer by binding directly to the specified region.

Binding can be either by covalent or non-covalent interactions, or both. Examples of non-covalent interactions include electrostatic interactions, van der Waals interactions, hydrophobic interactions and hydrophilic interactions.

When a compound interacts with Aβ-IgNAR and Aβ monomer, dimer, or tetramer, it preferably "modulates" Aβ-IgNAR and Aβ monomer, dimer, or tetramer activity respectively. By "modulate" we mean that the compound changes an activity of Aβ-IgNAR and Aβmonomer, dimer, or tetramer by at least 10%. Suitably, a compound modulates Aβ-IgNAR and Aβ monomer, dimer, or tetramer by decreasing oligomerization or toxicity. The phrase "decrease oligomerization or toxicity" is intended to encompass partial or complete inhibition of oligomerization or toxicity. The ability of a candidate compound to increase or decrease activity can be assessed by any one of the Aβ oligomerization or toxicity assays described herein.

As mentioned above one of the assay protocols involves assessment of binding using the actual crystal. Binding of chemical fragments/compounds is assessed by soaking or co-crystallizing such fragments/compounds into crystals provided by the invention and then subjecting these to an X-ray beam and obtaining diffraction data. Difference Fourier techniques are readily applied by those skilled in the art to determine the location within the Aβ-IgNAR and Aβ monomer, dimer, or tetramer structure at which these fragments/compounds bind.

Typically compounds derived from the various screening protocols described herein are subjected to biological testing. There are a number of such test and a useful review is provided in Rahimi, F., Shanmugam, A. & Bitan, G.; Structure-function relationships of pre-fibrillar protein assemblies in Alzheimer's disease and related disorders. Current Alzheimer research 5, 319-341 (2008) The disclosure of which is incorporated herein by reference.

Other methods involving the use of the crystal or A3-IgNAR protein include:

Assays utilising the Aβ-IgNAR protein and crystals/structure:

Recombinant Protein Production and SDS-Page/Western Blot

Assessment of dimerisation and tetramerisation of recombinant Aβ-IgNAR proteins.

Analysis of affect of familial/in vitro determined/structurally predicted/experimentally derived mutations on Aβ-IgNAR folding, oligomerization, and toxicity.

Analysis of action of peptides/compounds/fragments/metals/antibodies on oligomerization of Aβ peptide.

Figure 2A:
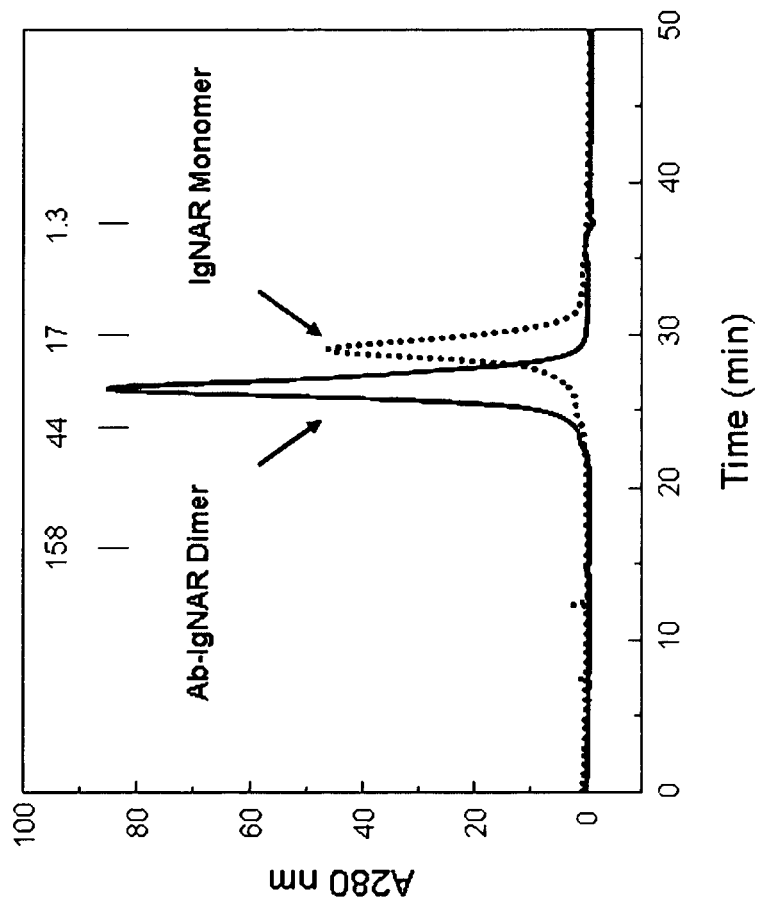
FIG. 2 Aβ-IgNAR fusions form a stable dimer. a, Affinity purified Aβ-IgNAR-G1 elutes as a dimer by gel filtration (solid line) in comparison to 12Y-2 IgNAR monomer (dotted line), b, SDS-PAGE of affinity-purified Aβ-IgNAR-G1 under reducing (R) and non-reducing (U) conditions, illustrating formation of tetrameric (arrowed) species in the absence of heating/reducing agent.

An example of this method is shown in FIG. 2a where the monomer-dimer ratio is used an assay tool ie using ability of compounds to disrupt formation of dimer, and assaying by SDS-PAGE and western blot.

Size Exclusion Chromatography

Assessment of dimerisation and tetramerisation of recombinant Aβ-IgNAR proteins.

Analysis of affect of familial/in vitro determined/structurally predicted/experimentally derived mutations on Aβ-IgNAR folding, oligomerization, and toxicity.

Analysis of action of peptides/compounds/fragments/antibodies on dimerisation and tetramerisation of Aβ-IgNAR.

Analysis of action of peptides/compounds/fragments/metals/antibodies on oligomerization of Aβ-IgNAR.

BIAcore Biosensor

Determination of binding affinities for peptides/compounds/fragments/antibodies targeting the Aβ-IgNAR structure.

Protein Crystallography

Analysis of affect of familial/in vitro determined/structurally predicted/experimentally derived mutations on Aβ-IgNAR structure and oligomerization.

Determination of binding site of peptides/compounds/fragments/metals/antibodies in the Aβ-IgNAR structure.

X-Ray Absorption Spectrometry

Determination of binding sites of metals, stoichiometry and oxidation state in the Aβ-IgNAR structure using X-ray Absorption Near-Edge Spectroscopy (XANES) and Extended X-ray Absorption Fine Structure (EXAFS) methods.

Assaying derived/selected peptides/compounds/fragments/antibodies for activity

Electron Microscopy

Analysis of action of peptides/compounds/fragments/metals/antibodies on oligomerization of Aβ peptide.

Yeast Cell Toxicity Assays

Analysis of affect of peptides/compounds/fragments/antibodies on oligomerization of Aβ peptide in yeast systems.

Analysis of action of peptides/compounds/fragments/metals/antibodies in reducing Aβ-mediated cellular toxicity in yeast systems.

Neuronal Cell Toxicity Assays

Analysis of action of peptides/compounds/fragments/metals/antibodies in reducing Aβ-mediated cellular toxicity in neuronal cell lines.

In vitro neuroprotection (MTT) assay against oligomer-mediated toxicity

Animal Studies

Analysis of action of peptides/compounds/fragments/metals/antibodies in reducing Aβ-mediated cellular toxicity in animal model systems.

Further information regarding these and other methods which may be usefully applied in the present invention is provided in the following references the disclosures of which is incorporated herein by reference Streltsov, V. A. (2008). "X-ray absorption and diffraction studies of the metal binding sites in amyloid β-peptide." *Eur Biophys J* 37(3): 257-263.

Streltsov, V. A. and J. N. Varghese (2008). "Substrate mediated reduction of copper-amyloid-β complex in Alzheimer's disease." *Chem Commun (Camb)*(27): 3169-3171.

Streltsov, V. A. Titmuss, S. J., Epa, V. C., Barnham, K. J., Masters, C. L., Varghese, J. N. (2008). "The structure of the Amyloid β-peptide high affinity Copper II binding site in Alzheimer's Disease." *Biophysical Journal*. (2008) 95 (7) 3447-3456

Caine, J., et al. Alzheimer's Ab fused to green fluorescent protein induces growth stress and a heat shock response. FEMS Yeast Res 7, 1230-1236 (2007).

Bharadwaj, P., Waddington, L., Varghese, J. & Macreadie, I. G. A new method to measure cellular toxicity of non-fibrillar and fibrillar Alzheimer's Abeta using yeast. J Alzheimers Dis 13, 147-150 (2008).

Mosmann, T. Rapid colorimetric assay for cellular growth and survival: application to proliferation and cytotoxicity assays. *Journal of immunological methods* 65, 55-63 (1983).

Maynard C J, Cappai R, Volitakis I, Cherny R A, Masters C L, Li Q X, Bush A I. Gender and genetic background effects on brain metal levels in APP transgenic and normal mice: implications for Alzheimer beta-amyloid pathology. J Inorg Biochem. 2006 May; 100(5-6):952-62.

Gotz, J., et al. A decade of tau transgenic animal models and beyond. *Brain pathology* (Zurich, Switzerland) 17, 91-103 (2007).

Direct binding of compounds to Aβ-IgNAR and Aβ monomer, dimer, or tetramer can also be assessed by Surface Plasmon Resonance (BIAcore) (reviewed in Morton & Myszka, 1998). Here Aβ-IgNAR and Aβ monomer, dimer, or tetramer is immobilized on a CM5 or other sensor chip by either direct chemical coupling using amine or thiol-disulphide exchange coupling (Nice & Catimel, 1999) or by capturing as a fusion protein to an appropriately derivatised sensor surface (Morten & Myszka, 1998). The potential binding molecule (called an analyte) is passed over the sensor surface at an appropriate flow rate and a range of concentrations. The classical method of analysis is to collect responses for a wide range of analyte concentrations. A range of concentrations provides sufficient information about the reaction, and by using a fitting algorithm such as CLAMP (see Morton & Myszka, 1998), rate constants can be determined (Morton & Myszka, 1998; Nice & Catimel, 1999). Normally, the ligand surface is regenerated at the end of each analyte binding cycle. Surface regeneration ensures that the same number of ligand binding sites is accessible to the analyte at the beginning of each cycle.

Incubation periods are selected for optimum activity, but may also be optimized to facilitate rapid high-throughput screening. Normally, between 0.1 and 1 hour will be sufficient. In general, a plurality of assay mixtures is run in parallel with different test agent concentrations to obtain a differential response to these concentrations. Typically, one of these concentrations serves as a negative control, i.e. at zero concentration or below the level of detection.

The basic format of oligomerization and toxicity assays are as follows:

(i) gel filtration; and western blot/SDS-PAGE
(ii) cellular assays
(iii) electron microscopy and oligomerization
(iv) yeast assays
(v) animal studies The compounds/chemical entities of the present invention may be used to modulate Aβ oligomerization and/or toxicity in cells, by direct binding of the chemical entity to an interface or region of Aβ-IgNAR and Aβ monomer, dimer, or tetramer and/or by an allosteric interaction elsewhere.

Given that Aβ monomer, dimer, or tetramer or oligomerization activity and toxicity is implicated in neuronal disfunction and a range of disorders, the compounds of the present invention may also be used to treat, ameliorate or prevent disorders associated with Alzheimer's disease and/or other amyloidogenic neuropathies.

The compounds which interact with Aβ-IgNAR and Aβ monomer, dimer, or tetramer and in particular to interact with the target interfaces, are useful as agonists or antagonists against the action of Aβ on other yet to be identified ligands. The compounds are useful as assay reagents for identifying other useful ligands by, for example as research tools for further analysis of Aβ oligomerization and as potential therapeutics in pharmaceutical compositions.

Aβ-IgNAR and Aβ monomer, dimer, or tetramer antagonists provided by this invention are potentially useful as therapeutics. For example, compounds are potentially useful as treatments for Alzheimers disease. These antagonists may also be used to detect the presence of Ab dimers in biological samples in particular blood and CSF. In this regard the biological sample is contacted with the compound and the level of binding assessed.

As will be evident to the skilled person, the crystal structures presented herein have enabled, for the first time, the identification of critical regions and conformations of Aβ involved in folding, dimerisation, tetramerisation, and oligermisation leading to fibril formation and toxicity.

Using a variety of known modelling techniques, the crystal structure of the present invention can be used to produce a model for at least part of Aβ monomer, dimer, or tetramer, and higher order oligomers.

As used herein, the term "modelling" includes the quantitative and qualitative analysis of molecular structure and/or function based on atomic structural information and interaction models. The term "modelling" includes conventional numeric-based molecular dynamic and energy minimisation models, interactive computer graphic models, modified molecular mechanics models, distance geometry and other structure-based constraint models.

Molecular modelling techniques can be applied to the atomic coordinates of the Aβ-IgNAR and Aβ monomer, dimer, or tetramer or a region thereof to derive a range of 3D models and to investigate the structure of interfaces and binding sites, such as the binding sites of monoclonal antibodies, nonimmunoglobulin binding proteins and inhibitory peptides.

These techniques may also be used to screen for or design small and large chemical entities which are capable of binding Aβ-IgNAR and Aβ monomer, dimer, or tetramer, their respective interfaces, and affecting oligomerization and toxicity. The screen may employ a solid 3D screening system or a computational screening system.

Such modelling methods are to design or select chemical entities that possess stereochemical complementary to particular regions of Aβ-IgNAR and Aβ monomer, dimer, or tetramer. By "stereochemical complementarity" we mean that the compound or a portion thereof makes a sufficient number of energetically favourable contacts with Aβ as to have a net reduction of free energy on binding.

Such stereochemical complementarity is characteristic of a molecule that matches intra-site surface residues located at
 (i) amino acids V18-I41;
 (ii) amino acids N27, K28, I31, L34, (dimer interface)
 (iii) amino acids G33, L34, M35, V36; (tetramer interface)
 (iv) amino acids V18, F20, S26, K28, G29, I32, M35, V39, I41 (amyloid interface),
 Or combinations thereof.
 Additional intra-site residues include:
 amino acids F19, A21, G25, N27, K28, G29, I31, L34 (dimer interface)
 amino acids I32, G33, L34, M35, V36 (tetramer interface)
 amino acids V18, F20, D23, S26, K28, A30, I32, M35, G37, V39, I41 (amyloid interface)

By "match" we mean that the identified portions interact with the surface residues, for example, via hydrogen bonding or by non-covalent Van der Waals and Coulomb interactions (with surface or residue) which promote desolvation of the molecule within the site, in such a way that retention of the molecule at the binding site is favoured energetically.

It is preferred that the stereochemical complementarity is such that the compound has a $K_d$ for the site of less than $10^{-4}$M, more preferably less than $10^{-5}$M and more preferably $10^{-6}$M. In a most preferred embodiment, the $K_d$ value is less than $10^{-8}$M and more preferably less than $10^{-9}$M.

Chemical entities which are complementary to the shape and electrostatics or chemistry of the sites characterised by amino acids positioned at atomic coordinates set out in Appendix I will be able to bind to the regions given above, either independently or in combination and when the binding is sufficiently strong, substantially inhibit oligomerization and/or toxicity.

It will be appreciated that it is not necessary that the complementarity between chemical entities and the site(s) extend over all residues of the site(s) in order to inhibit oligomerization and/or toxicity.

A number of methods may be used to identify chemical entities possessing stereo-complementarity to a region of the Aβ-IgNAR and Aβ monomer, dimer, or tetramer. For instance, the process may begin by visual inspection of potential interface sites, on the computer screen based on the Aβ-IgNAR and Aβ monomer, dimer, or tetramer structures, or region thereof, coordinates in Appendix I generated from the machine-readable storage medium. Alternatively, selected fragments or chemical entities may then be positioned in a variety of orientations, or docked, within an individual binding site of Aβ-IgNAR and Aβ monomer, dimer, or tetramer, as defined supra. Modelling software that is well known and available in the art may be used (Guida, 1994). These include QUANTA and InsightII [Molecular Simulations, Inc., San Diego, Calif., a division of Pharmacopiea, Inc., Princeton, N.J., 1992], SYBYL [Molecular Modeling Software, Tripos Associates, Inc., St. Louis, Mo., 1992]. This modelling step may be followed by energy minimization with standard molecular mechanics force fields such as AMBER (Weiner et al., 1984), and CHARMM (Brooks et al., 1983). In addition, there are a number of more specialized computer programs to assist in the process of selecting the binding moieties of this invention.

Specialised computer programs may also assist in the process of selecting fragments or chemical entities. These include, inter alia:
 1. GRID (Goodford, 1985). GRID is available from Oxford University, Oxford, UK.
 2. MCSS (MXXXanker & Karplus, 1991). MCSS is available from Molecular Simulations, Burlington, Mass.

3. AUTODOCK (Goodsell & Olsen, 1990). AUTODOCK is available from Scripps Research Institute, La Jolla, Calif.

4. DOCK (Kuntz et al., 1982). DOCK is available from University of California, San Francisco, Calif.

Once suitable chemical entities or fragments have been selected, they can be assembled into a single compound. In one embodiment, assembly may proceed by visual inspection of the relationship of the fragments to each other on the three-dimensional image displayed on a computer screen in relation to the structure coordinates of Aβ-IgNAR and Aβ monomer, dimer, or tetramer. This is followed by manual model building using software such as Quanta or Sybyl. Alternatively, fragments may be joined to additional atoms using standard chemical geometry.

The above-described evaluation process for chemical entities may be performed in a similar fashion for chemical compounds.

Useful programs to aid one skilled in the art in connecting the individual chemical entities or fragments include:

1. CAVEAT (Bartlett et al., 1989). CAVEAT is available from the University of California, Berkeley, Calif.

2. 3D Database systems such as MACCS-3D (MDL Information Systems, San Leandro, Calif.). This area is reviewed in Martin (1992).

3. HOOK (available from Molecular Simulations, Burlington, Mass.).

Other molecular modeling techniques may also be employed in accordance with this invention, see, e.g., Cohen et al. (1990) and Navia & Murcko (1992).

There are two preferred approaches to designing a molecule, according to the present invention, that complement the stereochemistry of Aβ-IgNAR and Aβ monomer, dimer, or tetramer. The first approach is to in silico directly dock molecules from a three-dimensional structural database, to the interface site(s), using mostly, but not exclusively, geometric criteria to assess the goodness-of-fit of a particular molecule to the site. In this approach, the number of internal degrees of freedom (and the corresponding local minima in the molecular conformation space) is reduced by considering only the geometric (hard-sphere) interactions of two rigid bodies, where one body (the active site) contains "pockets" or "grooves" that form binding sites for the second body (the complementing molecule).

This approach is illustrated by Kuntz et al. (1982) and Ewing et al. (2001), the contents of which are hereby incorporated by reference, whose algorithm for ligand design is implemented in a commercial software package, DOCK version 4.0, distributed by the Regents of the University of California and further described in a document, provided by the distributor, which is entitled "Overview of the DOCK program suite" the contents of which are hereby incorporated by reference. Pursuant to the Kuntz algorithm, the shape of the interface represented by a site on the Aβ-IgNAR and Aβ monomer, dimer, or tetramer is defined as a series of overlapping spheres of different radii. One or more extant databases of crystallographic data, such as the Cambridge Structural Database System maintained by Cambridge University (University Chemical Laboratory, Lensfield Road, Cambridge, U.K.), the Protein Data Bank maintained by the Research Collaboratory for Structural Bioinformatics (Rutgers University, N.J., U.S.A.), LeadQuest (Tripos Associates, Inc., St. Louis, Mo.), Available Chemicals DXXXectory (Molecular Design Ltd., San Leandro, Calif.), and the NCI database (National Cancer Institute, U.S.A) is then searched for molecules which approximate the shape thus defined.

Molecules identified on the basis of geometric parameters, can then be modified to satisfy criteria associated with chemical complementarity, such as hydrogen bonding, ionic interactions and Van der Waals interactions. Different scoring functions can be employed to rank and select the best molecule from a database. See for example Bohm & Stahl (1999). The software package FlexX, marketed by Tripos Associates, Inc. (St. Louis, Mo.) is another program that can be used in this direct docking approach (see Rarey et al., 1996).

The second preferred approach entails an assessment of the interaction of respective chemical groups ("probes") with the active site at sample positions within and around the site, resulting in an array of energy values from which three-dimensional contour surfaces at selected energy levels can be generated. The chemical-probe approach to ligand design is described, for example, by Goodford, (1985), the contents of which are hereby incorporated by reference, and is implemented in several commercial software packages, such as GRID (product of Molecular Discovery Ltd., West Way House, Elms Parade, Oxford OX2 9LL, U.K.).

Pursuant to this approach, the chemical prerequisites for a site-complementing molecule are identified at the outset, by probing the active site with different chemical probes, e.g., water, a methyl group, an amine nitrogen, a carboxyl oxygen, or a hydroxyl. Favoured sites for interaction between the active site and each probe are thus determined, and from the resulting three-dimensional pattern of such sites a putative complementary molecule can be generated. This may be done either by programs that can search three-dimensional databases to identify molecules incorporating desired pharmacophore patterns or by programs which use the favoured sites and probes as input to perform de novo design. Suitable programs for determining and designing pharmacophores include CATALYST (including HypoGen or HipHop) (Molecular Simulations, Inc), and CERIUS2, DISCO (Abbott Laboratories, Abbott Park, Ill.) and ChemDBS-3D (Chemical Design Ltd., Oxford, U.K.).

The pharmacophore can be used to screen in silico compound libraries/three-dimensional databases, using a program such as CATALYST (Molecular Simulations, Inc); MACCS-3D and ISIS/3D (Molecular Design Ltd., San Leandro, Calif.), ChemDBS-3D (Chemical Design Ltd., Oxford, U.K.), and Sybyl/3DB Unity (Tripos Associates, Inc., St. Louis, Mo.).

Databases of chemical structures are available from a number of sources including Cambridge Crystallographic Data Centre (Cambridge, U.K.), Molecular Design, Ltd., (San Leandro, Calif.), Tripos Associates, Inc. (St. Louis, Mo.), Chemical Abstracts Service (Columbus, Ohio), the Available Chemical DXXXectory (MDL Inc), the Derwent World Drug Index (WDI), BioByteMasterFile, the National Cancer Institute database (NCI), and the Maybridge catalogue.

De novo design programs include LUDI (Biosym Technologies Inc., San Diego, Calif.), Leapfrog (Tripos Associates, Inc.), Aladdin (Daylight Chemical Information Systems, Irvine, Calif.), and LigBuilder (Peking University, China).

Once an entity or compound has been designed or selected by the above methods, the efficiency with which that entity or compound may bind to Aβ-IgNAR and Aβ monomer, dimer, or tetramer can be tested and optimised by computational evaluation. An effective Aβ-IgNAR and Aβ monomer, dimer, or tetramer binding compound must preferably demonstrate a relatively small difference in energy between its bound and free states (i.e., a small deformation energy of binding). Thus, the most efficient Aβ-IgNAR and Aβ monomer, dimer, or tetramer binding compound should preferably be designed with a deformation energy of binding of not greater than about 10 kcal/mole, preferably, not greater than 7 kcal/mole.

Binding compounds may interact with Aβ-IgNAR and Aβ monomer, dimer, or tetramer in more than one conformation that are similar in overall binding energy. In those cases, the deformation energy of binding is taken to be the difference between the energy of the free compound and the average energy of the conformations observed when the compound binds to the protein.

A compound designed or selected as binding to Aβ-IgNAR and Aβ monomer, dimer, or tetramer may be further computationally optimised so that in its bound state it would preferably lack repulsive electrostatic interaction with the target protein. Such non-complementary (e.g., electrostatic) interactions include repulsive charge-charge, dipole-dipole and charge-dipole interactions. Specifically, the sum of all electrostatic interactions between the compound and the protein when the compound is bound to Aβ-IgNAR and Aβ monomer, dimer, or tetramer, preferably make a neutral or favourable contribution to the enthalpy of binding.

Once an Aβ-IgNAR and Aβ monomer, dimer, or tetramer-binding compound has been optimally selected or designed, as described above, substitutions may then be made in some of its atoms or side groups to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analysed for efficiency of fit to Aβ-IgNAR and Aβ monomer, dimer, or tetramer by the same computer methods described in detail above.

Specific computer software is available in the art to evaluate compound deformation energy and electrostatic interaction. Examples of programs designed for such uses include: Gaussian 92, revision C (Frisch, Gaussian, Inc., Pittsburgh, Pa.); AMBER, version 4.0 (Kollman, University of California at San Francisco); QUANTA/CHARMM (Molecular Simulations, Inc., Burlington, Mass.); and Insight II/Discover (Biosysm Technologies Inc., San Diego, Calif.).

The screening/design methods may be implemented in hardware or software, or a combination of both. However, preferably, the methods are implemented in computer programs executing on programmable computers each comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program is preferably implemented in a high level procedural or object-oriented programming language to communicate with a computer system. However, the programs can be implemented in assembly or machine language, if desired. In any case, the language may be compiled or interpreted language.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

Screening Assays and Confirmation of Binding and Biological Activity

Compounds selected or designed in accordance with the in silico methods of the invention may be subjected to further confirmation of binding to Aβ-IgNAR and Aβ monomer, dimer, or tetramer by cocrystallization of the compound with Aβ-IgNAR and Aβ monomer, dimer, or tetramer and structural determination, as described herein.

Libraries may be screened in solution by methods generally known in the art for determining whether ligands competitively bind at a common site. Such methods may include screening libraries in solution (e.g.; Houghten, 1992), or on beads (Lam, 1991), chips (Fodor, 1993), bacteria or spores (U.S. Pat. No. 5,223,409: Lardner), plasmids (Cull et al., 1992), or on phage (Scott & Smith, 1990; Devlin, 1990; CwXXXla et al., 1990; Felici, 1991; U.S. Pat. No. 5,223,409: Lardner).

Where the screening assay is a binding assay, Aβ-IgNAR and Aβ monomer, dimer, or tetramer may be joined to a label, where the label can directly or indirectly provide a detectable signal. Various labels include radioisotopes, fluorescent molecules, chemiluminescent molecules, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g., albumin, detergents, etc., which are used to facilitate optimal protein-protein binding and/or reduce non-specific or background interactions. Reagents that improve the efficiency of the assay, such as protease inhibitors, nuclease inhibitors, antimicrobial agents, etc., may be used. The components are added in any order that produces the requisite binding. Incubations are performed at any temperature that facilitates optimal activity, typically between 4 and 40° C.

The Aβ-IgNAR molecule may be used in its own right as a sink or tool to mop up oligomers both in vivo and in vitro ie as a therapeutic.

The Aβ-IgNAR molecule of the present invention may also be used as an antigen to raise antibodies against Aβ.

In a fifteenth aspect the present invention provides the use of an Aβ-IgNAR molecule of any one SEQ ID NOs 2, 4, 5, 6, 13, 15, 16, 17 or 18 to raise antibodies against Aβ wherein the antibodies bind to residues 18 to 41 of SEQ ID NO 1 when presented in the Aβ-IgNAR molecule of any one of SEQ ID NOs 2, 4, 5, 6, 15, 16, 17 or 18 but not to an isolated linear peptide having a sequence of residues 18 to 41 of SEQ ID NO 1.

In a sixteenth aspect the present invention provides an antibody which specifically binds to residues antibodies bind to residues 18 to 41 of SEQ ID NO 1 when presented in the Aβ-IgNAR molecule of any one of SEQ ID NOs 2, 4, 5, 6, 13, 15, 16, 17 or 18 but not to an isolated linear peptide having a sequence of residues 18 to 41 of SEQ ID NO 1.

In a preferred embodiment the antibody is a monoclonal antibody.

As will be understood by persons skilled in the art the antibodies of the present invention are directed to conformational epitopes of 18-41 of Aβ which are presented when Aβ

18-41 is positioned within the Aβ-IgNAR molecule. Such conformational epitopes will not be present in the isolated linear Aβ 18-41 peptide.

In addition to therapeutic uses the antibodies of the present invention may also be used in diagnostic assays to detect the presence of Aβ dimers in biological samples in particular blood and CSF. In this regard the biological sample is contacted with the antibody and the level of binding assessed.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

In order that the nature of the present invention may be more clearly understood, preferred forms thereof will now be described with reference to the following non-limiting examples.

EXAMPLE 1

Methods Summary

Construction of Aβ-IgNAR chimeras. Aβ-IgNAR-G1/G3/G6 and G1-Leu$^{34}$Pro coding sequences were constructed by splice-overlap PCR using IgNAR 12Y-2 DNA template (Nuttall, Humberstone et al. 2004), cloned into *E. coli* periplasmic expression vector pGC, and verified by DNA sequencing.

Protein purification and crystallization. Recombinant proteins were expressed into the *E. coli* periplasmic space, purified by affinity chromatography through an anti-FLAG Ig/Sepharose column equilibrated in TBS, and collected as single peaks by gel filtration. Proteins (~4-5 mg/ml in 20 mM Tris.HCl, pH 8.0) were set up as 0.4 μl sitting drops. Aβ-IgNAR-G1 (SEQ ID NO: 2) crystallised under a wide range of conditions (biased towards PEG 6000; PEG 3350; and PEG MME 2000 at neutral pH). Final crystallisation conditions were 0.2 M ammonium chloride, 20% polyethylene glycol (PEG) 6000, 0.1 M MES pH 6, with diffraction quality crystals (Space Group P3$_2$ and cell parameters a=b=79.40, c=84.89 Å) obtained after 9 days. No crystals were obtained for Aβ-IgNAR-G3 (SEQ ID NO: 4) or Aβ-IgNAR-G6 (SEQ ID NO: 5).

Structure determination. A full data set (93% completeness) was collected at the Australian Synchrotron 3-BM1 beam line to 2.2 Å resolution. Data were collected at −160° C. and processed using the HKL2000 suite (Otwinowski and Minor 1997). Diffraction data statistics are summarized in Table 1. The structure was solved by molecular replacement MOLREP (Vagin and Teplyakov 1997) using IgNAR 12Y-2 (PDB 1VES) minus CDR3 region as search template. Four independent molecules (A, B, C and D) were found in the asymmetric unit. The final refinement converged to R/R$_{free}$ values of 0.164/0.246. In total, 97.8% residues are in the most favoured regions of the Ramachandran plot, with 1.6% residues in the additionally allowed regions.

TABLE 1

| X-ray refinement statistics | |
|---|---|
| Resolution (Å) | 26.17-2.20 |
| R$_{work}$/R$_{free}$ | 16.4/24.6 |
| Number of | |
| Protein amino acids | 503 |
| Water | 394 |
| B-factors | |
| Overall | 46.5 |
| Protein | 46.0 |
| Water | 51.7 |
| R.m.s deviations | |
| Bond lengths (Å) | 0.019 |
| Bond angles (°) | 1.958 |

Results

Figure 2B:
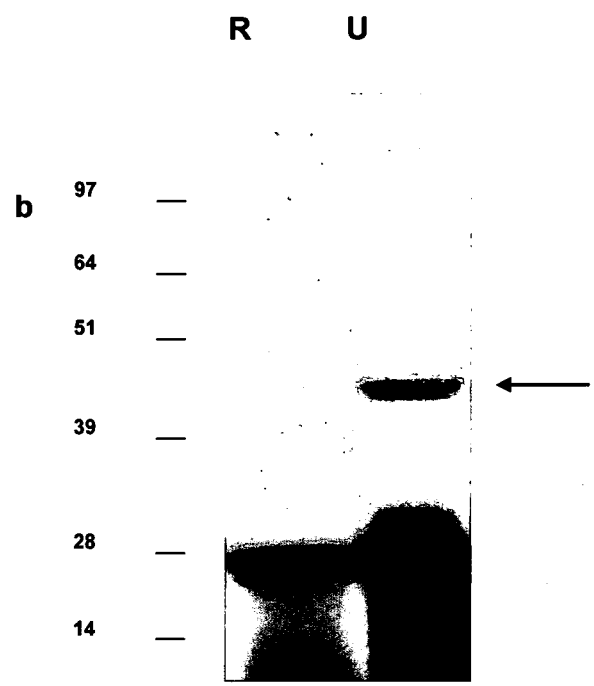
Figure 3:
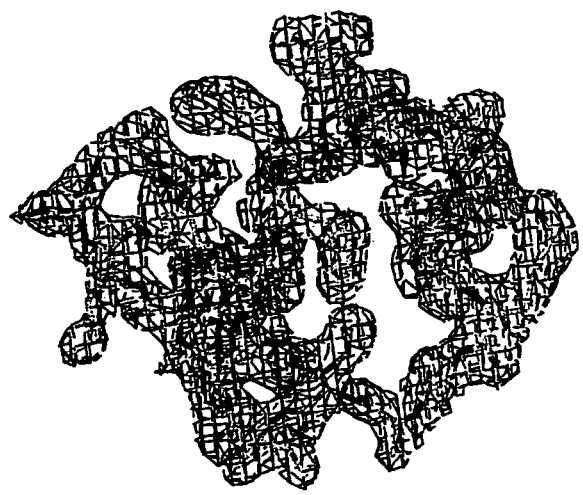
FIG. 3 Representative electron density for Aβ-IgNAR-G1. Electron density $2F_o-F_c$ for residues 18-41 of Aβ-IgNAR-G1 chain A. The map is contoured at 1.0σ.

The crystallographic structures of the IgNAR single variable domain antibody 12Y-2(Streltsov, Varghese et al. 2004) (PDB: 1VES) reveal self-stabilized extended β-hairpin CDR3 loop regions. We hypothesized that engineering the amyloidogenic component of Aβ peptide (residues Val$^{17}$-Ala$^{42}$) within this loop would (1) allow formation of an amyloid protofilament structure; while (2) preventing uncontrolled fibril formation and polymerisation by trapping the amyloid moiety in a cage of IgNAR domains that are amenable to crystallization. Three chimeric proteins were modelled based on existing NMR β-hairpin models of amyloid plaques (Luhrs, Ritter et al. 2005), incorporating variable N- and C-terminal glycine linkers to allow in-register transition from the immunoglobulin framework β-sheets to the Aβ peptide. These constructs, designated Aβ-IgNAR-G1 (SEQ ID NO. 2); Aβ-IgNAR-G3 (SEQ ID NO. 4); and Aβ-IgNAR-G6 (SEQ ID NO. 5), were expressed as recombinant proteins in *E. coli* and tested for oligomer formation. SDS and β-mercaptoethanol-stable dimers were observed in the bacterial periplasmic space by Western blot for all three chimeric proteins but not the unmodified IgNAR. The greater conformational flexibility for the glycine-3 and glycine-6 versions appeared to allow more rapid dimer formation, and protein induction at higher temperature tended to promote a higher dimer:monomer ratio. Upon affinity purification all 3 variants behaved as dimers, rather than the monomer observed for the wild type IgNAR, and tetrameric species were also apparent. (FIGS. 2a and 2b). Trigonal crystals of Aβ-IgNAR-G1 (SEQ ID NO: 2), but not the other two chimeric proteins, grew under a variety of conditions and diffracted to 2.2 Å resolution. The structure was solved by molecular replacement using IgNAR 12Y-2 (SEQ ID NO: 3) with removed CDR3 region as the search model, and refinement completed with R/R$_{free}$ factors of 16.4/24.6% (Table 1). Representative regions of electron density are shown in FIG. 3.

Figure 4:
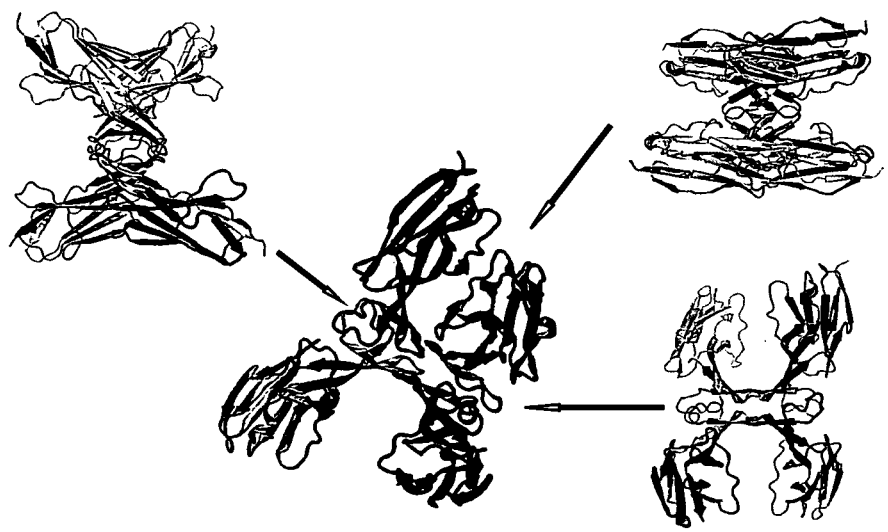
FIG. 4 Aβ-IgNAR-G1 tetramer. Three aspects of the Aβ-IgNAR-G1 tetramer are shown, illustrating the axis of approximate symmetry through dimeric and tetrameric forms.

The Aβ-IgNAR-G1 (SEQ ID NO: 2) quaternary structure consists of four independent molecules (A, B, C and D) in the asymmetric unit (FIG. 4), which form a tight tetramer (dimer of dimers) through interactions predominantly mediated by the Aβ peptide component. The inter-chain association for each dimer (A-C and B-D) is extremely robust, as indicated by an average surface of interaction (buried surface) of 580 Å$^2$ and an average shape correlation statistic (Lawrence and Colman 1993) (S$_c$)=0.64 (Tables 2 & 3). The dimer-dimer interaction (AC-BD) which forms the crystallographic tetramer is somewhat less extensive (buried surface of 546 Å$^2$). The underlying IgNAR scaffold monomers are very closely overlaid with each-other and with the previously described 12Y-2 structure.

TABLE 2

Aβ-IgNAR-G1 buried surface areas[1].

| Chain | A | B | C | D | Total[2] |
|---|---|---|---|---|---|
| A | — | 215.7 | 589.0 | 290.8 | 1095.5 |
| B | 215.7 | — | 254.9 | 563.8 | 1034.4 |
| C | 578.2 | 250.2 | — | 215.8 | 1044.2 |
| D | 296.5 | 569.6 | 221.5 | — | 1087.6 |
| Average | | | | | 1065.4 |

[1]For Aβ regions only.
[2]Area excluded on first molecule due to interaction with second (in Angstroms squared). Calculated using point density = 10 points/square Å; Probe sphere radius = 1.7 Å.

TABLE 3

Aβ-IgNAR-G1 shape complementarity statistics [1].

| Sc | A | B | C | D |
|---|---|---|---|---|
| A | 1 | 0.590 | 0.709 | 0.786 |
| B | | 1 | 0.742 | 0.567 |
| C | | | 1 | 0.717 |
| D | | | | 1 |

[1]Calculated using the Sc program with a 1.7 Å probe radius.

The Aβ-IgNAR-G1 structure reveals the Aβ peptide region (Val$^{18}$-Ile$^{41}$) as comprising two adjacent and connected loop motifs, rather than the expected extended β-hairpin structure. The first motif consists of residues Val$^{18}$-Ile$^{31}$ which adopt a 10-11 Å wide β-α structure, stabilised by intra-molecular and inter-molecular contacts and consisting of one β strand (Val$^{18}$-Ala$^{21}$) plus a 3$_{10}$-helical turn (Val$^{24}$-Ser$^{26}$)(chains A) and similar but distorted helix in chain B or an extended loop (chains C and D). The second motif consists of residues Ile$^{32}$-Ile$^{41}$ and is a β-hairpin consisting of two anti-parallel β-strands which form a 3-strand β-sheet with the parallel β-strand of the first loop motif. The overlaid Aβ loops have an average r.m.s.d.=1.19 Å$^2$, and as can be seen from FIG. 2d the greatest divergence occurs between residues Val$^{24}$-Asn$^{27}$, where chains A and B adopt a different conformation from chains C and D. Consequently, for the A/B chain conformations the Lys$^{28}$ side-chain is directed out of the plane of the loop and forms intramolecular contacts with Val$^{24}$ (2.6 Å) and Asn$^{27}$ (3.6 Å) (chain A) and helps maintain the helical conformation of Val$^{24}$-Ser$^{26}$. In contrast, for the C/D chains the Lys$^{28}$ side chain is now directed internally and forms two intra-molecular contacts with the carbonyl oxygens of Asp$^{23}$ (3.0 and 3.5 Å) and Ser$^{26}$ (4.0 and 3.0 Å) and two intermolecular contacts with carbonyl oxygens of chain A/B: Gly$^{29}$ (2.6 and 3.3 Å) and Asn$^{27}$ (2.8 and 3.6 Å). The transition between the two states for Lys$^{28}$ appears pivotal to crystallisation, and may represent a vital mechanism (and energy minimum) for Aβ oligomer formation. In NMR-based structures of amyloid plaques, residues Leu$^{17}$-Ala$^{42}$ form parallel, in-register β-sheets (Petkova, Ishii et al. 2002; Luhrs, Ritter et al. 2005; Sato, Kienlen-Campard et al. 2006), with Lys$^{28}$ facing outward in the first Aβ chain of the adjacently stacked peptides, while subsequent Aβ peptides have the Lys$^{28}$ side-chain directed internally and forming intermolecular contacts (salt bridges) with residue Asp$^{23}$ (Luhrs, Ritter et al. 2005; Petkova, Yau et al. 2006; Sato, Kienlen-Campard et al. 2006). Thus our structure is consistent with NMR data for this position.

Overall, the dimers (AC and BD), each related by an pseudo 2-fold axis running through the long axis of the tetramer, are stabilized around the Asp$^{23}$-Ala$^{30}$ loop by the carbonyl oxygen charges neutralizing the buried Lys$^{28}$ amide group and by the amide group of Asp$^{27}$ forming a hydrogen bonding network with the neighbouring dimer's carbonyl oxygen of Gly$^{29}$ and carboxy oxygen of Asp$^{27}$. The surface towards the tetramer interface is stabilized by the hydrophobic residues Ile$^{31}$, Val$^{40}$, and Leu$^{34}$. The tetramer interface is stabilized by two 3-stranded β-sheets of the monomer forming a single 6-stranded β-sheet with a pseudo-2-fold axis running perpendicular to and through the centroid of the extended β-sheets. The Leu$^{34}$ side-chains face each other: two from each side of the tetramer, rotated by ~90° (see later). Similarly, the respective Met$^{35}$ side-chains are surrounded by hydrophobic residues Ile$^{32}$, Val$^{39}$ and Ile$^{41}$. Intermolecular contacts seen by NMR such as Ala$^{21}$/Val$^{36}$ (Luhrs, Ritter et al. 2005) and Ile$^{32}$/Leu$^{34}$/Val$^{36}$ (Petkova, Yau et al. 2006) are also observed for this motif. An earlier crystallographic structure of Aβ(28-42) fused C-terminally to Tk-RNase HII (Takano, Endo et al. 2006) also suggested formation of a limited β-hairpin conformation which partially overlaps with the Aβ-IgNAR-G1 β-hairpin motif (r.m.s.d.=1.9 Å for 13 atoms).

Figure 5:
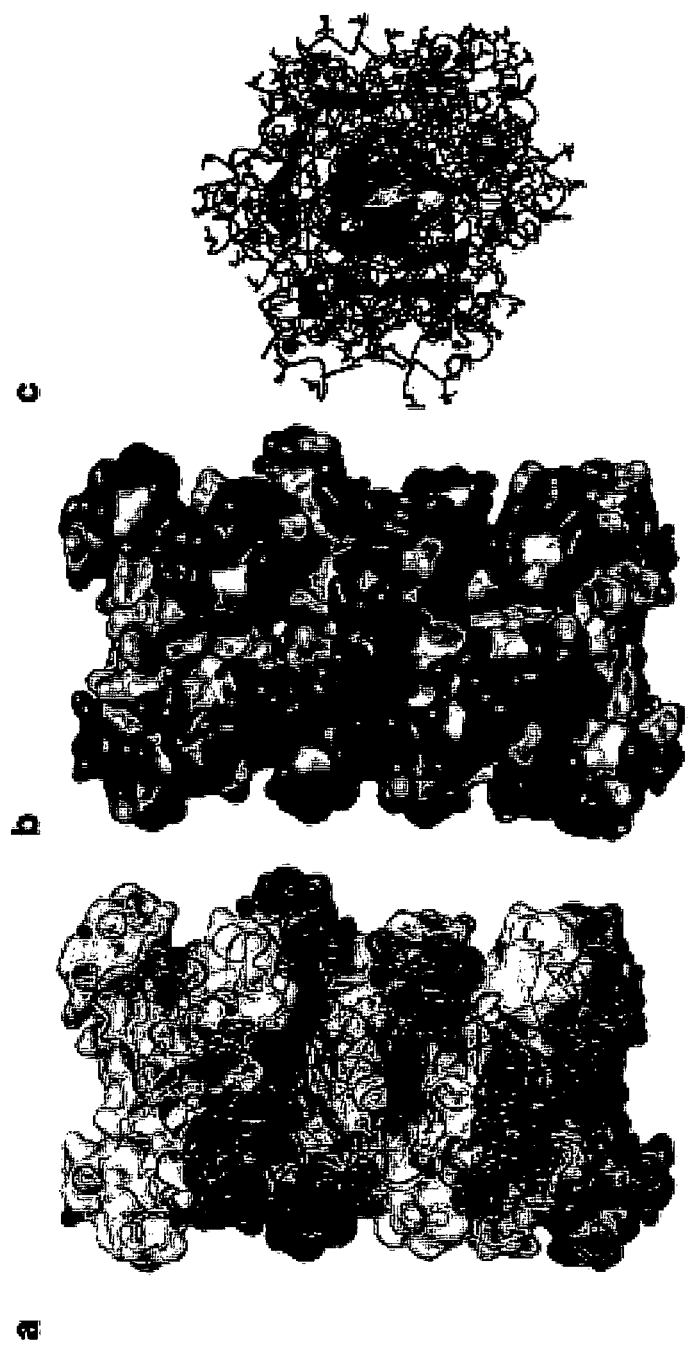
FIG. 5 Models of amyloid fibril formation. a, Construction of Aβ oligomer model based on the Aβ-IgNAR-G1 tetramer, incorporating six Aβ (1-41) metal-binding tetramers. The cartoon representation is overlayed with surfaces shaded by chains. Black spheres represent metals (Zn, Cu etc). b, As for a, represented as solubility surface (dark—hydrophilic; light—hydrophobic) c, View along the oligomer axis.
Figure 6:
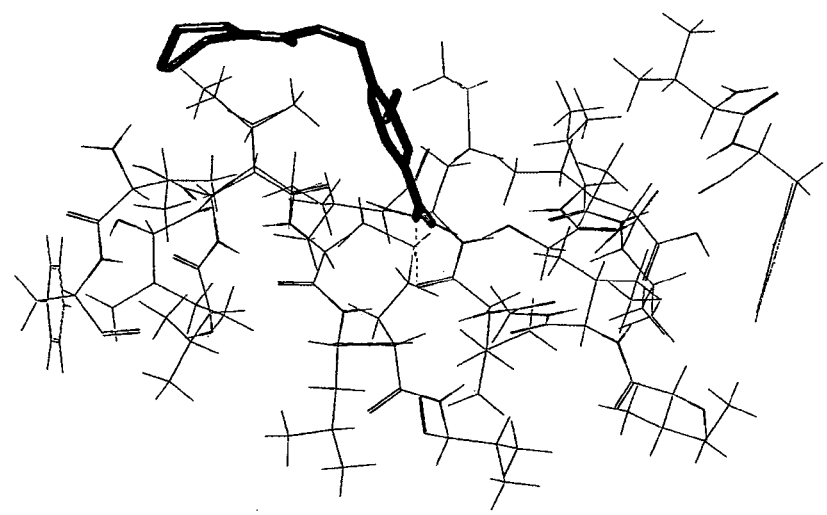
FIG. 6 In silico docking of ChemBridge 9124833 to the Aβ-IgNAR-G1 structure. The compound 3-methoxy-4-[2-(4-morpholinyl)-2-oxoethoxy]aniline (dark shading) docked within the Aβ-IgNAR-G1 structure (wireframe).
Figure 7:
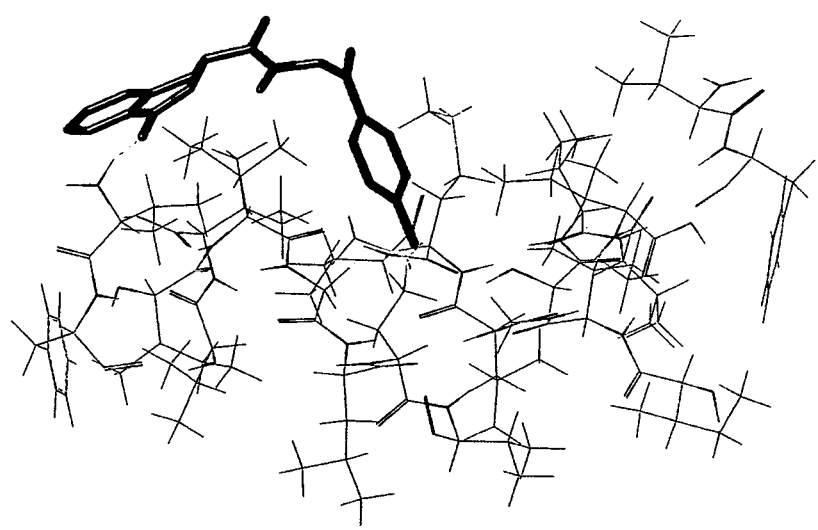
FIG. 7 In silico docking of ChemBridge 7996209 to the Aβ-IgNAR-G1 structure. The compound N-[2-(4-methylphenyl)-2-oxoethyl]-1-oxo-3,4-dihydro-1H-isochromene-3-carboxamide (dark shading) docked within the Aβ-IgNAR-G1 structure (wireframe).
Figure 8:
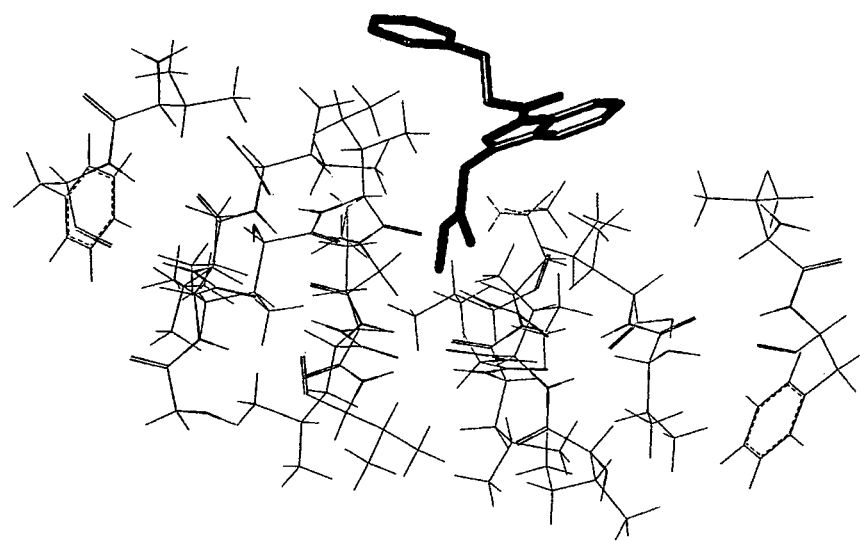
FIG. 8 In silico docking of ChemBridge 7949851 to the Aβ-IgNAR-G1 structure. The compound methyl [3-(phenoxyacetyl)-1H-indol-1-yl]acetate (dark shading) docked within the Aβ-IgNAR-G1 structure (wireframe).
Figure 9:
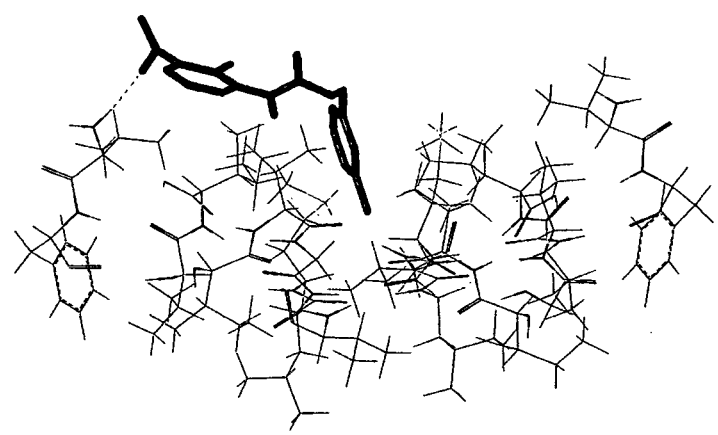
FIG. 9 In silico docking of ChemBridge 7780327 to the Aβ-IgNAR-G1 structure. The compound 2-methyl-3-{[(3-methylphenoxy)acetyl]amino}benzoic acid (dark shading) docked within the Aβ-IgNAR-G1 structure (wireframe).
Figure 10:
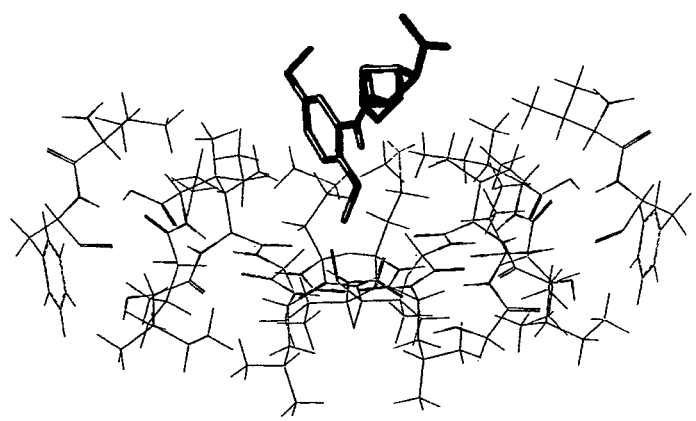
FIG. 10 In silico docking of ChemBridge 7302096 to the Aβ-IgNAR-G1 structure. The compound 3-{[(2,5-dimethoxyphenyl)amino]carbonyl}-7-oxabicyclo[2.2.1]hept-5-ene-2-carboxylic acid (dark shading) docked within the Aβ-IgNAR-G1 structure (wireframe).
Figure 11:
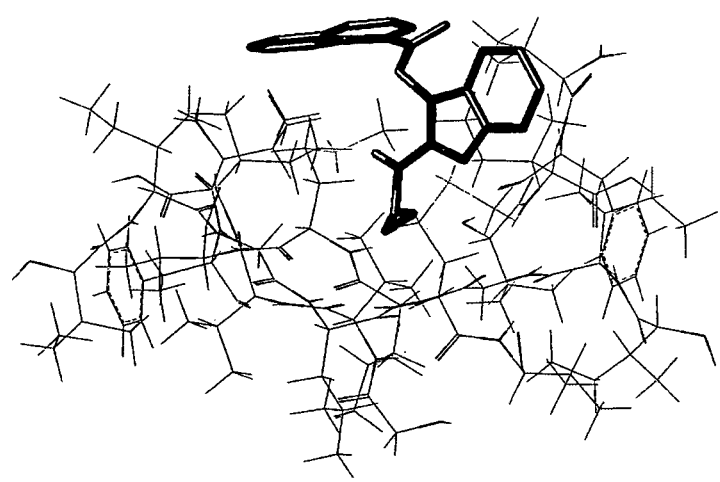
FIG. 11 In silico docking of ChemBridge 5785027 to the Aβ-IgNAR-G1 structure. The compound 2-{2-[(2-hydroxyethyl)amino]-1H-benzimidazol-1-yl}-1-(1-naphthyl)ethanone hydrobromide (dark shading) docked within the Aβ-IgNAR-G1 structure (wireframe).

The tetrameric structure displays features described for various models of both Aβ protofilaments (Malinchik, Inouye et al. 1998; Losic, Martin et al. 2006) and soluble globulomers (Barghorn, Nimmrich et al. 2005) and shows strong correlation with other independently obtained structural data for Aβ fragments and fibrils(Rahimi, Shanmugam et al. 2008). The top and bottom of the tetramer is covered by a contiguous hydrophobic surface with a girdle of hydrophilic residues) ($^{22}$EDVGSNKGA$^{30}$) (SEQ ID NO:25) running along the sides. The wedged-shape interface visible in our structure also suggest a possible mechanism for membrane-spanning pore formation(Jang, Zheng et al. 2008). Thus, we hypothesised that the observed dimer or tetramer may be a common structural motif in Aβ oligomerization, and modelled the Aβ tetramers minus the IgNAR domain as a building block of high order oligomers. By aligning Aβ tetramers on top of each other along the polar axis, utilising the interaction pattern observed between parallel Aβ stacks by NMR structure(Petkova, Yau et al. 2006), a series of multimeric constructs were generated (FIG. 5a-c). Sequential tetramers in this model are rotated by ~30° along the oligomer axis creating a twisted (coiled) cylinder up to ~40 Å wide. While the N-terminal residue Val$^{18}$ appears to be too close to the next tetramer in this configuration, this probably results from constraints imposed by the IgNAR scaffold, which would be absent in a soluble oligomeric form. Adding N-terminal Aβ peptides residues Ala$^1$-Lys$^{16}$, as described by XAFS data(Streltsov 2008), onto the crystallographic tetramer results in a model whereby this unstructured metal-binding fragment is ideally oriented to mediate reactive oxygen species toxicity. Mechanistically, neighbouring tetramers as shown in FIG. 3a-c align Glu$^{22}$ and Asp$^{23}$ side chains (from different tetramers) to form a belt of 4 potential metal-binding sites (Glu$^{22}$-G1u$^{22}$=10-12 Å; Asp$^{23}$-Asp$^{23}$=5.5-7 Å). With contributions from oxygen and nitrogens atoms this may conceivably produce one additional low affinity binding site per Ap monomer in the aggregate. Upon metal binding to the Aβ N-terminus (Asp$^1$; Glu$^{11}$; His$^6$; His$^{13}$; His$^{14}$), the adjacent Val$^{18}$-Ala$^{21}$ fragment should be stabilized, facilitating tetramer-tetramer interactions and accelerating oligomer (fibril) growth.

Familial and in vitro-generated mutations represent valuable tools for dissecting Aβ peptide function. For example the major pathogenic familial Aβ mutations (Walsh 2005), i.e. Ala$^{21}$Gly (Flemish), Glu$^{22}$Gly (Arctic), Glu$^{22}$Lys (Italian) and Asp$^{23}$Asn (Iowa) are localized within a β-turn stabilized by hydrogen bonds between Asp$^{23}$ (OD1) and Ser$^{26}$ (OG) (2.8 Å), and Asp$^{23}$ (OD2) and Gly$^{25}$ (N) (3.4 Å). Interactions with Phe$^{20}$ also appear important for loop stability: Asp$^{23}$ (OD1) is at 2.6 Å from an intra-loop water molecule which is at 3.1 Å from Phe$^{20}$ (N), an interaction which FAD mutation Asp$^{23}$ Asn is predicted break. Similarly, the "Wurth" mutations (Wurth, Guimard et al. 2002), derived in vitro from studies of the folding of Aβ(1-42)-GFP fusions (Wurth, Guimard et al. 2002), signpost residues important in aggregation. These mutations map into the surface residues of the monomer that interfere with formation of the dimer or tetramer interfaces and the amylogenic surface. For example mutation Leu$^{34}$Pro is described to markedly decrease Aβ aggregation, both alone and in combination with other variants. Here, the four Leu$^{34}$ side-chains form a universal type joint, leading to our prediction that a Leu$^{34}$Pro substitution would here (1) disrupts the central hydrophobic core of the tetramer; and (2) break the β-sheets formed by residues Ile$^{32}$-Val$^{36}$ between adjacent dimers. To test this theory, we produced the variant Aβ-IgNAR-G1 (Leu$^{34}$Pro) (SEQ ID NO. 7) and assessed the affect of this change on dimerisation. We observed marked reversion to monomeric form, of similar magnitude (~30%) to that originally described for this mutation in vitro (Wurth, Guimard et al. 2002). Upon affinity purification, this variant tended toward dimerisation, but in contrast to the parental Aβ-IgNAR-G1 was not resistant to β-mercaptoethanol treatment and failed to crystallise, suggesting that the tetramer interface had indeed been compromised.

The mechanistic basis of Aβ-mediated toxicity remains controversial and unresolved. Currently popular candidate mechanisms include: neuronal damage mediated by reactive oxygen species (ROS)(Bush 2000; Streltsov 2008); membrane destabilisation and/or pore formation (Jang, Zheng et al. 2008); and activation or modification of the apotopic pathway (Culmsee and Landshamer 2006). Most probably the final disease aetiology will prove to be multi-factorial. By developing a crystallographic model for amyloidogenic Aβ, we hoped to devise a system to test such hypotheses. Surprisingly, our structures revealed not the expected β-turn-βextended loop, but rather an unusual and compact four-lobed cloverleaf structure, which may prove to be the proto-oligomeric building block. To the best of our knowledge, this "cloverleaf" model is the first full x-ray crystallographic structure of the amyloidogenic component of the Aβ peptide.

Simplistically, our structure can be envisaged as presenting three aspects, which we describe as the dimer interface, the tetramer interface, and the amyloid-extension face. Each potentially represents a viable target for interventionist agents aimed at disrupting oligomer formation and toxic activity. Such moieties may extend beyond imaging agents to novel chemical and biological entities, including chemical compounds and peptidomimetic constructs. In this sense, we believe our structure represents a possible novel paradigm for Aβ folding, which will engender testable hypotheses for the protein folding and toxicity of this medically important peptide and its associated forms.

EXAMPLE 2

Familial Mutations

A series of variants for Aβ-IgNAR-G1 were produced (Table 4), with the aim of determining the affect of so-called "familial mutations" upon the Aβ-IgNAR-G1 structure. All these mutation map to residues 21-23. All variants displayed the characteristic Aβ dimerization predicted from the structure.

TABLE 4

| Protein | Description | Mutation | MW (Da) | Tag | SEQ ID NO: |
|---|---|---|---|---|---|
| 35A-1 | Aβ-IgNAR | — | 15,654 | FLAG × 2 | 2 |
| 12Y-2 | IgNAR wt | — | 14,878 | FLAG × 2 | 3 |
| 37A-1 | Aβ-IgNAR | Gly3 | 15,953 | FLAG × 2 | 4 |
| 37Q-6 | Aβ-IgNAR | Gly6 | 16,123 | FLAG × 2 | 5 |
| 37P-3 | Aβ-IgNAR | Gly2 | 15,768 | FLAG × 2 | 6 |
| 37D-4 | Aβ-IgNAR | Leu34Pro | 15,638 | FLAG × 2 | 7 |
| 37F-2 | Aβ-IgNAR | Asp23Asn | 15,653 | FLAG × 2 | 8 |
| 37K-1 | Aβ-IgNAR | Glu22Gln | 15,653 | FLAG × 2 | 9 |
| 37L-2 | Aβ-IgNAR | Ala21Gly | 15,640 | FLAG × 2 | 10 |
| 37R-1 | Aβ-IgNAR | ΔGlu22 | 15,525 | FLAG × 2 | 11 |
| 37M-4 | Aβ-IgNAR | Ser26Cys | 15,670 | FLAG × 2 | 12 |
| 37V-2 | Aβ-IgNAR | — | 14,345 | His | 13 |
| 37Y-1 | IgNAR wt | — | 13,553 | His | 14 |

A Western blot showed the characteristic dimerization for the familial mutants compared to wild type Aβ-IgNAR-G1 (35A-1) and the non-dimerizing wild type IgNAR (12Y-2) and "Wurth" mutant 37D-4. Familial mutants of Aβ-IgNAR-G1 reveal the presence of dimeric species at ~30 kDa, in contrast to the wild type IgNAR (12Y-2) and the mutant Leu34Pro (37D-4)

EXAMPLE 3

In Silico Screening

The crystallographic structure co-ordinates were taken and screened in silico against a database of compounds.

The crystal structure of the tetramer was examined disregarding the IgNAR domains. A site (cavity) on the 'amyloidogenic' surface, bounded by residues (chain B and chain C and Aβ amino acid residue number within these chains) B18, B32, B33, B34, B35, B41, C18, C32, C33, C34, C35, and C41 was selected as the target for docking molecules from the chemical database. The 'Clean lead-like' subset (approx. 1136000 compounds) from the ZINC database (http://zinc.docking.org; J. J. Irwin and B. K. Shoichet, J. Chem. Inf. Model, (2005), 45, 177-182) was used for the virtual screening or docking.

First, the program DOCK v. 6.2 (Univ. of California at San Francisco, USA; T. J. A. Ewing et al., J. Comput.-Aided Molec. Design, (2001), 15, 411-428.) was used to dock a segment of approx. 25000 compounds (molecules) from the database to the selected docking site on the tetramer surface. The force-field grid energy (sum of van der Waals and Coulomb energies) was used as the primary scoring function while the Zou GB/SA score (H-Y. Liu et al., J. Phys. Chem. B, (2004), 108, 5453-5462)) was used as the secondary scoring function. The DOCK output .mol2 files for each compound, giving the scores (energies) and the docked poses, were then processed by the program Binding Response (S. Zhong and A. D. MacKerell, J. Chem. Inf. Model., (2007), 47, 2302-2315) to obtain n, the number of docked molecule atoms enclosed by the docking site. Sorting the output, a total of 361 compounds were chosen for the second stage of virtual screening on the basis of the highest grid score, GB/SA score, and n.

The second stage of virtual screening was done with the program Surflex-Dock v.2.3 (A. N. Jain, J. Comput.-Aided Mol. Design, (2007), 21, 281-306), within Sybyl v.8.1 (Tripos Inc., St. Louis, USA). In docking with this program, the GeomX docking option was used with the number of additional starting conformations per molecule increased to 10 and the soft grid treatment turned off. From the docked poses, the top scoring molecules (Total score greater than 4.0, 'Crash' component of the score greater than −1.0) were visually examined and 6 compounds available from ChemBridge Corp. (San Diego, USA) were selected for purchase. These compounds are set out in Table 5.

TABLE 5

| Compound ID | Molecular Name | Molecular Weight |
|---|---|---|
| 7996209 | N-[2-(4-methylphenyl)-2-oxoethyl]-1-oxo-3,4-dihydro-1H-isochromene-3-carboxamide | 323.3 |
| 7780327 | 2-methyl-3-{[(3-methylphenoxy)acetyl]amino}benzoic acid | 299.2 |
| 7302096 | 3-{[(2,5-dimethoxyphenyl)amino]carbonyl}-7-oxabicyclo[2.2.1]hept-5-ene-2-carboxylic acid | 319.3 |
| 5785027 | 2-{2-[(2-hydroxyethyl)amino]-1H-benzimidazol-1-yl}-1-(1-naphthyl)ethanone hydrobromide | 426.3 |
| 9124833 | 3-methoxy-4-[2-(4-morpholinyl)-2-oxoethoxy]aniline | 266.3 |
| 7949851 | methyl [3-(phenoxyacetyl)-1H-indol-1-yl]acetate | 323.3 |

Illustrations of these compounds binding to Ab-IgNAR structure are shown in FIGS. 6 to 11.

These 6 compounds were purchased and tested for binding to the Aβ-IgNAR-G1 dimer and IgNAR alone by BIAcore biosensor. No binding definitively above background was observed, perhaps due to the interface targeted ie dimer immobilized, but the cavity targeted was formed by the dimer-tetramer interface.

Figure 12:
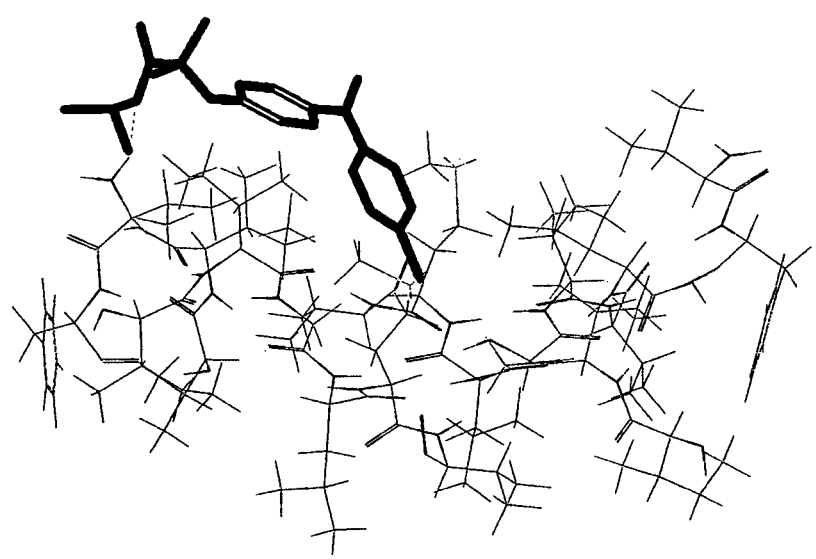
FIG. 12 In silico docking of fenofibrate to the Aβ-IgNAR-G1 structure. Fenofibrate (dark shading) docked within the Aβ-IgNAR-G1 structure (wireframe).

By way of comparison, docking performed for the anti-inflammatory drug fenofibrate which has been shown to bind Aβ (Kukar et al. Nature 453, 925-929 (2008) Substrate-targeting -secretase modulators). Docking experiments performed using the structure and a possible modelled solution presented in FIG. 12. No biochemical data for fenofibrate as soaking into crystals cracked the protein crystals, and the insolubility of fenofibrate precluded definitive biosensor experimentation.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

References

Barghorn, S., V. Nimmrich, et al. (2005). "Globular amyloid b-peptide oligomer—a homogenous and stable neuropathological protein in Alzheimer's disease." *J. Neurochem.* 95β): 834-847.

Bush, A. I. (2000). "Metals and neuroscience." *Curr Opin Chem Biol* 4(2): 184-191.

Crouch, P. J., S.-M. E. Harding, et al. (2008). "Mechanisms of Ab mediated neurodegeneration in Alzheimer's disease." *Int J Biochem Cell Biol* 40(2): 181-198.

Culmsee, C. and S. Landshamer (2006). "Molecular insights into mechanisms of the cell death program: role in the progression of neurodegenerative disorders." *Curr Alzheimer Res* 3(4): 269-83.

Henderson, K. A., V. A. Streltsov, et al. (2007). "Structure of an IgNAR-AMA1 complex: targeting a conserved hydrophobic cleft broadens malarial strain recognition." *Structure* 15(11): 1452-66.

Jang, H., J. Zheng, et al. (2008). "New structures help the modeling of toxic amyloidbeta ion channels." *Trends Biochem Sci* 33(2): 91-100.

Kajava, A. V., J. M. Squire, et al. (2006). "b-structures in fibrous proteins." *Adv Protein Chem* 73: 1-15.

Lawrence, M. C. and P. M. Colman (1993). "Shape complementarity at protein/protein interfaces." *J Mol Biol* 234(4): 946-950.

Losic, D., L. L. Martin, et al. (2006). "High resolution scanning tunnelling microscopy of the b-amyloid protein (Ab1-40) of Alzheimer's disease suggests a novel mechanism of oligomer assembly." *Journal of Structural Biology* 155(1): 104-110.

Luhrs, T., C. Ritter, et al. (2005). "3D structure of Alzheimer's amyloid-b(1-42) fibrils." *Proc Natl Acad Sci USA* 102(48): 17342-17347.

Malinchik, S. B., H. Inouye, et al. (1998). "Structural analysis of Alzheimer's b(1-40) amyloid: protofilament assembly of tubular fibrils." *Biophys. J.* 74(1): 537-745.

Nelson, R. and D. Eisenberg (2006). "Recent atomic models of amyloid fibril structure." *Curr Opin Struct Biol* 16(2): 260-265.

Nelson, R. and D. Eisenberg (2006). "Structural models of amyloid-like fibrils." *Adv Protein Chem* 73: 235-282.

Nuttall, S. D., K. S. Humberstone, et al. (2004). "Selection and affinity maturation of IgNAR variable domains targeting *Plasmodium falciparum* AMA1." *Proteins* 55(1): 187-97.

Otwinowski, Z. and W. Minor (1997). "Processing of X-ray Diffraction Data Collected in Oscillation Mode." *Methods in Enzymology:* 307-326.

Petkova, A. T., Y. Ishii, et al. (2002). "A structural model for Alzheimer's b-amyloid fibrils based on experimental constraints from solid state NMR." *Proc Natl Acad Sci USA* 99(26): 16742-16747.

Petkova, A. T., W. M. Yau, et al. (2006). "Experimental constraints on quaternary structure in Alzheimer's b-amyloid fibrils." *Biochemistry* 45(2): 498-512.

Rahimi, F., A. Shanmugam, et al. (2008). "Structure-function relationships of pre-fibrillar protein assemblies in Alzheimer's disease and related disorders." *Curr Alzheimer Res* 5β): 319-41.

Sato, T., P. Kienlen-Campard, et al. (2006). "Inhibitors of amyloid toxicity based on b-sheet packing of Ab40 and Ab42." *Biochemistry* 45(17): 5503-5516.

Shankar, G. M., S. Li, et al. (2008). "Amyloid-beta protein dimers isolated directly from Alzheimer's brains impair synaptic plasticity and memory." *Nat. Med.*

Streltsov, V. (2008). "X-ray absorption and diffraction studies of the metal binding sites in amyloid b-peptide." *Eur Biophys J* 37β): 257-263.

Streltsov, V. A., J. N. Varghese, et al. (2004). "Structural evidence for evolution of shark Ig new antigen receptor variable domain antibodies from a cell-surface receptor." *Proc Natl Acad Sci USA* 101(34): 12444-12449.

Takano, K., S. Endo, et al. (2006). "Structure of amyloid-b fragments in aqueous environments." *Febs J* 273(1): 150-158.

Vagin, A. and A. Teplyakov (1997). "MOLREP: an automated program for molecular replacement." *J. Appl. Crystallogr.* 30: 1022-1025.

Walsh, D. M. (2005). "Disease-associated intra-Ab mutations." *Alzheimer Research Forum*: Available at: http://www.alzgene.org.

Walsh, D. M. and D. J. Selkoe (2007). "Ab oligomers—a decade of discovery." *J. Neurochem.* 101(5): 1172-1184.

Wurth, C., N. K. Guimard, et al. (2002). "Mutations that reduce aggregation of the Alzheimer's Ab42 peptide: an unbiased search for the sequence determinants of Ab amyloidogenesis." *J Mol Biol* 319(5): 1279-1290.

APPENDIX I

```
HEADER    Ab-IgNAR
REMARK   3
REMARK   3  REFINEMENT.
REMARK   3    PROGRAM:     REFMAC 5.3.0040
REMARK   3
REMARK   3    REFINEMENT TARGET:  MAXIMUM LIKELIHOOD
REMARK   3
REMARK   3  DATA USED IN REFINEMENT.
REMARK   3    RESOLUTION RANGE HIGH      (ANGSTROMS):   2.20
REMARK   3    RESOLUTION RANGE LOW       (ANGSTROMS):   68.84
REMARK   3    DATA CUTOFF       (SIGMA(F)):            NONE
REMARK   3    COMPLETENESS FOR RANGE           (%):    93.45
REMARK   3    NUMBER OF REFLECTIONS:                  26860
REMARK   3
REMARK   3  FIT TO DATA USED IN REFINEMENT.
REMARK   3    CROSS-VALIDATION METHOD:              THROUGHOUT
REMARK   3    FREE R VALUE TEST SET SELECTION:         RANDOM
REMARK   3    R VALUE     (WORKING + TEST SET):        0.16841
REMARK   3    R VALUE        (WORKING SET):     0.16431
REMARK   3    FREE R VALUE:                     0.24650
REMARK   3    FREE R VALUE TEST SET SIZE   (%):    5.1
REMARK   3    FREE R VALUE TEST SET COUNT:        1439
REMARK   3
REMARK   3  FIT IN THE HIGHEST RESOLUTION BIN.
REMARK   3    TOTAL NUMBER OF BINS USED:             20
REMARK   3    BIN RESOLUTION RANGE HIGH:           2.202
REMARK   3    BIN RESOLUTION RANGE LOW:            2.260
REMARK   3    REFLECTION IN BIN        (WORKING SET):    1219
REMARK   3    BIN COMPLETENESS    (WORKING + TEST)  (%):  56.98
REMARK   3    BIN R VALUE         (WORKING SET):   0.229
REMARK   3    BIN FREE R VALUE SET COUNT:               55
REMARK   3    BIN FREE R VALUE:                      0.307
REMARK   3
REMARK   3  NUMBER OF NON-HYDROGEN ATOMS USED IN REFINEMENT.
REMARK   3    ALL ATOMS:                     4173
REMARK   3
REMARK   3  B VALUES.
REMARK   3    FROM WILSON PLOT       (A**2): NULL
REMARK   3    MEAN B VALUE      (OVERALL, A**2):  46.544
REMARK   3    OVERALL ANISOTROPIC B VALUE.
REMARK   3     B11 (A**2):    0.05
REMARK   3     B22 (A**2):    0.05
REMARK   3     B33 (A**2):   -0.08
REMARK   3     B12 (A**2):    0.03
REMARK   3     B13 (A**2):    0.00
REMARK   3     B23 (A**2):    0.00
REMARK   3
REMARK   3  ESTIMATED OVERALL COORDINATE ERROR.
REMARK   3    ESU BASED ON R VALUE                 (A):  0.241
REMARK   3    ESU BASED ON FREE R VALUE            (A):  0.223
REMARK   3    ESU BASED ON MAXIMUM LIKELIHOOD      (A):  0.152
REMARK   3    ESU FOR B VALUES BASED ON MAXIMUM LIKELIHOOD   (A**2):   11.557
REMARK   3
REMARK   3  CORRELATION COEFFICIENTS.
REMARK   3    CORRELATION COEFFICIENT FO-FC:       0.968
REMARK   3    CORRELATION COEFFICIENT FO-FC FREE:  0.930
REMARK   3
REMARK   3  RMS DEVIATIONS FROM IDEAL VALUES              COUNT   RMS   WEIGHT
REMARK   3    BOND LENGTHS REFINED ATOMS           (A):  3835 ; 0.022 ;  0.022
REMARK   3    BOND ANGLES REFINED ATOMS      (DEGREES):  5173 ; 1.994 ;  1.953
REMARK   3    TORSION ANGLES, PERIOD 1       (DEGREES):   499 ; 7.067 ;  5.000
REMARK   3    TORSION ANGLES, PERIOD 2       (DEGREES):   152 ; 35.901 ; 23.947
REMARK   3    TORSION ANGLES, PERIOD 3       (DEGREES):   664 ; 21.119 ; 15.000
REMARK   3    TORSION ANGLES, PERIOD 4       (DEGREES):    24 ; 14.991 ; 15.000
REMARK   3    CHIRAL-CENTER RESTRAINTS         (A**3):   591 ; 0.179 ;  0.200
REMARK   3    GENERAL PLANES REFINED ATOMS         (A):  2832 ; 0.008 ;  0.020
REMARK   3    NON-BONDED CONTACTS REFINED ATOMS    (A):  1537 ; 0.228 ;  0.200
REMARK   3    NON-BONDED TORSION REFINED ATOMS     (A):  2516 ; 0.311 ;  0.200
REMARK   3    H-BOND (X ... Y) REFINED ATOMS       (A):   292 ; 0.240 ;  0.200
REMARK   3    SYMMETRY VDW REFINED ATOMS           (A):    52 ; 0.222 ;  0.200
REMARK   3    SYMMETRY H-BOND REFINED ATOMS        (A):    22 ; 0.298 ;  0.200
REMARK   3
REMARK   3  ISOTROPIC THERMAL FACTOR RESTRAINTS.          COUNT   RMS   WEIGHT
REMARK   3    MAIN-CHAIN BOND REFINED ATOMS     (A**2):  2501 ; 1.051 ;  1.500
REMARK   3    MAIN-CHAIN ANGLE REFINED ATOMS    (A**2):  3921 ; 1.795 ;  2.000
REMARK   3    SIDE-CHAIN BOND REFINED ATOMS     (A**2):  1515 ; 3.032 ;  3.000
REMARK   3    SIDE-CHAIN ANGLE REFINED ATOMS    (A**2):  1252 ; 4.656 ;  4.500
REMARK   3
REMARK   3  NCS RESTRAINTS STATISTICS
REMARK   3    NUMBER OF NCS GROUPS: NULL
```

APPENDIX I-continued

```
REMARK   3
REMARK   3  TLS DETAILS
REMARK   3   NUMBER OF TLS GROUPS:     4
REMARK   3   ATOM RECORD CONTAINS RESIDUAL B FACTORS ONLY
REMARK   3
REMARK   3   TLS GROUP:      1
REMARK   3    NUMBER OF COMPONENTS GROUP:    1
REMARK   3    COMPONENTS        C SSSEQI    TO   C   SSSEQI
REMARK   3    RESIDUE RANGE:      A        1        A       126
REMARK   3    ORIGIN FOR THE GROUP (A):     63.8110    0.9650   -21.6740
REMARK   3    T TENSOR
REMARK   3      T11:   -0.1980 T22:    -0.2050
REMARK   3      T33:   -0.1620 T12:     0.0369
REMARK   3      T13:    0.0437 T23:     0.0680
REMARK   3    L TENSOR
REMARK   3      L11:    2.9649 L22:     2.1492
REMARK   3      L33:    5.5016 L12:     1.6240
REMARK   3      L13:   -3.1186 L23:    -1.7013
REMARK   3    S TENSOR
REMARK   3      S11:   -0.1563 S12:     0.1452 S13:    -0.2168
REMARK   3      S21:   -0.3866 S22:     0.0489 S23:    -0.3471
REMARK   3      S31:    0.2723 S32:    -0.1279 S33:     0.1075
REMARK   3
REMARK   3   TLS GROUP:      2
REMARK   3    NUMBER OF COMPONENTS GROUP:    1
REMARK   3    COMPONENTS        C SSSEQI    TO   C   SSSEQI
REMARK   3    RESIDUE RANGE:      B        1        B       126
REMARK   3    ORIGIN FOR THE GROUP (A):     22.5770  -14.1900   -12.2800
REMARK   3    T TENSOR
REMARK   3      T11:   -0.0751 T22:    -0.1155
REMARK   3      T33:   -0.1816 T12:    -0.0421
REMARK   3      T13:   -0.0399 T23:    -0.0558
REMARK   3    L TENSOR
REMARK   3      L11:   10.1470 L22:     1.3573
REMARK   3      L33:    3.5880 L12:     1.6659
REMARK   3      L13:    3.8599 L23:     0.8640
REMARK   3    S TENSOR
REMARK   3      S11:    0.2336 S12:    -0.7625 S13:    -0.3980
REMARK   3      S21:    0.2329 S22:    -0.2032 S23:    -0.1926
REMARK   3      S31:    0.0115 S32:    -0.2069 S33:    -0.0305
REMARK   3
REMARK   3   TLS GROUP:      3
REMARK   3    NUMBER OF COMPONENTS GROUP:    1
REMARK   3    COMPONENTS        C SSSEQI    TO   C   SSSEQI
REMARK   3    RESIDUE RANGE:      C        1        C       126
REMARK   3    ORIGIN FOR THE GROUP (A):     35.8140    7.3450    5.8670
REMARK   3    T TENSOR
REMARK   3      T11:   -0.1853 T22:    -0.1041
REMARK   3      T33:   -0.2449 T12:     0.0111
REMARK   3      T13:   -0.0203 T23:    -0.0062
REMARK   3    L TENSOR
REMARK   3      L11:    2.6982 L22:     1.5248
REMARK   3      L33:    3.8494 L12:    -1.7131
REMARK   3      L13:   -3.2164 L23:     2.1240
REMARK   3    S TENSOR
REMARK   3      S11:   -0.1201 S12:    -0.0335 S13:     0.0035
REMARK   3      S21:    0.0881 S22:    -0.0407 S23:     0.0913
REMARK   3      S31:    0.1124 S32:     0.0662 S33:     0.1608
REMARK   3
REMARK   3   TLS GROUP:      4
REMARK   3    NUMBER OF COMPONENTS GROUP:    1
REMARK   3    COMPONENTS        C SSSEQI    TO   C   SSSEQI
REMARK   3    RESIDUE RANGE:      D        1        D       125
REMARK   3    ORIGIN FOR THE GROUP (A):     59.5290  -29.2800    -4.2380
REMARK   3    T TENSOR
REMARK   3      T11:    0.0220 T22:    -0.0010
REMARK   3      T33:   -0.1489 T12:     0.0046
REMARK   3      T13:    0.0795 T23:     0.0694
REMARK   3    L TENSOR
REMARK   3      L11:    2.7989 L22:     9.7864
REMARK   3      L33:    4.7502 L12:    -4.5612
REMARK   3      L13:    2.9365 L23:    -5.7275
REMARK   3    S TENSOR
REMARK   3      S11:    0.4188 S12:     0.4905 S13:     0.0482
REMARK   3      S21:   -0.7846 S22:    -0.4194 S23:     0.2228
REMARK   3      S31:    0.4959 S32:     0.5328 S33:     0.0006
REMARK   3
REMARK   3   BULK SOLVENT MODELLING.
REMARK   3    METHOD USED:   MASK
REMARK   3    PARAMETERS FOR MASK CALCULATION
```

APPENDIX I-continued

| REMARK | 3 | VDW PROBE RADIUS: | 1.20 | | | | | | |
|---|---|---|---|---|---|---|---|---|---|
| REMARK | 3 | ION PROBE RADIUS: | 0.80 | | | | | | |
| REMARK | 3 | SHRINKAGE RADIUS: | 0.80 | | | | | | |
| REMARK | 3 | | | | | | | | |
| REMARK | 3 | OTHER REFINEMENT REMARKS: | | | | | | | |
| REMARK | 3 | HYDROGENS HAVE BEEN ADDED IN THE RIDING POSITIONS | | | | | | | |
| REMARK | 3 | | | | | | | | |
| SSBOND | 1 | CYS | A | 22 | CYS | A | 83 | | |
| SSBOND | 2 | CYS | B | 22 | CYS | B | 83 | | |
| SSBOND | 3 | CYS | C | 22 | CYS | C | 83 | | |
| SSBOND | 4 | CYS | D | 22 | CYS | D | 83 | | |
| CISPEP | 1 | THR | A | 6 | PRO | A | 7 | 0.00 | |
| CISPEP | 2 | THR | D | 6 | PRO | D | 7 | 0.00 | |
| CISPEP | 3 | THR | B | 6 | PRO | B | 7 | 0.00 | |
| CISPEP | 4 | THR | C | 6 | PRO | C | 7 | 0.00 | |
| CRYST1 | 79.399 | | 79.399 | | 84.890 | 90.00 | 90.00 | 120.00 | P 32 |
| SCALE1 | 0.012595 | 0.007272 | 0.000000 | | 0.00000 | | | | |
| SCALE2 | 0.000000 | 0.014543 | 0.000000 | | 0.00000 | | | | |
| SCALE3 | 0.000000 | 0.000000 | 0.011780 | | 0.00000 | | | | |
| ATOM | 1 | N | ALA | A | 1 | 61.749 | 8.643 | −7.895 | 1.00 | 40.15 | N |
| ATOM | 2 | CA | ALA | A | 1 | 62.634 | 7.902 | −8.884 | 1.00 | 40.18 | C |
| ATOM | 3 | CB | ALA | A | 1 | 62.339 | 6.518 | −8.853 | 1.00 | 39.79 | C |
| ATOM | 4 | C | ALA | A | 1 | 62.285 | 8.403 | −10.269 | 1.00 | 40.24 | C |
| ATOM | 5 | O | ALA | A | 1 | 61.183 | 8.874 | −10.490 | 1.00 | 40.36 | O |
| ATOM | 6 | N | TRP | A | 2 | 63.195 | 8.273 | −11.213 | 1.00 | 39.60 | N |
| ATOM | 7 | CA | TRP | A | 2 | 62.842 | 8.487 | −12.631 | 1.00 | 39.57 | C |
| ATOM | 8 | CB | TRP | A | 2 | 62.870 | 9.972 | −12.978 | 1.00 | 38.16 | C |
| ATOM | 9 | CG | TRP | A | 2 | 64.196 | 10.736 | −12.660 | 1.00 | 37.18 | C |
| ATOM | 10 | CD1 | TRP | A | 2 | 64.695 | 11.043 | −11.419 | 1.00 | 36.93 | C |
| ATOM | 11 | NE1 | TRP | A | 2 | 65.878 | 11.763 | −11.534 | 1.00 | 39.31 | N |
| ATOM | 12 | CE2 | TRP | A | 2 | 66.153 | 11.943 | −12.869 | 1.00 | 37.67 | C |
| ATOM | 13 | CD2 | TRP | A | 2 | 65.132 | 11.298 | −13.609 | 1.00 | 36.59 | C |
| ATOM | 14 | CE3 | TRP | A | 2 | 65.173 | 11.364 | −15.011 | 1.00 | 37.43 | C |
| ATOM | 15 | CZ3 | TRP | A | 2 | 66.223 | 12.030 | −15.622 | 1.00 | 37.01 | C |
| ATOM | 16 | CH2 | TRP | A | 2 | 67.259 | 12.614 | −14.864 | 1.00 | 37.70 | C |
| ATOM | 17 | CZ2 | TRP | A | 2 | 67.247 | 12.571 | −13.485 | 1.00 | 38.75 | C |
| ATOM | 18 | C | TRP | A | 2 | 63.930 | 7.731 | −13.337 | 1.00 | 40.62 | C |
| ATOM | 19 | O | TRP | A | 2 | 64.970 | 7.444 | −12.740 | 1.00 | 41.17 | O |
| ATOM | 20 | N | VAL | A | 3 | 63.713 | 7.420 | −14.598 | 1.00 | 41.79 | N |
| ATOM | 21 | CA | VAL | A | 3 | 64.712 | 6.737 | −15.393 | 1.00 | 41.23 | C |
| ATOM | 22 | CB | VAL | A | 3 | 64.067 | 5.575 | −16.107 | 1.00 | 42.49 | C |
| ATOM | 23 | CG1 | VAL | A | 3 | 65.010 | 5.042 | −17.208 | 1.00 | 41.14 | C |
| ATOM | 24 | CG2 | VAL | A | 3 | 63.708 | 4.417 | −15.072 | 1.00 | 42.49 | C |
| ATOM | 25 | C | VAL | A | 3 | 65.240 | 7.752 | −16.400 | 1.00 | 42.26 | C |
| ATOM | 26 | O | VAL | A | 3 | 64.461 | 8.371 | −17.135 | 1.00 | 39.69 | O |
| ATOM | 27 | N | ASP | A | 4 | 66.560 | 7.946 | −16.388 | 1.00 | 42.27 | N |
| ATOM | 28 | CA | ASP | A | 4 | 67.259 | 8.833 | −17.277 | 1.00 | 42.47 | C |
| ATOM | 29 | CB | ASP | A | 4 | 68.484 | 9.335 | −16.509 | 1.00 | 44.28 | C |
| ATOM | 30 | CG | ASP | A | 4 | 69.123 | 10.573 | −17.112 | 1.00 | 43.29 | C |
| ATOM | 31 | OD1 | ASP | A | 4 | 68.608 | 11.128 | −18.107 | 1.00 | 41.54 | O |
| ATOM | 32 | OD2 | ASP | A | 4 | 70.150 | 10.991 | −16.507 | 1.00 | 47.28 | O |
| ATOM | 33 | C | ASP | A | 4 | 67.725 | 8.103 | −18.544 | 1.00 | 42.79 | C |
| ATOM | 34 | O | ASP | A | 4 | 68.709 | 7.350 | −18.523 | 1.00 | 43.97 | O |
| ATOM | 35 | N | GLN | A | 5 | 67.048 | 8.361 | −19.639 | 1.00 | 42.16 | N |
| ATOM | 36 | CA | GLN | A | 5 | 67.299 | 7.703 | −20.903 | 1.00 | 43.25 | C |
| ATOM | 37 | CB | GLN | A | 5 | 65.983 | 7.258 | −21.571 | 1.00 | 42.36 | C |
| ATOM | 38 | CG | GLN | A | 5 | 66.230 | 6.429 | −22.844 | 1.00 | 43.49 | C |
| ATOM | 39 | CD | GLN | A | 5 | 64.959 | 5.836 | −23.412 | 1.00 | 43.79 | C |
| ATOM | 40 | OE1 | GLN | A | 5 | 63.975 | 5.772 | −22.714 | 1.00 | 45.41 | O |
| ATOM | 41 | NE2 | GLN | A | 5 | 64.976 | 5.402 | −24.693 | 1.00 | 41.11 | N |
| ATOM | 42 | C | GLN | A | 5 | 68.052 | 8.629 | −21.864 | 1.00 | 42.68 | C |
| ATOM | 43 | O | GLN | A | 5 | 67.584 | 9.724 | −22.191 | 1.00 | 41.82 | O |
| ATOM | 44 | N | THR | A | 6 | 69.198 | 8.157 | −22.354 | 1.00 | 42.97 | N |
| ATOM | 45 | CA | THR | A | 6 | 69.971 | 8.908 | −23.364 | 1.00 | 42.86 | C |
| ATOM | 46 | CB | THR | A | 6 | 71.203 | 9.619 | −22.713 | 1.00 | 43.54 | C |
| ATOM | 47 | OG1 | THR | A | 6 | 71.985 | 8.617 | −22.080 | 1.00 | 44.91 | O |
| ATOM | 48 | CG2 | THR | A | 6 | 70.801 | 10.670 | −21.649 | 1.00 | 41.18 | C |
| ATOM | 49 | C | THR | A | 6 | 70.442 | 8.007 | −24.507 | 1.00 | 43.00 | C |
| ATOM | 50 | O | THR | A | 6 | 70.734 | 6.818 | −24.262 | 1.00 | 44.11 | O |
| ATOM | 51 | N | PRO | A | 7 | 70.571 | 8.561 | −25.757 | 1.00 | 42.63 | N |
| ATOM | 52 | CA | PRO | A | 7 | 70.323 | 9.961 | −26.145 | 1.00 | 42.77 | C |
| ATOM | 53 | CB | PRO | A | 7 | 71.057 | 10.081 | −27.477 | 1.00 | 41.46 | C |
| ATOM | 54 | CG | PRO | A | 7 | 70.903 | 8.752 | −28.078 | 1.00 | 41.46 | C |
| ATOM | 55 | CD | PRO | A | 7 | 71.052 | 7.779 | −26.918 | 1.00 | 43.08 | C |
| ATOM | 56 | C | PRO | A | 7 | 68.835 | 10.178 | −26.359 | 1.00 | 43.23 | C |
| ATOM | 57 | O | PRO | A | 7 | 68.177 | 9.198 | −26.651 | 1.00 | 44.91 | O |
| ATOM | 58 | N | ARG | A | 8 | 68.302 | 11.392 | −26.222 | 1.00 | 43.41 | N |
| ATOM | 59 | CA | ARG | A | 8 | 66.868 | 11.625 | −26.493 | 1.00 | 44.08 | C |
| ATOM | 60 | CB | ARG | A | 8 | 66.349 | 12.944 | −25.869 | 1.00 | 43.76 | C |
| ATOM | 61 | CG | ARG | A | 8 | 64.763 | 13.006 | −25.738 | 1.00 | 46.28 | C |

APPENDIX I-continued

| ATOM | 62 | CD | ARG | A | 8 | 64.248 | 13.844 | −24.561 | 1.00 | 48.21 | C |
|---|---|---|---|---|---|---|---|---|---|---|---|
| ATOM | 63 | NE | ARG | A | 8 | 64.530 | 13.270 | −23.235 | 1.00 | 51.99 | N |
| ATOM | 64 | CZ | ARG | A | 8 | 64.574 | 13.982 | −22.102 | 1.00 | 49.58 | C |
| ATOM | 65 | NH1 | ARG | A | 8 | 64.388 | 15.306 | −22.123 | 1.00 | 45.49 | N |
| ATOM | 66 | NH2 | ARG | A | 8 | 64.817 | 13.367 | −20.953 | 1.00 | 50.31 | N |
| ATOM | 67 | C | ARG | A | 8 | 66.538 | 11.587 | −27.988 | 1.00 | 43.51 | C |
| ATOM | 68 | O | ARG | A | 8 | 65.418 | 11.284 | −28.370 | 1.00 | 43.05 | O |
| ATOM | 69 | N | THR | A | 9 | 67.498 | 11.929 | −28.846 | 1.00 | 42.86 | N |
| ATOM | 70 | CA | THR | A | 9 | 67.285 | 11.777 | −30.274 | 1.00 | 43.57 | C |
| ATOM | 71 | CB | THR | A | 9 | 66.814 | 13.095 | −30.939 | 1.00 | 43.56 | C |
| ATOM | 72 | OG1 | THR | A | 9 | 67.858 | 14.036 | −30.821 | 1.00 | 48.77 | O |
| ATOM | 73 | CG2 | THR | A | 9 | 65.563 | 13.731 | −30.225 | 1.00 | 43.75 | C |
| ATOM | 74 | C | THR | A | 9 | 68.564 | 11.279 | −30.904 | 1.00 | 42.93 | C |
| ATOM | 75 | O | THR | A | 9 | 69.650 | 11.556 | −30.398 | 1.00 | 43.89 | O |
| ATOM | 76 | N | ALA | A | 10 | 68.453 | 10.511 | −31.978 | 1.00 | 42.78 | N |
| ATOM | 77 | CA | ALA | A | 10 | 69.619 | 9.970 | −32.667 | 1.00 | 42.32 | C |
| ATOM | 78 | CB | ALA | A | 10 | 69.994 | 8.627 | −32.086 | 1.00 | 42.83 | C |
| ATOM | 79 | C | ALA | A | 10 | 69.314 | 9.859 | −34.149 | 1.00 | 43.20 | C |
| ATOM | 80 | O | ALA | A | 10 | 68.155 | 9.623 | −34.518 | 1.00 | 43.17 | O |
| ATOM | 81 | N | THR | A | 11 | 70.318 | 10.143 | −34.992 | 1.00 | 42.97 | N |
| ATOM | 82 | CA | THR | A | 11 | 70.225 | 9.915 | −36.444 | 1.00 | 43.50 | C |
| ATOM | 83 | CB | THR | A | 11 | 70.189 | 11.203 | −37.289 | 1.00 | 43.99 | C |
| ATOM | 84 | OG1 | THR | A | 11 | 69.173 | 12.071 | −36.792 | 1.00 | 46.81 | O |
| ATOM | 85 | CG2 | THR | A | 11 | 69.888 | 10.919 | −38.782 | 1.00 | 44.63 | C |
| ATOM | 86 | C | THR | A | 11 | 71.394 | 9.035 | −36.818 | 1.00 | 42.68 | C |
| ATOM | 87 | O | THR | A | 11 | 72.527 | 9.265 | −36.405 | 1.00 | 42.50 | O |
| ATOM | 88 | N | LYS | A | 12 | 71.095 | 7.988 | −37.565 | 1.00 | 42.11 | N |
| ATOM | 89 | CA | LYS | A | 12 | 72.062 | 6.984 | −37.863 | 1.00 | 41.61 | C |
| ATOM | 90 | CB | LYS | A | 12 | 71.742 | 5.752 | −37.024 | 1.00 | 42.20 | C |
| ATOM | 91 | CG | LYS | A | 12 | 72.682 | 5.566 | −35.832 | 1.00 | 42.69 | C |
| ATOM | 92 | CD | LYS | A | 12 | 72.462 | 6.488 | −34.722 | 1.00 | 42.75 | C |
| ATOM | 93 | CE | LYS | A | 12 | 73.785 | 6.938 | −34.193 | 1.00 | 45.64 | C |
| ATOM | 94 | NZ | LYS | A | 12 | 74.413 | 5.947 | −33.372 | 1.00 | 45.06 | N |
| ATOM | 95 | C | LYS | A | 12 | 72.005 | 6.639 | −39.319 | 1.00 | 41.13 | C |
| ATOM | 96 | O | LYS | A | 12 | 70.939 | 6.763 | −39.917 | 1.00 | 40.78 | O |
| ATOM | 97 | N | GLU | A | 13 | 73.148 | 6.221 | −39.886 | 1.00 | 41.13 | N |
| ATOM | 98 | CA | GLU | A | 13 | 73.217 | 5.639 | −41.224 | 1.00 | 41.27 | C |
| ATOM | 99 | CB | GLU | A | 13 | 74.632 | 5.698 | −41.828 | 1.00 | 42.20 | C |
| ATOM | 100 | CG | GLU | A | 13 | 75.229 | 7.083 | −41.972 | 1.00 | 45.88 | C |
| ATOM | 101 | CD | GLU | A | 13 | 74.375 | 8.034 | −42.822 | 1.00 | 46.51 | C |
| ATOM | 102 | OE1 | GLU | A | 13 | 74.450 | 9.257 | −42.598 | 1.00 | 46.46 | O |
| ATOM | 103 | OE2 | GLU | A | 13 | 73.643 | 7.546 | −43.710 | 1.00 | 49.37 | O |
| ATOM | 104 | C | GLU | A | 13 | 72.800 | 4.187 | −41.192 | 1.00 | 40.83 | C |
| ATOM | 105 | O | GLU | A | 13 | 72.992 | 3.508 | −40.169 | 1.00 | 41.54 | O |
| ATOM | 106 | N | THR | A | 14 | 72.215 | 3.721 | −42.301 | 1.00 | 40.03 | N |
| ATOM | 107 | CA | THR | A | 14 | 71.940 | 2.318 | −42.489 | 1.00 | 39.84 | C |
| ATOM | 108 | CB | THR | A | 14 | 71.377 | 2.042 | −43.909 | 1.00 | 40.21 | C |
| ATOM | 109 | OG1 | THR | A | 14 | 69.983 | 2.377 | −43.955 | 1.00 | 37.92 | O |
| ATOM | 110 | CG2 | THR | A | 14 | 71.526 | 0.563 | −44.299 | 1.00 | 39.74 | C |
| ATOM | 111 | C | THR | A | 14 | 73.270 | 1.599 | −42.243 | 1.00 | 40.13 | C |
| ATOM | 112 | O | THR | A | 14 | 74.324 | 2.000 | −42.791 | 1.00 | 39.27 | O |
| ATOM | 113 | N | GLY | A | 15 | 73.233 | 0.613 | −41.342 | 1.00 | 40.34 | N |
| ATOM | 114 | CA | GLY | A | 15 | 74.396 | −0.218 | −41.032 | 1.00 | 40.42 | C |
| ATOM | 115 | C | GLY | A | 15 | 75.117 | 0.128 | −39.748 | 1.00 | 40.96 | C |
| ATOM | 116 | O | GLY | A | 15 | 75.788 | −0.709 | −39.224 | 1.00 | 41.04 | O |
| ATOM | 117 | N | GLU | A | 16 | 74.989 | 1.365 | −39.256 | 1.00 | 41.99 | N |
| ATOM | 118 | CA | GLU | A | 16 | 75.598 | 1.850 | −38.014 | 1.00 | 43.51 | C |
| ATOM | 119 | CB | GLU | A | 16 | 75.343 | 3.359 | −37.860 | 1.00 | 43.93 | C |
| ATOM | 120 | CG | GLU | A | 16 | 76.304 | 4.377 | −38.538 | 1.00 | 45.03 | C |
| ATOM | 121 | CD | GLU | A | 16 | 76.197 | 5.807 | −37.839 | 1.00 | 46.94 | C |
| ATOM | 122 | OE1 | GLU | A | 16 | 75.428 | 6.678 | −38.323 | 1.00 | 43.22 | O |
| ATOM | 123 | OE2 | GLU | A | 16 | 76.837 | 6.036 | −36.754 | 1.00 | 52.94 | O |
| ATOM | 124 | C | GLU | A | 16 | 74.854 | 1.177 | −36.872 | 1.00 | 43.56 | C |
| ATOM | 125 | O | GLU | A | 16 | 73.865 | 0.509 | −37.092 | 1.00 | 43.77 | O |
| ATOM | 126 | N | SER | A | 17 | 75.282 | 1.388 | −35.641 | 1.00 | 43.74 | N |
| ATOM | 127 | CA | SER | A | 17 | 74.492 | 0.923 | −34.544 | 1.00 | 44.40 | C |
| ATOM | 128 | CB | SER | A | 17 | 75.215 | −0.229 | −33.873 | 1.00 | 44.97 | C |
| ATOM | 129 | OG | SER | A | 17 | 76.123 | 0.270 | −32.945 | 1.00 | 50.00 | O |
| ATOM | 130 | C | SER | A | 17 | 74.111 | 2.054 | −33.578 | 1.00 | 44.40 | C |
| ATOM | 131 | O | SER | A | 17 | 74.564 | 3.183 | −33.740 | 1.00 | 43.42 | O |
| ATOM | 132 | N | LEU | A | 18 | 73.218 | 1.768 | −32.623 | 1.00 | 44.29 | N |
| ATOM | 133 | CA | LEU | A | 18 | 72.750 | 2.743 | −31.631 | 1.00 | 43.42 | C |
| ATOM | 134 | CB | LEU | A | 18 | 71.264 | 3.018 | −31.857 | 1.00 | 44.02 | C |
| ATOM | 135 | CG | LEU | A | 18 | 70.458 | 4.188 | −31.246 | 1.00 | 45.03 | C |
| ATOM | 136 | CD1 | LEU | A | 18 | 69.189 | 3.777 | −30.570 | 1.00 | 43.77 | C |
| ATOM | 137 | CD2 | LEU | A | 18 | 71.201 | 5.339 | −30.494 | 1.00 | 43.20 | C |
| ATOM | 138 | C | LEU | A | 18 | 72.893 | 2.116 | −30.251 | 1.00 | 43.15 | C |
| ATOM | 139 | O | LEU | A | 18 | 72.533 | 0.967 | −30.042 | 1.00 | 42.50 | O |
| ATOM | 140 | N | THR | A | 19 | 73.396 | 2.881 | −29.305 | 1.00 | 42.18 | N |
| ATOM | 141 | CA | THR | A | 19 | 73.367 | 2.460 | −27.919 | 1.00 | 42.94 | C |

APPENDIX I-continued

| ATOM | 142 | CB | THR | A | 19 | 74.762 | 2.333 | −27.352 | 1.00 | 41.91 | C |
|---|---|---|---|---|---|---|---|---|---|---|---|
| ATOM | 143 | OG1 | THR | A | 19 | 75.459 | 1.366 | −28.144 | 1.00 | 46.16 | O |
| ATOM | 144 | CG2 | THR | A | 19 | 74.690 | 1.835 | −25.920 | 1.00 | 43.14 | C |
| ATOM | 145 | C | THR | A | 19 | 72.566 | 3.445 | −27.107 | 1.00 | 42.46 | C |
| ATOM | 146 | O | THR | A | 19 | 72.838 | 4.656 | −27.120 | 1.00 | 42.53 | O |
| ATOM | 147 | N | ILE | A | 20 | 71.548 | 2.927 | −26.451 | 1.00 | 42.31 | N |
| ATOM | 148 | CA | ILE | A | 20 | 70.689 | 3.706 | −25.552 | 1.00 | 43.03 | C |
| ATOM | 149 | CB | ILE | A | 20 | 69.201 | 3.335 | −25.767 | 1.00 | 43.33 | C |
| ATOM | 150 | CG1 | ILE | A | 20 | 68.800 | 3.502 | −27.256 | 1.00 | 44.11 | C |
| ATOM | 151 | CD1 | ILE | A | 20 | 67.399 | 2.948 | −27.600 | 1.00 | 44.88 | C |
| ATOM | 152 | CG2 | ILE | A | 20 | 68.302 | 4.141 | −24.822 | 1.00 | 42.84 | C |
| ATOM | 153 | C | ILE | A | 20 | 71.077 | 3.333 | −24.134 | 1.00 | 42.61 | C |
| ATOM | 154 | O | ILE | A | 20 | 71.157 | 2.147 | −23.843 | 1.00 | 41.82 | O |
| ATOM | 155 | N | ASN | A | 21 | 71.379 | 4.327 | −23.294 | 1.00 | 43.17 | N |
| ATOM | 156 | CA | ASN | A | 21 | 71.708 | 4.102 | −21.860 | 1.00 | 44.83 | C |
| ATOM | 157 | CB | ASN | A | 21 | 72.990 | 4.831 | −21.455 | 1.00 | 44.74 | C |
| ATOM | 158 | CG | ASN | A | 21 | 74.197 | 4.409 | −22.296 | 1.00 | 50.81 | C |
| ATOM | 159 | OD1 | ASN | A | 21 | 74.786 | 3.335 | −22.070 | 1.00 | 57.38 | O |
| ATOM | 160 | ND2 | ASN | A | 21 | 74.594 | 5.257 | −23.256 | 1.00 | 52.86 | N |
| ATOM | 161 | C | ASN | A | 21 | 70.569 | 4.588 | −20.961 | 1.00 | 45.00 | C |
| ATOM | 162 | O | ASN | A | 21 | 70.033 | 5.670 | −21.182 | 1.00 | 44.50 | O |
| ATOM | 163 | N | CYS | A | 22 | 70.208 | 3.816 | −19.949 | 1.00 | 44.60 | N |
| ATOM | 164 | CA | CYS | A | 22 | 69.167 | 4.237 | −19.029 | 1.00 | 45.32 | C |
| ATOM | 165 | CB | CYS | A | 22 | 67.909 | 3.372 | −19.165 | 1.00 | 45.74 | C |
| ATOM | 166 | SG | CYS | A | 22 | 66.995 | 3.746 | −20.639 | 1.00 | 54.23 | S |
| ATOM | 167 | C | CYS | A | 22 | 69.658 | 4.101 | −17.624 | 1.00 | 44.15 | C |
| ATOM | 168 | O | CYS | A | 22 | 70.236 | 3.107 | −17.289 | 1.00 | 43.54 | O |
| ATOM | 169 | N | VAL | A | 23 | 69.395 | 5.085 | −16.785 | 1.00 | 43.49 | N |
| ATOM | 170 | CA | VAL | A | 23 | 69.643 | 4.909 | −15.365 | 1.00 | 42.35 | C |
| ATOM | 171 | CB | VAL | A | 23 | 71.085 | 5.352 | −14.883 | 1.00 | 43.00 | C |
| ATOM | 172 | CG1 | VAL | A | 23 | 71.963 | 6.041 | −15.953 | 1.00 | 41.73 | C |
| ATOM | 173 | CG2 | VAL | A | 23 | 71.199 | 5.917 | −13.413 | 1.00 | 42.45 | C |
| ATOM | 174 | C | VAL | A | 23 | 68.417 | 5.249 | −14.481 | 1.00 | 42.71 | C |
| ATOM | 175 | O | VAL | A | 23 | 67.709 | 6.260 | −14.671 | 1.00 | 41.74 | O |
| ATOM | 176 | N | LEU | A | 24 | 68.123 | 4.344 | −13.563 | 1.00 | 42.36 | N |
| ATOM | 177 | CA | LEU | A | 24 | 67.057 | 4.563 | −12.645 | 1.00 | 43.14 | C |
| ATOM | 178 | CB | LEU | A | 24 | 66.608 | 3.213 | −12.068 | 1.00 | 43.10 | C |
| ATOM | 179 | CG | LEU | A | 24 | 65.662 | 3.260 | −10.863 | 1.00 | 44.67 | C |
| ATOM | 180 | CD1 | LEU | A | 24 | 64.281 | 3.811 | −11.337 | 1.00 | 42.56 | C |
| ATOM | 181 | CD2 | LEU | A | 24 | 65.508 | 1.885 | −10.150 | 1.00 | 44.14 | C |
| ATOM | 182 | C | LEU | A | 24 | 67.691 | 5.476 | −11.592 | 1.00 | 42.20 | C |
| ATOM | 183 | O | LEU | A | 24 | 68.575 | 5.053 | −10.877 | 1.00 | 42.62 | O |
| ATOM | 184 | N | ARG | A | 25 | 67.261 | 6.734 | −11.531 | 1.00 | 41.75 | N |
| ATOM | 185 | CA | ARG | A | 25 | 67.859 | 7.731 | −10.598 | 1.00 | 40.94 | C |
| ATOM | 186 | CB | ARG | A | 25 | 68.196 | 9.032 | −11.327 | 1.00 | 39.67 | C |
| ATOM | 187 | CG | ARG | A | 25 | 69.067 | 8.832 | −12.554 | 1.00 | 39.63 | C |
| ATOM | 188 | CD | ARG | A | 25 | 69.891 | 10.080 | −12.859 | 1.00 | 38.88 | C |
| ATOM | 189 | NE | ARG | A | 25 | 70.828 | 9.833 | −13.950 | 1.00 | 44.89 | N |
| ATOM | 190 | CZ | ARG | A | 25 | 72.121 | 9.535 | −13.783 | 1.00 | 47.29 | C |
| ATOM | 191 | NH1 | ARG | A | 25 | 72.620 | 9.447 | −12.539 | 1.00 | 46.01 | N |
| ATOM | 192 | NH2 | ARG | A | 25 | 72.924 | 9.391 | −14.850 | 1.00 | 43.92 | N |
| ATOM | 193 | C | ARG | A | 25 | 66.903 | 8.056 | −9.468 | 1.00 | 41.31 | C |
| ATOM | 194 | O | ARG | A | 25 | 65.691 | 7.828 | −9.600 | 1.00 | 39.67 | O |
| ATOM | 195 | N | ASP | A | 26 | 67.466 | 8.586 | −8.375 | 1.00 | 41.32 | N |
| ATOM | 196 | CA | ASP | A | 26 | 66.756 | 8.989 | −7.190 | 1.00 | 43.62 | C |
| ATOM | 197 | CB | ASP | A | 26 | 66.179 | 10.401 | −7.349 | 1.00 | 45.00 | C |
| ATOM | 198 | CG | ASP | A | 26 | 67.224 | 11.395 | −7.953 | 1.00 | 52.91 | C |
| ATOM | 199 | OD1 | ASP | A | 26 | 66.854 | 12.215 | −8.853 | 1.00 | 59.13 | O |
| ATOM | 200 | OD2 | ASP | A | 26 | 68.436 | 11.347 | −7.556 | 1.00 | 60.06 | O |
| ATOM | 201 | C | ASP | A | 26 | 65.732 | 7.986 | −6.674 | 1.00 | 43.23 | C |
| ATOM | 202 | O | ASP | A | 26 | 64.635 | 8.350 | −6.232 | 1.00 | 43.09 | O |
| ATOM | 203 | N | ALA | A | 27 | 66.114 | 6.708 | −6.710 | 1.00 | 43.21 | N |
| ATOM | 204 | CA | ALA | A | 27 | 65.231 | 5.600 | −6.311 | 1.00 | 42.66 | C |
| ATOM | 205 | CB | ALA | A | 27 | 65.081 | 4.609 | −7.466 | 1.00 | 40.95 | C |
| ATOM | 206 | C | ALA | A | 27 | 65.800 | 4.898 | −5.058 | 1.00 | 43.66 | C |
| ATOM | 207 | O | ALA | A | 27 | 66.997 | 4.563 | −4.986 | 1.00 | 43.64 | O |
| ATOM | 208 | N | SER | A | 28 | 64.929 | 4.643 | −4.097 | 1.00 | 44.63 | N |
| ATOM | 209 | CA | SER | A | 28 | 65.301 | 3.945 | −2.860 | 1.00 | 46.25 | C |
| ATOM | 210 | CB | SER | A | 28 | 64.306 | 4.340 | −1.793 | 1.00 | 46.62 | C |
| ATOM | 211 | OG | SER | A | 28 | 62.989 | 4.076 | −2.343 | 1.00 | 51.66 | O |
| ATOM | 212 | C | SER | A | 28 | 65.244 | 2.424 | −3.024 | 1.00 | 45.27 | C |
| ATOM | 213 | O | SER | A | 28 | 65.753 | 1.699 | −2.204 | 1.00 | 45.50 | O |
| ATOM | 214 | N | PHE | A | 29 | 64.597 | 1.951 | −4.080 | 1.00 | 44.65 | N |
| ATOM | 215 | CA | PHE | A | 29 | 64.428 | 0.515 | −4.320 | 1.00 | 44.66 | C |
| ATOM | 216 | CB | PHE | A | 29 | 63.026 | 0.206 | −4.853 | 1.00 | 44.20 | C |
| ATOM | 217 | CG | PHE | A | 29 | 62.491 | 1.236 | −5.821 | 1.00 | 43.80 | C |
| ATOM | 218 | CD1 | PHE | A | 29 | 61.557 | 2.181 | −5.392 | 1.00 | 42.75 | C |
| ATOM | 219 | CE1 | PHE | A | 29 | 61.055 | 3.155 | −6.275 | 1.00 | 42.50 | C |
| ATOM | 220 | CZ | PHE | A | 29 | 61.457 | 3.156 | −7.641 | 1.00 | 42.43 | C |
| ATOM | 221 | CE2 | PHE | A | 29 | 62.376 | 2.202 | −8.074 | 1.00 | 43.56 | C |

APPENDIX I-continued

| ATOM | 222 | CD2 | PHE | A | 29 | 62.895 | 1.243 | −7.168 | 1.00 | 40.83 | C |
|---|---|---|---|---|---|---|---|---|---|---|---|
| ATOM | 223 | C | PHE | A | 29 | 65.444 | 0.022 | −5.324 | 1.00 | 44.85 | C |
| ATOM | 224 | O | PHE | A | 29 | 66.046 | 0.816 | −6.017 | 1.00 | 45.13 | O |
| ATOM | 225 | N | GLU | A | 30 | 65.606 | −1.292 | −5.428 | 1.00 | 44.65 | N |
| ATOM | 226 | CA | GLU | A | 30 | 66.616 | −1.829 | −6.302 | 1.00 | 45.34 | C |
| ATOM | 227 | CB | GLU | A | 30 | 67.141 | −3.148 | −5.719 | 1.00 | 46.03 | C |
| ATOM | 228 | CG | GLU | A | 30 | 67.484 | −3.139 | −4.182 | 1.00 | 51.87 | C |
| ATOM | 229 | CD | GLU | A | 30 | 68.905 | −2.718 | −3.833 | 1.00 | 61.36 | C |
| ATOM | 230 | OE1 | GLU | A | 30 | 69.655 | −3.533 | −3.218 | 1.00 | 64.71 | O |
| ATOM | 231 | OE2 | GLU | A | 30 | 69.283 | −1.554 | −4.132 | 1.00 | 66.90 | O |
| ATOM | 232 | C | GLU | A | 30 | 66.040 | −2.045 | −7.710 | 1.00 | 44.87 | C |
| ATOM | 233 | O | GLU | A | 30 | 64.804 | −2.206 | −7.902 | 1.00 | 43.77 | O |
| ATOM | 234 | N | LEU | A | 31 | 66.933 | −2.100 | −8.692 | 1.00 | 44.05 | N |
| ATOM | 235 | CA | LEU | A | 31 | 66.527 | −2.480 | −10.022 | 1.00 | 44.47 | C |
| ATOM | 236 | CB | LEU | A | 31 | 67.529 | −1.966 | −11.057 | 1.00 | 44.35 | C |
| ATOM | 237 | CG | LEU | A | 31 | 67.302 | −2.279 | −12.541 | 1.00 | 44.08 | C |
| ATOM | 238 | CD1 | LEU | A | 31 | 68.569 | −2.051 | −13.351 | 1.00 | 41.58 | C |
| ATOM | 239 | CD2 | LEU | A | 31 | 66.136 | −1.523 | −13.132 | 1.00 | 41.76 | C |
| ATOM | 240 | C | LEU | A | 31 | 66.373 | −4.001 | −10.047 | 1.00 | 45.45 | C |
| ATOM | 241 | O | LEU | A | 31 | 67.337 | −4.736 | −9.819 | 1.00 | 46.74 | O |
| ATOM | 242 | N | LYS | A | 32 | 65.139 | −4.478 | −10.238 | 1.00 | 45.05 | N |
| ATOM | 243 | CA | LYS | A | 32 | 64.876 | −5.919 | −10.271 | 1.00 | 44.49 | C |
| ATOM | 244 | CB | LYS | A | 32 | 63.509 | −6.221 | −9.649 | 1.00 | 44.92 | C |
| ATOM | 245 | CG | LYS | A | 32 | 63.393 | −5.867 | −8.121 | 1.00 | 46.76 | C |
| ATOM | 246 | CD | LYS | A | 32 | 64.441 | −6.598 | −7.239 | 1.00 | 46.19 | C |
| ATOM | 247 | CE | LYS | A | 32 | 63.953 | −6.546 | −5.816 | 1.00 | 50.58 | C |
| ATOM | 248 | NZ | LYS | A | 32 | 64.928 | −7.103 | −4.883 | 1.00 | 53.68 | N |
| ATOM | 249 | C | LYS | A | 32 | 64.934 | −6.509 | −11.676 | 1.00 | 44.11 | C |
| ATOM | 250 | O | LYS | A | 32 | 65.328 | −7.643 | −11.858 | 1.00 | 42.45 | O |
| ATOM | 251 | N | ASP | A | 33 | 64.509 | −5.743 | −12.676 | 1.00 | 44.84 | N |
| ATOM | 252 | CA | ASP | A | 33 | 64.436 | −6.261 | −14.076 | 1.00 | 44.80 | C |
| ATOM | 253 | CB | ASP | A | 33 | 63.261 | −7.211 | −14.233 | 1.00 | 45.40 | C |
| ATOM | 254 | CG | ASP | A | 33 | 63.419 | −8.179 | −15.400 | 1.00 | 49.24 | C |
| ATOM | 255 | OD1 | ASP | A | 33 | 64.455 | −8.192 | −16.141 | 1.00 | 47.77 | O |
| ATOM | 256 | OD2 | ASP | A | 33 | 62.433 | −8.933 | −15.577 | 1.00 | 55.63 | O |
| ATOM | 257 | C | ASP | A | 33 | 64.293 | −5.127 | −15.063 | 1.00 | 44.19 | C |
| ATOM | 258 | O | ASP | A | 33 | 64.063 | −3.981 | −14.671 | 1.00 | 42.88 | O |
| ATOM | 259 | N | THR | A | 34 | 64.481 | −5.431 | −16.348 | 1.00 | 43.32 | N |
| ATOM | 260 | CA | THR | A | 34 | 64.513 | −4.362 | −17.365 | 1.00 | 42.96 | C |
| ATOM | 261 | CB | THR | A | 34 | 65.977 | −4.082 | −17.816 | 1.00 | 43.35 | C |
| ATOM | 262 | OG1 | THR | A | 34 | 66.616 | −5.313 | −18.245 | 1.00 | 46.20 | O |
| ATOM | 263 | CG2 | THR | A | 34 | 66.799 | −3.582 | −16.631 | 1.00 | 42.87 | C |
| ATOM | 264 | C | THR | A | 34 | 63.634 | −4.801 | −18.566 | 1.00 | 42.17 | C |
| ATOM | 265 | O | THR | A | 34 | 63.395 | −6.018 | −18.771 | 1.00 | 40.33 | O |
| ATOM | 266 | N | GLY | A | 35 | 63.143 | −3.820 | −19.318 | 1.00 | 40.76 | N |
| ATOM | 267 | CA | GLY | A | 35 | 62.446 | −4.100 | −20.554 | 1.00 | 40.48 | C |
| ATOM | 268 | C | GLY | A | 35 | 62.659 | −2.980 | −21.531 | 1.00 | 40.71 | C |
| ATOM | 269 | O | GLY | A | 35 | 63.001 | −1.868 | −21.139 | 1.00 | 41.72 | O |
| ATOM | 270 | N | TRP | A | 36 | 62.465 | −3.294 | −22.815 | 1.00 | 40.28 | N |
| ATOM | 271 | CA | TRP | A | 36 | 62.674 | −2.399 | −23.935 | 1.00 | 40.14 | C |
| ATOM | 272 | CB | TRP | A | 36 | 63.993 | −2.767 | −24.656 | 1.00 | 38.78 | C |
| ATOM | 273 | CG | TRP | A | 36 | 65.201 | −2.495 | −23.763 | 1.00 | 37.14 | C |
| ATOM | 274 | CD1 | TRP | A | 36 | 65.778 | −3.349 | −22.867 | 1.00 | 36.99 | C |
| ATOM | 275 | NE1 | TRP | A | 36 | 66.846 | −2.715 | −22.216 | 1.00 | 37.64 | N |
| ATOM | 276 | CE2 | TRP | A | 36 | 66.915 | −1.410 | −22.659 | 1.00 | 37.73 | C |
| ATOM | 277 | CD2 | TRP | A | 36 | 65.912 | −1.233 | −23.632 | 1.00 | 35.75 | C |
| ATOM | 278 | CE3 | TRP | A | 36 | 65.771 | 0.021 | −24.231 | 1.00 | 38.30 | C |
| ATOM | 279 | CZ3 | TRP | A | 36 | 66.662 | 1.028 | −23.895 | 1.00 | 38.55 | C |
| ATOM | 280 | CH2 | TRP | A | 36 | 67.669 | 0.808 | −22.922 | 1.00 | 38.11 | C |
| ATOM | 281 | CZ2 | TRP | A | 36 | 67.803 | −0.388 | −22.308 | 1.00 | 39.69 | C |
| ATOM | 282 | C | TRP | A | 36 | 61.462 | −2.494 | −24.882 | 1.00 | 40.45 | C |
| ATOM | 283 | O | TRP | A | 36 | 60.900 | −3.575 | −25.086 | 1.00 | 37.84 | O |
| ATOM | 284 | N | TYR | A | 37 | 61.082 | −1.350 | −25.466 | 1.00 | 40.70 | N |
| ATOM | 285 | CA | TYR | A | 37 | 59.866 | −1.236 | −26.308 | 1.00 | 41.93 | C |
| ATOM | 286 | CB | TYR | A | 37 | 58.685 | −0.707 | −25.468 | 1.00 | 42.76 | C |
| ATOM | 287 | CG | TYR | A | 37 | 58.563 | −1.427 | −24.194 | 1.00 | 42.14 | C |
| ATOM | 288 | CD1 | TYR | A | 37 | 57.719 | −2.520 | −24.075 | 1.00 | 40.34 | C |
| ATOM | 289 | CE1 | TYR | A | 37 | 57.646 | −3.242 | −22.868 | 1.00 | 41.85 | C |
| ATOM | 290 | CZ | TYR | A | 37 | 58.426 | −2.826 | −21.801 | 1.00 | 42.69 | C |
| ATOM | 291 | OH | TYR | A | 37 | 58.379 | −3.479 | −20.599 | 1.00 | 47.21 | O |
| ATOM | 292 | CE2 | TYR | A | 37 | 59.238 | −1.728 | −21.895 | 1.00 | 42.12 | C |
| ATOM | 293 | CD2 | TYR | A | 37 | 59.307 | −1.027 | −23.098 | 1.00 | 41.52 | C |
| ATOM | 294 | C | TYR | A | 37 | 60.081 | −0.257 | −27.427 | 1.00 | 42.18 | C |
| ATOM | 295 | O | TYR | A | 37 | 60.936 | 0.595 | −27.346 | 1.00 | 41.61 | O |
| ATOM | 296 | N | ARG | A | 38 | 59.267 | −0.357 | −28.453 | 1.00 | 43.78 | N |
| ATOM | 297 | CA | ARG | A | 38 | 59.532 | 0.406 | −29.648 | 1.00 | 46.16 | C |
| ATOM | 298 | CB | ARG | A | 38 | 60.599 | −0.320 | −30.467 | 1.00 | 45.76 | C |
| ATOM | 299 | CG | ARG | A | 38 | 60.521 | −0.353 | −31.940 | 1.00 | 49.53 | C |
| ATOM | 300 | CD | ARG | A | 38 | 61.333 | −1.543 | −32.436 | 1.00 | 50.13 | C |
| ATOM | 301 | NE | ARG | A | 38 | 60.989 | −1.847 | −33.794 | 1.00 | 52.73 | N |

APPENDIX I-continued

| ATOM | 302 | CZ | ARG | A | 38 | 61.856 | −1.891 | −34.805 | 1.00 | 60.11 | C |
| --- | --- | --- | --- | --- | --- | --- | --- | --- | --- | --- | --- |
| ATOM | 303 | NH1 | ARG | A | 38 | 61.402 | −2.162 | −36.023 | 1.00 | 59.27 | N |
| ATOM | 304 | NH2 | ARG | A | 38 | 63.172 | −1.662 | −34.620 | 1.00 | 60.83 | N |
| ATOM | 305 | C | ARG | A | 38 | 58.216 | 0.686 | −30.345 | 1.00 | 46.60 | C |
| ATOM | 306 | O | ARG | A | 38 | 57.320 | −0.172 | −30.373 | 1.00 | 46.42 | O |
| ATOM | 307 | N | THR | A | 39 | 58.077 | 1.929 | −30.802 | 1.00 | 46.84 | N |
| ATOM | 308 | CA | THR | A | 39 | 56.980 | 2.339 | −31.664 | 1.00 | 47.57 | C |
| ATOM | 309 | CB | THR | A | 39 | 56.261 | 3.586 | −31.110 | 1.00 | 47.10 | C |
| ATOM | 310 | OG1 | THR | A | 39 | 55.916 | 3.378 | −29.750 | 1.00 | 50.61 | O |
| ATOM | 311 | CG2 | THR | A | 39 | 54.999 | 3.839 | −31.858 | 1.00 | 49.14 | C |
| ATOM | 312 | C | THR | A | 39 | 57.637 | 2.703 | −32.961 | 1.00 | 47.84 | C |
| ATOM | 313 | O | THR | A | 39 | 58.482 | 3.618 | −32.983 | 1.00 | 46.61 | O |
| ATOM | 314 | N | LYS | A | 40 | 57.283 | 1.980 | −34.034 | 1.00 | 49.00 | N |
| ATOM | 315 | CA | LYS | A | 40 | 57.849 | 2.253 | −35.349 | 1.00 | 51.32 | C |
| ATOM | 316 | CB | LYS | A | 40 | 57.656 | 1.095 | −36.329 | 1.00 | 51.60 | C |
| ATOM | 317 | CG | LYS | A | 40 | 58.368 | −0.180 | −35.877 | 1.00 | 54.32 | C |
| ATOM | 318 | CD | LYS | A | 40 | 58.208 | −1.327 | −36.858 | 1.00 | 55.56 | C |
| ATOM | 319 | CE | LYS | A | 40 | 59.149 | −1.119 | −38.039 | 1.00 | 55.54 | C |
| ATOM | 320 | NZ | LYS | A | 40 | 59.491 | −2.440 | −38.640 | 1.00 | 58.58 | N |
| ATOM | 321 | C | LYS | A | 40 | 57.310 | 3.555 | −35.909 | 1.00 | 51.81 | C |
| ATOM | 322 | O | LYS | A | 40 | 56.245 | 4.013 | −35.513 | 1.00 | 51.60 | O |
| ATOM | 323 | N | LEU | A | 41 | 58.073 | 4.166 | −36.805 | 1.00 | 53.16 | N |
| ATOM | 324 | CA | LEU | A | 41 | 57.623 | 5.383 | −37.454 | 1.00 | 54.73 | C |
| ATOM | 325 | CB | LEU | A | 41 | 58.735 | 5.951 | −38.319 | 1.00 | 55.27 | C |
| ATOM | 326 | CG | LEU | A | 41 | 58.569 | 7.373 | −38.833 | 1.00 | 56.10 | C |
| ATOM | 327 | CD1 | LEU | A | 41 | 59.828 | 7.743 | −39.616 | 1.00 | 54.91 | C |
| ATOM | 328 | CD2 | LEU | A | 41 | 58.320 | 8.338 | −37.636 | 1.00 | 58.13 | C |
| ATOM | 329 | C | LEU | A | 41 | 56.385 | 5.086 | −38.311 | 1.00 | 55.70 | C |
| ATOM | 330 | O | LEU | A | 41 | 56.424 | 4.238 | −39.228 | 1.00 | 55.38 | O |
| ATOM | 331 | N | GLY | A | 42 | 55.290 | 5.778 | −38.001 | 1.00 | 56.61 | N |
| ATOM | 332 | CA | GLY | A | 42 | 54.043 | 5.583 | −38.715 | 1.00 | 57.83 | C |
| ATOM | 333 | C | GLY | A | 42 | 53.064 | 4.709 | −37.968 | 1.00 | 59.16 | C |
| ATOM | 334 | O | GLY | A | 42 | 51.849 | 4.803 | −38.199 | 1.00 | 59.45 | O |
| ATOM | 335 | N | SER | A | 43 | 53.587 | 3.873 | −37.060 | 1.00 | 60.41 | N |
| ATOM | 336 | CA | SER | A | 43 | 52.775 | 2.988 | −36.198 | 1.00 | 61.00 | C |
| ATOM | 337 | CB | SER | A | 43 | 53.550 | 1.722 | −35.781 | 1.00 | 60.84 | C |
| ATOM | 338 | OG | SER | A | 43 | 53.706 | 0.833 | −36.880 | 1.00 | 61.59 | O |
| ATOM | 339 | C | SER | A | 43 | 52.239 | 3.671 | −34.956 | 1.00 | 61.22 | C |
| ATOM | 340 | O | SER | A | 43 | 52.845 | 4.581 | −34.387 | 1.00 | 61.91 | O |
| ATOM | 341 | N | THR | A | 44 | 51.092 | 3.206 | −34.507 | 1.00 | 61.44 | N |
| ATOM | 342 | CA | THR | A | 44 | 50.502 | 3.811 | −33.352 | 1.00 | 61.38 | C |
| ATOM | 343 | CB | THR | A | 44 | 48.964 | 3.869 | −33.493 | 1.00 | 61.80 | C |
| ATOM | 344 | OG1 | THR | A | 44 | 48.650 | 4.479 | −34.762 | 1.00 | 60.23 | O |
| ATOM | 345 | CG2 | THR | A | 44 | 48.307 | 4.653 | −32.316 | 1.00 | 59.36 | C |
| ATOM | 346 | C | THR | A | 44 | 50.973 | 3.105 | −32.083 | 1.00 | 61.97 | C |
| ATOM | 347 | O | THR | A | 44 | 51.440 | 3.773 | −31.146 | 1.00 | 62.38 | O |
| ATOM | 348 | N | ASN | A | 45 | 50.885 | 1.770 | −32.064 | 1.00 | 61.54 | N |
| ATOM | 349 | CA | ASN | A | 45 | 51.100 | 1.020 | −30.825 | 1.00 | 61.43 | C |
| ATOM | 350 | CB | ASN | A | 45 | 50.127 | −0.173 | −30.705 | 1.00 | 61.50 | C |
| ATOM | 351 | CG | ASN | A | 45 | 48.642 | 0.221 | −30.958 | 1.00 | 62.37 | C |
| ATOM | 352 | OD1 | ASN | A | 45 | 48.185 | 1.305 | −30.582 | 1.00 | 62.72 | O |
| ATOM | 353 | ND2 | ASN | A | 45 | 47.896 | −0.683 | −31.590 | 1.00 | 61.46 | N |
| ATOM | 354 | C | ASN | A | 45 | 52.560 | 0.609 | −30.523 | 1.00 | 60.98 | C |
| ATOM | 355 | O | ASN | A | 45 | 53.299 | 0.149 | −31.394 | 1.00 | 61.08 | O |
| ATOM | 356 | N | GLU | A | 46 | 52.938 | 0.823 | −29.265 | 1.00 | 60.78 | N |
| ATOM | 357 | CA | GLU | A | 46 | 54.210 | 0.400 | −28.672 | 1.00 | 60.71 | C |
| ATOM | 358 | CB | GLU | A | 46 | 54.284 | 0.954 | −27.266 | 1.00 | 60.85 | C |
| ATOM | 359 | CG | GLU | A | 46 | 55.575 | 0.708 | −26.576 | 1.00 | 63.83 | C |
| ATOM | 360 | CD | GLU | A | 46 | 55.497 | 1.029 | −25.103 | 1.00 | 70.18 | C |
| ATOM | 361 | OE1 | GLU | A | 46 | 54.694 | 0.349 | −24.389 | 1.00 | 72.55 | O |
| ATOM | 362 | OE2 | GLU | A | 46 | 56.254 | 1.940 | −24.657 | 1.00 | 73.06 | O |
| ATOM | 363 | C | GLU | A | 46 | 54.333 | −1.121 | −28.614 | 1.00 | 59.83 | C |
| ATOM | 364 | O | GLU | A | 46 | 53.389 | −1.791 | −28.220 | 1.00 | 60.32 | O |
| ATOM | 365 | N | GLN | A | 47 | 55.485 | −1.669 | −29.007 | 1.00 | 58.86 | N |
| ATOM | 366 | CA | GLN | A | 47 | 55.685 | −3.121 | −28.999 | 1.00 | 57.92 | C |
| ATOM | 367 | CB | GLN | A | 47 | 55.601 | −3.679 | −30.411 | 1.00 | 58.34 | C |
| ATOM | 368 | CG | GLN | A | 47 | 56.948 | −3.889 | −31.081 | 1.00 | 61.68 | C |
| ATOM | 369 | CD | GLN | A | 47 | 56.886 | −3.720 | −32.595 | 1.00 | 68.07 | C |
| ATOM | 370 | OE1 | GLN | A | 47 | 57.774 | −3.090 | −33.219 | 1.00 | 69.58 | O |
| ATOM | 371 | NE2 | GLN | A | 47 | 55.838 | −4.288 | −33.204 | 1.00 | 69.32 | N |
| ATOM | 372 | C | GLN | A | 47 | 56.991 | −3.546 | −28.291 | 1.00 | 56.40 | C |
| ATOM | 373 | O | GLN | A | 47 | 57.991 | −2.855 | −28.403 | 1.00 | 56.16 | O |
| ATOM | 374 | N | SER | A | 48 | 56.973 | −4.691 | −27.599 | 1.00 | 53.86 | N |
| ATOM | 375 | CA | SER | A | 48 | 58.112 | −5.136 | −26.806 | 1.00 | 53.14 | C |
| ATOM | 376 | CB | SER | A | 48 | 57.759 | −6.239 | −25.793 | 1.00 | 52.59 | C |
| ATOM | 377 | OG | SER | A | 48 | 56.373 | −6.331 | −25.659 | 1.00 | 55.97 | O |
| ATOM | 378 | C | SER | A | 48 | 59.210 | −5.658 | −27.672 | 1.00 | 51.60 | C |
| ATOM | 379 | O | SER | A | 48 | 58.968 | −6.329 | −28.679 | 1.00 | 51.19 | O |
| ATOM | 380 | N | ILE | A | 49 | 60.433 | −5.380 | −27.229 | 1.00 | 50.47 | N |
| ATOM | 381 | CA | ILE | A | 49 | 61.627 | −5.856 | −27.920 | 1.00 | 49.33 | C |

APPENDIX I-continued

| ATOM | 382 | CB | ILE | A | 49 | 62.710 | −4.755 | −28.005 | 1.00 | 48.45 | C |
|---|---|---|---|---|---|---|---|---|---|---|---|
| ATOM | 383 | CG1 | ILE | A | 49 | 62.251 | −3.636 | −28.919 | 1.00 | 48.57 | C |
| ATOM | 384 | CD1 | ILE | A | 49 | 62.995 | −2.348 | −28.670 | 1.00 | 47.03 | C |
| ATOM | 385 | CG2 | ILE | A | 49 | 64.064 | −5.362 | −28.492 | 1.00 | 47.35 | C |
| ATOM | 386 | C | ILE | A | 49 | 62.198 | −7.054 | −27.160 | 1.00 | 48.70 | C |
| ATOM | 387 | O | ILE | A | 49 | 62.555 | −6.911 | −25.986 | 1.00 | 48.29 | O |
| ATOM | 388 | N | SER | A | 50 | 62.293 | −8.198 | −27.849 | 1.00 | 49.00 | N |
| ATOM | 389 | CA | SER | A | 50 | 62.998 | −9.436 | −27.400 | 1.00 | 49.52 | C |
| ATOM | 390 | CB | SER | A | 50 | 62.551 | −10.647 | −28.223 | 1.00 | 49.72 | C |
| ATOM | 391 | OG | SER | A | 50 | 61.213 | −10.968 | −27.948 | 1.00 | 52.50 | O |
| ATOM | 392 | C | SER | A | 50 | 64.507 | −9.299 | −27.621 | 1.00 | 48.65 | C |
| ATOM | 393 | O | SER | A | 50 | 64.944 | −9.131 | −28.735 | 1.00 | 48.05 | O |
| ATOM | 394 | N | ILE | A | 51 | 65.270 | −9.397 | −26.540 | 1.00 | 47.94 | N |
| ATOM | 395 | CA | ILE | A | 51 | 66.706 | −9.224 | −26.516 | 1.00 | 47.34 | C |
| ATOM | 396 | CB | ILE | A | 51 | 67.134 | −9.131 | −25.012 | 1.00 | 47.28 | C |
| ATOM | 397 | CG1 | ILE | A | 51 | 66.616 | −7.835 | −24.342 | 1.00 | 47.48 | C |
| ATOM | 398 | CD1 | ILE | A | 51 | 66.759 | −6.511 | −25.185 | 1.00 | 46.22 | C |
| ATOM | 399 | CG2 | ILE | A | 51 | 68.618 | −9.405 | −24.815 | 1.00 | 49.45 | C |
| ATOM | 400 | C | ILE | A | 51 | 67.332 | −10.427 | −27.229 | 1.00 | 46.82 | C |
| ATOM | 401 | O | ILE | A | 51 | 66.976 | −11.538 | −26.927 | 1.00 | 46.57 | O |
| ATOM | 402 | N | GLY | A | 52 | 68.227 | −10.219 | −28.197 | 1.00 | 46.54 | N |
| ATOM | 403 | CA | GLY | A | 52 | 68.790 | −11.324 | −28.979 | 1.00 | 45.30 | C |
| ATOM | 404 | C | GLY | A | 52 | 69.129 | −10.786 | −30.354 | 1.00 | 46.43 | C |
| ATOM | 405 | O | GLY | A | 52 | 68.603 | −9.736 | −30.754 | 1.00 | 47.18 | O |
| ATOM | 406 | N | GLY | A | 53 | 70.047 | −11.446 | −31.054 | 1.00 | 45.33 | N |
| ATOM | 407 | CA | GLY | A | 53 | 70.408 | −11.065 | −32.399 | 1.00 | 45.72 | C |
| ATOM | 408 | C | GLY | A | 53 | 71.007 | −9.680 | −32.446 | 1.00 | 45.66 | C |
| ATOM | 409 | O | GLY | A | 53 | 72.039 | −9.435 | −31.823 | 1.00 | 46.03 | O |
| ATOM | 410 | N | ARG | A | 54 | 70.359 | −8.794 | −33.207 | 1.00 | 45.46 | N |
| ATOM | 411 | CA | ARG | A | 54 | 70.681 | −7.360 | −33.292 | 1.00 | 45.57 | C |
| ATOM | 412 | CB | ARG | A | 54 | 69.802 | −6.697 | −34.364 | 1.00 | 45.77 | C |
| ATOM | 413 | CG | ARG | A | 54 | 70.428 | −6.723 | −35.756 | 1.00 | 47.80 | C |
| ATOM | 414 | CD | ARG | A | 54 | 69.460 | −6.515 | −36.962 | 1.00 | 47.13 | C |
| ATOM | 415 | NE | ARG | A | 54 | 68.139 | −5.901 | −36.699 | 1.00 | 48.21 | N |
| ATOM | 416 | CZ | ARG | A | 54 | 67.854 | −4.597 | −36.739 | 1.00 | 48.23 | C |
| ATOM | 417 | NH1 | ARG | A | 54 | 68.788 | −3.680 | −36.949 | 1.00 | 47.12 | N |
| ATOM | 418 | NH2 | ARG | A | 54 | 66.614 | −4.205 | −36.539 | 1.00 | 47.74 | N |
| ATOM | 419 | C | ARG | A | 54 | 70.538 | −6.549 | −31.994 | 1.00 | 44.48 | C |
| ATOM | 420 | O | ARG | A | 54 | 71.102 | −5.455 | −31.899 | 1.00 | 45.01 | O |
| ATOM | 421 | N | TYR | A | 55 | 69.760 | −7.042 | −31.028 | 1.00 | 43.84 | N |
| ATOM | 422 | CA | TYR | A | 55 | 69.450 | −6.305 | −29.788 | 1.00 | 43.35 | C |
| ATOM | 423 | CB | TYR | A | 55 | 67.958 | −6.426 | −29.448 | 1.00 | 44.35 | C |
| ATOM | 424 | CG | TYR | A | 55 | 67.074 | −5.915 | −30.548 | 1.00 | 46.48 | C |
| ATOM | 425 | CD1 | TYR | A | 55 | 66.572 | −6.774 | −31.512 | 1.00 | 49.83 | C |
| ATOM | 426 | CE1 | TYR | A | 55 | 65.784 | −6.314 | −32.555 | 1.00 | 49.58 | C |
| ATOM | 427 | CZ | TYR | A | 55 | 65.477 | −4.973 | −32.627 | 1.00 | 50.34 | C |
| ATOM | 428 | OH | TYR | A | 55 | 64.687 | −4.523 | −33.663 | 1.00 | 50.81 | O |
| ATOM | 429 | CE2 | TYR | A | 55 | 65.965 | −4.079 | −31.681 | 1.00 | 48.69 | C |
| ATOM | 430 | CD2 | TYR | A | 55 | 66.772 | −4.557 | −30.655 | 1.00 | 48.63 | C |
| ATOM | 431 | C | TYR | A | 55 | 70.266 | −6.876 | −28.651 | 1.00 | 42.80 | C |
| ATOM | 432 | O | TYR | A | 55 | 69.952 | −7.955 | −28.191 | 1.00 | 42.93 | O |
| ATOM | 433 | N | VAL | A | 56 | 71.355 | −6.232 | −28.240 | 1.00 | 41.64 | N |
| ATOM | 434 | CA | VAL | A | 56 | 72.001 | −6.733 | −27.046 | 1.00 | 40.80 | C |
| ATOM | 435 | CB | VAL | A | 56 | 73.464 | −7.357 | −27.245 | 1.00 | 42.17 | C |
| ATOM | 436 | CG1 | VAL | A | 56 | 73.841 | −7.600 | −28.748 | 1.00 | 38.54 | C |
| ATOM | 437 | CG2 | VAL | A | 56 | 74.538 | −6.558 | −26.522 | 1.00 | 43.83 | C |
| ATOM | 438 | C | VAL | A | 56 | 71.827 | −5.785 | −25.862 | 1.00 | 41.18 | C |
| ATOM | 439 | O | VAL | A | 56 | 71.910 | −4.546 | −25.990 | 1.00 | 39.41 | O |
| ATOM | 440 | N | GLU | A | 57 | 71.512 | −6.367 | −24.712 | 1.00 | 40.70 | N |
| ATOM | 441 | CA | GLU | A | 57 | 71.286 | −5.580 | −23.520 | 1.00 | 41.90 | C |
| ATOM | 442 | CB | GLU | A | 57 | 69.900 | −5.898 | −22.929 | 1.00 | 42.24 | C |
| ATOM | 443 | CG | GLU | A | 57 | 69.600 | −5.062 | −21.704 | 1.00 | 42.95 | C |
| ATOM | 444 | CD | GLU | A | 57 | 68.308 | −5.403 | −20.974 | 1.00 | 42.25 | C |
| ATOM | 445 | OE1 | GLU | A | 57 | 67.949 | −6.577 | −20.900 | 1.00 | 38.99 | O |
| ATOM | 446 | OE2 | GLU | A | 57 | 67.670 | −4.457 | −20.460 | 1.00 | 44.79 | O |
| ATOM | 447 | C | GLU | A | 57 | 72.384 | −5.881 | −22.492 | 1.00 | 42.34 | C |
| ATOM | 448 | O | GLU | A | 57 | 72.798 | −7.042 | −22.344 | 1.00 | 42.11 | O |
| ATOM | 449 | N | THR | A | 58 | 72.877 | −4.831 | −21.831 | 1.00 | 42.68 | N |
| ATOM | 450 | CA | THR | A | 58 | 73.858 | −4.957 | −20.757 | 1.00 | 43.59 | C |
| ATOM | 451 | CB | THR | A | 58 | 75.189 | −4.212 | −21.077 | 1.00 | 43.40 | C |
| ATOM | 452 | OG1 | THR | A | 58 | 75.624 | −4.579 | −22.385 | 1.00 | 44.66 | O |
| ATOM | 453 | CG2 | THR | A | 58 | 76.359 | −4.628 | −20.109 | 1.00 | 43.34 | C |
| ATOM | 454 | C | THR | A | 58 | 73.158 | −4.367 | −19.552 | 1.00 | 44.00 | C |
| ATOM | 455 | O | THR | A | 58 | 72.617 | −3.287 | −19.658 | 1.00 | 44.75 | O |
| ATOM | 456 | N | VAL | A | 59 | 73.085 | −5.096 | −18.435 | 1.00 | 45.31 | N |
| ATOM | 457 | CA | VAL | A | 59 | 72.445 | −4.573 | −17.188 | 1.00 | 46.32 | C |
| ATOM | 458 | CB | VAL | A | 59 | 71.193 | −5.433 | −16.756 | 1.00 | 46.73 | C |
| ATOM | 459 | CG1 | VAL | A | 59 | 70.611 | −4.939 | −15.416 | 1.00 | 45.96 | C |
| ATOM | 460 | CG2 | VAL | A | 59 | 70.109 | −5.392 | −17.855 | 1.00 | 46.73 | C |
| ATOM | 461 | C | VAL | A | 59 | 73.470 | −4.509 | −16.019 | 1.00 | 46.15 | C |

APPENDIX I-continued

| | | | | | | | | | | | |
|---|---|---|---|---|---|---|---|---|---|---|---|
| ATOM | 462 | O | VAL | A | 59 | 74.107 | −5.492 | −15.742 | 1.00 | 45.02 | O |
| ATOM | 463 | N | ASN | A | 60 | 73.646 | −3.357 | −15.368 | 1.00 | 46.21 | N |
| ATOM | 464 | CA | ASN | A | 60 | 74.410 | −3.289 | −14.091 | 1.00 | 47.08 | C |
| ATOM | 465 | CB | ASN | A | 60 | 75.582 | −2.282 | −14.177 | 1.00 | 46.82 | C |
| ATOM | 466 | CG | ASN | A | 60 | 76.468 | −2.280 | −12.923 | 1.00 | 49.00 | C |
| ATOM | 467 | OD1 | ASN | A | 60 | 75.999 | −2.345 | −11.785 | 1.00 | 52.76 | O |
| ATOM | 468 | ND2 | ASN | A | 60 | 77.757 | −2.224 | −13.138 | 1.00 | 49.31 | N |
| ATOM | 469 | C | ASN | A | 60 | 73.440 | −2.923 | −12.955 | 1.00 | 47.32 | C |
| ATOM | 470 | O | ASN | A | 60 | 73.134 | −1.773 | −12.726 | 1.00 | 46.07 | O |
| ATOM | 471 | N | LYS | A | 61 | 72.939 | −3.925 | −12.255 | 1.00 | 48.72 | N |
| ATOM | 472 | CA | LYS | A | 61 | 71.962 | −3.707 | −11.182 | 1.00 | 49.59 | C |
| ATOM | 473 | CB | LYS | A | 61 | 71.378 | −5.055 | −10.716 | 1.00 | 49.75 | C |
| ATOM | 474 | CG | LYS | A | 61 | 70.215 | −5.564 | −11.593 | 1.00 | 50.68 | C |
| ATOM | 475 | CD | LYS | A | 61 | 69.812 | −6.983 | −11.174 | 1.00 | 50.86 | C |
| ATOM | 476 | CE | LYS | A | 61 | 68.695 | −7.504 | −12.055 | 1.00 | 54.11 | C |
| ATOM | 477 | NZ | LYS | A | 61 | 68.044 | −8.687 | −11.416 | 1.00 | 56.87 | N |
| ATOM | 478 | C | LYS | A | 61 | 72.560 | −2.919 | −10.000 | 1.00 | 49.82 | C |
| ATOM | 479 | O | LYS | A | 61 | 71.854 | −2.143 | −9.371 | 1.00 | 50.15 | O |
| ATOM | 480 | N | GLY | A | 62 | 73.848 | −3.134 | −9.718 | 1.00 | 49.68 | N |
| ATOM | 481 | CA | GLY | A | 62 | 74.606 | −2.382 | −8.706 | 1.00 | 49.85 | C |
| ATOM | 482 | C | GLY | A | 62 | 74.552 | −0.878 | −8.922 | 1.00 | 49.84 | C |
| ATOM | 483 | O | GLY | A | 62 | 74.322 | −0.121 | −7.980 | 1.00 | 50.26 | O |
| ATOM | 484 | N | SER | A | 63 | 74.731 | −0.433 | −10.169 | 1.00 | 48.77 | N |
| ATOM | 485 | CA | SER | A | 63 | 74.577 | 0.986 | −10.490 | 1.00 | 47.70 | C |
| ATOM | 486 | CB | SER | A | 63 | 75.754 | 1.436 | −11.342 | 1.00 | 47.84 | C |
| ATOM | 487 | OG | SER | A | 63 | 75.593 | 0.909 | −12.632 | 1.00 | 51.09 | O |
| ATOM | 488 | C | SER | A | 63 | 73.200 | 1.385 | −11.111 | 1.00 | 46.97 | C |
| ATOM | 489 | O | SER | A | 63 | 73.043 | 2.490 | −11.649 | 1.00 | 47.21 | O |
| ATOM | 490 | N | LYS | A | 64 | 72.209 | 0.497 | −11.007 | 1.00 | 44.94 | N |
| ATOM | 491 | CA | LYS | A | 64 | 70.843 | 0.715 | −11.475 | 1.00 | 44.84 | C |
| ATOM | 492 | CB | LYS | A | 64 | 70.057 | 1.625 | −10.509 | 1.00 | 43.86 | C |
| ATOM | 493 | CG | LYS | A | 64 | 70.033 | 1.170 | −9.029 | 1.00 | 47.25 | C |
| ATOM | 494 | CD | LYS | A | 64 | 69.005 | 2.001 | −8.219 | 1.00 | 44.70 | C |
| ATOM | 495 | CE | LYS | A | 64 | 69.247 | 1.819 | −6.729 | 1.00 | 44.99 | C |
| ATOM | 496 | NZ | LYS | A | 64 | 68.112 | 2.477 | −6.068 | 1.00 | 44.40 | N |
| ATOM | 497 | C | LYS | A | 64 | 70.804 | 1.247 | −12.917 | 1.00 | 44.07 | C |
| ATOM | 498 | O | LYS | A | 64 | 70.049 | 2.146 | −13.280 | 1.00 | 43.97 | O |
| ATOM | 499 | N | SER | A | 65 | 71.587 | 0.626 | −13.752 | 1.00 | 43.50 | N |
| ATOM | 500 | CA | SER | A | 65 | 71.940 | 1.168 | −15.069 | 1.00 | 44.29 | C |
| ATOM | 501 | CB | SER | A | 65 | 73.362 | 1.691 | −14.968 | 1.00 | 44.32 | C |
| ATOM | 502 | OG | SER | A | 65 | 73.875 | 1.947 | −16.238 | 1.00 | 50.36 | O |
| ATOM | 503 | C | SER | A | 65 | 71.865 | 0.026 | −16.097 | 1.00 | 43.54 | C |
| ATOM | 504 | O | SER | A | 65 | 72.276 | −1.068 | −15.818 | 1.00 | 44.78 | O |
| ATOM | 505 | N | PHE | A | 66 | 71.310 | 0.273 | −17.268 | 1.00 | 43.55 | N |
| ATOM | 506 | CA | PHE | A | 66 | 71.086 | −0.763 | −18.282 | 1.00 | 42.34 | C |
| ATOM | 507 | CB | PHE | A | 66 | 69.779 | −1.568 | −18.040 | 1.00 | 41.29 | C |
| ATOM | 508 | CG | PHE | A | 66 | 68.550 | −0.738 | −17.764 | 1.00 | 43.12 | C |
| ATOM | 509 | CD1 | PHE | A | 66 | 68.427 | 0.051 | −16.599 | 1.00 | 42.71 | C |
| ATOM | 510 | CE1 | PHE | A | 66 | 67.241 | 0.790 | −16.358 | 1.00 | 44.02 | C |
| ATOM | 511 | CZ | PHE | A | 66 | 66.195 | 0.688 | −17.257 | 1.00 | 45.56 | C |
| ATOM | 512 | CE2 | PHE | A | 66 | 66.300 | −0.135 | −18.391 | 1.00 | 43.21 | C |
| ATOM | 513 | CD2 | PHE | A | 66 | 67.444 | −0.813 | −18.639 | 1.00 | 43.36 | C |
| ATOM | 514 | C | PHE | A | 66 | 71.113 | −0.110 | −19.662 | 1.00 | 42.27 | C |
| ATOM | 515 | O | PHE | A | 66 | 70.725 | 1.063 | −19.818 | 1.00 | 40.59 | O |
| ATOM | 516 | N | SER | A | 67 | 71.578 | −0.848 | −20.661 | 1.00 | 42.12 | N |
| ATOM | 517 | CA | SER | A | 67 | 71.575 | −0.287 | −22.008 | 1.00 | 42.94 | C |
| ATOM | 518 | CB | SER | A | 67 | 72.871 | 0.482 | −22.245 | 1.00 | 44.09 | C |
| ATOM | 519 | OG | SER | A | 67 | 73.943 | −0.414 | −22.195 | 1.00 | 46.13 | O |
| ATOM | 520 | C | SER | A | 67 | 71.318 | −1.326 | −23.109 | 1.00 | 42.30 | C |
| ATOM | 521 | O | SER | A | 67 | 71.475 | −2.518 | −22.887 | 1.00 | 41.64 | O |
| ATOM | 522 | N | LEU | A | 68 | 70.843 | −0.857 | −24.259 | 1.00 | 42.72 | N |
| ATOM | 523 | CA | LEU | A | 68 | 70.479 | −1.706 | −25.376 | 1.00 | 42.24 | C |
| ATOM | 524 | CB | LEU | A | 68 | 69.032 | −1.415 | −25.795 | 1.00 | 42.06 | C |
| ATOM | 525 | CG | LEU | A | 68 | 68.062 | −2.356 | −26.561 | 1.00 | 42.82 | C |
| ATOM | 526 | CD1 | LEU | A | 68 | 67.123 | −1.619 | −27.518 | 1.00 | 37.15 | C |
| ATOM | 527 | CD2 | LEU | A | 68 | 68.630 | −3.617 | −27.193 | 1.00 | 45.54 | C |
| ATOM | 528 | C | LEU | A | 68 | 71.342 | −1.215 | −26.521 | 1.00 | 42.90 | C |
| ATOM | 529 | O | LEU | A | 68 | 71.347 | −0.010 | −26.820 | 1.00 | 41.46 | O |
| ATOM | 530 | N | ARG | A | 69 | 72.031 | −2.141 | −27.196 | 1.00 | 42.96 | N |
| ATOM | 531 | CA | ARG | A | 69 | 72.635 | −1.810 | −28.465 | 1.00 | 43.33 | C |
| ATOM | 532 | CB | ARG | A | 69 | 74.071 | −2.295 | −28.521 | 1.00 | 44.06 | C |
| ATOM | 533 | CG | ARG | A | 69 | 74.908 | −1.467 | −29.419 | 1.00 | 44.93 | C |
| ATOM | 534 | CD | ARG | A | 69 | 76.347 | −1.648 | −29.074 | 1.00 | 51.01 | C |
| ATOM | 535 | NE | ARG | A | 69 | 77.032 | −2.495 | −30.046 | 1.00 | 55.03 | N |
| ATOM | 536 | CZ | ARG | A | 69 | 77.938 | −2.041 | −30.924 | 1.00 | 59.47 | C |
| ATOM | 537 | NH1 | ARG | A | 69 | 78.259 | −0.733 | −30.942 | 1.00 | 59.92 | N |
| ATOM | 538 | NH2 | ARG | A | 69 | 78.520 | −2.876 | −31.794 | 1.00 | 52.94 | N |
| ATOM | 539 | C | ARG | A | 69 | 71.867 | −2.458 | −29.589 | 1.00 | 43.41 | C |
| ATOM | 540 | O | ARG | A | 69 | 71.684 | −3.661 | −29.590 | 1.00 | 42.37 | O |
| ATOM | 541 | N | ILE | A | 70 | 71.416 | −1.646 | −30.545 | 1.00 | 43.65 | N |

APPENDIX I-continued

| ATOM | 542 | CA | ILE | A | 70 | 70.858 | −2.153 | −31.779 | 1.00 | 44.23 | C |
|------|-----|-----|-----|---|----|--------|--------|---------|------|-------|---|
| ATOM | 543 | CB | ILE | A | 70 | 69.492 | −1.515 | −32.157 | 1.00 | 44.17 | C |
| ATOM | 544 | CG1 | ILE | A | 70 | 68.603 | −1.333 | −30.942 | 1.00 | 45.74 | C |
| ATOM | 545 | CD1 | ILE | A | 70 | 67.758 | −0.131 | −31.117 | 1.00 | 46.30 | C |
| ATOM | 546 | CG2 | ILE | A | 70 | 68.756 | −2.351 | −33.172 | 1.00 | 43.47 | C |
| ATOM | 547 | C | ILE | A | 70 | 71.856 | −1.934 | −32.893 | 1.00 | 44.58 | C |
| ATOM | 548 | O | ILE | A | 70 | 72.153 | −0.792 | −33.282 | 1.00 | 45.70 | O |
| ATOM | 549 | N | SER | A | 71 | 72.376 | −3.022 | −33.425 | 1.00 | 45.40 | N |
| ATOM | 550 | CA | SER | A | 71 | 73.387 | −2.879 | −34.435 | 1.00 | 46.26 | C |
| ATOM | 551 | CB | SER | A | 71 | 74.597 | −3.736 | −34.104 | 1.00 | 46.66 | C |
| ATOM | 552 | OG | SER | A | 71 | 74.223 | −5.080 | −34.154 | 1.00 | 46.90 | O |
| ATOM | 553 | C | SER | A | 71 | 72.788 | −3.238 | −35.776 | 1.00 | 46.26 | C |
| ATOM | 554 | O | SER | A | 71 | 71.702 | −3.811 | −35.833 | 1.00 | 45.27 | O |
| ATOM | 555 | N | ASP | A | 72 | 73.491 | −2.855 | −36.845 | 1.00 | 47.04 | N |
| ATOM | 556 | CA | ASP | A | 72 | 73.083 | −3.164 | −38.220 | 1.00 | 47.40 | C |
| ATOM | 557 | CB | ASP | A | 72 | 73.125 | −4.671 | −38.470 | 1.00 | 47.74 | C |
| ATOM | 558 | CG | ASP | A | 72 | 73.180 | −5.019 | −39.934 | 1.00 | 51.59 | C |
| ATOM | 559 | OD1 | ASP | A | 72 | 73.693 | −4.202 | −40.771 | 1.00 | 53.46 | O |
| ATOM | 560 | OD2 | ASP | A | 72 | 72.705 | −6.140 | −40.238 | 1.00 | 56.93 | O |
| ATOM | 561 | C | ASP | A | 72 | 71.704 | −2.556 | −38.534 | 1.00 | 46.75 | C |
| ATOM | 562 | O | ASP | A | 72 | 70.796 | −3.217 | −39.079 | 1.00 | 46.48 | O |
| ATOM | 563 | N | LEU | A | 73 | 71.601 | −1.275 | −38.183 | 1.00 | 46.13 | N |
| ATOM | 564 | CA | LEU | A | 73 | 70.406 | −0.467 | −38.296 | 1.00 | 45.96 | C |
| ATOM | 565 | CB | LEU | A | 73 | 70.745 | 0.931 | −37.780 | 1.00 | 45.33 | C |
| ATOM | 566 | CG | LEU | A | 73 | 70.287 | 1.479 | −36.425 | 1.00 | 48.34 | C |
| ATOM | 567 | CD1 | LEU | A | 73 | 69.586 | 0.448 | −35.493 | 1.00 | 42.67 | C |
| ATOM | 568 | CD2 | LEU | A | 73 | 71.423 | 2.297 | −35.755 | 1.00 | 49.05 | C |
| ATOM | 569 | C | LEU | A | 73 | 69.946 | −0.366 | −39.742 | 1.00 | 46.10 | C |
| ATOM | 570 | O | LEU | A | 73 | 70.764 | −0.352 | −40.660 | 1.00 | 44.78 | O |
| ATOM | 571 | N | ARG | A | 74 | 68.631 | −0.281 | −39.934 | 1.00 | 46.57 | N |
| ATOM | 572 | CA | ARG | A | 74 | 68.040 | −0.106 | −41.264 | 1.00 | 47.37 | C |
| ATOM | 573 | CB | ARG | A | 74 | 67.637 | −1.474 | −41.849 | 1.00 | 46.77 | C |
| ATOM | 574 | CG | ARG | A | 74 | 66.719 | −2.239 | −40.899 | 1.00 | 49.24 | C |
| ATOM | 575 | CD | ARG | A | 74 | 66.663 | −3.759 | −41.079 | 1.00 | 50.32 | C |
| ATOM | 576 | NE | ARG | A | 74 | 67.971 | −4.409 | −40.931 | 1.00 | 53.80 | N |
| ATOM | 577 | CZ | ARG | A | 74 | 68.136 | −5.671 | −40.534 | 1.00 | 55.17 | C |
| ATOM | 578 | NH1 | ARG | A | 74 | 67.079 | −6.433 | −40.214 | 1.00 | 53.89 | N |
| ATOM | 579 | NH2 | ARG | A | 74 | 69.367 | −6.169 | −40.440 | 1.00 | 55.31 | N |
| ATOM | 580 | C | ARG | A | 74 | 66.851 | 0.854 | −41.114 | 1.00 | 46.54 | C |
| ATOM | 581 | O | ARG | A | 74 | 66.367 | 1.069 | −39.989 | 1.00 | 46.24 | O |
| ATOM | 582 | N | VAL | A | 75 | 66.407 | 1.456 | −42.221 | 1.00 | 46.74 | N |
| ATOM | 583 | CA | VAL | A | 75 | 65.304 | 2.453 | −42.211 | 1.00 | 47.37 | C |
| ATOM | 584 | CB | VAL | A | 75 | 64.850 | 2.870 | −43.638 | 1.00 | 47.20 | C |
| ATOM | 585 | CG1 | VAL | A | 75 | 63.727 | 3.897 | −43.563 | 1.00 | 48.39 | C |
| ATOM | 586 | CG2 | VAL | A | 75 | 65.979 | 3.477 | −44.373 | 1.00 | 45.91 | C |
| ATOM | 587 | C | VAL | A | 75 | 64.073 | 2.053 | −41.387 | 1.00 | 47.49 | C |
| ATOM | 588 | O | VAL | A | 75 | 63.434 | 2.919 | −40.786 | 1.00 | 48.41 | O |
| ATOM | 589 | N | GLU | A | 76 | 63.774 | 0.748 | −41.340 | 1.00 | 47.38 | N |
| ATOM | 590 | CA | GLU | A | 76 | 62.578 | 0.186 | −40.682 | 1.00 | 47.03 | C |
| ATOM | 591 | CB | GLU | A | 76 | 62.327 | −1.264 | −41.122 | 1.00 | 46.90 | C |
| ATOM | 592 | CG | GLU | A | 76 | 62.075 | −1.440 | −42.631 | 1.00 | 50.85 | C |
| ATOM | 593 | CD | GLU | A | 76 | 63.370 | −1.574 | −43.459 | 1.00 | 56.49 | C |
| ATOM | 594 | OE1 | GLU | A | 76 | 64.438 | −1.844 | −42.855 | 1.00 | 56.84 | O |
| ATOM | 595 | OE2 | GLU | A | 76 | 63.321 | −1.414 | −44.721 | 1.00 | 60.06 | O |
| ATOM | 596 | C | GLU | A | 76 | 62.681 | 0.239 | −39.173 | 1.00 | 46.09 | C |
| ATOM | 597 | O | GLU | A | 76 | 61.694 | 0.020 | −38.485 | 1.00 | 46.19 | O |
| ATOM | 598 | N | ASP | A | 77 | 63.880 | 0.526 | −38.662 | 1.00 | 45.73 | N |
| ATOM | 599 | CA | ASP | A | 77 | 64.123 | 0.677 | −37.224 | 1.00 | 44.49 | C |
| ATOM | 600 | CB | ASP | A | 77 | 65.557 | 0.277 | −36.855 | 1.00 | 44.34 | C |
| ATOM | 601 | CG | ASP | A | 77 | 65.839 | −1.207 | −37.086 | 1.00 | 47.06 | C |
| ATOM | 602 | OD1 | ASP | A | 77 | 64.964 | −2.086 | −36.810 | 1.00 | 51.98 | O |
| ATOM | 603 | OD2 | ASP | A | 77 | 66.959 | −1.515 | −37.546 | 1.00 | 50.67 | O |
| ATOM | 604 | C | ASP | A | 77 | 63.820 | 2.086 | −36.705 | 1.00 | 44.17 | C |
| ATOM | 605 | O | ASP | A | 77 | 63.795 | 2.288 | −35.501 | 1.00 | 43.66 | O |
| ATOM | 606 | N | SER | A | 78 | 63.606 | 3.056 | −37.601 | 1.00 | 43.76 | N |
| ATOM | 607 | CA | SER | A | 78 | 63.254 | 4.403 | −37.176 | 1.00 | 43.69 | C |
| ATOM | 608 | CB | SER | A | 78 | 62.975 | 5.334 | −38.352 | 1.00 | 43.43 | C |
| ATOM | 609 | OG | SER | A | 78 | 64.074 | 5.409 | −39.232 | 1.00 | 42.84 | O |
| ATOM | 610 | C | SER | A | 78 | 62.026 | 4.342 | −36.304 | 1.00 | 44.36 | C |
| ATOM | 611 | O | SER | A | 78 | 61.112 | 3.604 | −36.591 | 1.00 | 45.78 | O |
| ATOM | 612 | N | GLY | A | 79 | 62.009 | 5.134 | −35.239 | 1.00 | 44.36 | N |
| ATOM | 613 | CA | GLY | A | 79 | 60.931 | 5.138 | −34.284 | 1.00 | 43.30 | C |
| ATOM | 614 | C | GLY | A | 79 | 61.435 | 5.586 | −32.936 | 1.00 | 43.00 | C |
| ATOM | 615 | O | GLY | A | 79 | 62.541 | 6.110 | −32.830 | 1.00 | 43.25 | O |
| ATOM | 616 | N | THR | A | 80 | 60.585 | 5.415 | −31.929 | 1.00 | 42.21 | N |
| ATOM | 617 | CA | THR | A | 80 | 60.837 | 5.861 | −30.587 | 1.00 | 42.60 | C |
| ATOM | 618 | CB | THR | A | 80 | 59.658 | 6.697 | −30.047 | 1.00 | 43.53 | C |
| ATOM | 619 | OG1 | THR | A | 80 | 59.501 | 7.860 | −30.873 | 1.00 | 45.61 | O |
| ATOM | 620 | CG2 | THR | A | 80 | 59.869 | 7.123 | −28.565 | 1.00 | 44.78 | C |
| ATOM | 621 | C | THR | A | 80 | 61.047 | 4.587 | −29.775 | 1.00 | 42.21 | C |

APPENDIX I-continued

| ATOM | 622 | O | THR | A | 80 | 60.308 | 3.637 | −29.924 | 1.00 | 41.06 | O |
|---|---|---|---|---|---|---|---|---|---|---|---|
| ATOM | 623 | N | TYR | A | 81 | 62.115 | 4.578 | −28.973 | 1.00 | 41.77 | N |
| ATOM | 624 | CA | TYR | A | 81 | 62.463 | 3.459 | −28.122 | 1.00 | 40.78 | C |
| ATOM | 625 | CB | TYR | A | 81 | 63.891 | 2.998 | −28.407 | 1.00 | 39.74 | C |
| ATOM | 626 | CG | TYR | A | 81 | 64.031 | 2.350 | −29.774 | 1.00 | 40.54 | C |
| ATOM | 627 | CD1 | TYR | A | 81 | 64.286 | 0.993 | −29.909 | 1.00 | 38.77 | C |
| ATOM | 628 | CE1 | TYR | A | 81 | 64.400 | 0.414 | −31.226 | 1.00 | 42.36 | C |
| ATOM | 629 | CZ | TYR | A | 81 | 64.245 | 1.208 | −32.347 | 1.00 | 37.03 | C |
| ATOM | 630 | OH | TYR | A | 81 | 64.353 | 0.685 | −33.633 | 1.00 | 39.33 | O |
| ATOM | 631 | CE2 | TYR | A | 81 | 63.975 | 2.523 | −32.218 | 1.00 | 38.69 | C |
| ATOM | 632 | CD2 | TYR | A | 81 | 63.891 | 3.106 | −30.932 | 1.00 | 40.06 | C |
| ATOM | 633 | C | TYR | A | 81 | 62.382 | 3.935 | −26.715 | 1.00 | 40.90 | C |
| ATOM | 634 | O | TYR | A | 81 | 62.766 | 5.033 | −26.462 | 1.00 | 40.58 | O |
| ATOM | 635 | N | LYS | A | 82 | 61.896 | 3.088 | −25.819 | 1.00 | 41.29 | N |
| ATOM | 636 | CA | LYS | A | 82 | 61.850 | 3.350 | −24.388 | 1.00 | 42.71 | C |
| ATOM | 637 | CB | LYS | A | 82 | 60.422 | 3.634 | −23.944 | 1.00 | 42.24 | C |
| ATOM | 638 | CG | LYS | A | 82 | 59.994 | 4.963 | −24.379 | 1.00 | 44.27 | C |
| ATOM | 639 | CD | LYS | A | 82 | 58.731 | 5.424 | −23.596 | 1.00 | 45.18 | C |
| ATOM | 640 | CE | LYS | A | 82 | 58.202 | 6.727 | −24.265 | 1.00 | 46.00 | C |
| ATOM | 641 | NZ | LYS | A | 82 | 57.117 | 7.194 | −23.357 | 1.00 | 56.94 | N |
| ATOM | 642 | C | LYS | A | 82 | 62.315 | 2.107 | −23.650 | 1.00 | 42.18 | C |
| ATOM | 643 | O | LYS | A | 82 | 62.061 | 1.027 | −24.094 | 1.00 | 40.76 | O |
| ATOM | 644 | N | CYS | A | 83 | 63.042 | 2.318 | −22.560 | 1.00 | 43.46 | N |
| ATOM | 645 | CA | CYS | A | 83 | 63.439 | 1.309 | −21.629 | 1.00 | 44.61 | C |
| ATOM | 646 | CB | CYS | A | 83 | 64.761 | 1.693 | −20.986 | 1.00 | 45.96 | C |
| ATOM | 647 | SG | CYS | A | 83 | 64.973 | 3.375 | −20.311 | 1.00 | 48.94 | S |
| ATOM | 648 | C | CYS | A | 83 | 62.409 | 1.325 | −20.534 | 1.00 | 45.71 | C |
| ATOM | 649 | O | CYS | A | 83 | 61.631 | 2.271 | −20.456 | 1.00 | 46.30 | O |
| ATOM | 650 | N | GLN | A | 84 | 62.385 | 0.287 | −19.692 | 1.00 | 43.77 | N |
| ATOM | 651 | CA | GLN | A | 84 | 61.568 | 0.350 | −18.534 | 1.00 | 42.92 | C |
| ATOM | 652 | CB | GLN | A | 84 | 60.203 | −0.292 | −18.790 | 1.00 | 42.16 | C |
| ATOM | 653 | CG | GLN | A | 84 | 59.330 | −0.191 | −17.551 | 1.00 | 43.09 | C |
| ATOM | 654 | CD | GLN | A | 84 | 57.821 | −0.376 | −17.766 | 1.00 | 46.36 | C |
| ATOM | 655 | OE1 | GLN | A | 84 | 57.016 | 0.257 | −17.094 | 1.00 | 50.63 | O |
| ATOM | 656 | NE2 | GLN | A | 84 | 57.443 | −1.260 | −18.660 | 1.00 | 44.97 | N |
| ATOM | 657 | C | GLN | A | 84 | 62.286 | −0.351 | −17.413 | 1.00 | 42.33 | C |
| ATOM | 658 | O | GLN | A | 84 | 62.766 | −1.454 | −17.614 | 1.00 | 40.11 | O |
| ATOM | 659 | N | ALA | A | 85 | 62.403 | 0.310 | −16.256 | 1.00 | 42.76 | N |
| ATOM | 660 | CA | ALA | A | 85 | 62.992 | −0.323 | −15.027 | 1.00 | 43.66 | C |
| ATOM | 661 | CB | ALA | A | 85 | 63.803 | 0.674 | −14.213 | 1.00 | 42.44 | C |
| ATOM | 662 | C | ALA | A | 85 | 61.854 | −0.875 | −14.159 | 1.00 | 43.77 | C |
| ATOM | 663 | O | ALA | A | 85 | 60.904 | −0.143 | −13.877 | 1.00 | 42.85 | O |
| ATOM | 664 | N | PHE | A | 86 | 61.986 | −2.140 | −13.760 | 1.00 | 42.59 | N |
| ATOM | 665 | CA | PHE | A | 86 | 61.015 | −2.843 | −12.918 | 1.00 | 43.37 | C |
| ATOM | 666 | CB | PHE | A | 86 | 60.674 | −4.222 | −13.484 | 1.00 | 41.48 | C |
| ATOM | 667 | CG | PHE | A | 86 | 60.048 | −4.178 | −14.879 | 1.00 | 43.52 | C |
| ATOM | 668 | CD1 | PHE | A | 86 | 58.751 | −3.695 | −15.063 | 1.00 | 40.20 | C |
| ATOM | 669 | CE1 | PHE | A | 86 | 58.158 | −3.672 | −16.327 | 1.00 | 38.57 | C |
| ATOM | 670 | CZ | PHE | A | 86 | 58.871 | −4.088 | −17.428 | 1.00 | 42.08 | C |
| ATOM | 671 | CE2 | PHE | A | 86 | 60.178 | −4.538 | −17.273 | 1.00 | 43.63 | C |
| ATOM | 672 | CD2 | PHE | A | 86 | 60.765 | −4.568 | −15.998 | 1.00 | 42.39 | C |
| ATOM | 673 | C | PHE | A | 86 | 61.564 | −2.990 | −11.487 | 1.00 | 44.25 | C |
| ATOM | 674 | O | PHE | A | 86 | 62.745 | −3.227 | −11.275 | 1.00 | 45.17 | O |
| ATOM | 675 | N | TYR | A | 87 | 60.673 | −2.891 | −10.514 | 1.00 | 44.26 | N |
| ATOM | 676 | CA | TYR | A | 87 | 61.056 | −2.955 | −9.127 | 1.00 | 42.81 | C |
| ATOM | 677 | CB | TYR | A | 87 | 61.591 | −1.595 | −8.705 | 1.00 | 42.95 | C |
| ATOM | 678 | CG | TYR | A | 87 | 60.589 | −0.506 | −9.034 | 1.00 | 44.84 | C |
| ATOM | 679 | CD1 | TYR | A | 87 | 60.593 | 0.094 | −10.300 | 1.00 | 44.05 | C |
| ATOM | 680 | CE1 | TYR | A | 87 | 59.685 | 1.047 | −10.640 | 1.00 | 46.61 | C |
| ATOM | 681 | CZ | TYR | A | 87 | 58.730 | 1.425 | −9.702 | 1.00 | 45.72 | C |
| ATOM | 682 | OH | TYR | A | 87 | 57.877 | 2.355 | −10.081 | 1.00 | 48.88 | O |
| ATOM | 683 | CE2 | TYR | A | 87 | 58.659 | 0.878 | −8.442 | 1.00 | 45.57 | C |
| ATOM | 684 | CD2 | TYR | A | 87 | 59.622 | −0.126 | −8.110 | 1.00 | 45.85 | C |
| ATOM | 685 | C | TYR | A | 87 | 59.820 | −3.359 | −8.308 | 1.00 | 42.27 | C |
| ATOM | 686 | O | TYR | A | 87 | 58.694 | −3.482 | −8.832 | 1.00 | 42.84 | O |
| ATOM | 687 | N | VAL | A | 88 | 60.017 | −3.599 | −7.022 | 1.00 | 41.80 | N |
| ATOM | 688 | CA | VAL | A | 88 | 58.912 | −3.966 | −6.147 | 1.00 | 40.05 | C |
| ATOM | 689 | CB | VAL | A | 88 | 59.180 | −5.357 | −5.568 | 1.00 | 40.65 | C |
| ATOM | 690 | CG1 | VAL | A | 88 | 60.622 | −5.432 | −4.904 | 1.00 | 34.41 | C |
| ATOM | 691 | CG2 | VAL | A | 88 | 59.093 | −6.416 | −6.658 | 1.00 | 36.97 | C |
| ATOM | 692 | C | VAL | A | 88 | 58.720 | −2.893 | −5.015 | 1.00 | 41.14 | C |
| ATOM | 693 | O | VAL | A | 88 | 59.646 | −2.140 | −4.619 | 1.00 | 42.19 | O |
| ATOM | 694 | N | PHE | A | 89 | 57.529 | −2.846 | −4.472 | 1.00 | 40.69 | N |
| ATOM | 695 | CA | PHE | A | 89 | 57.239 | −1.957 | −3.367 | 1.00 | 38.05 | C |
| ATOM | 696 | CB | PHE | A | 89 | 57.064 | −0.483 | −3.841 | 1.00 | 37.66 | C |
| ATOM | 697 | CG | PHE | A | 89 | 55.841 | −0.218 | −4.771 | 1.00 | 35.47 | C |
| ATOM | 698 | CD1 | PHE | A | 89 | 55.948 | −0.343 | −6.141 | 1.00 | 34.15 | C |
| ATOM | 699 | CE1 | PHE | A | 89 | 54.868 | −0.074 | −6.984 | 1.00 | 30.34 | C |
| ATOM | 700 | CZ | PHE | A | 89 | 53.716 | 0.379 | −6.408 | 1.00 | 38.20 | C |
| ATOM | 701 | CE2 | PHE | A | 89 | 53.627 | 0.586 | −4.999 | 1.00 | 30.74 | C |

APPENDIX I-continued

| | | | | | | | | | | | |
|---|---|---|---|---|---|---|---|---|---|---|---|
| ATOM | 702 | CD2 | PHE | A | 89 | 54.662 | 0.290 | −4.241 | 1.00 | 36.54 | C |
| ATOM | 703 | C | PHE | A | 89 | 56.012 | −2.518 | −2.694 | 1.00 | 39.07 | C |
| ATOM | 704 | O | PHE | A | 89 | 55.218 | −3.234 | −3.341 | 1.00 | 35.78 | O |
| ATOM | 705 | N | PHE | A | 90 | 55.886 | −2.215 | −1.394 | 1.00 | 38.51 | N |
| ATOM | 706 | CA | PHE | A | 90 | 54.693 | −2.576 | −0.621 | 1.00 | 39.88 | C |
| ATOM | 707 | CB | PHE | A | 90 | 54.993 | −2.528 | 0.874 | 1.00 | 37.98 | C |
| ATOM | 708 | CG | PHE | A | 90 | 55.700 | −3.740 | 1.386 | 1.00 | 37.62 | C |
| ATOM | 709 | CD1 | PHE | A | 90 | 55.078 | −5.003 | 1.336 | 1.00 | 35.79 | C |
| ATOM | 710 | CE1 | PHE | A | 90 | 55.688 | −6.126 | 1.895 | 1.00 | 37.83 | C |
| ATOM | 711 | CZ | PHE | A | 90 | 56.950 | −6.030 | 2.476 | 1.00 | 38.12 | C |
| ATOM | 712 | CE2 | PHE | A | 90 | 57.601 | −4.739 | 2.526 | 1.00 | 38.60 | C |
| ATOM | 713 | CD2 | PHE | A | 90 | 56.922 | −3.620 | 1.998 | 1.00 | 37.29 | C |
| ATOM | 714 | C | PHE | A | 90 | 53.467 | −1.698 | −0.981 | 1.00 | 40.53 | C |
| ATOM | 715 | O | PHE | A | 90 | 53.605 | −0.502 | −1.196 | 1.00 | 40.32 | O |
| ATOM | 716 | N | ALA | A | 91 | 52.277 | −2.306 | −0.985 | 1.00 | 41.27 | N |
| ATOM | 717 | CA | ALA | A | 91 | 51.067 | −1.617 | −1.372 | 1.00 | 41.84 | C |
| ATOM | 718 | CB | ALA | A | 91 | 49.892 | −2.513 | −1.182 | 1.00 | 42.15 | C |
| ATOM | 719 | C | ALA | A | 91 | 50.860 | −0.249 | −0.668 | 1.00 | 43.70 | C |
| ATOM | 720 | O | ALA | A | 91 | 50.328 | 0.664 | −1.280 | 1.00 | 43.35 | O |
| ATOM | 721 | N | GLU | A | 92 | 51.321 | −0.091 | 0.581 | 1.00 | 44.95 | N |
| ATOM | 722 | CA | GLU | A | 92 | 51.195 | 1.188 | 1.293 | 1.00 | 45.93 | C |
| ATOM | 723 | CB | GLU | A | 92 | 50.780 | 0.942 | 2.711 | 1.00 | 46.65 | C |
| ATOM | 724 | CG | GLU | A | 92 | 49.555 | 0.079 | 2.779 | 1.00 | 48.11 | C |
| ATOM | 725 | CD | GLU | A | 92 | 48.913 | 0.127 | 4.131 | 1.00 | 57.18 | C |
| ATOM | 726 | OE1 | GLU | A | 92 | 48.562 | 1.252 | 4.563 | 1.00 | 59.80 | O |
| ATOM | 727 | OE2 | GLU | A | 92 | 48.750 | −0.953 | 4.764 | 1.00 | 56.56 | O |
| ATOM | 728 | C | GLU | A | 92 | 52.446 | 2.067 | 1.252 | 1.00 | 47.30 | C |
| ATOM | 729 | O | GLU | A | 92 | 52.450 | 3.195 | 1.756 | 1.00 | 48.77 | O |
| ATOM | 730 | N | ASP | A | 93 | 53.503 | 1.616 | 0.598 | 1.00 | 46.55 | N |
| ATOM | 731 | CA | ASP | A | 93 | 54.636 | 2.501 | 0.483 | 1.00 | 46.41 | C |
| ATOM | 732 | CB | ASP | A | 93 | 55.884 | 1.692 | 0.182 | 1.00 | 45.51 | C |
| ATOM | 733 | CG | ASP | A | 93 | 57.082 | 2.561 | −0.131 | 1.00 | 44.76 | C |
| ATOM | 734 | OD1 | ASP | A | 93 | 58.026 | 2.046 | −0.789 | 1.00 | 42.86 | O |
| ATOM | 735 | OD2 | ASP | A | 93 | 57.072 | 3.754 | 0.253 | 1.00 | 42.99 | O |
| ATOM | 736 | C | ASP | A | 93 | 54.344 | 3.551 | −0.605 | 1.00 | 46.69 | C |
| ATOM | 737 | O | ASP | A | 93 | 54.653 | 3.334 | −1.774 | 1.00 | 46.46 | O |
| ATOM | 738 | N | VAL | A | 94 | 53.716 | 4.660 | −0.218 | 1.00 | 46.68 | N |
| ATOM | 739 | CA | VAL | A | 94 | 53.276 | 5.672 | −1.199 | 1.00 | 47.78 | C |
| ATOM | 740 | CB | VAL | A | 94 | 52.240 | 6.690 | −0.629 | 1.00 | 47.50 | C |
| ATOM | 741 | CG1 | VAL | A | 94 | 52.844 | 7.591 | 0.471 | 1.00 | 48.03 | C |
| ATOM | 742 | CG2 | VAL | A | 94 | 51.023 | 5.941 | −0.088 | 1.00 | 48.45 | C |
| ATOM | 743 | C | VAL | A | 94 | 54.439 | 6.375 | −1.893 | 1.00 | 47.62 | C |
| ATOM | 744 | O | VAL | A | 94 | 54.323 | 6.822 | −3.039 | 1.00 | 48.80 | O |
| ATOM | 745 | N | GLY | A | 95 | 55.577 | 6.444 | −1.228 | 1.00 | 47.46 | N |
| ATOM | 746 | CA | GLY | A | 95 | 56.743 | 7.084 | −1.829 | 1.00 | 46.54 | C |
| ATOM | 747 | C | GLY | A | 95 | 57.216 | 6.371 | −3.077 | 1.00 | 46.80 | C |
| ATOM | 748 | O | GLY | A | 95 | 57.971 | 6.944 | −3.858 | 1.00 | 48.77 | O |
| ATOM | 749 | N | SER | A | 96 | 56.789 | 5.125 | −3.282 | 1.00 | 45.12 | N |
| ATOM | 750 | CA | SER | A | 96 | 57.316 | 4.299 | −4.367 | 1.00 | 43.91 | C |
| ATOM | 751 | CB | SER | A | 96 | 57.806 | 2.951 | −3.774 | 1.00 | 43.86 | C |
| ATOM | 752 | OG | SER | A | 96 | 59.082 | 3.050 | −3.170 | 1.00 | 45.47 | O |
| ATOM | 753 | C | SER | A | 96 | 56.280 | 3.976 | −5.464 | 1.00 | 43.04 | C |
| ATOM | 754 | O | SER | A | 96 | 56.556 | 3.141 | −6.333 | 1.00 | 41.97 | O |
| ATOM | 755 | N | ASN | A | 97 | 55.083 | 4.582 | −5.411 | 1.00 | 42.62 | N |
| ATOM | 756 | CA | ASN | A | 97 | 53.955 | 4.125 | −6.262 | 1.00 | 41.42 | C |
| ATOM | 757 | CB | ASN | A | 97 | 52.664 | 3.995 | −5.411 | 1.00 | 41.08 | C |
| ATOM | 758 | CG | ASN | A | 97 | 52.129 | 5.344 | −4.941 | 1.00 | 42.94 | C |
| ATOM | 759 | OD1 | ASN | A | 97 | 52.503 | 6.365 | −5.465 | 1.00 | 46.83 | O |
| ATOM | 760 | ND2 | ASN | A | 97 | 51.255 | 5.342 | −3.965 | 1.00 | 40.83 | N |
| ATOM | 761 | C | ASN | A | 97 | 53.666 | 4.932 | −7.525 | 1.00 | 42.28 | C |
| ATOM | 762 | O | ASN | A | 97 | 52.585 | 4.750 | −8.141 | 1.00 | 41.82 | O |
| ATOM | 763 | N | LYS | A | 98 | 54.573 | 5.850 | −7.915 | 1.00 | 42.02 | N |
| ATOM | 764 | CA | LYS | A | 98 | 54.248 | 6.732 | −9.041 | 1.00 | 43.43 | C |
| ATOM | 765 | CB | LYS | A | 98 | 54.942 | 8.098 | −8.900 | 1.00 | 44.23 | C |
| ATOM | 766 | CG | LYS | A | 98 | 55.210 | 8.508 | −7.418 | 1.00 | 46.17 | C |
| ATOM | 767 | CD | LYS | A | 98 | 54.021 | 9.049 | −6.764 | 1.00 | 48.50 | C |
| ATOM | 768 | CE | LYS | A | 98 | 54.408 | 9.875 | −5.559 | 1.00 | 45.50 | C |
| ATOM | 769 | NZ | LYS | A | 98 | 54.697 | 8.979 | −4.390 | 1.00 | 48.43 | N |
| ATOM | 770 | C | LYS | A | 98 | 54.460 | 6.112 | −10.439 | 1.00 | 43.17 | C |
| ATOM | 771 | O | LYS | A | 98 | 54.025 | 6.663 | −11.415 | 1.00 | 42.52 | O |
| ATOM | 772 | N | GLY | A | 99 | 55.057 | 4.929 | −10.498 | 1.00 | 43.81 | N |
| ATOM | 773 | CA | GLY | A | 99 | 55.295 | 4.242 | −11.742 | 1.00 | 43.60 | C |
| ATOM | 774 | C | GLY | A | 99 | 54.052 | 3.507 | −12.181 | 1.00 | 42.19 | C |
| ATOM | 775 | O | GLY | A | 99 | 53.008 | 3.607 | −11.544 | 1.00 | 42.85 | O |
| ATOM | 776 | N | ALA | A | 100 | 54.151 | 2.775 | −13.283 | 1.00 | 40.39 | N |
| ATOM | 777 | CA | ALA | A | 100 | 53.014 | 1.974 | −13.753 | 1.00 | 39.22 | C |
| ATOM | 778 | CB | ALA | A | 100 | 53.278 | 1.513 | −15.205 | 1.00 | 36.47 | C |
| ATOM | 779 | C | ALA | A | 100 | 52.932 | 0.751 | −12.819 | 1.00 | 38.50 | C |
| ATOM | 780 | O | ALA | A | 100 | 53.913 | 0.368 | −12.262 | 1.00 | 38.16 | O |
| ATOM | 781 | N | ILE | A | 101 | 51.772 | 0.140 | −12.652 | 1.00 | 38.62 | N |

APPENDIX I-continued

| ATOM | 782 | CA | ILE | A | 101 | 51.638 | −1.134 | −11.945 | 1.00 | 38.55 | C |
|---|---|---|---|---|---|---|---|---|---|---|---|
| ATOM | 783 | CB | ILE | A | 101 | 50.190 | −1.269 | −11.405 | 1.00 | 40.06 | C |
| ATOM | 784 | CG1 | ILE | A | 101 | 49.797 | 0.015 | −10.598 | 1.00 | 42.79 | C |
| ATOM | 785 | CD1 | ILE | A | 101 | 50.554 | 0.261 | −9.310 | 1.00 | 39.48 | C |
| ATOM | 786 | CG2 | ILE | A | 101 | 49.959 | −2.667 | −10.762 | 1.00 | 36.33 | C |
| ATOM | 787 | C | ILE | A | 101 | 51.767 | −2.274 | −12.951 | 1.00 | 39.19 | C |
| ATOM | 788 | O | ILE | A | 101 | 50.995 | −2.357 | −13.950 | 1.00 | 36.64 | O |
| ATOM | 789 | N | ILE | A | 102 | 52.677 | −3.191 | −12.663 | 1.00 | 39.81 | N |
| ATOM | 790 | CA | ILE | A | 102 | 52.909 | −4.348 | −13.578 | 1.00 | 39.64 | C |
| ATOM | 791 | CB | ILE | A | 102 | 54.454 | −4.487 | −13.734 | 1.00 | 39.59 | C |
| ATOM | 792 | CG1 | ILE | A | 102 | 55.089 | −3.117 | −14.157 | 1.00 | 38.41 | C |
| ATOM | 793 | CD1 | ILE | A | 102 | 54.460 | −2.524 | −15.511 | 1.00 | 33.86 | C |
| ATOM | 794 | CG2 | ILE | A | 102 | 54.819 | −5.583 | −14.725 | 1.00 | 40.76 | C |
| ATOM | 795 | C | ILE | A | 102 | 52.195 | −5.647 | −13.073 | 1.00 | 39.13 | C |
| ATOM | 796 | O | ILE | A | 102 | 51.854 | −6.530 | −13.816 | 1.00 | 39.94 | O |
| ATOM | 797 | N | GLY | A | 103 | 52.050 | −5.776 | −11.775 | 1.00 | 39.01 | N |
| ATOM | 798 | CA | GLY | A | 103 | 51.334 | −6.885 | −11.213 | 1.00 | 38.49 | C |
| ATOM | 799 | C | GLY | A | 103 | 51.324 | −6.752 | −9.716 | 1.00 | 37.24 | C |
| ATOM | 800 | O | GLY | A | 103 | 51.882 | −5.833 | −9.130 | 1.00 | 36.17 | O |
| ATOM | 801 | N | LEU | A | 104 | 50.749 | −7.742 | −9.089 | 1.00 | 37.99 | N |
| ATOM | 802 | CA | LEU | A | 104 | 50.493 | −7.683 | −7.688 | 1.00 | 39.66 | C |
| ATOM | 803 | CB | LEU | A | 104 | 49.031 | −7.210 | −7.355 | 1.00 | 37.53 | C |
| ATOM | 804 | CG | LEU | A | 104 | 48.649 | −7.290 | −5.842 | 1.00 | 40.70 | C |
| ATOM | 805 | CD1 | LEU | A | 104 | 47.171 | −7.118 | −5.505 | 1.00 | 39.27 | C |
| ATOM | 806 | CD2 | LEU | A | 104 | 49.430 | −6.275 | −4.991 | 1.00 | 38.45 | C |
| ATOM | 807 | C | LEU | A | 104 | 50.744 | −9.080 | −7.236 | 1.00 | 40.91 | C |
| ATOM | 808 | O | LEU | A | 104 | 50.123 | −10.019 | −7.747 | 1.00 | 40.88 | O |
| ATOM | 809 | N | MET | A | 105 | 51.687 | −9.213 | −6.306 | 1.00 | 43.27 | N |
| ATOM | 810 | CA | MET | A | 105 | 51.982 | −10.471 | −5.649 | 1.00 | 45.57 | C |
| ATOM | 811 | CB | MET | A | 105 | 53.480 | −10.581 | −5.502 | 1.00 | 47.53 | C |
| ATOM | 812 | CG | MET | A | 105 | 54.143 | −11.586 | −6.445 | 1.00 | 56.01 | C |
| ATOM | 813 | SD | MET | A | 105 | 53.858 | −11.477 | −8.250 | 1.00 | 66.51 | S |
| ATOM | 814 | CE | MET | A | 105 | 54.839 | −12.860 | −8.841 | 1.00 | 57.93 | C |
| ATOM | 815 | C | MET | A | 105 | 51.291 | −10.529 | −4.289 | 1.00 | 44.27 | C |
| ATOM | 816 | O | MET | A | 105 | 51.143 | −9.509 | −3.650 | 1.00 | 43.68 | O |
| ATOM | 817 | N | VAL | A | 106 | 50.826 | −11.700 | −3.870 | 1.00 | 44.78 | N |
| ATOM | 818 | CA | VAL | A | 106 | 50.387 | −11.916 | −2.462 | 1.00 | 46.00 | C |
| ATOM | 819 | CB | VAL | A | 106 | 50.185 | −13.396 | −2.124 | 1.00 | 46.66 | C |
| ATOM | 820 | CG1 | VAL | A | 106 | 51.551 | −14.154 | −2.328 | 1.00 | 47.69 | C |
| ATOM | 821 | CG2 | VAL | A | 106 | 49.015 | −13.959 | −2.921 | 1.00 | 45.00 | C |
| ATOM | 822 | C | VAL | A | 106 | 51.431 | −11.451 | −1.442 | 1.00 | 46.49 | C |
| ATOM | 823 | O | VAL | A | 106 | 52.639 | −11.733 | −1.590 | 1.00 | 46.05 | O |
| ATOM | 824 | N | GLY | A | 107 | 50.942 | −10.795 | −0.390 | 1.00 | 45.74 | N |
| ATOM | 825 | CA | GLY | A | 107 | 51.799 | −10.227 | 0.629 | 1.00 | 44.85 | C |
| ATOM | 826 | C | GLY | A | 107 | 51.784 | −8.730 | 0.425 | 1.00 | 44.68 | C |
| ATOM | 827 | O | GLY | A | 107 | 52.526 | −8.029 | 1.054 | 1.00 | 45.42 | O |
| ATOM | 828 | N | GLY | A | 108 | 50.939 | −8.247 | −0.480 | 1.00 | 43.98 | N |
| ATOM | 829 | CA | GLY | A | 108 | 50.840 | −6.821 | −0.790 | 1.00 | 43.08 | C |
| ATOM | 830 | C | GLY | A | 108 | 52.084 | −6.255 | −1.442 | 1.00 | 42.91 | C |
| ATOM | 831 | O | GLY | A | 108 | 52.434 | −5.089 | −1.242 | 1.00 | 42.44 | O |
| ATOM | 832 | N | VAL | A | 109 | 52.719 | −7.046 | −2.291 | 1.00 | 43.26 | N |
| ATOM | 833 | CA | VAL | A | 109 | 53.948 | −6.599 | −2.957 | 1.00 | 42.66 | C |
| ATOM | 834 | CB | VAL | A | 109 | 55.000 | −7.751 | −2.883 | 1.00 | 43.69 | C |
| ATOM | 835 | CG1 | VAL | A | 109 | 56.193 | −7.522 | −3.854 | 1.00 | 42.19 | C |
| ATOM | 836 | CG2 | VAL | A | 109 | 55.408 | −8.004 | −1.423 | 1.00 | 42.91 | C |
| ATOM | 837 | C | VAL | A | 109 | 53.554 | −6.242 | −4.387 | 1.00 | 42.97 | C |
| ATOM | 838 | O | VAL | A | 109 | 53.096 | −7.113 | −5.167 | 1.00 | 42.03 | O |
| ATOM | 839 | N | VAL | A | 110 | 53.665 | −4.958 | −4.723 | 1.00 | 42.17 | N |
| ATOM | 840 | CA | VAL | A | 110 | 53.415 | −4.541 | −6.054 | 1.00 | 40.80 | C |
| ATOM | 841 | CB | VAL | A | 110 | 52.310 | −3.424 | −6.153 | 1.00 | 44.02 | C |
| ATOM | 842 | CG1 | VAL | A | 110 | 52.372 | −2.549 | −7.365 | 1.00 | 42.03 | C |
| ATOM | 843 | CG2 | VAL | A | 110 | 51.848 | −2.769 | −4.779 | 1.00 | 41.33 | C |
| ATOM | 844 | C | VAL | A | 110 | 54.630 | −4.554 | −6.979 | 1.00 | 41.32 | C |
| ATOM | 845 | O | VAL | A | 110 | 55.745 | −4.275 | −6.542 | 1.00 | 41.11 | O |
| ATOM | 846 | N | ILE | A | 111 | 54.454 | −4.937 | −8.242 | 1.00 | 40.50 | N |
| ATOM | 847 | CA | ILE | A | 111 | 55.520 | −4.758 | −9.218 | 1.00 | 39.74 | C |
| ATOM | 848 | CB | ILE | A | 111 | 55.693 | −6.002 | −10.151 | 1.00 | 42.13 | C |
| ATOM | 849 | CG1 | ILE | A | 111 | 55.947 | −7.264 | −9.286 | 1.00 | 44.65 | C |
| ATOM | 850 | CD1 | ILE | A | 111 | 55.492 | −8.577 | −9.969 | 1.00 | 51.14 | C |
| ATOM | 851 | CG2 | ILE | A | 111 | 56.814 | −5.793 | −11.241 | 1.00 | 39.84 | C |
| ATOM | 852 | C | ILE | A | 111 | 55.308 | −3.462 | −9.981 | 1.00 | 38.67 | C |
| ATOM | 853 | O | ILE | A | 111 | 54.231 | −3.209 | −10.519 | 1.00 | 39.08 | O |
| ATOM | 854 | N | GLY | A | 112 | 56.314 | −2.594 | −9.989 | 1.00 | 37.53 | N |
| ATOM | 855 | CA | GLY | A | 112 | 56.135 | −1.251 | −10.626 | 1.00 | 36.49 | C |
| ATOM | 856 | C | GLY | A | 112 | 57.100 | −1.138 | −11.758 | 1.00 | 37.46 | C |
| ATOM | 857 | O | GLY | A | 112 | 58.065 | −1.929 | −11.859 | 1.00 | 37.41 | O |
| ATOM | 858 | N | GLY | A | 113 | 56.787 | −0.246 | −12.688 | 1.00 | 38.41 | N |
| ATOM | 859 | CA | GLY | A | 113 | 57.674 | 0.011 | −13.832 | 1.00 | 39.24 | C |
| ATOM | 860 | C | GLY | A | 113 | 57.818 | 1.473 | −14.008 | 1.00 | 38.63 | C |
| ATOM | 861 | O | GLY | A | 113 | 56.810 | 2.152 | −13.932 | 1.00 | 40.39 | O |

APPENDIX I-continued

| | | | | | | | | | | | |
|---|---|---|---|---|---|---|---|---|---|---|---|
| ATOM | 862 | N | GLU | A | 114 | 59.046 | 1.981 | −14.149 | 1.00 | 40.63 | N |
| ATOM | 863 | CA | GLU | A | 114 | 59.293 | 3.395 | −14.613 | 1.00 | 42.64 | C |
| ATOM | 864 | CB | GLU | A | 114 | 60.340 | 4.176 | −13.800 | 1.00 | 42.87 | C |
| ATOM | 865 | CG | GLU | A | 114 | 59.955 | 4.975 | −12.595 | 1.00 | 50.17 | C |
| ATOM | 866 | CD | GLU | A | 114 | 58.981 | 6.134 | −12.814 | 1.00 | 55.34 | C |
| ATOM | 867 | OE1 | GLU | A | 114 | 59.160 | 6.926 | −13.769 | 1.00 | 61.09 | O |
| ATOM | 868 | OE2 | GLU | A | 114 | 58.080 | 6.310 | −11.959 | 1.00 | 57.31 | O |
| ATOM | 869 | C | GLU | A | 114 | 59.949 | 3.324 | −15.964 | 1.00 | 42.42 | C |
| ATOM | 870 | O | GLU | A | 114 | 60.953 | 2.626 | −16.132 | 1.00 | 43.93 | O |
| ATOM | 871 | N | LYS | A | 115 | 59.503 | 4.152 | −16.876 | 1.00 | 42.38 | N |
| ATOM | 872 | CA | LYS | A | 115 | 60.016 | 4.192 | −18.240 | 1.00 | 42.73 | C |
| ATOM | 873 | CB | LYS | A | 115 | 58.829 | 4.219 | −19.234 | 1.00 | 44.06 | C |
| ATOM | 874 | CG | LYS | A | 115 | 58.069 | 2.975 | −19.365 | 1.00 | 47.53 | C |
| ATOM | 875 | CD | LYS | A | 115 | 57.203 | 3.006 | −20.629 | 1.00 | 53.24 | C |
| ATOM | 876 | CE | LYS | A | 115 | 56.289 | 1.786 | −20.589 | 1.00 | 54.45 | C |
| ATOM | 877 | NZ | LYS | A | 115 | 55.402 | 1.783 | −21.803 | 1.00 | 61.37 | N |
| ATOM | 878 | C | LYS | A | 115 | 60.796 | 5.484 | −18.507 | 1.00 | 41.16 | C |
| ATOM | 879 | O | LYS | A | 115 | 60.463 | 6.586 | −18.007 | 1.00 | 40.33 | O |
| ATOM | 880 | N | GLY | A | 116 | 61.804 | 5.356 | −19.341 | 1.00 | 40.59 | N |
| ATOM | 881 | CA | GLY | A | 116 | 62.579 | 6.518 | −19.817 | 1.00 | 39.49 | C |
| ATOM | 882 | C | GLY | A | 116 | 61.717 | 7.400 | −20.692 | 1.00 | 40.21 | C |
| ATOM | 883 | O | GLY | A | 116 | 60.615 | 6.997 | −21.112 | 1.00 | 38.64 | O |
| ATOM | 884 | N | ALA | A | 117 | 62.212 | 8.605 | −20.987 | 1.00 | 41.52 | N |
| ATOM | 885 | CA | ALA | A | 117 | 61.472 | 9.547 | −21.817 | 1.00 | 42.80 | C |
| ATOM | 886 | CB | ALA | A | 117 | 62.048 | 10.974 | −21.662 | 1.00 | 44.34 | C |
| ATOM | 887 | C | ALA | A | 117 | 61.451 | 9.187 | −23.295 | 1.00 | 43.54 | C |
| ATOM | 888 | O | ALA | A | 117 | 60.687 | 9.767 | −24.039 | 1.00 | 44.55 | O |
| ATOM | 889 | N | GLY | A | 118 | 62.303 | 8.280 | −23.760 | 1.00 | 43.70 | N |
| ATOM | 890 | CA | GLY | A | 118 | 62.260 | 7.966 | −25.184 | 1.00 | 41.16 | C |
| ATOM | 891 | C | GLY | A | 118 | 63.528 | 8.367 | −25.883 | 1.00 | 41.11 | C |
| ATOM | 892 | O | GLY | A | 118 | 64.195 | 9.321 | −25.473 | 1.00 | 41.17 | O |
| ATOM | 893 | N | THR | A | 119 | 63.870 | 7.617 | −26.927 | 1.00 | 40.36 | N |
| ATOM | 894 | CA | THR | A | 119 | 64.921 | 7.982 | −27.896 | 1.00 | 39.93 | C |
| ATOM | 895 | CB | THR | A | 119 | 66.082 | 6.926 | −27.933 | 1.00 | 39.67 | C |
| ATOM | 896 | OG1 | THR | A | 119 | 66.775 | 6.941 | −26.682 | 1.00 | 36.77 | O |
| ATOM | 897 | CG2 | THR | A | 119 | 67.130 | 7.237 | −29.078 | 1.00 | 37.93 | C |
| ATOM | 898 | C | THR | A | 119 | 64.168 | 7.915 | −29.198 | 1.00 | 40.54 | C |
| ATOM | 899 | O | THR | A | 119 | 63.610 | 6.841 | −29.510 | 1.00 | 41.01 | O |
| ATOM | 900 | N | ALA | A | 120 | 64.042 | 9.058 | −29.886 | 1.00 | 39.18 | N |
| ATOM | 901 | CA | ALA | A | 120 | 63.474 | 9.123 | −31.240 | 1.00 | 39.16 | C |
| ATOM | 902 | CB | ALA | A | 120 | 62.887 | 10.544 | −31.521 | 1.00 | 39.16 | C |
| ATOM | 903 | C | ALA | A | 120 | 64.617 | 8.819 | −32.234 | 1.00 | 38.85 | C |
| ATOM | 904 | O | ALA | A | 120 | 65.576 | 9.562 | −32.300 | 1.00 | 37.63 | O |
| ATOM | 905 | N | LEU | A | 121 | 64.560 | 7.680 | −32.925 | 1.00 | 39.42 | N |
| ATOM | 906 | CA | LEU | A | 121 | 65.634 | 7.279 | −33.798 | 1.00 | 39.83 | C |
| ATOM | 907 | CB | LEU | A | 121 | 66.049 | 5.819 | −33.513 | 1.00 | 40.42 | C |
| ATOM | 908 | CG | LEU | A | 121 | 66.974 | 5.144 | −34.569 | 1.00 | 40.59 | C |
| ATOM | 909 | CD1 | LEU | A | 121 | 68.396 | 5.751 | −34.587 | 1.00 | 38.95 | C |
| ATOM | 910 | CD2 | LEU | A | 121 | 67.007 | 3.604 | −34.288 | 1.00 | 41.03 | C |
| ATOM | 911 | C | LEU | A | 121 | 65.256 | 7.492 | −35.280 | 1.00 | 40.22 | C |
| ATOM | 912 | O | LEU | A | 121 | 64.147 | 7.165 | −35.705 | 1.00 | 39.00 | O |
| ATOM | 913 | N | THR | A | 122 | 66.171 | 8.081 | −36.057 | 1.00 | 40.54 | N |
| ATOM | 914 | CA | THR | A | 122 | 65.968 | 8.199 | −37.476 | 1.00 | 40.45 | C |
| ATOM | 915 | CB | THR | A | 122 | 65.896 | 9.701 | −37.936 | 1.00 | 41.48 | C |
| ATOM | 916 | OG1 | THR | A | 122 | 64.702 | 10.294 | −37.406 | 1.00 | 44.87 | O |
| ATOM | 917 | CG2 | THR | A | 122 | 65.878 | 9.852 | −39.480 | 1.00 | 39.71 | C |
| ATOM | 918 | C | THR | A | 122 | 67.138 | 7.487 | −38.092 | 1.00 | 40.29 | C |
| ATOM | 919 | O | THR | A | 122 | 68.279 | 7.874 | −37.877 | 1.00 | 39.60 | O |
| ATOM | 920 | N | VAL | A | 123 | 66.875 | 6.408 | −38.818 | 1.00 | 40.92 | N |
| ATOM | 921 | CA | VAL | A | 123 | 67.930 | 5.869 | −39.707 | 1.00 | 41.20 | C |
| ATOM | 922 | CB | VAL | A | 123 | 68.359 | 4.405 | −39.388 | 1.00 | 41.03 | C |
| ATOM | 923 | CG1 | VAL | A | 123 | 67.511 | 3.799 | −38.233 | 1.00 | 39.09 | C |
| ATOM | 924 | CG2 | VAL | A | 123 | 68.518 | 3.549 | −40.620 | 1.00 | 40.22 | C |
| ATOM | 925 | C | VAL | A | 123 | 67.788 | 6.260 | −41.186 | 1.00 | 42.10 | C |
| ATOM | 926 | O | VAL | A | 123 | 66.767 | 6.047 | −41.842 | 1.00 | 42.13 | O |
| ATOM | 927 | N | LYS | A | 124 | 68.836 | 6.892 | −41.677 | 1.00 | 43.39 | N |
| ATOM | 928 | CA | LYS | A | 124 | 68.864 | 7.415 | −43.030 | 1.00 | 44.97 | C |
| ATOM | 929 | CB | LYS | A | 124 | 70.047 | 8.388 | −43.187 | 1.00 | 44.33 | C |
| ATOM | 930 | CG | LYS | A | 124 | 69.902 | 9.697 | −42.471 | 1.00 | 43.86 | C |
| ATOM | 931 | CD | LYS | A | 124 | 71.265 | 10.355 | −42.186 | 1.00 | 42.06 | C |
| ATOM | 932 | CE | LYS | A | 124 | 71.842 | 11.023 | −43.404 | 1.00 | 46.07 | C |
| ATOM | 933 | NZ | LYS | A | 124 | 73.312 | 11.366 | −43.269 | 1.00 | 46.30 | N |
| ATOM | 934 | C | LYS | A | 124 | 68.989 | 6.198 | −43.984 | 1.00 | 45.36 | C |
| ATOM | 935 | O | LYS | A | 124 | 69.693 | 5.235 | −43.663 | 1.00 | 45.33 | O |
| ATOM | 936 | N | ALA | A | 125 | 68.274 | 6.214 | −45.110 | 1.00 | 46.08 | N |
| ATOM | 937 | CA | ALA | A | 125 | 68.489 | 5.175 | −46.141 | 1.00 | 47.11 | C |
| ATOM | 938 | CB | ALA | A | 125 | 67.648 | 5.451 | −47.384 | 1.00 | 46.76 | C |
| ATOM | 939 | C | ALA | A | 125 | 69.972 | 5.123 | −46.500 | 1.00 | 47.33 | C |
| ATOM | 940 | O | ALA | A | 125 | 70.618 | 6.175 | −46.508 | 1.00 | 47.44 | O |
| ATOM | 941 | N | ALA | A | 126 | 70.528 | 3.890 | −46.738 | 1.00 | 48.74 | N |

APPENDIX I-continued

| | | | | | | | | | | | |
|---|---|---|---|---|---|---|---|---|---|---|---|
| ATOM | 942 | CA | ALA | A | 126 | 71.863 | 3.817 | −47.444 | 1.00 | 49.81 | C |
| ATOM | 943 | CB | ALA | A | 126 | 72.337 | 2.362 | −47.714 | 1.00 | 49.59 | C |
| ATOM | 944 | C | ALA | A | 126 | 71.800 | 4.577 | −48.758 | 1.00 | 49.59 | C |
| ATOM | 945 | O | ALA | A | 126 | 70.772 | 4.531 | −49.478 | 1.00 | 51.31 | O |
| ATOM | 946 | OXT | ALA | A | 126 | 72.764 | 5.235 | −49.161 | 1.00 | 51.16 | O |
| ATOM | 947 | N | ALA | B | 1 | 32.574 | −25.808 | −7.345 | 1.00 | 54.95 | N |
| ATOM | 948 | CA | ALA | B | 1 | 31.899 | −24.453 | −7.214 | 1.00 | 54.95 | C |
| ATOM | 949 | CB | ALA | B | 1 | 32.851 | −23.438 | −6.634 | 1.00 | 55.01 | C |
| ATOM | 950 | C | ALA | B | 1 | 31.283 | −23.899 | −8.498 | 1.00 | 54.51 | C |
| ATOM | 951 | O | ALA | B | 1 | 31.993 | −23.349 | −9.338 | 1.00 | 55.95 | O |
| ATOM | 952 | N | TRP | B | 2 | 29.963 | −23.999 | −8.630 | 1.00 | 53.08 | N |
| ATOM | 953 | CA | TRP | B | 2 | 29.268 | −23.472 | −9.820 | 1.00 | 50.94 | C |
| ATOM | 954 | CB | TRP | B | 2 | 29.049 | −24.605 | −10.808 | 1.00 | 51.28 | C |
| ATOM | 955 | CG | TRP | B | 2 | 28.244 | −25.758 | −10.275 | 1.00 | 51.82 | C |
| ATOM | 956 | CD1 | TRP | B | 2 | 28.645 | −26.700 | −9.352 | 1.00 | 52.56 | C |
| ATOM | 957 | NE1 | TRP | B | 2 | 27.625 | −27.612 | −9.141 | 1.00 | 53.31 | N |
| ATOM | 958 | CE2 | TRP | B | 2 | 26.550 | −27.281 | −9.932 | 1.00 | 51.80 | C |
| ATOM | 959 | CD2 | TRP | B | 2 | 26.903 | −26.123 | −10.670 | 1.00 | 51.84 | C |
| ATOM | 960 | CE3 | TRP | B | 2 | 25.970 | −25.573 | −11.562 | 1.00 | 51.22 | C |
| ATOM | 961 | CZ3 | TRP | B | 2 | 24.719 | −26.207 | −11.705 | 1.00 | 52.11 | C |
| ATOM | 962 | CH2 | TRP | B | 2 | 24.404 | −27.365 | −10.954 | 1.00 | 52.45 | C |
| ATOM | 963 | CZ2 | TRP | B | 2 | 25.303 | −27.907 | −10.064 | 1.00 | 51.92 | C |
| ATOM | 964 | C | TRP | B | 2 | 27.938 | −22.763 | −9.508 | 1.00 | 49.34 | C |
| ATOM | 965 | O | TRP | B | 2 | 27.440 | −22.864 | −8.388 | 1.00 | 48.53 | O |
| ATOM | 966 | N | VAL | B | 3 | 27.368 | −22.056 | −10.497 | 1.00 | 47.43 | N |
| ATOM | 967 | CA | VAL | B | 3 | 26.076 | −21.354 | −10.319 | 1.00 | 45.64 | C |
| ATOM | 968 | CB | VAL | B | 3 | 26.099 | −19.865 | −10.731 | 1.00 | 45.32 | C |
| ATOM | 969 | CG1 | VAL | B | 3 | 24.721 | −19.227 | −10.539 | 1.00 | 42.93 | C |
| ATOM | 970 | CG2 | VAL | B | 3 | 27.168 | −19.097 | −9.887 | 1.00 | 45.26 | C |
| ATOM | 971 | C | VAL | B | 3 | 24.945 | −22.081 | −11.021 | 1.00 | 45.65 | C |
| ATOM | 972 | O | VAL | B | 3 | 24.996 | −22.334 | −12.239 | 1.00 | 45.33 | O |
| ATOM | 973 | N | ASP | B | 4 | 23.951 | −22.435 | −10.211 | 1.00 | 44.65 | N |
| ATOM | 974 | CA | ASP | B | 4 | 22.792 | −23.198 | −10.608 | 1.00 | 44.39 | C |
| ATOM | 975 | CB | ASP | B | 4 | 22.440 | −24.131 | −9.458 | 1.00 | 44.31 | C |
| ATOM | 976 | CG | ASP | B | 4 | 21.422 | −25.186 | −9.834 | 1.00 | 48.07 | C |
| ATOM | 977 | OD1 | ASP | B | 4 | 20.972 | −25.212 | −11.005 | 1.00 | 48.90 | O |
| ATOM | 978 | OD2 | ASP | B | 4 | 21.052 | −25.997 | −8.932 | 1.00 | 51.27 | O |
| ATOM | 979 | C | ASP | B | 4 | 21.621 | −22.242 | −10.868 | 1.00 | 44.17 | C |
| ATOM | 980 | O | ASP | B | 4 | 20.926 | −21.829 | −9.913 | 1.00 | 45.13 | O |
| ATOM | 981 | N | GLN | B | 5 | 21.411 | −21.881 | −12.140 | 1.00 | 41.99 | N |
| ATOM | 982 | CA | GLN | B | 5 | 20.330 | −20.945 | −12.536 | 1.00 | 40.63 | C |
| ATOM | 983 | CB | GLN | B | 5 | 20.776 | −20.017 | −13.679 | 1.00 | 38.50 | C |
| ATOM | 984 | CG | GLN | B | 5 | 19.743 | −18.908 | −14.001 | 1.00 | 38.32 | C |
| ATOM | 985 | CD | GLN | B | 5 | 20.265 | −17.971 | −15.026 | 1.00 | 40.18 | C |
| ATOM | 986 | OE1 | GLN | B | 5 | 21.484 | −17.928 | −15.203 | 1.00 | 40.72 | O |
| ATOM | 987 | NE2 | GLN | B | 5 | 19.367 | −17.207 | −15.738 | 1.00 | 32.03 | N |
| ATOM | 988 | C | GLN | B | 5 | 19.078 | −21.717 | −12.978 | 1.00 | 40.31 | C |
| ATOM | 989 | O | GLN | B | 5 | 19.183 | −22.575 | −13.867 | 1.00 | 40.15 | O |
| ATOM | 990 | N | THR | B | 6 | 17.928 | −21.407 | −12.360 | 1.00 | 40.19 | N |
| ATOM | 991 | CA | THR | B | 6 | 16.597 | −21.960 | −12.747 | 1.00 | 41.32 | C |
| ATOM | 992 | CB | THR | B | 6 | 16.104 | −23.106 | −11.802 | 1.00 | 42.19 | C |
| ATOM | 993 | OG1 | THR | B | 6 | 16.242 | −22.695 | −10.438 | 1.00 | 45.35 | O |
| ATOM | 994 | CG2 | THR | B | 6 | 16.930 | −24.421 | −11.980 | 1.00 | 42.80 | C |
| ATOM | 995 | C | THR | B | 6 | 15.521 | −20.844 | −12.901 | 1.00 | 40.56 | C |
| ATOM | 996 | O | THR | B | 6 | 15.543 | −19.855 | −12.194 | 1.00 | 41.21 | O |
| ATOM | 997 | N | PRO | B | 7 | 14.605 | −20.982 | −13.859 | 1.00 | 40.24 | N |
| ATOM | 998 | CA | PRO | B | 7 | 14.476 | −22.120 | −14.793 | 1.00 | 39.70 | C |
| ATOM | 999 | CB | PRO | B | 7 | 13.018 | −22.018 | −15.237 | 1.00 | 38.51 | C |
| ATOM | 1000 | CG | PRO | B | 7 | 12.763 | −20.573 | −15.267 | 1.00 | 37.58 | C |
| ATOM | 1001 | CD | PRO | B | 7 | 13.570 | −19.975 | −14.102 | 1.00 | 39.88 | C |
| ATOM | 1002 | C | PRO | B | 7 | 15.428 | −21.915 | −15.952 | 1.00 | 39.21 | C |
| ATOM | 1003 | O | PRO | B | 7 | 15.772 | −20.760 | −16.237 | 1.00 | 40.93 | O |
| ATOM | 1004 | N | ARG | B | 8 | 15.863 | −22.985 | −16.598 | 1.00 | 39.22 | N |
| ATOM | 1005 | CA | ARG | B | 8 | 16.691 | −22.864 | −17.793 | 1.00 | 41.90 | C |
| ATOM | 1006 | CB | ARG | B | 8 | 17.582 | −24.141 | −17.979 | 1.00 | 40.92 | C |
| ATOM | 1007 | CG | ARG | B | 8 | 19.021 | −23.843 | −17.244 | 1.00 | 46.48 | C |
| ATOM | 1008 | CD | ARG | B | 8 | 20.003 | −25.051 | −17.078 | 1.00 | 49.30 | C |
| ATOM | 1009 | NE | ARG | B | 8 | 20.903 | −25.344 | −18.231 | 1.00 | 58.14 | N |
| ATOM | 1010 | CZ | ARG | B | 8 | 21.129 | −24.550 | −19.298 | 1.00 | 60.29 | C |
| ATOM | 1011 | NH1 | ARG | B | 8 | 21.970 | −24.991 | −20.239 | 1.00 | 62.88 | N |
| ATOM | 1012 | NH2 | ARG | B | 8 | 20.541 | −23.343 | −19.446 | 1.00 | 55.02 | N |
| ATOM | 1013 | C | ARG | B | 8 | 15.916 | −22.266 | −19.062 | 1.00 | 41.20 | C |
| ATOM | 1014 | O | ARG | B | 8 | 16.488 | −21.531 | −19.915 | 1.00 | 39.59 | O |
| ATOM | 1015 | N | THR | B | 9 | 14.594 | −22.472 | −19.057 | 1.00 | 40.29 | N |
| ATOM | 1016 | CA | THR | B | 9 | 13.687 | −22.185 | −20.154 | 1.00 | 41.50 | C |
| ATOM | 1017 | CB | THR | B | 9 | 13.369 | −23.496 | −20.870 | 1.00 | 41.08 | C |
| ATOM | 1018 | OG1 | THR | B | 9 | 14.478 | −23.831 | −21.716 | 1.00 | 44.54 | O |
| ATOM | 1019 | CG2 | THR | B | 9 | 12.186 | −23.397 | −21.691 | 1.00 | 44.46 | C |
| ATOM | 1020 | C | THR | B | 9 | 12.420 | −21.625 | −19.532 | 1.00 | 41.17 | C |
| ATOM | 1021 | O | THR | B | 9 | 11.988 | −22.105 | −18.486 | 1.00 | 42.29 | O |

APPENDIX I-continued

| | | | | | | | | | | | |
|---|---|---|---|---|---|---|---|---|---|---|---|
| ATOM | 1022 | N | ALA | B | 10 | 11.863 | −20.577 | −20.120 | 1.00 | 39.83 | N |
| ATOM | 1023 | CA | ALA | B | 10 | 10.527 | −20.109 | −19.709 | 1.00 | 39.81 | C |
| ATOM | 1024 | CB | ALA | B | 10 | 10.636 | −19.150 | −18.520 | 1.00 | 39.10 | C |
| ATOM | 1025 | C | ALA | B | 10 | 9.708 | −19.486 | −20.865 | 1.00 | 39.00 | C |
| ATOM | 1026 | O | ALA | B | 10 | 10.218 | −18.783 | −21.709 | 1.00 | 37.05 | O |
| ATOM | 1027 | N | THR | B | 11 | 8.433 | −19.807 | −20.926 | 1.00 | 41.44 | N |
| ATOM | 1028 | CA | THR | B | 11 | 7.504 | −19.035 | −21.763 | 1.00 | 42.21 | C |
| ATOM | 1029 | CB | THR | B | 11 | 7.116 | −19.744 | −23.092 | 1.00 | 43.19 | C |
| ATOM | 1030 | OG1 | THR | B | 11 | 5.708 | −19.620 | −23.359 | 1.00 | 45.57 | O |
| ATOM | 1031 | CG2 | THR | B | 11 | 7.568 | −21.172 | −23.089 | 1.00 | 43.44 | C |
| ATOM | 1032 | C | THR | B | 11 | 6.410 | −18.391 | −20.904 | 1.00 | 43.25 | C |
| ATOM | 1033 | O | THR | B | 11 | 5.846 | −19.026 | −20.001 | 1.00 | 42.68 | O |
| ATOM | 1034 | N | LYS | B | 12 | 6.255 | −17.074 | −21.067 | 1.00 | 43.20 | N |
| ATOM | 1035 | CA | LYS | B | 12 | 5.257 | −16.353 | −20.305 | 1.00 | 43.24 | C |
| ATOM | 1036 | CB | LYS | B | 12 | 5.922 | −15.425 | −19.313 | 1.00 | 43.55 | C |
| ATOM | 1037 | CG | LYS | B | 12 | 6.850 | −16.125 | −18.282 | 1.00 | 43.71 | C |
| ATOM | 1038 | CD | LYS | B | 12 | 6.045 | −16.918 | −17.255 | 1.00 | 46.08 | C |
| ATOM | 1039 | CE | LYS | B | 12 | 6.956 | −17.432 | −16.177 | 1.00 | 46.77 | C |
| ATOM | 1040 | NZ | LYS | B | 12 | 6.207 | −18.212 | −15.178 | 1.00 | 48.14 | N |
| ATOM | 1041 | C | LYS | B | 12 | 4.323 | −15.587 | −21.224 | 1.00 | 43.67 | C |
| ATOM | 1042 | O | LYS | B | 12 | 4.603 | −15.377 | −22.399 | 1.00 | 43.55 | O |
| ATOM | 1043 | N | GLU | B | 13 | 3.196 | −15.198 | −20.670 | 1.00 | 44.88 | N |
| ATOM | 1044 | CA | GLU | B | 13 | 2.183 | −14.407 | −21.349 | 1.00 | 45.97 | C |
| ATOM | 1045 | CB | GLU | B | 13 | 0.819 | −14.763 | −20.763 | 1.00 | 45.50 | C |
| ATOM | 1046 | CG | GLU | B | 13 | −0.252 | −14.954 | −21.805 | 1.00 | 51.14 | C |
| ATOM | 1047 | CD | GLU | B | 13 | −1.672 | −15.025 | −21.223 | 1.00 | 52.49 | C |
| ATOM | 1048 | OE1 | GLU | B | 13 | −2.214 | −13.977 | −20.736 | 1.00 | 56.84 | O |
| ATOM | 1049 | OE2 | GLU | B | 13 | −2.268 | −16.136 | −21.318 | 1.00 | 61.96 | O |
| ATOM | 1050 | C | GLU | B | 13 | 2.512 | −12.959 | −21.020 | 1.00 | 43.04 | C |
| ATOM | 1051 | O | GLU | B | 13 | 3.028 | −12.701 | −19.945 | 1.00 | 41.31 | O |
| ATOM | 1052 | N | THR | B | 14 | 2.223 | −12.015 | −21.916 | 1.00 | 41.79 | N |
| ATOM | 1053 | CA | THR | B | 14 | 2.424 | −10.600 | −21.549 | 1.00 | 41.84 | C |
| ATOM | 1054 | CB | THR | B | 14 | 2.091 | −9.590 | −22.653 | 1.00 | 41.46 | C |
| ATOM | 1055 | OG1 | THR | B | 14 | 0.695 | −9.668 | −22.914 | 1.00 | 46.96 | O |
| ATOM | 1056 | CG2 | THR | B | 14 | 2.850 | −9.885 | −23.954 | 1.00 | 39.14 | C |
| ATOM | 1057 | C | THR | B | 14 | 1.601 | −10.261 | −20.284 | 1.00 | 41.06 | C |
| ATOM | 1058 | O | THR | B | 14 | 0.519 | −10.798 | −20.082 | 1.00 | 39.53 | O |
| ATOM | 1059 | N | GLY | B | 15 | 2.167 | −9.424 | −19.419 | 1.00 | 39.95 | N |
| ATOM | 1060 | CA | GLY | B | 15 | 1.531 | −9.033 | −18.178 | 1.00 | 39.59 | C |
| ATOM | 1061 | C | GLY | B | 15 | 1.928 | −9.927 | −17.032 | 1.00 | 39.94 | C |
| ATOM | 1062 | O | GLY | B | 15 | 1.745 | −9.553 | −15.861 | 1.00 | 40.01 | O |
| ATOM | 1063 | N | GLU | B | 16 | 2.448 | −11.112 | −17.347 | 1.00 | 40.07 | N |
| ATOM | 1064 | CA | GLU | B | 16 | 2.963 | −12.013 | −16.311 | 1.00 | 41.17 | C |
| ATOM | 1065 | CB | GLU | B | 16 | 3.024 | −13.455 | −16.850 | 1.00 | 40.57 | C |
| ATOM | 1066 | CG | GLU | B | 16 | 1.656 | −14.146 | −16.761 | 1.00 | 41.94 | C |
| ATOM | 1067 | CD | GLU | B | 16 | 1.562 | −15.517 | −17.442 | 1.00 | 43.73 | C |
| ATOM | 1068 | OE1 | GLU | B | 16 | 2.530 | −16.134 | −17.948 | 1.00 | 43.61 | O |
| ATOM | 1069 | OE2 | GLU | B | 16 | 0.432 | −16.009 | −17.477 | 1.00 | 54.01 | O |
| ATOM | 1070 | C | GLU | B | 16 | 4.321 | −11.577 | −15.715 | 1.00 | 40.58 | C |
| ATOM | 1071 | O | GLU | B | 16 | 4.936 | −10.595 | −16.140 | 1.00 | 41.16 | O |
| ATOM | 1072 | N | SER | B | 17 | 4.803 | −12.311 | −14.732 | 1.00 | 40.31 | N |
| ATOM | 1073 | CA | SER | B | 17 | 6.133 | −12.054 | −14.205 | 1.00 | 39.94 | C |
| ATOM | 1074 | CB | SER | B | 17 | 5.987 | −11.519 | −12.797 | 1.00 | 40.72 | C |
| ATOM | 1075 | OG | SER | B | 17 | 5.762 | −12.588 | −11.942 | 1.00 | 41.64 | O |
| ATOM | 1076 | C | SER | B | 17 | 7.004 | −13.346 | −14.277 | 1.00 | 39.37 | C |
| ATOM | 1077 | O | SER | B | 17 | 6.488 | −14.426 | −14.552 | 1.00 | 39.99 | O |
| ATOM | 1078 | N | LEU | B | 18 | 8.320 | −13.220 | −14.120 | 1.00 | 39.17 | N |
| ATOM | 1079 | CA | LEU | B | 18 | 9.270 | −14.346 | −14.176 | 1.00 | 39.40 | C |
| ATOM | 1080 | CB | LEU | B | 18 | 10.217 | −14.269 | −15.412 | 1.00 | 39.88 | C |
| ATOM | 1081 | CG | LEU | B | 18 | 10.975 | −15.464 | −16.093 | 1.00 | 39.25 | C |
| ATOM | 1082 | CD1 | LEU | B | 18 | 12.361 | −15.081 | −16.621 | 1.00 | 36.41 | C |
| ATOM | 1083 | CD2 | LEU | B | 18 | 11.031 | −16.801 | −15.375 | 1.00 | 36.79 | C |
| ATOM | 1084 | C | LEU | B | 18 | 10.151 | −14.217 | −12.952 | 1.00 | 39.21 | C |
| ATOM | 1085 | O | LEU | B | 18 | 10.648 | −13.131 | −12.684 | 1.00 | 38.56 | O |
| ATOM | 1086 | N | THR | B | 19 | 10.350 | −15.309 | −12.208 | 1.00 | 39.51 | N |
| ATOM | 1087 | CA | THR | B | 19 | 11.356 | −15.331 | −11.145 | 1.00 | 38.61 | C |
| ATOM | 1088 | CB | THR | B | 19 | 10.745 | −15.681 | −9.777 | 1.00 | 39.40 | C |
| ATOM | 1089 | OG1 | THR | B | 19 | 9.596 | −14.859 | −9.569 | 1.00 | 40.21 | O |
| ATOM | 1090 | CG2 | THR | B | 19 | 11.734 | −15.391 | −8.613 | 1.00 | 37.97 | C |
| ATOM | 1091 | C | THR | B | 19 | 12.481 | −16.291 | −11.544 | 1.00 | 39.08 | C |
| ATOM | 1092 | O | THR | B | 19 | 12.242 | −17.425 | −11.918 | 1.00 | 38.36 | O |
| ATOM | 1093 | N | ILE | B | 20 | 13.713 | −15.795 | −11.510 | 1.00 | 39.84 | N |
| ATOM | 1094 | CA | ILE | B | 20 | 14.881 | −16.577 | −11.832 | 1.00 | 40.37 | C |
| ATOM | 1095 | CB | ILE | B | 20 | 15.752 | −15.886 | −12.869 | 1.00 | 41.04 | C |
| ATOM | 1096 | CG1 | ILE | B | 20 | 14.963 | −15.656 | −14.189 | 1.00 | 41.04 | C |
| ATOM | 1097 | CD1 | ILE | B | 20 | 15.801 | −14.744 | −15.167 | 1.00 | 40.82 | C |
| ATOM | 1098 | CG2 | ILE | B | 20 | 17.039 | −16.690 | −13.157 | 1.00 | 37.32 | C |
| ATOM | 1099 | C | ILE | B | 20 | 15.653 | −16.721 | −10.544 | 1.00 | 42.32 | C |
| ATOM | 1100 | O | ILE | B | 20 | 15.910 | −15.743 | −9.821 | 1.00 | 42.02 | O |
| ATOM | 1101 | N | ASN | B | 21 | 16.009 | −17.959 | −10.235 | 1.00 | 43.42 | N |

APPENDIX I-continued

| | | | | | | | | | | | |
|---|---|---|---|---|---|---|---|---|---|---|---|
| ATOM | 1102 | CA | ASN | B | 21 | 16.750 | −18.232 | −9.028 | 1.00 | 44.99 | C |
| ATOM | 1103 | CB | ASN | B | 21 | 15.975 | −19.274 | −8.234 | 1.00 | 45.42 | C |
| ATOM | 1104 | CG | ASN | B | 21 | 14.760 | −18.676 | −7.544 | 1.00 | 49.78 | C |
| ATOM | 1105 | OD1 | ASN | B | 21 | 14.911 | −17.898 | −6.575 | 1.00 | 55.43 | O |
| ATOM | 1106 | ND2 | ASN | B | 21 | 13.546 | −19.031 | −8.021 | 1.00 | 48.66 | N |
| ATOM | 1107 | C | ASN | B | 21 | 18.162 | −18.714 | −9.316 | 1.00 | 45.15 | C |
| ATOM | 1108 | O | ASN | B | 21 | 18.355 | −19.604 | −10.139 | 1.00 | 46.04 | O |
| ATOM | 1109 | N | CYS | B | 22 | 19.145 | −18.141 | −8.642 | 1.00 | 45.51 | N |
| ATOM | 1110 | CA | CYS | B | 22 | 20.512 | −18.645 | −8.738 | 1.00 | 46.56 | C |
| ATOM | 1111 | CB | CYS | B | 22 | 21.398 | −17.616 | −9.407 | 1.00 | 46.01 | C |
| ATOM | 1112 | SG | CYS | B | 22 | 20.937 | −17.240 | −11.134 | 1.00 | 54.66 | S |
| ATOM | 1113 | C | CYS | B | 22 | 21.094 | −19.006 | −7.382 | 1.00 | 46.14 | C |
| ATOM | 1114 | O | CYS | B | 22 | 20.802 | −18.342 | −6.400 | 1.00 | 45.68 | O |
| ATOM | 1115 | N | VAL | B | 23 | 21.914 | −20.064 | −7.348 | 1.00 | 46.34 | N |
| ATOM | 1116 | CA | VAL | B | 23 | 22.574 | −20.552 | −6.137 | 1.00 | 45.67 | C |
| ATOM | 1117 | CB | VAL | B | 23 | 21.951 | −21.906 | −5.581 | 1.00 | 45.26 | C |
| ATOM | 1118 | CG1 | VAL | B | 23 | 22.335 | −22.151 | −4.112 | 1.00 | 44.69 | C |
| ATOM | 1119 | CG2 | VAL | B | 23 | 20.461 | −21.936 | −5.697 | 1.00 | 46.49 | C |
| ATOM | 1120 | C | VAL | B | 23 | 24.018 | −20.856 | −6.513 | 1.00 | 46.67 | C |
| ATOM | 1121 | O | VAL | B | 23 | 24.255 | −21.594 | −7.477 | 1.00 | 46.49 | O |
| ATOM | 1122 | N | LEU | B | 24 | 24.964 | −20.275 | −5.775 | 1.00 | 47.05 | N |
| ATOM | 1123 | CA | LEU | B | 24 | 26.379 | −20.661 | −5.783 | 1.00 | 49.11 | C |
| ATOM | 1124 | CB | LEU | B | 24 | 27.194 | −19.589 | −5.042 | 1.00 | 48.19 | C |
| ATOM | 1125 | CG | LEU | B | 24 | 28.539 | −19.018 | −5.483 | 1.00 | 50.04 | C |
| ATOM | 1126 | CD1 | LEU | B | 24 | 29.178 | −18.189 | −4.317 | 1.00 | 47.71 | C |
| ATOM | 1127 | CD2 | LEU | B | 24 | 29.500 | −20.085 | −5.957 | 1.00 | 51.22 | C |
| ATOM | 1128 | C | LEU | B | 24 | 26.508 | −21.967 | −4.994 | 1.00 | 50.50 | C |
| ATOM | 1129 | O | LEU | B | 24 | 26.243 | −21.987 | −3.785 | 1.00 | 50.47 | O |
| ATOM | 1130 | N | ARG | B | 25 | 26.902 | −23.047 | −5.670 | 1.00 | 52.28 | N |
| ATOM | 1131 | CA | ARG | B | 25 | 27.026 | −24.372 | −5.044 | 1.00 | 53.42 | C |
| ATOM | 1132 | CB | ARG | B | 25 | 26.429 | −25.461 | −5.933 | 1.00 | 53.07 | C |
| ATOM | 1133 | CG | ARG | B | 25 | 25.046 | −25.141 | −6.419 | 1.00 | 51.09 | C |
| ATOM | 1134 | CD | ARG | B | 25 | 24.139 | −26.318 | −6.287 | 1.00 | 51.67 | C |
| ATOM | 1135 | NE | ARG | B | 25 | 22.742 | −25.901 | −6.377 | 1.00 | 52.28 | N |
| ATOM | 1136 | CZ | ARG | B | 25 | 21.895 | −25.907 | −5.354 | 1.00 | 51.59 | C |
| ATOM | 1137 | NH1 | ARG | B | 25 | 22.299 | −26.334 | −4.157 | 1.00 | 51.61 | N |
| ATOM | 1138 | NH2 | ARG | B | 25 | 20.644 | −25.498 | −5.532 | 1.00 | 50.56 | N |
| ATOM | 1139 | C | ARG | B | 25 | 28.483 | −24.685 | −4.733 | 1.00 | 55.51 | C |
| ATOM | 1140 | O | ARG | B | 25 | 29.364 | −23.827 | −4.909 | 1.00 | 55.95 | O |
| ATOM | 1141 | N | ASP | B | 26 | 28.724 | −25.902 | −4.238 | 1.00 | 57.67 | N |
| ATOM | 1142 | CA | ASP | B | 26 | 30.064 | −26.414 | −3.891 | 1.00 | 59.47 | C |
| ATOM | 1143 | CB | ASP | B | 26 | 30.592 | −27.321 | −5.009 | 1.00 | 59.83 | C |
| ATOM | 1144 | CG | ASP | B | 26 | 29.669 | −28.511 | −5.285 | 1.00 | 61.62 | C |
| ATOM | 1145 | OD1 | ASP | B | 26 | 28.795 | −28.416 | −6.198 | 1.00 | 62.14 | O |
| ATOM | 1146 | OD2 | ASP | B | 26 | 29.814 | −29.530 | −4.572 | 1.00 | 62.86 | O |
| ATOM | 1147 | C | ASP | B | 26 | 31.052 | −25.293 | −3.599 | 1.00 | 60.27 | C |
| ATOM | 1148 | O | ASP | B | 26 | 32.103 | −25.207 | −4.225 | 1.00 | 60.76 | O |
| ATOM | 1149 | N | ALA | B | 27 | 30.693 | −24.433 | −2.646 | 1.00 | 61.28 | N |
| ATOM | 1150 | CA | ALA | B | 27 | 31.493 | −23.273 | −2.307 | 1.00 | 61.93 | C |
| ATOM | 1151 | CB | ALA | B | 27 | 30.784 | −22.014 | −2.708 | 1.00 | 61.89 | C |
| ATOM | 1152 | C | ALA | B | 27 | 31.863 | −23.212 | −0.829 | 1.00 | 62.84 | C |
| ATOM | 1153 | O | ALA | B | 27 | 30.991 | −23.186 | 0.053 | 1.00 | 63.36 | O |
| ATOM | 1154 | N | SER | B | 28 | 33.171 | −23.214 | −0.581 | 1.00 | 63.10 | N |
| ATOM | 1155 | CA | SER | B | 28 | 33.737 | −22.641 | 0.624 | 1.00 | 63.63 | C |
| ATOM | 1156 | CB | SER | B | 28 | 35.224 | −22.968 | 0.718 | 1.00 | 63.90 | C |
| ATOM | 1157 | OG | SER | B | 28 | 35.570 | −24.105 | −0.058 | 1.00 | 64.95 | O |
| ATOM | 1158 | C | SER | B | 28 | 33.601 | −21.129 | 0.427 | 1.00 | 63.77 | C |
| ATOM | 1159 | O | SER | B | 28 | 33.495 | −20.363 | 1.393 | 1.00 | 64.47 | O |
| ATOM | 1160 | N | PHE | B | 29 | 33.625 | −20.737 | −0.852 | 1.00 | 63.20 | N |
| ATOM | 1161 | CA | PHE | B | 29 | 33.530 | −19.355 | −1.334 | 1.00 | 62.45 | C |
| ATOM | 1162 | CB | PHE | B | 29 | 33.358 | −19.335 | −2.872 | 1.00 | 62.20 | C |
| ATOM | 1163 | CG | PHE | B | 29 | 34.395 | −20.140 | −3.656 | 1.00 | 60.55 | C |
| ATOM | 1164 | CD1 | PHE | B | 29 | 35.699 | −20.308 | −3.201 | 1.00 | 60.68 | C |
| ATOM | 1165 | CE1 | PHE | B | 29 | 36.646 | −21.025 | −3.950 | 1.00 | 60.56 | C |
| ATOM | 1166 | CZ | PHE | B | 29 | 36.304 | −21.564 | −5.173 | 1.00 | 60.35 | C |
| ATOM | 1167 | CE2 | PHE | B | 29 | 35.014 | −21.392 | −5.648 | 1.00 | 62.60 | C |
| ATOM | 1168 | CD2 | PHE | B | 29 | 34.066 | −20.671 | −4.891 | 1.00 | 61.14 | C |
| ATOM | 1169 | C | PHE | B | 29 | 32.352 | −18.604 | −0.706 | 1.00 | 62.55 | C |
| ATOM | 1170 | O | PHE | B | 29 | 31.268 | −19.188 | −0.504 | 1.00 | 62.53 | O |
| ATOM | 1171 | N | GLU | B | 30 | 32.545 | −17.315 | −0.411 | 1.00 | 61.80 | N |
| ATOM | 1172 | CA | GLU | B | 30 | 31.445 | −16.518 | 0.143 | 1.00 | 61.37 | C |
| ATOM | 1173 | CB | GLU | B | 30 | 31.797 | −15.884 | 1.497 | 1.00 | 61.71 | C |
| ATOM | 1174 | CG | GLU | B | 30 | 32.680 | −14.633 | 1.411 | 1.00 | 64.15 | C |
| ATOM | 1175 | CD | GLU | B | 30 | 32.153 | −13.451 | 2.233 | 1.00 | 65.74 | C |
| ATOM | 1176 | OE1 | GLU | B | 30 | 32.866 | −13.015 | 3.168 | 1.00 | 63.81 | O |
| ATOM | 1177 | OE2 | GLU | B | 30 | 31.033 | −12.963 | 1.925 | 1.00 | 66.59 | O |
| ATOM | 1178 | C | GLU | B | 30 | 30.920 | −15.470 | −0.836 | 1.00 | 59.86 | C |
| ATOM | 1179 | O | GLU | B | 30 | 31.681 | −14.655 | −1.343 | 1.00 | 59.82 | O |
| ATOM | 1180 | N | LEU | B | 31 | 29.606 | −15.497 | −1.069 | 1.00 | 58.15 | N |
| ATOM | 1181 | CA | LEU | B | 31 | 28.946 | −14.572 | −1.982 | 1.00 | 56.44 | C |

APPENDIX I-continued

| ATOM | 1182 | CB | LEU | B | 31 | 27.444 | −14.831 | −1.998 | 1.00 | 56.25 | C |
|---|---|---|---|---|---|---|---|---|---|---|---|
| ATOM | 1183 | CG | LEU | B | 31 | 26.669 | −14.204 | −3.148 | 1.00 | 54.16 | C |
| ATOM | 1184 | CD1 | LEU | B | 31 | 27.090 | −14.868 | −4.401 | 1.00 | 51.33 | C |
| ATOM | 1185 | CD2 | LEU | B | 31 | 25.183 | −14.389 | −2.910 | 1.00 | 53.29 | C |
| ATOM | 1186 | C | LEU | B | 31 | 29.187 | −13.136 | −1.575 | 1.00 | 55.70 | C |
| ATOM | 1187 | O | LEU | B | 31 | 28.791 | −12.748 | −0.489 | 1.00 | 55.50 | O |
| ATOM | 1188 | N | LYS | B | 32 | 29.831 | −12.354 | −2.436 | 1.00 | 54.55 | N |
| ATOM | 1189 | CA | LYS | B | 32 | 30.081 | −10.963 | −2.096 | 1.00 | 54.28 | C |
| ATOM | 1190 | CB | LYS | B | 32 | 31.576 | −10.589 | −2.202 | 1.00 | 54.33 | C |
| ATOM | 1191 | CG | LYS | B | 32 | 31.918 | −9.629 | −3.367 | 1.00 | 56.46 | C |
| ATOM | 1192 | CD | LYS | B | 32 | 33.271 | −8.944 | −3.278 | 1.00 | 55.97 | C |
| ATOM | 1193 | CE | LYS | B | 32 | 33.233 | −7.762 | −2.288 | 1.00 | 63.91 | C |
| ATOM | 1194 | NZ | LYS | B | 32 | 32.451 | −6.536 | −2.708 | 1.00 | 64.90 | N |
| ATOM | 1195 | C | LYS | B | 32 | 29.216 | −10.009 | −2.902 | 1.00 | 52.81 | C |
| ATOM | 1196 | O | LYS | B | 32 | 28.927 | −8.898 | −2.450 | 1.00 | 52.61 | O |
| ATOM | 1197 | N | ASP | B | 33 | 28.818 | −10.438 | −4.093 | 1.00 | 51.52 | N |
| ATOM | 1198 | CA | ASP | B | 33 | 28.077 | −9.585 | −5.000 | 1.00 | 50.34 | C |
| ATOM | 1199 | CB | ASP | B | 33 | 29.020 | −8.581 | −5.653 | 1.00 | 51.45 | C |
| ATOM | 1200 | CG | ASP | B | 33 | 28.458 | −7.192 | −5.654 | 1.00 | 54.79 | C |
| ATOM | 1201 | OD1 | ASP | B | 33 | 29.150 | −6.290 | −5.130 | 1.00 | 60.70 | O |
| ATOM | 1202 | OD2 | ASP | B | 33 | 27.308 | −6.997 | −6.126 | 1.00 | 60.01 | O |
| ATOM | 1203 | C | ASP | B | 33 | 27.349 | −10.349 | −6.103 | 1.00 | 48.37 | C |
| ATOM | 1204 | O | ASP | B | 33 | 27.618 | −11.514 | −6.338 | 1.00 | 47.51 | O |
| ATOM | 1205 | N | THR | B | 34 | 26.435 | −9.656 | −6.783 | 1.00 | 46.63 | N |
| ATOM | 1206 | CA | THR | B | 34 | 25.607 | −10.230 | −7.812 | 1.00 | 45.52 | C |
| ATOM | 1207 | CB | THR | B | 34 | 24.228 | −10.594 | −7.311 | 1.00 | 45.26 | C |
| ATOM | 1208 | OG1 | THR | B | 34 | 23.507 | −9.400 | −7.005 | 1.00 | 44.94 | O |
| ATOM | 1209 | CG2 | THR | B | 34 | 24.280 | −11.520 | −6.066 | 1.00 | 46.07 | C |
| ATOM | 1210 | C | THR | B | 34 | 25.396 | −9.238 | −8.924 | 1.00 | 45.83 | C |
| ATOM | 1211 | O | THR | B | 34 | 25.372 | −8.017 | −8.702 | 1.00 | 45.11 | O |
| ATOM | 1212 | N | GLY | B | 35 | 25.201 | −9.773 | −10.125 | 1.00 | 45.83 | N |
| ATOM | 1213 | CA | GLY | B | 35 | 24.725 | −8.972 | −11.249 | 1.00 | 44.82 | C |
| ATOM | 1214 | C | GLY | B | 35 | 23.816 | −9.785 | −12.153 | 1.00 | 43.28 | C |
| ATOM | 1215 | O | GLY | B | 35 | 23.801 | −11.019 | −12.111 | 1.00 | 42.32 | O |
| ATOM | 1216 | N | TRP | B | 36 | 23.074 | −9.070 | −12.992 | 1.00 | 42.69 | N |
| ATOM | 1217 | CA | TRP | B | 36 | 22.094 | −9.665 | −13.876 | 1.00 | 42.22 | C |
| ATOM | 1218 | CB | TRP | B | 36 | 20.695 | −9.393 | −13.321 | 1.00 | 41.99 | C |
| ATOM | 1219 | CG | TRP | B | 36 | 20.426 | −10.204 | −12.070 | 1.00 | 42.02 | C |
| ATOM | 1220 | CD1 | TRP | B | 36 | 20.606 | −9.809 | −10.785 | 1.00 | 39.92 | C |
| ATOM | 1221 | NE1 | TRP | B | 36 | 20.263 | −10.839 | −9.929 | 1.00 | 42.86 | N |
| ATOM | 1222 | CE2 | TRP | B | 36 | 19.869 | −11.931 | −10.660 | 1.00 | 41.27 | C |
| ATOM | 1223 | CD2 | TRP | B | 36 | 19.955 | −11.571 | −12.021 | 1.00 | 41.39 | C |
| ATOM | 1224 | CE3 | TRP | B | 36 | 19.601 | −12.520 | −13.014 | 1.00 | 42.24 | C |
| ATOM | 1225 | CZ3 | TRP | B | 36 | 19.161 | −13.779 | −12.616 | 1.00 | 42.06 | C |
| ATOM | 1226 | CH2 | TRP | B | 36 | 19.077 | −14.117 | −11.226 | 1.00 | 42.99 | C |
| ATOM | 1227 | CZ2 | TRP | B | 36 | 19.428 | −13.199 | −10.235 | 1.00 | 42.30 | C |
| ATOM | 1228 | C | TRP | B | 36 | 22.263 | −9.062 | −15.251 | 1.00 | 42.47 | C |
| ATOM | 1229 | O | TRP | B | 36 | 22.527 | −7.848 | −15.372 | 1.00 | 43.87 | O |
| ATOM | 1230 | N | TYR | B | 37 | 22.124 | −9.884 | −16.284 | 1.00 | 42.85 | N |
| ATOM | 1231 | CA | TYR | B | 37 | 22.396 | −9.464 | −17.688 | 1.00 | 44.60 | C |
| ATOM | 1232 | CB | TYR | B | 37 | 23.771 | −9.983 | −18.167 | 1.00 | 45.76 | C |
| ATOM | 1233 | CG | TYR | B | 37 | 24.857 | −9.689 | −17.146 | 1.00 | 47.71 | C |
| ATOM | 1234 | CD1 | TYR | B | 37 | 25.524 | −8.464 | −17.117 | 1.00 | 50.27 | C |
| ATOM | 1235 | CE1 | TYR | B | 37 | 26.524 | −8.179 | −16.125 | 1.00 | 51.99 | C |
| ATOM | 1236 | CZ | TYR | B | 37 | 26.825 | −9.195 | −15.183 | 1.00 | 53.06 | C |
| ATOM | 1237 | OH | TYR | B | 37 | 27.770 | −9.042 | −14.172 | 1.00 | 54.16 | O |
| ATOM | 1238 | CE2 | TYR | B | 37 | 26.137 | −10.395 | −15.213 | 1.00 | 54.10 | C |
| ATOM | 1239 | CD2 | TYR | B | 37 | 25.163 | −10.627 | −16.175 | 1.00 | 51.46 | C |
| ATOM | 1240 | C | TYR | B | 37 | 21.332 | −10.026 | −18.555 | 1.00 | 44.88 | C |
| ATOM | 1241 | O | TYR | B | 37 | 20.705 | −11.043 | −18.209 | 1.00 | 45.77 | O |
| ATOM | 1242 | N | ARG | B | 38 | 21.135 | −9.388 | −19.698 | 1.00 | 45.01 | N |
| ATOM | 1243 | CA | ARG | B | 38 | 20.136 | −9.799 | −20.689 | 1.00 | 44.85 | C |
| ATOM | 1244 | CB | ARG | B | 38 | 18.859 | −8.971 | −20.449 | 1.00 | 44.48 | C |
| ATOM | 1245 | CG | ARG | B | 38 | 17.818 | −8.990 | −21.512 | 1.00 | 49.57 | C |
| ATOM | 1246 | CD | ARG | B | 38 | 16.572 | −8.154 | −21.096 | 1.00 | 50.80 | C |
| ATOM | 1247 | NE | ARG | B | 38 | 16.808 | −6.728 | −20.931 | 1.00 | 59.29 | N |
| ATOM | 1248 | CZ | ARG | B | 38 | 16.791 | −5.849 | −21.929 | 1.00 | 65.43 | C |
| ATOM | 1249 | NH1 | ARG | B | 38 | 16.570 | −6.250 | −23.196 | 1.00 | 68.18 | N |
| ATOM | 1250 | NH2 | ARG | B | 38 | 17.020 | −4.560 | −21.670 | 1.00 | 66.70 | N |
| ATOM | 1251 | C | ARG | B | 38 | 20.678 | −9.588 | −22.100 | 1.00 | 43.70 | C |
| ATOM | 1252 | O | ARG | B | 38 | 21.291 | −8.573 | −22.413 | 1.00 | 43.08 | O |
| ATOM | 1253 | N | THR | B | 39 | 20.399 | −10.551 | −22.970 | 1.00 | 43.10 | N |
| ATOM | 1254 | CA | THR | B | 39 | 20.574 | −10.401 | −24.392 | 1.00 | 41.41 | C |
| ATOM | 1255 | CB | THR | B | 39 | 21.561 | −11.463 | −24.921 | 1.00 | 40.29 | C |
| ATOM | 1256 | OG1 | THR | B | 39 | 22.780 | −11.325 | −24.192 | 1.00 | 44.60 | C |
| ATOM | 1257 | CG2 | THR | B | 39 | 21.830 | −11.278 | −26.361 | 1.00 | 38.65 | C |
| ATOM | 1258 | C | THR | B | 39 | 19.209 | −10.611 | −25.023 | 1.00 | 40.66 | C |
| ATOM | 1259 | O | THR | B | 39 | 18.632 | −11.718 | −24.960 | 1.00 | 40.48 | O |
| ATOM | 1260 | N | LYS | B | 40 | 18.696 | −9.575 | −25.658 | 1.00 | 38.27 | N |
| ATOM | 1261 | CA | LYS | B | 40 | 17.420 | −9.673 | −26.286 | 1.00 | 40.05 | C |

APPENDIX I-continued

| | | | | | | | | | | | |
|---|---|---|---|---|---|---|---|---|---|---|---|
| ATOM | 1262 | CB | LYS | B | 40 | 16.985 | −8.329 | −26.866 | 1.00 | 40.66 | C |
| ATOM | 1263 | CG | LYS | B | 40 | 18.180 | −7.401 | −27.336 | 1.00 | 46.79 | C |
| ATOM | 1264 | CD | LYS | B | 40 | 19.495 | −7.235 | −26.337 | 1.00 | 45.68 | C |
| ATOM | 1265 | CE | LYS | B | 40 | 20.177 | −5.941 | −26.663 | 1.00 | 47.93 | C |
| ATOM | 1266 | NZ | LYS | B | 40 | 19.625 | −5.348 | −28.020 | 1.00 | 50.16 | N |
| ATOM | 1267 | C | LYS | B | 40 | 17.399 | −10.781 | −27.346 | 1.00 | 39.05 | C |
| ATOM | 1268 | O | LYS | B | 40 | 18.428 | −11.090 | −27.963 | 1.00 | 38.47 | O |
| ATOM | 1269 | N | LEU | B | 41 | 16.231 | −11.387 | −27.526 | 1.00 | 37.38 | N |
| ATOM | 1270 | CA | LEU | B | 41 | 16.110 | −12.482 | −28.447 | 1.00 | 36.97 | C |
| ATOM | 1271 | CB | LEU | B | 41 | 14.693 | −13.025 | −28.410 | 1.00 | 35.93 | C |
| ATOM | 1272 | CG | LEU | B | 41 | 14.361 | −14.498 | −28.751 | 1.00 | 38.03 | C |
| ATOM | 1273 | CD1 | LEU | B | 41 | 15.260 | −15.201 | −29.688 | 1.00 | 29.12 | C |
| ATOM | 1274 | CD2 | LEU | B | 41 | 12.935 | −14.628 | −29.245 | 1.00 | 34.95 | C |
| ATOM | 1275 | C | LEU | B | 41 | 16.456 | −12.015 | −29.853 | 1.00 | 37.90 | C |
| ATOM | 1276 | O | LEU | B | 41 | 15.750 | −11.171 | −30.429 | 1.00 | 38.11 | O |
| ATOM | 1277 | N | GLY | B | 42 | 17.516 | −12.596 | −30.428 | 1.00 | 38.84 | N |
| ATOM | 1278 | CA | GLY | B | 42 | 17.894 | −12.309 | −31.828 | 1.00 | 39.84 | C |
| ATOM | 1279 | C | GLY | B | 42 | 19.138 | −11.426 | −31.882 | 1.00 | 41.12 | C |
| ATOM | 1280 | O | GLY | B | 42 | 19.889 | −11.451 | −32.845 | 1.00 | 40.47 | O |
| ATOM | 1281 | N | SER | B | 43 | 19.398 | −10.703 | −30.795 | 1.00 | 42.54 | N |
| ATOM | 1282 | CA | SER | B | 43 | 20.505 | −9.752 | −30.700 | 1.00 | 43.80 | C |
| ATOM | 1283 | CB | SER | B | 43 | 20.102 | −8.627 | −29.733 | 1.00 | 43.55 | C |
| ATOM | 1284 | OG | SER | B | 43 | 21.263 | −8.058 | −29.131 | 1.00 | 47.40 | O |
| ATOM | 1285 | C | SER | B | 43 | 21.837 | −10.389 | −30.246 | 1.00 | 44.08 | C |
| ATOM | 1286 | O | SER | B | 43 | 21.850 | −11.442 | −29.639 | 1.00 | 43.11 | O |
| ATOM | 1287 | N | THR | B | 44 | 22.950 | −9.730 | −30.556 | 1.00 | 46.01 | N |
| ATOM | 1288 | CA | THR | B | 44 | 24.284 | −10.132 | −30.088 | 1.00 | 49.08 | C |
| ATOM | 1289 | CB | THR | B | 44 | 25.386 | −9.746 | −31.113 | 1.00 | 49.56 | C |
| ATOM | 1290 | OG1 | THR | B | 44 | 24.825 | −8.862 | −32.111 | 1.00 | 50.26 | O |
| ATOM | 1291 | CG2 | THR | B | 44 | 25.951 | −10.982 | −31.782 | 1.00 | 51.25 | C |
| ATOM | 1292 | C | THR | B | 44 | 24.609 | −9.414 | −28.788 | 1.00 | 50.25 | C |
| ATOM | 1293 | O | THR | B | 44 | 25.441 | −9.865 | −27.991 | 1.00 | 51.27 | O |
| ATOM | 1294 | N | ASN | B | 45 | 23.915 | −8.304 | −28.560 | 1.00 | 51.11 | N |
| ATOM | 1295 | CA | ASN | B | 45 | 24.288 | −7.373 | −27.522 | 1.00 | 51.61 | C |
| ATOM | 1296 | CB | ASN | B | 45 | 23.900 | −5.973 | −27.975 | 1.00 | 51.54 | C |
| ATOM | 1297 | CG | ASN | B | 45 | 24.666 | −5.532 | −29.257 | 1.00 | 52.45 | C |
| ATOM | 1298 | OD1 | ASN | B | 45 | 24.146 | −4.760 | −30.070 | 1.00 | 52.60 | O |
| ATOM | 1299 | ND2 | ASN | B | 45 | 25.895 | −6.033 | −29.433 | 1.00 | 53.59 | N |
| ATOM | 1300 | C | ASN | B | 45 | 23.809 | −7.699 | −26.105 | 1.00 | 51.58 | C |
| ATOM | 1301 | O | ASN | B | 45 | 22.632 | −7.837 | −25.840 | 1.00 | 52.48 | O |
| ATOM | 1302 | N | GLU | B | 46 | 24.750 | −7.844 | −25.189 | 1.00 | 51.92 | N |
| ATOM | 1303 | CA | GLU | B | 46 | 24.414 | −8.133 | −23.821 | 1.00 | 52.44 | C |
| ATOM | 1304 | CB | GLU | B | 46 | 25.368 | −9.161 | −23.221 | 1.00 | 52.91 | C |
| ATOM | 1305 | CG | GLU | B | 46 | 24.884 | −9.678 | −21.894 | 1.00 | 58.15 | C |
| ATOM | 1306 | CD | GLU | B | 46 | 25.957 | −10.405 | −21.123 | 1.00 | 66.36 | C |
| ATOM | 1307 | OE1 | GLU | B | 46 | 25.706 | −11.582 | −20.727 | 1.00 | 70.62 | O |
| ATOM | 1308 | OE2 | GLU | B | 46 | 27.039 | −9.793 | −20.894 | 1.00 | 69.30 | O |
| ATOM | 1309 | C | GLU | B | 46 | 24.380 | −6.860 | −22.976 | 1.00 | 51.53 | C |
| ATOM | 1310 | O | GLU | B | 46 | 25.327 | −6.088 | −22.964 | 1.00 | 53.42 | O |
| ATOM | 1311 | N | GLN | B | 47 | 23.278 | −6.642 | −22.286 | 1.00 | 49.40 | N |
| ATOM | 1312 | CA | GLN | B | 47 | 23.107 | −5.475 | −21.450 | 1.00 | 48.39 | C |
| ATOM | 1313 | CB | GLN | B | 47 | 21.867 | −4.713 | −21.877 | 1.00 | 48.97 | C |
| ATOM | 1314 | CG | GLN | B | 47 | 21.851 | −4.315 | −23.390 | 1.00 | 54.17 | C |
| ATOM | 1315 | CD | GLN | B | 47 | 22.859 | −3.187 | −23.733 | 1.00 | 58.95 | C |
| ATOM | 1316 | OE1 | GLN | B | 47 | 22.457 | −2.123 | −24.216 | 1.00 | 59.67 | O |
| ATOM | 1317 | NE2 | GLN | B | 47 | 24.167 | −3.430 | −23.488 | 1.00 | 56.36 | N |
| ATOM | 1318 | C | GLN | B | 47 | 22.954 | −5.913 | −20.012 | 1.00 | 46.93 | C |
| ATOM | 1319 | O | GLN | B | 47 | 22.368 | −6.955 | −19.731 | 1.00 | 45.54 | O |
| ATOM | 1320 | N | SER | B | 48 | 23.510 | −5.138 | −19.103 | 1.00 | 45.48 | N |
| ATOM | 1321 | CA | SER | B | 48 | 23.310 | −5.430 | −17.703 | 1.00 | 45.97 | C |
| ATOM | 1322 | CB | SER | B | 48 | 24.518 | −5.024 | −16.823 | 1.00 | 44.83 | C |
| ATOM | 1323 | OG | SER | B | 48 | 24.567 | −3.634 | −16.677 | 1.00 | 48.28 | O |
| ATOM | 1324 | C | SER | B | 48 | 21.996 | −4.775 | −17.260 | 1.00 | 45.25 | C |
| ATOM | 1325 | O | SER | B | 48 | 21.625 | −3.706 | −17.747 | 1.00 | 44.79 | O |
| ATOM | 1326 | N | ILE | B | 49 | 21.310 | −5.440 | −16.336 | 1.00 | 44.46 | N |
| ATOM | 1327 | CA | ILE | B | 49 | 19.994 | −5.034 | −15.879 | 1.00 | 43.57 | C |
| ATOM | 1328 | CB | ILE | B | 49 | 19.191 | −6.343 | −15.528 | 1.00 | 43.55 | C |
| ATOM | 1329 | CG1 | ILE | B | 49 | 18.786 | −7.071 | −16.799 | 1.00 | 41.77 | C |
| ATOM | 1330 | CD1 | ILE | B | 49 | 18.315 | −8.465 | −16.522 | 1.00 | 45.18 | C |
| ATOM | 1331 | CG2 | ILE | B | 49 | 17.998 | −6.077 | −14.627 | 1.00 | 42.15 | C |
| ATOM | 1332 | C | ILE | B | 49 | 20.202 | −4.130 | −14.678 | 1.00 | 43.36 | C |
| ATOM | 1333 | O | ILE | B | 49 | 20.937 | −4.516 | −13.800 | 1.00 | 43.25 | O |
| ATOM | 1334 | N | SER | B | 50 | 19.619 | −2.910 | −14.657 | 1.00 | 44.45 | N |
| ATOM | 1335 | CA | SER | B | 50 | 19.533 | −2.085 | −13.399 | 1.00 | 44.63 | C |
| ATOM | 1336 | CB | SER | B | 50 | 19.444 | −0.561 | −13.621 | 1.00 | 44.94 | C |
| ATOM | 1337 | OG | SER | B | 50 | 19.832 | −0.190 | −14.927 | 1.00 | 49.21 | O |
| ATOM | 1338 | C | SER | B | 50 | 18.328 | −2.500 | −12.603 | 1.00 | 43.86 | C |
| ATOM | 1339 | O | SER | B | 50 | 17.189 | −2.461 | −13.099 | 1.00 | 43.03 | O |
| ATOM | 1340 | N | ILE | B | 51 | 18.603 | −2.881 | −11.369 | 1.00 | 43.39 | N |
| ATOM | 1341 | CA | ILE | B | 51 | 17.624 | −3.379 | −10.447 | 1.00 | 43.30 | C |

APPENDIX I-continued

| ATOM | 1342 | CB | ILE | B | 51 | 18.340 | −3.979 | −9.224 | 1.00 | 43.57 | C |
|---|---|---|---|---|---|---|---|---|---|---|---|
| ATOM | 1343 | CG1 | ILE | B | 51 | 19.287 | −5.151 | −9.618 | 1.00 | 44.05 | C |
| ATOM | 1344 | CD1 | ILE | B | 51 | 18.667 | −6.326 | −10.418 | 1.00 | 35.96 | C |
| ATOM | 1345 | CG2 | ILE | B | 51 | 17.357 | −4.242 | −8.073 | 1.00 | 43.78 | C |
| ATOM | 1346 | C | ILE | B | 51 | 16.771 | −2.224 | −9.993 | 1.00 | 44.13 | C |
| ATOM | 1347 | O | ILE | B | 51 | 17.287 | −1.167 | −9.601 | 1.00 | 45.28 | O |
| ATOM | 1348 | N | GLY | B | 52 | 15.456 | −2.413 | −10.016 | 1.00 | 44.21 | N |
| ATOM | 1349 | CA | GLY | B | 52 | 14.540 | −1.395 | −9.504 | 1.00 | 43.63 | C |
| ATOM | 1350 | C | GLY | B | 52 | 13.381 | −1.293 | −10.469 | 1.00 | 43.28 | C |
| ATOM | 1351 | O | GLY | B | 52 | 13.460 | −1.784 | −11.585 | 1.00 | 43.58 | O |
| ATOM | 1352 | N | GLY | B | 53 | 12.310 | −0.656 | −10.035 | 1.00 | 43.27 | N |
| ATOM | 1353 | CA | GLY | B | 53 | 11.083 | −0.560 | −10.850 | 1.00 | 42.78 | C |
| ATOM | 1354 | C | GLY | B | 53 | 10.462 | −2.015 | −10.752 | 1.00 | 43.77 | C |
| ATOM | 1355 | O | GLY | B | 53 | 9.995 | −2.673 | −9.640 | 1.00 | 43.34 | O |
| ATOM | 1356 | N | ARG | B | 54 | 10.551 | −2.654 | −12.075 | 1.00 | 43.61 | N |
| ATOM | 1357 | CA | ARG | B | 54 | 9.886 | −3.914 | −12.251 | 1.00 | 42.86 | C |
| ATOM | 1358 | CB | ARG | B | 54 | 9.068 | −3.913 | −13.539 | 1.00 | 44.13 | C |
| ATOM | 1359 | CG | ARG | B | 54 | 9.889 | −3.906 | −14.830 | 1.00 | 42.33 | C |
| ATOM | 1360 | CD | ARG | B | 54 | 8.906 | −3.835 | −15.998 | 1.00 | 45.56 | C |
| ATOM | 1361 | NE | ARG | B | 54 | 9.580 | −3.821 | −17.288 | 1.00 | 47.32 | N |
| ATOM | 1362 | CZ | ARG | B | 54 | 9.650 | −4.835 | −18.148 | 1.00 | 47.04 | C |
| ATOM | 1363 | NH1 | ARG | B | 54 | 9.064 | −6.010 | −17.908 | 1.00 | 50.81 | N |
| ATOM | 1364 | NH2 | ARG | B | 54 | 10.306 | −4.664 | −19.280 | 1.00 | 46.49 | N |
| ATOM | 1365 | C | ARG | B | 54 | 10.892 | −5.077 | −12.274 | 1.00 | 44.33 | C |
| ATOM | 1366 | O | ARG | B | 54 | 10.498 | −6.291 | −12.483 | 1.00 | 44.77 | O |
| ATOM | 1367 | N | TYR | B | 55 | 12.186 | −4.751 | −12.152 | 1.00 | 43.57 | N |
| ATOM | 1368 | CA | TYR | B | 55 | 13.228 | −5.749 | −11.905 | 1.00 | 43.62 | C |
| ATOM | 1369 | CB | TYR | B | 55 | 14.498 | −5.407 | −12.673 | 1.00 | 44.46 | C |
| ATOM | 1370 | CG | TYR | B | 55 | 14.287 | −5.318 | −14.171 | 1.00 | 46.09 | C |
| ATOM | 1371 | CD1 | TYR | B | 55 | 14.032 | −4.088 | −14.784 | 1.00 | 48.85 | C |
| ATOM | 1372 | CE1 | TYR | B | 55 | 13.812 | −3.998 | −16.152 | 1.00 | 48.27 | C |
| ATOM | 1373 | CZ | TYR | B | 55 | 13.865 | −5.144 | −16.918 | 1.00 | 48.69 | C |
| ATOM | 1374 | OH | TYR | B | 55 | 13.655 | −5.041 | −18.268 | 1.00 | 47.96 | O |
| ATOM | 1375 | CE2 | TYR | B | 55 | 14.087 | −6.373 | −16.336 | 1.00 | 48.31 | C |
| ATOM | 1376 | CD2 | TYR | B | 55 | 14.296 | −6.448 | −14.959 | 1.00 | 45.72 | C |
| ATOM | 1377 | C | TYR | B | 55 | 13.511 | −5.706 | −10.398 | 1.00 | 43.55 | C |
| ATOM | 1378 | O | TYR | B | 55 | 14.064 | −4.715 | −9.878 | 1.00 | 42.28 | O |
| ATOM | 1379 | N | VAL | B | 56 | 13.071 | −6.744 | −9.689 | 1.00 | 43.19 | N |
| ATOM | 1380 | CA | VAL | B | 56 | 13.348 | −6.837 | −8.260 | 1.00 | 42.73 | C |
| ATOM | 1381 | CB | VAL | B | 56 | 12.127 | −6.516 | −7.293 | 1.00 | 42.21 | C |
| ATOM | 1382 | CG1 | VAL | B | 56 | 10.841 | −6.421 | −7.968 | 1.00 | 44.06 | C |
| ATOM | 1383 | CG2 | VAL | B | 56 | 12.051 | −7.448 | −6.048 | 1.00 | 45.27 | C |
| ATOM | 1384 | C | VAL | B | 56 | 14.263 | −8.013 | −7.898 | 1.00 | 42.60 | C |
| ATOM | 1385 | O | VAL | B | 56 | 13.991 | −9.173 | −8.224 | 1.00 | 41.88 | O |
| ATOM | 1386 | N | GLU | B | 57 | 15.388 | −7.664 | −7.277 | 1.00 | 42.73 | N |
| ATOM | 1387 | CA | GLU | B | 57 | 16.395 | −8.617 | −6.875 | 1.00 | 44.06 | C |
| ATOM | 1388 | CB | GLU | B | 57 | 17.815 | −8.148 | −7.214 | 1.00 | 42.94 | C |
| ATOM | 1389 | CG | GLU | B | 57 | 18.805 | −9.083 | −6.512 | 1.00 | 44.58 | C |
| ATOM | 1390 | CD | GLU | B | 57 | 20.228 | −9.094 | −7.028 | 1.00 | 48.71 | C |
| ATOM | 1391 | OE1 | GLU | B | 57 | 20.904 | −8.036 | −7.062 | 1.00 | 49.40 | O |
| ATOM | 1392 | OE2 | GLU | B | 57 | 20.704 | −10.204 | −7.334 | 1.00 | 49.94 | O |
| ATOM | 1393 | C | GLU | B | 57 | 16.271 | −8.867 | −5.374 | 1.00 | 44.37 | C |
| ATOM | 1394 | O | GLU | B | 57 | 16.096 | −7.910 | −4.621 | 1.00 | 43.80 | O |
| ATOM | 1395 | N | THR | B | 58 | 16.326 | −10.154 | −4.985 | 1.00 | 45.59 | N |
| ATOM | 1396 | CA | THR | B | 58 | 16.372 | −10.633 | −3.584 | 1.00 | 47.38 | C |
| ATOM | 1397 | CB | THR | B | 58 | 15.228 | −11.630 | −3.244 | 1.00 | 47.57 | C |
| ATOM | 1398 | OG1 | THR | B | 58 | 13.968 | −11.157 | −3.752 | 1.00 | 48.77 | O |
| ATOM | 1399 | CG2 | THR | B | 58 | 15.109 | −11.859 | −1.738 | 1.00 | 46.75 | C |
| ATOM | 1400 | C | THR | B | 58 | 17.694 | −11.404 | −3.420 | 1.00 | 48.37 | C |
| ATOM | 1401 | O | THR | B | 58 | 18.014 | −12.246 | −4.263 | 1.00 | 48.05 | O |
| ATOM | 1402 | N | VAL | B | 59 | 18.443 | −11.121 | −2.353 | 1.00 | 48.84 | N |
| ATOM | 1403 | CA | VAL | B | 59 | 19.708 | −11.814 | −2.089 | 1.00 | 50.27 | C |
| ATOM | 1404 | CB | VAL | B | 59 | 20.942 | −10.858 | −2.229 | 1.00 | 49.98 | C |
| ATOM | 1405 | CG1 | VAL | B | 59 | 22.241 | −11.607 | −1.987 | 1.00 | 48.98 | C |
| ATOM | 1406 | CG2 | VAL | B | 59 | 20.971 | −10.233 | −3.605 | 1.00 | 49.50 | C |
| ATOM | 1407 | C | VAL | B | 59 | 19.732 | −12.503 | −0.708 | 1.00 | 51.31 | C |
| ATOM | 1408 | O | VAL | B | 59 | 19.396 | −11.889 | 0.306 | 1.00 | 51.41 | O |
| ATOM | 1409 | N | ASN | B | 60 | 20.110 | −13.784 | −0.692 | 1.00 | 52.16 | N |
| ATOM | 1410 | CA | ASN | B | 60 | 20.417 | −14.503 | 0.550 | 1.00 | 52.82 | C |
| ATOM | 1411 | CB | ASN | B | 60 | 19.494 | −15.713 | 0.703 | 1.00 | 52.46 | C |
| ATOM | 1412 | CG | ASN | B | 60 | 19.190 | −16.052 | 2.165 | 1.00 | 53.85 | C |
| ATOM | 1413 | OD1 | ASN | B | 60 | 18.162 | −16.662 | 2.452 | 1.00 | 55.75 | O |
| ATOM | 1414 | ND2 | ASN | B | 60 | 20.069 | −15.657 | 3.083 | 1.00 | 51.06 | N |
| ATOM | 1415 | C | ASN | B | 60 | 21.917 | −14.916 | 0.621 | 1.00 | 53.15 | C |
| ATOM | 1416 | O | ASN | B | 60 | 22.307 | −16.018 | 0.189 | 1.00 | 53.51 | O |
| ATOM | 1417 | N | LYS | B | 61 | 22.758 | −14.024 | 1.159 | 1.00 | 53.07 | N |
| ATOM | 1418 | CA | LYS | B | 61 | 24.188 | −14.318 | 1.304 | 1.00 | 52.63 | C |
| ATOM | 1419 | CB | LYS | B | 61 | 24.962 | −13.086 | 1.789 | 1.00 | 52.57 | C |
| ATOM | 1420 | CG | LYS | B | 61 | 25.168 | −12.025 | 0.708 | 1.00 | 53.36 | C |
| ATOM | 1421 | CD | LYS | B | 61 | 25.866 | −10.798 | 1.240 | 1.00 | 53.65 | C |

APPENDIX I-continued

| ATOM | 1422 | CE | LYS | B | 61 | 26.365 | −9.877 | 0.126 | 1.00 | 53.16 | C |
|---|---|---|---|---|---|---|---|---|---|---|---|
| ATOM | 1423 | NZ | LYS | B | 61 | 27.560 | −9.116 | 0.657 | 1.00 | 54.11 | N |
| ATOM | 1424 | C | LYS | B | 61 | 24.443 | −15.537 | 2.211 | 1.00 | 52.22 | C |
| ATOM | 1425 | O | LYS | B | 61 | 25.476 | −16.199 | 2.070 | 1.00 | 52.39 | O |
| ATOM | 1426 | N | GLY | B | 62 | 23.489 | −15.827 | 3.105 | 1.00 | 51.07 | N |
| ATOM | 1427 | CA | GLY | B | 62 | 23.513 | −17.025 | 3.955 | 1.00 | 50.34 | C |
| ATOM | 1428 | C | GLY | B | 62 | 23.572 | −18.280 | 3.105 | 1.00 | 49.30 | C |
| ATOM | 1429 | O | GLY | B | 62 | 24.571 | −19.021 | 3.116 | 1.00 | 49.51 | O |
| ATOM | 1430 | N | SER | B | 63 | 22.498 | −18.488 | 2.327 | 1.00 | 48.43 | N |
| ATOM | 1431 | CA | SER | B | 63 | 22.370 | −19.683 | 1.482 | 1.00 | 47.02 | C |
| ATOM | 1432 | CB | SER | B | 63 | 20.884 | −19.978 | 1.224 | 1.00 | 46.83 | C |
| ATOM | 1433 | OG | SER | B | 63 | 20.078 | −19.136 | 2.232 | 1.00 | 47.96 | O |
| ATOM | 1434 | C | SER | B | 63 | 23.105 | −19.552 | 0.135 | 1.00 | 45.91 | C |
| ATOM | 1435 | O | SER | B | 63 | 23.128 | −20.499 | −0.652 | 1.00 | 45.61 | O |
| ATOM | 1436 | N | LYS | B | 64 | 23.718 | −18.402 | −0.122 | 1.00 | 44.87 | N |
| ATOM | 1437 | CA | LYS | B | 64 | 24.410 | −18.152 | −1.417 | 1.00 | 44.92 | C |
| ATOM | 1438 | CB | LYS | B | 64 | 25.586 | −19.115 | −1.651 | 1.00 | 44.61 | C |
| ATOM | 1439 | CG | LYS | B | 64 | 26.660 | −19.099 | −0.554 | 1.00 | 45.05 | C |
| ATOM | 1440 | CD | LYS | B | 64 | 27.665 | −20.213 | −0.805 | 1.00 | 44.56 | C |
| ATOM | 1441 | CE | LYS | B | 64 | 28.244 | −20.755 | 0.486 | 1.00 | 42.89 | C |
| ATOM | 1442 | NZ | LYS | B | 64 | 29.561 | −20.185 | 0.780 | 1.00 | 41.38 | N |
| ATOM | 1443 | C | LYS | B | 64 | 23.429 | −18.180 | −2.601 | 1.00 | 44.11 | C |
| ATOM | 1444 | O | LYS | B | 64 | 23.754 | −18.623 | −3.704 | 1.00 | 44.27 | O |
| ATOM | 1445 | N | SER | B | 65 | 22.219 | −17.710 | −2.358 | 1.00 | 43.78 | N |
| ATOM | 1446 | CA | SER | B | 65 | 21.231 | −17.677 | −3.417 | 1.00 | 45.07 | C |
| ATOM | 1447 | CB | SER | B | 65 | 20.157 | −18.737 | −3.220 | 1.00 | 45.06 | C |
| ATOM | 1448 | OG | SER | B | 65 | 19.602 | −18.635 | −1.939 | 1.00 | 46.48 | O |
| ATOM | 1449 | C | SER | B | 65 | 20.654 | −16.282 | −3.598 | 1.00 | 44.87 | C |
| ATOM | 1450 | O | SER | B | 65 | 20.725 | −15.444 | −2.695 | 1.00 | 46.30 | O |
| ATOM | 1451 | N | PHE | B | 66 | 20.165 | −16.024 | −4.795 | 1.00 | 43.98 | N |
| ATOM | 1452 | CA | PHE | B | 66 | 19.662 | −14.717 | −5.174 | 1.00 | 43.45 | C |
| ATOM | 1453 | CB | PHE | B | 66 | 20.794 | −13.716 | −5.484 | 1.00 | 43.22 | C |
| ATOM | 1454 | CG | PHE | B | 66 | 21.805 | −14.199 | −6.486 | 1.00 | 42.41 | C |
| ATOM | 1455 | CD1 | PHE | B | 66 | 22.667 | −15.256 | −6.188 | 1.00 | 41.96 | C |
| ATOM | 1456 | CE1 | PHE | B | 66 | 23.629 | −15.678 | −7.083 | 1.00 | 40.78 | C |
| ATOM | 1457 | CZ | PHE | B | 66 | 23.745 | −15.037 | −8.303 | 1.00 | 43.25 | C |
| ATOM | 1458 | CE2 | PHE | B | 66 | 22.909 | −13.946 | −8.609 | 1.00 | 42.43 | C |
| ATOM | 1459 | CD2 | PHE | B | 66 | 21.955 | −13.537 | −7.693 | 1.00 | 42.09 | C |
| ATOM | 1460 | C | PHE | B | 66 | 18.748 | −14.890 | −6.362 | 1.00 | 43.59 | C |
| ATOM | 1461 | O | PHE | B | 66 | 18.876 | −15.857 | −7.112 | 1.00 | 43.27 | O |
| ATOM | 1462 | N | SER | B | 67 | 17.813 | −13.966 | −6.521 | 1.00 | 43.46 | N |
| ATOM | 1463 | CA | SER | B | 67 | 16.872 | −14.080 | −7.599 | 1.00 | 43.95 | C |
| ATOM | 1464 | CB | SER | B | 67 | 15.647 | −14.891 | −7.177 | 1.00 | 44.17 | C |
| ATOM | 1465 | OG | SER | B | 67 | 14.969 | −14.198 | −6.173 | 1.00 | 47.70 | O |
| ATOM | 1466 | C | SER | B | 67 | 16.442 | −12.745 | −8.140 | 1.00 | 43.18 | C |
| ATOM | 1467 | O | SER | B | 67 | 16.571 | −11.715 | −7.497 | 1.00 | 42.89 | O |
| ATOM | 1468 | N | LEU | B | 68 | 15.918 | −12.787 | −9.347 | 1.00 | 42.60 | N |
| ATOM | 1469 | CA | LEU | B | 68 | 15.432 | −11.612 | −10.012 | 1.00 | 42.76 | C |
| ATOM | 1470 | CB | LEU | B | 68 | 16.174 | −11.461 | −11.336 | 1.00 | 41.93 | C |
| ATOM | 1471 | CG | LEU | B | 68 | 16.515 | −10.118 | −11.984 | 1.00 | 45.17 | C |
| ATOM | 1472 | CD1 | LEU | B | 68 | 16.440 | −10.205 | −13.537 | 1.00 | 43.08 | C |
| ATOM | 1473 | CD2 | LEU | B | 68 | 15.823 | −8.866 | −11.437 | 1.00 | 43.46 | C |
| ATOM | 1474 | C | LEU | B | 68 | 13.988 | −11.907 | −10.355 | 1.00 | 42.62 | C |
| ATOM | 1475 | O | LEU | B | 68 | 13.711 | −12.896 | −11.018 | 1.00 | 42.63 | O |
| ATOM | 1476 | N | ARG | B | 69 | 13.075 | −11.045 | −9.973 | 1.00 | 42.71 | N |
| ATOM | 1477 | CA | ARG | B | 69 | 11.746 | −11.161 | −10.528 | 1.00 | 44.20 | C |
| ATOM | 1478 | CB | ARG | B | 69 | 10.715 | −11.157 | −9.418 | 1.00 | 43.82 | C |
| ATOM | 1479 | CG | ARG | B | 69 | 9.300 | −11.193 | −9.930 | 1.00 | 44.98 | C |
| ATOM | 1480 | CD | ARG | B | 69 | 8.390 | −11.421 | −8.752 | 1.00 | 50.13 | C |
| ATOM | 1481 | NE | ARG | B | 69 | 7.015 | −11.124 | −9.113 | 1.00 | 58.36 | N |
| ATOM | 1482 | CZ | ARG | B | 69 | 6.457 | −9.914 | −9.010 | 1.00 | 61.11 | C |
| ATOM | 1483 | NH1 | ARG | B | 69 | 7.188 | −8.871 | −8.565 | 1.00 | 61.04 | N |
| ATOM | 1484 | NH2 | ARG | B | 69 | 5.170 | −9.750 | −9.367 | 1.00 | 59.12 | N |
| ATOM | 1485 | C | ARG | B | 69 | 11.485 | −10.025 | −11.500 | 1.00 | 43.87 | C |
| ATOM | 1486 | O | ARG | B | 69 | 11.692 | −8.876 | −11.157 | 1.00 | 45.00 | O |
| ATOM | 1487 | N | ILE | B | 70 | 11.026 | −10.355 | −12.699 | 1.00 | 43.46 | N |
| ATOM | 1488 | CA | ILE | B | 70 | 10.727 | −9.370 | −13.697 | 1.00 | 43.63 | C |
| ATOM | 1489 | CB | ILE | B | 70 | 11.407 | −9.689 | −15.035 | 1.00 | 45.10 | C |
| ATOM | 1490 | CG1 | ILE | B | 70 | 12.912 | −9.941 | −14.806 | 1.00 | 43.18 | C |
| ATOM | 1491 | CD1 | ILE | B | 70 | 13.478 | −10.890 | −15.730 | 1.00 | 45.17 | C |
| ATOM | 1492 | CG2 | ILE | B | 70 | 11.137 | −8.524 | −16.012 | 1.00 | 44.11 | C |
| ATOM | 1493 | C | ILE | B | 70 | 9.209 | −9.326 | −13.860 | 1.00 | 43.63 | C |
| ATOM | 1494 | O | ILE | B | 70 | 8.592 | −10.314 | −14.166 | 1.00 | 43.43 | O |
| ATOM | 1495 | N | SER | B | 71 | 8.610 | −8.175 | −13.579 | 1.00 | 44.13 | N |
| ATOM | 1496 | CA | SER | B | 71 | 7.177 | −8.025 | −13.678 | 1.00 | 44.47 | C |
| ATOM | 1497 | CB | SER | B | 71 | 6.659 | −7.217 | −12.519 | 1.00 | 43.71 | C |
| ATOM | 1498 | OG | SER | B | 71 | 6.974 | −7.938 | −11.370 | 1.00 | 45.34 | O |
| ATOM | 1499 | C | SER | B | 71 | 6.729 | −7.397 | −14.962 | 1.00 | 44.92 | C |
| ATOM | 1500 | O | SER | B | 71 | 7.546 | −6.909 | −15.731 | 1.00 | 43.62 | O |
| ATOM | 1501 | N | ASP | B | 72 | 5.398 | −7.295 | −15.068 | 1.00 | 46.93 | N |

APPENDIX I-continued

| ATOM | 1502 | CA | ASP | B | 72 | 4.640 | −7.266 | −16.317 | 1.00 | 47.72 | C |
|---|---|---|---|---|---|---|---|---|---|---|---|
| ATOM | 1503 | CB | ASP | B | 72 | 3.574 | −6.195 | −16.338 | 1.00 | 49.50 | C |
| ATOM | 1504 | CG | ASP | B | 72 | 4.135 | −4.834 | −16.302 | 1.00 | 54.38 | C |
| ATOM | 1505 | OD1 | ASP | B | 72 | 4.521 | −4.403 | −15.190 | 1.00 | 60.99 | O |
| ATOM | 1506 | OD2 | ASP | B | 72 | 4.146 | −4.186 | −17.381 | 1.00 | 60.20 | O |
| ATOM | 1507 | C | ASP | B | 72 | 5.411 | −7.335 | −17.615 | 1.00 | 46.39 | C |
| ATOM | 1508 | O | ASP | B | 72 | 5.706 | −6.316 | −18.250 | 1.00 | 46.34 | O |
| ATOM | 1509 | N | LEU | B | 73 | 5.653 | −8.569 | −18.014 | 1.00 | 45.38 | N |
| ATOM | 1510 | CA | LEU | B | 73 | 6.476 | −8.921 | −19.147 | 1.00 | 44.12 | C |
| ATOM | 1511 | CB | LEU | B | 73 | 6.686 | −10.447 | −19.152 | 1.00 | 43.05 | C |
| ATOM | 1512 | CG | LEU | B | 73 | 7.513 | −11.022 | −17.984 | 1.00 | 42.55 | C |
| ATOM | 1513 | CD1 | LEU | B | 73 | 7.264 | −12.505 | −17.805 | 1.00 | 37.65 | C |
| ATOM | 1514 | CD2 | LEU | B | 73 | 9.037 | −10.729 | −18.116 | 1.00 | 40.53 | C |
| ATOM | 1515 | C | LEU | B | 73 | 5.861 | −8.430 | −20.443 | 1.00 | 44.58 | C |
| ATOM | 1516 | O | LEU | B | 73 | 4.637 | −8.415 | −20.594 | 1.00 | 44.57 | O |
| ATOM | 1517 | N | ARG | B | 74 | 6.712 | −8.006 | −21.370 | 1.00 | 44.91 | N |
| ATOM | 1518 | CA | ARG | B | 74 | 6.279 | −7.680 | −22.737 | 1.00 | 45.45 | C |
| ATOM | 1519 | CB | ARG | B | 74 | 6.565 | −6.224 | −23.047 | 1.00 | 45.64 | C |
| ATOM | 1520 | CG | ARG | B | 74 | 6.164 | −5.286 | −22.019 | 1.00 | 49.91 | C |
| ATOM | 1521 | CD | ARG | B | 74 | 7.106 | −4.109 | −22.126 | 1.00 | 57.66 | C |
| ATOM | 1522 | NE | ARG | B | 74 | 7.462 | −3.603 | −20.811 | 1.00 | 60.89 | N |
| ATOM | 1523 | CZ | ARG | B | 74 | 6.724 | −2.746 | −20.101 | 1.00 | 64.00 | C |
| ATOM | 1524 | NH1 | ARG | B | 74 | 5.571 | −2.278 | −20.587 | 1.00 | 65.92 | N |
| ATOM | 1525 | NH2 | ARG | B | 74 | 7.155 | −2.334 | −18.909 | 1.00 | 64.22 | N |
| ATOM | 1526 | C | ARG | B | 74 | 7.067 | −8.497 | −23.727 | 1.00 | 44.79 | C |
| ATOM | 1527 | O | ARG | B | 74 | 8.042 | −9.136 | −23.365 | 1.00 | 45.02 | O |
| ATOM | 1528 | N | VAL | B | 75 | 6.666 | −8.466 | −24.983 | 1.00 | 45.42 | N |
| ATOM | 1529 | CA | VAL | B | 75 | 7.276 | −9.328 | −26.006 | 1.00 | 45.62 | C |
| ATOM | 1530 | CB | VAL | B | 75 | 6.624 | −9.140 | −27.368 | 1.00 | 45.40 | C |
| ATOM | 1531 | CG1 | VAL | B | 75 | 5.223 | −9.671 | −27.324 | 1.00 | 46.53 | C |
| ATOM | 1532 | CG2 | VAL | B | 75 | 7.440 | −9.851 | −28.447 | 1.00 | 45.91 | C |
| ATOM | 1533 | C | VAL | B | 75 | 8.765 | −9.030 | −26.108 | 1.00 | 44.93 | C |
| ATOM | 1534 | O | VAL | B | 75 | 9.578 | −9.937 | −26.234 | 1.00 | 45.36 | O |
| ATOM | 1535 | N | GLU | B | 76 | 9.105 | −7.760 | −25.986 | 1.00 | 44.44 | N |
| ATOM | 1536 | CA | GLU | B | 76 | 10.458 | −7.282 | −26.127 | 1.00 | 44.58 | C |
| ATOM | 1537 | CB | GLU | B | 76 | 10.449 | −5.771 | −26.372 | 1.00 | 45.85 | C |
| ATOM | 1538 | CG | GLU | B | 76 | 9.328 | −5.317 | −27.417 | 1.00 | 51.77 | C |
| ATOM | 1539 | CD | GLU | B | 76 | 7.931 | −5.030 | −26.766 | 1.00 | 59.07 | C |
| ATOM | 1540 | OE1 | GLU | B | 76 | 6.879 | −5.154 | −27.462 | 1.00 | 60.29 | O |
| ATOM | 1541 | OE2 | GLU | B | 76 | 7.898 | −4.661 | −25.557 | 1.00 | 62.06 | O |
| ATOM | 1542 | C | GLU | B | 76 | 11.389 | −7.671 | −24.957 | 1.00 | 43.89 | C |
| ATOM | 1543 | O | GLU | B | 76 | 12.627 | −7.513 | −25.082 | 1.00 | 42.88 | O |
| ATOM | 1544 | N | ASP | B | 77 | 10.817 | −8.202 | −23.859 | 1.00 | 42.42 | N |
| ATOM | 1545 | CA | ASP | B | 77 | 11.618 | −8.761 | −22.766 | 1.00 | 41.98 | C |
| ATOM | 1546 | CB | ASP | B | 77 | 10.833 | −8.835 | −21.468 | 1.00 | 42.23 | C |
| ATOM | 1547 | CG | ASP | B | 77 | 10.458 | −7.483 | −20.905 | 1.00 | 44.50 | C |
| ATOM | 1548 | OD1 | ASP | B | 77 | 11.179 | −6.460 | −21.084 | 1.00 | 48.11 | O |
| ATOM | 1549 | OD2 | ASP | B | 77 | 9.417 | −7.454 | −20.227 | 1.00 | 47.95 | O |
| ATOM | 1550 | C | ASP | B | 77 | 12.117 | −10.205 | −23.101 | 1.00 | 42.26 | C |
| ATOM | 1551 | O | ASP | B | 77 | 12.839 | −10.816 | −22.314 | 1.00 | 42.73 | O |
| ATOM | 1552 | N | SER | B | 78 | 11.679 | −10.742 | −24.230 | 1.00 | 40.74 | N |
| ATOM | 1553 | CA | SER | B | 78 | 12.145 | −12.007 | −24.758 | 1.00 | 40.45 | C |
| ATOM | 1554 | CB | SER | B | 78 | 11.467 | −12.307 | −26.105 | 1.00 | 37.71 | C |
| ATOM | 1555 | OG | SER | B | 78 | 10.070 | −12.574 | −25.878 | 1.00 | 37.58 | O |
| ATOM | 1556 | C | SER | B | 78 | 13.660 | −11.964 | −24.910 | 1.00 | 40.32 | C |
| ATOM | 1557 | O | SER | B | 78 | 14.208 | −11.100 | −25.589 | 1.00 | 40.12 | O |
| ATOM | 1558 | N | GLY | B | 79 | 14.328 | −12.910 | −24.280 | 1.00 | 39.35 | N |
| ATOM | 1559 | CA | GLY | B | 79 | 15.758 | −13.031 | −24.490 | 1.00 | 39.80 | C |
| ATOM | 1560 | C | GLY | B | 79 | 16.392 | −13.943 | −23.466 | 1.00 | 38.99 | C |
| ATOM | 1561 | O | GLY | B | 79 | 15.697 | −14.690 | −22.788 | 1.00 | 39.42 | O |
| ATOM | 1562 | N | THR | B | 80 | 17.706 | −13.880 | −23.381 | 1.00 | 38.30 | N |
| ATOM | 1563 | CA | THR | B | 80 | 18.493 | −14.660 | −22.436 | 1.00 | 39.61 | C |
| ATOM | 1564 | CB | THR | B | 80 | 19.765 | −15.195 | −23.148 | 1.00 | 39.70 | C |
| ATOM | 1565 | OG1 | THR | B | 80 | 19.339 | −16.052 | −24.190 | 1.00 | 38.59 | O |
| ATOM | 1566 | CG2 | THR | B | 80 | 20.688 | −15.994 | −22.197 | 1.00 | 37.90 | C |
| ATOM | 1567 | C | THR | B | 80 | 18.929 | −13.821 | −21.246 | 1.00 | 40.30 | C |
| ATOM | 1568 | O | THR | B | 80 | 19.531 | −12.776 | −21.414 | 1.00 | 39.92 | O |
| ATOM | 1569 | N | TYR | B | 81 | 18.642 | −14.329 | −20.060 | 1.00 | 41.21 | N |
| ATOM | 1570 | CA | TYR | B | 81 | 18.921 | −13.698 | −18.817 | 1.00 | 41.29 | C |
| ATOM | 1571 | CB | TYR | B | 81 | 17.654 | −13.633 | −17.949 | 1.00 | 41.37 | C |
| ATOM | 1572 | CG | TYR | B | 81 | 16.647 | −12.664 | −18.510 | 1.00 | 41.48 | C |
| ATOM | 1573 | CD1 | TYR | B | 81 | 16.562 | −11.381 | −18.023 | 1.00 | 40.06 | C |
| ATOM | 1574 | CE1 | TYR | B | 81 | 15.644 | −10.454 | −18.583 | 1.00 | 44.06 | C |
| ATOM | 1575 | CZ | TYR | B | 81 | 14.846 | −10.857 | −19.675 | 1.00 | 43.01 | C |
| ATOM | 1576 | OH | TYR | B | 81 | 13.959 | −9.992 | −20.249 | 1.00 | 42.85 | O |
| ATOM | 1577 | CE2 | TYR | B | 81 | 14.913 | −12.137 | −20.160 | 1.00 | 37.03 | C |
| ATOM | 1578 | CD2 | TYR | B | 81 | 15.798 | −13.043 | −19.604 | 1.00 | 38.04 | C |
| ATOM | 1579 | C | TYR | B | 81 | 19.940 | −14.563 | −18.132 | 1.00 | 43.06 | C |
| ATOM | 1580 | O | TYR | B | 81 | 19.798 | −15.785 | −18.103 | 1.00 | 43.90 | O |
| ATOM | 1581 | N | LYS | B | 82 | 20.990 | −13.924 | −17.631 | 1.00 | 43.98 | N |

APPENDIX I-continued

| | | | | | | | | | | | |
|---|---|---|---|---|---|---|---|---|---|---|---|
| ATOM | 1582 | CA | LYS | B | 82 | 22.054 | −14.585 | −16.866 | 1.00 | 45.48 | C |
| ATOM | 1583 | CB | LYS | B | 82 | 23.331 | −14.667 | −17.693 | 1.00 | 46.06 | C |
| ATOM | 1584 | CG | LYS | B | 82 | 23.440 | −16.011 | −18.369 | 1.00 | 48.70 | C |
| ATOM | 1585 | CD | LYS | B | 82 | 24.530 | −16.006 | −19.412 | 1.00 | 54.28 | C |
| ATOM | 1586 | CE | LYS | B | 82 | 24.476 | −17.315 | −20.209 | 1.00 | 53.81 | C |
| ATOM | 1587 | NZ | LYS | B | 82 | 25.735 | −17.388 | −20.957 | 1.00 | 57.58 | N |
| ATOM | 1588 | C | LYS | B | 82 | 22.308 | −13.867 | −15.552 | 1.00 | 44.33 | C |
| ATOM | 1589 | O | LYS | B | 82 | 22.201 | −12.664 | −15.484 | 1.00 | 44.79 | O |
| ATOM | 1590 | N | CYS | B | 83 | 22.566 | −14.626 | −14.507 | 1.00 | 43.87 | N |
| ATOM | 1591 | CA | CYS | B | 83 | 22.995 | −14.054 | −13.266 | 1.00 | 44.81 | C |
| ATOM | 1592 | CB | CYS | B | 83 | 22.327 | −14.739 | −12.098 | 1.00 | 44.27 | C |
| ATOM | 1593 | SG | CYS | B | 83 | 22.696 | −16.465 | −11.941 | 1.00 | 45.41 | S |
| ATOM | 1594 | C | CYS | B | 83 | 24.497 | −14.258 | −13.210 | 1.00 | 46.24 | C |
| ATOM | 1595 | O | CYS | B | 83 | 25.008 | −15.105 | −13.936 | 1.00 | 46.71 | O |
| ATOM | 1596 | N | GLN | B | 84 | 25.197 | −13.440 | −12.415 | 1.00 | 46.76 | N |
| ATOM | 1597 | CA | GLN | B | 84 | 26.617 | −13.650 | −12.077 | 1.00 | 46.51 | C |
| ATOM | 1598 | CB | GLN | B | 84 | 27.526 | −12.679 | −12.810 | 1.00 | 47.55 | C |
| ATOM | 1599 | CG | GLN | B | 84 | 29.032 | −12.902 | −12.495 | 1.00 | 50.71 | C |
| ATOM | 1600 | CD | GLN | B | 84 | 29.953 | −12.348 | −13.563 | 1.00 | 54.90 | C |
| ATOM | 1601 | OE1 | GLN | B | 84 | 30.999 | −12.943 | −13.851 | 1.00 | 61.33 | O |
| ATOM | 1602 | NE2 | GLN | B | 84 | 29.584 | −11.212 | −14.160 | 1.00 | 54.98 | N |
| ATOM | 1603 | C | GLN | B | 84 | 26.829 | −13.518 | −10.569 | 1.00 | 45.81 | C |
| ATOM | 1604 | O | GLN | B | 84 | 26.324 | −12.604 | −9.944 | 1.00 | 44.81 | O |
| ATOM | 1605 | N | ALA | B | 85 | 27.532 | −14.488 | −9.993 | 1.00 | 44.59 | N |
| ATOM | 1606 | CA | ALA | B | 85 | 27.840 | −14.484 | −8.590 | 1.00 | 43.83 | C |
| ATOM | 1607 | CB | ALA | B | 85 | 27.646 | −15.884 | −8.031 | 1.00 | 43.38 | C |
| ATOM | 1608 | C | ALA | B | 85 | 29.316 | −14.014 | −8.479 | 1.00 | 43.84 | C |
| ATOM | 1609 | O | ALA | B | 85 | 30.172 | −14.539 | −9.175 | 1.00 | 45.10 | O |
| ATOM | 1610 | N | PHE | B | 86 | 29.603 | −12.990 | −7.689 | 1.00 | 43.41 | N |
| ATOM | 1611 | CA | PHE | B | 86 | 30.985 | −12.634 | −7.399 | 1.00 | 43.48 | C |
| ATOM | 1612 | CB | PHE | B | 86 | 31.195 | −11.139 | −7.499 | 1.00 | 43.25 | C |
| ATOM | 1613 | CG | PHE | B | 86 | 30.922 | −10.598 | −8.863 | 1.00 | 45.60 | C |
| ATOM | 1614 | CD1 | PHE | B | 86 | 29.695 | −9.993 | −9.153 | 1.00 | 46.99 | C |
| ATOM | 1615 | CE1 | PHE | B | 86 | 29.434 | −9.498 | −10.461 | 1.00 | 49.94 | C |
| ATOM | 1616 | CZ | PHE | B | 86 | 30.427 | −9.610 | −11.452 | 1.00 | 47.51 | C |
| ATOM | 1617 | CE2 | PHE | B | 86 | 31.649 | −10.207 | −11.143 | 1.00 | 46.33 | C |
| ATOM | 1618 | CD2 | PHE | B | 86 | 31.874 | −10.723 | −9.877 | 1.00 | 43.78 | C |
| ATOM | 1619 | C | PHE | B | 86 | 31.291 | −13.124 | −6.015 | 1.00 | 44.35 | C |
| ATOM | 1620 | O | PHE | B | 86 | 30.508 | −12.925 | −5.066 | 1.00 | 44.86 | O |
| ATOM | 1621 | N | TYR | B | 87 | 32.427 | −13.779 | −5.866 | 1.00 | 43.59 | N |
| ATOM | 1622 | CA | TYR | B | 87 | 32.679 | −14.421 | −4.604 | 1.00 | 43.44 | C |
| ATOM | 1623 | CB | TYR | B | 87 | 32.251 | −15.913 | −4.633 | 1.00 | 43.50 | C |
| ATOM | 1624 | CG | TYR | B | 87 | 32.810 | −16.691 | −5.817 | 1.00 | 44.45 | C |
| ATOM | 1625 | CD1 | TYR | B | 87 | 34.022 | −17.351 | −5.704 | 1.00 | 46.50 | C |
| ATOM | 1626 | CE1 | TYR | B | 87 | 34.574 | −18.044 | −6.759 | 1.00 | 45.78 | C |
| ATOM | 1627 | CZ | TYR | B | 87 | 33.918 | −18.111 | −7.953 | 1.00 | 46.91 | C |
| ATOM | 1628 | OH | TYR | B | 87 | 34.547 | −18.831 | −8.957 | 1.00 | 48.61 | O |
| ATOM | 1629 | CE2 | TYR | B | 87 | 32.684 | −17.477 | −8.120 | 1.00 | 45.59 | C |
| ATOM | 1630 | CD2 | TYR | B | 87 | 32.130 | −16.777 | −7.031 | 1.00 | 43.90 | C |
| ATOM | 1631 | C | TYR | B | 87 | 34.139 | −14.221 | −4.248 | 1.00 | 42.55 | C |
| ATOM | 1632 | O | TYR | B | 87 | 34.935 | −13.761 | −5.046 | 1.00 | 42.89 | O |
| ATOM | 1633 | N | VAL | B | 88 | 34.468 | −14.599 | −3.037 | 1.00 | 41.90 | N |
| ATOM | 1634 | CA | VAL | B | 88 | 35.747 | −14.320 | −2.484 | 1.00 | 40.38 | C |
| ATOM | 1635 | CB | VAL | B | 88 | 35.563 | −13.113 | −1.524 | 1.00 | 41.09 | C |
| ATOM | 1636 | CG1 | VAL | B | 88 | 36.089 | −13.331 | −0.157 | 1.00 | 39.39 | C |
| ATOM | 1637 | CG2 | VAL | B | 88 | 36.117 | −11.869 | −2.206 | 1.00 | 41.64 | C |
| ATOM | 1638 | C | VAL | B | 88 | 36.321 | −15.611 | −1.910 | 1.00 | 39.32 | C |
| ATOM | 1639 | O | VAL | B | 88 | 35.617 | −16.392 | −1.274 | 1.00 | 39.48 | O |
| ATOM | 1640 | N | PHE | B | 89 | 37.584 | −15.880 | −2.214 | 1.00 | 38.33 | N |
| ATOM | 1641 | CA | PHE | B | 89 | 38.325 | −16.946 | −1.527 | 1.00 | 36.70 | C |
| ATOM | 1642 | CB | PHE | B | 89 | 38.362 | −18.233 | −2.346 | 1.00 | 35.81 | C |
| ATOM | 1643 | CG | PHE | B | 89 | 38.830 | −18.069 | −3.773 | 1.00 | 33.80 | C |
| ATOM | 1644 | CD1 | PHE | B | 89 | 40.156 | −18.343 | −4.112 | 1.00 | 33.47 | C |
| ATOM | 1645 | CE1 | PHE | B | 89 | 40.606 | −18.225 | −5.403 | 1.00 | 30.77 | C |
| ATOM | 1646 | CZ | PHE | B | 89 | 39.726 | −17.835 | −6.426 | 1.00 | 31.68 | C |
| ATOM | 1647 | CE2 | PHE | B | 89 | 38.387 | −17.583 | −6.134 | 1.00 | 33.87 | C |
| ATOM | 1648 | CD2 | PHE | B | 89 | 37.946 | −17.711 | −4.782 | 1.00 | 36.04 | C |
| ATOM | 1649 | C | PHE | B | 89 | 39.704 | −16.451 | −1.269 | 1.00 | 37.19 | C |
| ATOM | 1650 | O | PHE | B | 89 | 40.059 | −15.356 | −1.701 | 1.00 | 36.81 | O |
| ATOM | 1651 | N | PHE | B | 90 | 40.484 | −17.258 | −0.565 | 1.00 | 38.03 | N |
| ATOM | 1652 | CA | PHE | B | 90 | 41.842 | −16.928 | −0.180 | 1.00 | 38.04 | C |
| ATOM | 1653 | CB | PHE | B | 90 | 42.075 | −17.297 | 1.280 | 1.00 | 39.75 | C |
| ATOM | 1654 | CG | PHE | B | 90 | 41.328 | −16.416 | 2.209 | 1.00 | 43.37 | C |
| ATOM | 1655 | CD1 | PHE | B | 90 | 39.930 | −16.435 | 2.223 | 1.00 | 47.99 | C |
| ATOM | 1656 | CE1 | PHE | B | 90 | 39.208 | −15.584 | 3.055 | 1.00 | 50.22 | C |
| ATOM | 1657 | CZ | PHE | B | 90 | 39.893 | −14.691 | 3.875 | 1.00 | 46.73 | C |
| ATOM | 1658 | CE2 | PHE | B | 90 | 41.285 | −14.653 | 3.848 | 1.00 | 49.56 | C |
| ATOM | 1659 | CD2 | PHE | B | 90 | 41.992 | −15.504 | 2.998 | 1.00 | 47.02 | C |
| ATOM | 1660 | C | PHE | B | 90 | 42.831 | −17.568 | −1.103 | 1.00 | 37.73 | C |
| ATOM | 1661 | O | PHE | B | 90 | 42.675 | −18.723 | −1.455 | 1.00 | 35.86 | O |

APPENDIX I-continued

| | | | | | | | | | | | |
|---|---|---|---|---|---|---|---|---|---|---|---|
| ATOM | 1662 | N | ALA | B | 91 | 43.808 | −16.766 | −1.541 | 1.00 | 38.81 | N |
| ATOM | 1663 | CA | ALA | B | 91 | 44.880 | −17.186 | −2.450 | 1.00 | 41.01 | C |
| ATOM | 1664 | CB | ALA | B | 91 | 45.887 | −16.050 | −2.613 | 1.00 | 41.04 | C |
| ATOM | 1665 | C | ALA | B | 91 | 45.610 | −18.459 | −1.997 | 1.00 | 42.55 | C |
| ATOM | 1666 | O | ALA | B | 91 | 46.126 | −19.208 | −2.826 | 1.00 | 41.40 | O |
| ATOM | 1667 | N | GLU | B | 92 | 45.643 | −18.675 | −0.677 | 1.00 | 45.64 | N |
| ATOM | 1668 | CA | GLU | B | 92 | 46.278 | −19.854 | −0.067 | 1.00 | 49.34 | C |
| ATOM | 1669 | CB | GLU | B | 92 | 46.339 | −19.765 | 1.468 | 1.00 | 49.34 | C |
| ATOM | 1670 | CG | GLU | B | 92 | 47.103 | −18.578 | 2.047 | 1.00 | 53.21 | C |
| ATOM | 1671 | CD | GLU | B | 92 | 46.215 | −17.331 | 2.266 | 1.00 | 57.21 | C |
| ATOM | 1672 | OE1 | GLU | B | 92 | 45.848 | −17.086 | 3.448 | 1.00 | 59.01 | O |
| ATOM | 1673 | OE2 | GLU | B | 92 | 45.901 | −16.599 | 1.280 | 1.00 | 55.91 | O |
| ATOM | 1674 | C | GLU | B | 92 | 45.529 | −21.121 | −0.433 | 1.00 | 50.92 | C |
| ATOM | 1675 | O | GLU | B | 92 | 46.163 | −22.112 | −0.803 | 1.00 | 51.36 | O |
| ATOM | 1676 | N | ASP | B | 93 | 44.198 | −21.098 | −0.315 | 1.00 | 52.93 | N |
| ATOM | 1677 | CA | ASP | B | 93 | 43.454 | −22.356 | −0.337 | 1.00 | 55.69 | C |
| ATOM | 1678 | CB | ASP | B | 93 | 41.992 | −22.280 | 0.238 | 1.00 | 55.85 | C |
| ATOM | 1679 | CG | ASP | B | 93 | 40.982 | −21.501 | −0.651 | 1.00 | 58.02 | C |
| ATOM | 1680 | OD1 | ASP | B | 93 | 40.972 | −21.667 | −1.896 | 1.00 | 60.03 | O |
| ATOM | 1681 | OD2 | ASP | B | 93 | 40.134 | −20.749 | −0.080 | 1.00 | 58.21 | O |
| ATOM | 1682 | C | ASP | B | 93 | 43.647 | −23.117 | −1.659 | 1.00 | 57.09 | C |
| ATOM | 1683 | O | ASP | B | 93 | 43.222 | −22.670 | −2.731 | 1.00 | 56.60 | O |
| ATOM | 1684 | N | VAL | B | 94 | 44.381 | −24.231 | −1.542 | 1.00 | 59.08 | N |
| ATOM | 1685 | CA | VAL | B | 94 | 44.863 | −25.029 | −2.673 | 1.00 | 61.07 | C |
| ATOM | 1686 | CB | VAL | B | 94 | 46.088 | −25.913 | −2.271 | 1.00 | 61.32 | C |
| ATOM | 1687 | CG1 | VAL | B | 94 | 46.489 | −26.881 | −3.404 | 1.00 | 61.77 | C |
| ATOM | 1688 | CG2 | VAL | B | 94 | 47.300 | −25.062 | −1.795 | 1.00 | 61.40 | C |
| ATOM | 1689 | C | VAL | B | 94 | 43.755 | −25.952 | −3.125 | 1.00 | 62.29 | C |
| ATOM | 1690 | O | VAL | B | 94 | 42.925 | −26.361 | −2.312 | 1.00 | 62.77 | O |
| ATOM | 1691 | N | GLY | B | 95 | 43.738 | −26.286 | −4.410 | 1.00 | 63.72 | N |
| ATOM | 1692 | CA | GLY | B | 95 | 42.849 | −27.341 | −4.889 | 1.00 | 65.63 | C |
| ATOM | 1693 | C | GLY | B | 95 | 41.366 | −26.996 | −4.820 | 1.00 | 66.94 | C |
| ATOM | 1694 | O | GLY | B | 95 | 40.503 | −27.897 | −4.790 | 1.00 | 67.35 | O |
| ATOM | 1695 | N | SER | B | 96 | 41.082 | −25.693 | −4.764 | 1.00 | 67.66 | N |
| ATOM | 1696 | CA | SER | B | 96 | 39.752 | −25.126 | −5.019 | 1.00 | 68.33 | C |
| ATOM | 1697 | CB | SER | B | 96 | 38.719 | −25.490 | −3.934 | 1.00 | 68.30 | C |
| ATOM | 1698 | OG | SER | B | 96 | 39.096 | −25.003 | −2.655 | 1.00 | 69.15 | O |
| ATOM | 1699 | C | SER | B | 96 | 39.951 | −23.610 | −5.149 | 1.00 | 68.57 | C |
| ATOM | 1700 | O | SER | B | 96 | 40.232 | −22.909 | −4.161 | 1.00 | 68.47 | O |
| ATOM | 1701 | N | ASN | B | 97 | 39.872 | −23.144 | −6.399 | 1.00 | 68.54 | N |
| ATOM | 1702 | CA | ASN | B | 97 | 40.063 | −21.737 | −6.798 | 1.00 | 67.90 | C |
| ATOM | 1703 | CB | ASN | B | 97 | 41.539 | −21.450 | −7.190 | 1.00 | 67.64 | C |
| ATOM | 1704 | CG | ASN | B | 97 | 42.549 | −21.839 | −6.102 | 1.00 | 67.80 | C |
| ATOM | 1705 | OD1 | ASN | B | 97 | 43.346 | −21.010 | −5.642 | 1.00 | 68.17 | O |
| ATOM | 1706 | ND2 | ASN | B | 97 | 42.535 | −23.103 | −5.706 | 1.00 | 67.46 | N |
| ATOM | 1707 | C | ASN | B | 97 | 39.164 | −21.548 | −8.020 | 1.00 | 67.37 | C |
| ATOM | 1708 | O | ASN | B | 97 | 39.474 | −20.763 | −8.918 | 1.00 | 67.83 | O |
| ATOM | 1709 | N | LYS | B | 98 | 38.028 | −22.246 | −8.012 | 1.00 | 66.43 | N |
| ATOM | 1710 | CA | LYS | B | 98 | 37.501 | −22.902 | −9.221 | 1.00 | 65.41 | C |
| ATOM | 1711 | CB | LYS | B | 98 | 36.489 | −24.003 | −8.837 | 1.00 | 65.75 | C |
| ATOM | 1712 | CG | LYS | B | 98 | 37.167 | −25.283 | −8.285 | 1.00 | 67.70 | C |
| ATOM | 1713 | CD | LYS | B | 98 | 36.292 | −26.019 | −7.266 | 1.00 | 70.57 | C |
| ATOM | 1714 | CE | LYS | B | 98 | 36.108 | −25.188 | −5.992 | 1.00 | 71.50 | C |
| ATOM | 1715 | NZ | LYS | B | 98 | 35.816 | −26.004 | −4.778 | 1.00 | 71.51 | N |
| ATOM | 1716 | C | LYS | B | 98 | 37.036 | −22.104 | −10.467 | 1.00 | 64.00 | C |
| ATOM | 1717 | O | LYS | B | 98 | 37.100 | −22.642 | −11.587 | 1.00 | 64.50 | O |
| ATOM | 1718 | N | GLY | B | 99 | 36.583 | −20.861 | −10.313 | 1.00 | 61.92 | N |
| ATOM | 1719 | CA | GLY | B | 99 | 35.934 | −20.173 | −11.453 | 1.00 | 58.65 | C |
| ATOM | 1720 | C | GLY | B | 99 | 36.850 | −19.277 | −12.268 | 1.00 | 56.59 | C |
| ATOM | 1721 | O | GLY | B | 99 | 38.048 | −19.538 | −12.374 | 1.00 | 56.84 | O |
| ATOM | 1722 | N | ALA | B | 100 | 36.282 | −18.223 | −12.849 | 1.00 | 53.87 | N |
| ATOM | 1723 | CA | ALA | B | 100 | 37.065 | −17.133 | −13.429 | 1.00 | 51.62 | C |
| ATOM | 1724 | CB | ALA | B | 100 | 36.164 | −16.245 | −14.269 | 1.00 | 51.17 | C |
| ATOM | 1725 | C | ALA | B | 100 | 37.690 | −16.294 | −12.312 | 1.00 | 49.55 | C |
| ATOM | 1726 | O | ALA | B | 100 | 36.987 | −15.896 | −11.373 | 1.00 | 49.34 | O |
| ATOM | 1727 | N | ILE | B | 101 | 38.985 | −16.005 | −12.395 | 1.00 | 47.31 | N |
| ATOM | 1728 | CA | ILE | B | 101 | 39.533 | −14.981 | −11.484 | 1.00 | 45.25 | C |
| ATOM | 1729 | CB | ILE | B | 101 | 40.904 | −15.345 | −10.756 | 1.00 | 45.80 | C |
| ATOM | 1730 | CG1 | ILE | B | 101 | 42.016 | −14.358 | −11.079 | 1.00 | 46.05 | C |
| ATOM | 1731 | CD1 | ILE | B | 101 | 42.324 | −13.495 | −9.928 | 1.00 | 46.13 | C |
| ATOM | 1732 | CG2 | ILE | B | 101 | 41.319 | −16.849 | −10.843 | 1.00 | 44.18 | C |
| ATOM | 1733 | C | ILE | B | 101 | 39.355 | −13.542 | −12.031 | 1.00 | 44.02 | C |
| ATOM | 1734 | O | ILE | B | 101 | 39.651 | −13.227 | −13.209 | 1.00 | 43.07 | O |
| ATOM | 1735 | N | ILE | B | 102 | 38.734 | −12.724 | −11.185 | 1.00 | 41.55 | N |
| ATOM | 1736 | CA | ILE | B | 102 | 38.307 | −11.368 | −11.482 | 1.00 | 40.42 | C |
| ATOM | 1737 | CB | ILE | B | 102 | 36.935 | −11.028 | −10.777 | 1.00 | 41.20 | C |
| ATOM | 1738 | CG1 | ILE | B | 102 | 35.748 | −11.863 | −11.308 | 1.00 | 43.88 | C |
| ATOM | 1739 | CD1 | ILE | B | 102 | 35.773 | −12.274 | −12.825 | 1.00 | 43.26 | C |
| ATOM | 1740 | CG2 | ILE | B | 102 | 36.582 | −9.531 | −10.871 | 1.00 | 44.23 | C |
| ATOM | 1741 | C | ILE | B | 102 | 39.378 | −10.376 | −10.971 | 1.00 | 39.32 | C |

APPENDIX I-continued

| | | | | | | | | | | | |
|---|---|---|---|---|---|---|---|---|---|---|---|
| ATOM | 1742 | O | ILE | B | 102 | 39.623 | −9.342 | −11.614 | 1.00 | 39.71 | O |
| ATOM | 1743 | N | GLY | B | 103 | 40.002 | −10.670 | −9.810 | 1.00 | 36.32 | N |
| ATOM | 1744 | CA | GLY | B | 103 | 41.079 | −9.842 | −9.312 | 1.00 | 32.38 | C |
| ATOM | 1745 | C | GLY | B | 103 | 41.673 | −10.369 | −8.038 | 1.00 | 31.16 | C |
| ATOM | 1746 | O | GLY | B | 103 | 41.199 | −11.372 | −7.457 | 1.00 | 31.39 | O |
| ATOM | 1747 | N | LEU | B | 104 | 42.706 | −9.670 | −7.578 | 1.00 | 29.03 | N |
| ATOM | 1748 | CA | LEU | B | 104 | 43.424 | −10.049 | −6.423 | 1.00 | 27.58 | C |
| ATOM | 1749 | CB | LEU | B | 104 | 44.839 | −10.544 | −6.818 | 1.00 | 26.53 | C |
| ATOM | 1750 | CG | LEU | B | 104 | 45.829 | −10.943 | −5.733 | 1.00 | 26.78 | C |
| ATOM | 1751 | CD1 | LEU | B | 104 | 47.232 | −11.015 | −6.252 | 1.00 | 30.47 | C |
| ATOM | 1752 | CD2 | LEU | B | 104 | 45.473 | −12.251 | −5.078 | 1.00 | 27.53 | C |
| ATOM | 1753 | C | LEU | B | 104 | 43.459 | −8.841 | −5.496 | 1.00 | 28.83 | C |
| ATOM | 1754 | O | LEU | B | 104 | 43.870 | −7.752 | −5.901 | 1.00 | 27.59 | O |
| ATOM | 1755 | N | MET | B | 105 | 43.067 | −9.055 | −4.233 | 1.00 | 29.96 | N |
| ATOM | 1756 | CA | MET | B | 105 | 43.136 | −8.031 | −3.177 | 1.00 | 31.39 | C |
| ATOM | 1757 | CB | MET | B | 105 | 41.918 | −8.182 | −2.270 | 1.00 | 33.00 | C |
| ATOM | 1758 | CG | MET | B | 105 | 41.063 | −6.942 | −2.145 | 1.00 | 38.80 | C |
| ATOM | 1759 | SD | MET | B | 105 | 40.356 | −6.594 | −3.753 | 1.00 | 41.80 | S |
| ATOM | 1760 | CE | MET | B | 105 | 39.143 | −7.874 | −3.693 | 1.00 | 49.56 | C |
| ATOM | 1761 | C | MET | B | 105 | 44.336 | −8.189 | −2.319 | 1.00 | 31.71 | C |
| ATOM | 1762 | O | MET | B | 105 | 44.667 | −9.305 | −1.911 | 1.00 | 31.15 | O |
| ATOM | 1763 | N | VAL | B | 106 | 44.991 | −7.075 | −2.006 | 1.00 | 31.47 | N |
| ATOM | 1764 | CA | VAL | B | 106 | 45.960 | −7.056 | −0.929 | 1.00 | 33.12 | C |
| ATOM | 1765 | CB | VAL | B | 106 | 46.528 | −5.649 | −0.736 | 1.00 | 32.05 | C |
| ATOM | 1766 | CG1 | VAL | B | 106 | 47.526 | −5.649 | 0.323 | 1.00 | 32.12 | C |
| ATOM | 1767 | CG2 | VAL | B | 106 | 47.164 | −5.186 | −2.013 | 1.00 | 31.80 | C |
| ATOM | 1768 | C | VAL | B | 106 | 45.287 | −7.601 | 0.368 | 1.00 | 34.62 | C |
| ATOM | 1769 | O | VAL | B | 106 | 44.032 | −7.384 | 0.577 | 1.00 | 34.28 | O |
| ATOM | 1770 | N | GLY | B | 107 | 46.126 | −8.309 | 1.212 | 1.00 | 34.95 | N |
| ATOM | 1771 | CA | GLY | B | 107 | 45.566 | −9.209 | 2.267 | 1.00 | 34.64 | C |
| ATOM | 1772 | C | GLY | B | 107 | 45.048 | −10.613 | 1.825 | 1.00 | 35.04 | C |
| ATOM | 1773 | O | GLY | B | 107 | 44.566 | −11.404 | 2.676 | 1.00 | 36.55 | O |
| ATOM | 1774 | N | GLY | B | 108 | 45.122 | −10.929 | 0.525 | 1.00 | 32.55 | N |
| ATOM | 1775 | CA | GLY | B | 108 | 45.225 | −12.307 | 0.075 | 1.00 | 30.81 | C |
| ATOM | 1776 | C | GLY | B | 108 | 43.925 | −12.886 | −0.359 | 1.00 | 30.73 | C |
| ATOM | 1777 | O | GLY | B | 108 | 43.812 | −14.091 | −0.489 | 1.00 | 31.42 | O |
| ATOM | 1778 | N | VAL | B | 109 | 42.963 | −12.006 | −0.622 | 1.00 | 30.06 | N |
| ATOM | 1779 | CA | VAL | B | 109 | 41.610 | −12.332 | −1.113 | 1.00 | 29.98 | C |
| ATOM | 1780 | CB | VAL | B | 109 | 40.595 | −11.330 | −0.447 | 1.00 | 29.82 | C |
| ATOM | 1781 | CG1 | VAL | B | 109 | 39.238 | −11.415 | −0.954 | 1.00 | 27.30 | C |
| ATOM | 1782 | CG2 | VAL | B | 109 | 40.579 | −11.519 | 1.073 | 1.00 | 31.58 | C |
| ATOM | 1783 | C | VAL | B | 109 | 41.576 | −12.271 | −2.652 | 1.00 | 30.22 | C |
| ATOM | 1784 | O | VAL | B | 109 | 41.988 | −11.285 | −3.280 | 1.00 | 29.55 | O |
| ATOM | 1785 | N | VAL | B | 110 | 41.103 | −13.354 | −3.257 | 1.00 | 31.00 | N |
| ATOM | 1786 | CA | VAL | B | 110 | 40.832 | −13.376 | −4.656 | 1.00 | 30.34 | C |
| ATOM | 1787 | CB | VAL | B | 110 | 41.760 | −14.318 | −5.501 | 1.00 | 30.78 | C |
| ATOM | 1788 | CG1 | VAL | B | 110 | 41.079 | −14.939 | −6.663 | 1.00 | 27.57 | C |
| ATOM | 1789 | CG2 | VAL | B | 110 | 42.605 | −15.240 | −4.676 | 1.00 | 28.92 | C |
| ATOM | 1790 | C | VAL | B | 110 | 39.376 | −13.342 | −4.934 | 1.00 | 32.42 | C |
| ATOM | 1791 | O | VAL | B | 110 | 38.617 | −13.904 | −4.193 | 1.00 | 32.63 | O |
| ATOM | 1792 | N | ILE | B | 111 | 38.986 | −12.596 | −5.962 | 1.00 | 34.25 | N |
| ATOM | 1793 | CA | ILE | B | 111 | 37.608 | −12.418 | −6.360 | 1.00 | 36.25 | C |
| ATOM | 1794 | CB | ILE | B | 111 | 37.377 | −10.966 | −6.834 | 1.00 | 37.63 | C |
| ATOM | 1795 | CG1 | ILE | B | 111 | 38.177 | −9.980 | −5.960 | 1.00 | 39.86 | C |
| ATOM | 1796 | CD1 | ILE | B | 111 | 37.582 | −9.749 | −4.568 | 1.00 | 44.15 | C |
| ATOM | 1797 | CG2 | ILE | B | 111 | 35.871 | −10.598 | −6.970 | 1.00 | 35.86 | C |
| ATOM | 1798 | C | ILE | B | 111 | 37.401 | −13.299 | −7.581 | 1.00 | 37.45 | C |
| ATOM | 1799 | O | ILE | B | 111 | 38.116 | −13.150 | −8.569 | 1.00 | 38.10 | O |
| ATOM | 1800 | N | GLY | B | 112 | 36.478 | −14.244 | −7.487 | 1.00 | 37.85 | N |
| ATOM | 1801 | CA | GLY | B | 112 | 36.044 | −15.026 | −8.625 | 1.00 | 39.55 | C |
| ATOM | 1802 | C | GLY | B | 112 | 34.660 | −14.536 | −9.031 | 1.00 | 40.92 | C |
| ATOM | 1803 | O | GLY | B | 112 | 33.991 | −13.833 | −8.279 | 1.00 | 40.69 | O |
| ATOM | 1804 | N | GLY | B | 113 | 34.240 | −14.877 | −10.241 | 1.00 | 41.72 | N |
| ATOM | 1805 | CA | GLY | B | 113 | 32.878 | −14.675 | −10.631 | 1.00 | 42.68 | C |
| ATOM | 1806 | C | GLY | B | 113 | 32.526 | −15.932 | −11.369 | 1.00 | 44.53 | C |
| ATOM | 1807 | O | GLY | B | 113 | 33.385 | −16.523 | −12.033 | 1.00 | 45.28 | O |
| ATOM | 1808 | N | GLU | B | 114 | 31.281 | −16.352 | −11.230 | 1.00 | 45.00 | N |
| ATOM | 1809 | CA | GLU | B | 114 | 30.721 | −17.475 | −11.954 | 1.00 | 46.79 | C |
| ATOM | 1810 | CB | GLU | B | 114 | 30.486 | −18.650 | −11.003 | 1.00 | 47.57 | C |
| ATOM | 1811 | CG | GLU | B | 114 | 31.481 | −19.777 | −11.016 | 1.00 | 54.05 | C |
| ATOM | 1812 | CD | GLU | B | 114 | 31.681 | −20.428 | −12.384 | 1.00 | 60.74 | C |
| ATOM | 1813 | OE1 | GLU | B | 114 | 32.730 | −21.116 | −12.540 | 1.00 | 65.24 | O |
| ATOM | 1814 | OE2 | GLU | B | 114 | 30.834 | −20.241 | −13.294 | 1.00 | 62.06 | O |
| ATOM | 1815 | C | GLU | B | 114 | 29.349 | −16.990 | −12.451 | 1.00 | 46.24 | C |
| ATOM | 1816 | O | GLU | B | 114 | 28.600 | −16.427 | −11.683 | 1.00 | 45.45 | O |
| ATOM | 1817 | N | LYS | B | 115 | 29.048 | −17.210 | −13.730 | 1.00 | 47.57 | N |
| ATOM | 1818 | CA | LYS | B | 115 | 27.705 | −16.986 | −14.306 | 1.00 | 47.63 | C |
| ATOM | 1819 | CB | LYS | B | 115 | 27.868 | −16.442 | −15.716 | 1.00 | 49.05 | C |
| ATOM | 1820 | CG | LYS | B | 115 | 28.285 | −14.990 | −15.769 | 1.00 | 49.49 | C |
| ATOM | 1821 | CD | LYS | B | 115 | 28.457 | −14.608 | −17.209 | 1.00 | 58.06 | C |

APPENDIX I-continued

| ATOM | 1822 | CE | LYS | B | 115 | 28.325 | −13.100 | −17.425 | 1.00 | 62.98 | C |
|---|---|---|---|---|---|---|---|---|---|---|---|
| ATOM | 1823 | NZ | LYS | B | 115 | 29.569 | −12.371 | −16.971 | 1.00 | 67.39 | N |
| ATOM | 1824 | C | LYS | B | 115 | 26.831 | −18.235 | −14.341 | 1.00 | 46.96 | C |
| ATOM | 1825 | O | LYS | B | 115 | 27.328 | −19.359 | −14.475 | 1.00 | 46.33 | O |
| ATOM | 1826 | N | GLY | B | 116 | 25.522 | −18.055 | −14.202 | 1.00 | 46.82 | N |
| ATOM | 1827 | CA | GLY | B | 116 | 24.551 | −19.156 | −14.429 | 1.00 | 45.94 | C |
| ATOM | 1828 | C | GLY | B | 116 | 24.477 | −19.549 | −15.896 | 1.00 | 46.06 | C |
| ATOM | 1829 | O | GLY | B | 116 | 24.948 | −18.798 | −16.764 | 1.00 | 46.74 | O |
| ATOM | 1830 | N | ALA | B | 117 | 23.929 | −20.732 | −16.203 | 1.00 | 44.78 | N |
| ATOM | 1831 | CA | ALA | B | 117 | 23.856 | −21.181 | −17.602 | 1.00 | 43.54 | C |
| ATOM | 1832 | CB | ALA | B | 117 | 23.609 | −22.733 | −17.710 | 1.00 | 42.15 | C |
| ATOM | 1833 | C | ALA | B | 117 | 22.804 | −20.377 | −18.395 | 1.00 | 43.36 | C |
| ATOM | 1834 | O | ALA | B | 117 | 22.765 | −20.473 | −19.619 | 1.00 | 44.57 | O |
| ATOM | 1835 | N | GLY | B | 118 | 22.009 | −19.543 | −17.711 | 1.00 | 42.01 | N |
| ATOM | 1836 | CA | GLY | B | 118 | 21.041 | −18.672 | −18.374 | 1.00 | 40.50 | C |
| ATOM | 1837 | C | GLY | B | 118 | 19.638 | −19.226 | −18.447 | 1.00 | 40.45 | C |
| ATOM | 1838 | O | GLY | B | 118 | 19.440 | −20.454 | −18.385 | 1.00 | 39.63 | O |
| ATOM | 1839 | N | THR | B | 119 | 18.689 | −18.293 | −18.609 | 1.00 | 39.73 | N |
| ATOM | 1840 | CA | THR | B | 119 | 17.267 | −18.517 | −18.728 | 1.00 | 39.06 | C |
| ATOM | 1841 | CB | THR | B | 119 | 16.494 | −17.767 | −17.648 | 1.00 | 39.37 | C |
| ATOM | 1842 | OG1 | THR | B | 119 | 16.867 | −18.298 | −16.359 | 1.00 | 42.58 | O |
| ATOM | 1843 | CG2 | THR | B | 119 | 14.985 | −17.926 | −17.817 | 1.00 | 36.37 | C |
| ATOM | 1844 | C | THR | B | 119 | 16.846 | −18.000 | −20.086 | 1.00 | 40.30 | C |
| ATOM | 1845 | O | THR | B | 119 | 17.046 | −16.827 | −20.386 | 1.00 | 40.23 | O |
| ATOM | 1846 | N | ALA | B | 120 | 16.306 | −18.881 | −20.930 | 1.00 | 40.46 | N |
| ATOM | 1847 | CA | ALA | B | 120 | 15.808 | −18.450 | −22.232 | 1.00 | 39.96 | C |
| ATOM | 1848 | CB | ALA | B | 120 | 16.032 | −19.546 | −23.327 | 1.00 | 38.10 | C |
| ATOM | 1849 | C | ALA | B | 120 | 14.333 | −18.107 | −22.056 | 1.00 | 39.39 | C |
| ATOM | 1850 | O | ALA | B | 120 | 13.514 | −18.995 | −21.874 | 1.00 | 39.20 | O |
| ATOM | 1851 | N | LEU | B | 121 | 14.018 | −16.811 | −22.058 | 1.00 | 38.26 | N |
| ATOM | 1852 | CA | LEU | B | 121 | 12.655 | −16.366 | −21.893 | 1.00 | 38.37 | C |
| ATOM | 1853 | CB | LEU | B | 121 | 12.552 | −15.321 | −20.816 | 1.00 | 37.24 | C |
| ATOM | 1854 | CG | LEU | B | 121 | 11.223 | −14.563 | −20.800 | 1.00 | 39.25 | C |
| ATOM | 1855 | CD1 | LEU | B | 121 | 10.056 | −15.389 | −20.199 | 1.00 | 38.60 | C |
| ATOM | 1856 | CD2 | LEU | B | 121 | 11.327 | −13.202 | −20.149 | 1.00 | 34.33 | C |
| ATOM | 1857 | C | LEU | B | 121 | 11.955 | −15.883 | −23.237 | 1.00 | 39.04 | C |
| ATOM | 1858 | O | LEU | B | 121 | 12.473 | −15.020 | −23.955 | 1.00 | 40.91 | O |
| ATOM | 1859 | N | THR | B | 122 | 10.811 | −16.491 | −23.548 | 1.00 | 38.34 | N |
| ATOM | 1860 | CA | THR | B | 122 | 9.930 | −16.055 | −24.614 | 1.00 | 39.43 | C |
| ATOM | 1861 | CB | THR | B | 122 | 9.552 | −17.214 | −25.559 | 1.00 | 39.02 | C |
| ATOM | 1862 | OG1 | THR | B | 122 | 10.738 | −17.917 | −25.949 | 1.00 | 39.58 | O |
| ATOM | 1863 | CG2 | THR | B | 122 | 8.846 | −16.654 | −26.785 | 1.00 | 40.51 | C |
| ATOM | 1864 | C | THR | B | 122 | 8.660 | −15.512 | −23.988 | 1.00 | 38.05 | C |
| ATOM | 1865 | O | THR | B | 122 | 8.034 | −16.192 | −23.186 | 1.00 | 38.30 | O |
| ATOM | 1866 | N | VAL | B | 123 | 8.343 | −14.258 | −24.283 | 1.00 | 38.09 | N |
| ATOM | 1867 | CA | VAL | B | 123 | 7.093 | −13.650 | −23.812 | 1.00 | 38.38 | C |
| ATOM | 1868 | CB | VAL | B | 123 | 7.274 | −12.260 | −23.225 | 1.00 | 37.30 | C |
| ATOM | 1869 | CG1 | VAL | B | 123 | 5.940 | −11.665 | −22.754 | 1.00 | 38.24 | C |
| ATOM | 1870 | CG2 | VAL | B | 123 | 8.307 | −12.240 | −22.120 | 1.00 | 35.68 | C |
| ATOM | 1871 | C | VAL | B | 123 | 6.172 | −13.609 | −25.055 | 1.00 | 40.09 | C |
| ATOM | 1872 | O | VAL | B | 123 | 6.580 | −13.168 | −26.152 | 1.00 | 38.15 | O |
| ATOM | 1873 | N | LYS | B | 124 | 4.948 | −14.096 | −24.870 | 1.00 | 42.46 | N |
| ATOM | 1874 | CA | LYS | B | 124 | 3.962 | −14.184 | −25.947 | 1.00 | 45.11 | C |
| ATOM | 1875 | CB | LYS | B | 124 | 3.596 | −15.645 | −26.162 | 1.00 | 44.65 | C |
| ATOM | 1876 | CG | LYS | B | 124 | 4.855 | −16.487 | −26.597 | 1.00 | 44.00 | C |
| ATOM | 1877 | CD | LYS | B | 124 | 4.562 | −17.860 | −27.095 | 1.00 | 41.77 | C |
| ATOM | 1878 | CE | LYS | B | 124 | 5.855 | −18.519 | −27.544 | 1.00 | 40.51 | C |
| ATOM | 1879 | NZ | LYS | B | 124 | 5.576 | −19.819 | −28.207 | 1.00 | 47.63 | N |
| ATOM | 1880 | C | LYS | B | 124 | 2.734 | −13.382 | −25.557 | 1.00 | 47.91 | C |
| ATOM | 1881 | O | LYS | B | 124 | 2.298 | −13.441 | −24.407 | 1.00 | 48.54 | O |
| ATOM | 1882 | N | ALA | B | 125 | 2.192 | −12.603 | −26.488 | 1.00 | 50.80 | N |
| ATOM | 1883 | CA | ALA | B | 125 | 0.849 | −12.034 | −26.276 | 1.00 | 53.80 | C |
| ATOM | 1884 | CB | ALA | B | 125 | 0.556 | −10.903 | −27.275 | 1.00 | 53.63 | C |
| ATOM | 1885 | C | ALA | B | 125 | −0.163 | −13.137 | −26.440 | 1.00 | 55.22 | C |
| ATOM | 1886 | O | ALA | B | 125 | −0.164 | −13.791 | −27.472 | 1.00 | 56.23 | O |
| ATOM | 1887 | N | ALA | B | 126 | −1.002 | −13.379 | −25.438 | 1.00 | 57.49 | N |
| ATOM | 1888 | CA | ALA | B | 126 | −2.254 | −14.133 | −25.698 | 1.00 | 59.24 | C |
| ATOM | 1889 | CB | ALA | B | 126 | −3.063 | −14.300 | −24.393 | 1.00 | 59.45 | C |
| ATOM | 1890 | C | ALA | B | 126 | −3.111 | −13.414 | −26.810 | 1.00 | 60.27 | C |
| ATOM | 1891 | O | ALA | B | 126 | −3.505 | −13.983 | −27.865 | 1.00 | 59.50 | O |
| ATOM | 1892 | OXT | ALA | B | 126 | −3.391 | −12.183 | −26.675 | 1.00 | 60.56 | O |
| ATOM | 1893 | N | ALA | C | 1 | 47.894 | 12.704 | −2.969 | 1.00 | 49.41 | N |
| ATOM | 1894 | CA | ALA | C | 1 | 46.483 | 12.845 | −2.525 | 1.00 | 48.69 | C |
| ATOM | 1895 | CB | ALA | C | 1 | 45.612 | 11.926 | −3.320 | 1.00 | 49.22 | C |
| ATOM | 1896 | C | ALA | C | 1 | 46.345 | 12.555 | −1.040 | 1.00 | 49.03 | C |
| ATOM | 1897 | O | ALA | C | 1 | 47.219 | 11.950 | −0.422 | 1.00 | 48.45 | O |
| ATOM | 1898 | N | TRP | C | 2 | 45.241 | 12.989 | −0.442 | 1.00 | 48.83 | N |
| ATOM | 1899 | CA | TRP | C | 2 | 45.029 | 12.703 | 0.970 | 1.00 | 47.92 | C |
| ATOM | 1900 | CB | TRP | C | 2 | 45.920 | 13.592 | 1.858 | 1.00 | 46.22 | C |
| ATOM | 1901 | CG | TRP | C | 2 | 45.728 | 15.092 | 1.734 | 1.00 | 46.85 | C |

APPENDIX I-continued

| | | | | | | | | | | | |
|---|---|---|---|---|---|---|---|---|---|---|---|
| ATOM | 1902 | CD1 | TRP | C | 2 | 46.068 | 15.895 | 0.653 | 1.00 | 46.02 | C |
| ATOM | 1903 | NE1 | TRP | C | 2 | 45.753 | 17.216 | 0.924 | 1.00 | 45.63 | N |
| ATOM | 1904 | CE2 | TRP | C | 2 | 45.233 | 17.303 | 2.191 | 1.00 | 46.81 | C |
| ATOM | 1905 | CD2 | TRP | C | 2 | 45.200 | 15.983 | 2.737 | 1.00 | 47.63 | C |
| ATOM | 1906 | CE3 | TRP | C | 2 | 44.719 | 15.802 | 4.053 | 1.00 | 46.87 | C |
| ATOM | 1907 | CZ3 | TRP | C | 2 | 44.289 | 16.918 | 4.769 | 1.00 | 46.19 | C |
| ATOM | 1908 | CH2 | TRP | C | 2 | 44.326 | 18.226 | 4.185 | 1.00 | 45.94 | C |
| ATOM | 1909 | CZ2 | TRP | C | 2 | 44.781 | 18.428 | 2.907 | 1.00 | 46.39 | C |
| ATOM | 1910 | C | TRP | C | 2 | 43.560 | 12.862 | 1.314 | 1.00 | 48.15 | C |
| ATOM | 1911 | O | TRP | C | 2 | 42.877 | 13.673 | 0.702 | 1.00 | 47.92 | O |
| ATOM | 1912 | N | VAL | C | 3 | 43.077 | 12.104 | 2.304 | 1.00 | 48.14 | N |
| ATOM | 1913 | CA | VAL | C | 3 | 41.713 | 12.343 | 2.793 | 1.00 | 47.09 | C |
| ATOM | 1914 | CB | VAL | C | 3 | 40.905 | 11.060 | 3.039 | 1.00 | 46.72 | C |
| ATOM | 1915 | CG1 | VAL | C | 3 | 39.538 | 11.402 | 3.680 | 1.00 | 44.65 | C |
| ATOM | 1916 | CG2 | VAL | C | 3 | 40.706 | 10.367 | 1.753 | 1.00 | 46.02 | C |
| ATOM | 1917 | C | VAL | C | 3 | 41.738 | 13.261 | 3.993 | 1.00 | 46.31 | C |
| ATOM | 1918 | O | VAL | C | 3 | 42.494 | 13.073 | 4.925 | 1.00 | 48.10 | O |
| ATOM | 1919 | N | ASP | C | 4 | 40.937 | 14.303 | 3.930 | 1.00 | 46.31 | N |
| ATOM | 1920 | CA | ASP | C | 4 | 40.908 | 15.306 | 4.965 | 1.00 | 45.27 | C |
| ATOM | 1921 | CB | ASP | C | 4 | 40.916 | 16.681 | 4.312 | 1.00 | 45.16 | C |
| ATOM | 1922 | CG | ASP | C | 4 | 40.888 | 17.815 | 5.312 | 1.00 | 46.64 | C |
| ATOM | 1923 | OD1 | ASP | C | 4 | 41.135 | 17.640 | 6.526 | 1.00 | 52.47 | O |
| ATOM | 1924 | OD2 | ASP | C | 4 | 40.594 | 18.933 | 4.886 | 1.00 | 48.46 | O |
| ATOM | 1925 | C | ASP | C | 4 | 39.615 | 15.025 | 5.728 | 1.00 | 44.41 | C |
| ATOM | 1926 | O | ASP | C | 4 | 38.534 | 15.276 | 5.260 | 1.00 | 43.86 | O |
| ATOM | 1927 | N | GLN | C | 5 | 39.777 | 14.424 | 6.883 | 1.00 | 43.38 | N |
| ATOM | 1928 | CA | GLN | C | 5 | 38.699 | 14.020 | 7.725 | 1.00 | 42.49 | C |
| ATOM | 1929 | CB | GLN | C | 5 | 38.951 | 12.585 | 8.184 | 1.00 | 43.25 | C |
| ATOM | 1930 | CG | GLN | C | 5 | 37.964 | 12.087 | 9.266 | 1.00 | 42.78 | C |
| ATOM | 1931 | CD | GLN | C | 5 | 38.117 | 10.629 | 9.568 | 1.00 | 43.36 | C |
| ATOM | 1932 | OE1 | GLN | C | 5 | 38.975 | 9.911 | 8.977 | 1.00 | 44.25 | O |
| ATOM | 1933 | NE2 | GLN | C | 5 | 37.341 | 10.171 | 10.522 | 1.00 | 41.48 | N |
| ATOM | 1934 | C | GLN | C | 5 | 38.612 | 14.947 | 8.919 | 1.00 | 41.74 | C |
| ATOM | 1935 | O | GLN | C | 5 | 39.573 | 15.107 | 9.659 | 1.00 | 41.18 | O |
| ATOM | 1936 | N | THR | C | 6 | 37.434 | 15.557 | 9.077 | 1.00 | 42.37 | N |
| ATOM | 1937 | CA | THR | C | 6 | 37.127 | 16.448 | 10.187 | 1.00 | 42.38 | C |
| ATOM | 1938 | CB | THR | C | 6 | 37.134 | 17.922 | 9.730 | 1.00 | 43.81 | C |
| ATOM | 1939 | OG1 | THR | C | 6 | 36.323 | 18.087 | 8.567 | 1.00 | 42.52 | O |
| ATOM | 1940 | CG2 | THR | C | 6 | 38.614 | 18.342 | 9.375 | 1.00 | 41.50 | C |
| ATOM | 1941 | C | THR | C | 6 | 35.801 | 16.006 | 10.801 | 1.00 | 42.03 | C |
| ATOM | 1942 | O | THR | C | 6 | 34.967 | 15.469 | 10.102 | 1.00 | 42.87 | O |
| ATOM | 1943 | N | PRO | C | 7 | 35.654 | 16.121 | 12.134 | 1.00 | 41.26 | N |
| ATOM | 1944 | CA | PRO | C | 7 | 36.674 | 16.605 | 13.095 | 1.00 | 39.68 | C |
| ATOM | 1945 | CB | PRO | C | 7 | 35.847 | 17.012 | 14.318 | 1.00 | 38.19 | C |
| ATOM | 1946 | CG | PRO | C | 7 | 34.571 | 16.163 | 14.235 | 1.00 | 39.85 | C |
| ATOM | 1947 | CD | PRO | C | 7 | 34.370 | 15.774 | 12.795 | 1.00 | 41.08 | C |
| ATOM | 1948 | C | PRO | C | 7 | 37.674 | 15.539 | 13.526 | 1.00 | 40.17 | C |
| ATOM | 1949 | O | PRO | C | 7 | 37.376 | 14.341 | 13.492 | 1.00 | 40.26 | O |
| ATOM | 1950 | N | ARG | C | 8 | 38.833 | 15.968 | 14.000 | 1.00 | 39.86 | N |
| ATOM | 1951 | CA | ARG | C | 8 | 39.787 | 15.015 | 14.450 | 1.00 | 42.27 | C |
| ATOM | 1952 | CB | ARG | C | 8 | 41.170 | 15.678 | 14.495 | 1.00 | 43.98 | C |
| ATOM | 1953 | CG | ARG | C | 8 | 42.321 | 14.715 | 14.708 | 1.00 | 50.28 | C |
| ATOM | 1954 | CD | ARG | C | 8 | 42.501 | 13.799 | 13.469 | 1.00 | 56.99 | C |
| ATOM | 1955 | NE | ARG | C | 8 | 43.131 | 14.492 | 12.357 | 1.00 | 59.34 | N |
| ATOM | 1956 | CZ | ARG | C | 8 | 44.447 | 14.636 | 12.274 | 1.00 | 64.10 | C |
| ATOM | 1957 | NH1 | ARG | C | 8 | 45.012 | 15.284 | 11.252 | 1.00 | 65.07 | N |
| ATOM | 1958 | NH2 | ARG | C | 8 | 45.200 | 14.117 | 13.239 | 1.00 | 67.46 | N |
| ATOM | 1959 | C | ARG | C | 8 | 39.357 | 14.418 | 15.816 | 1.00 | 41.81 | C |
| ATOM | 1960 | O | ARG | C | 8 | 39.638 | 13.250 | 16.123 | 1.00 | 41.61 | O |
| ATOM | 1961 | N | THR | C | 9 | 38.647 | 15.208 | 16.622 | 1.00 | 41.23 | N |
| ATOM | 1962 | CA | THR | C | 9 | 38.189 | 14.769 | 17.918 | 1.00 | 41.41 | C |
| ATOM | 1963 | CB | THR | C | 9 | 39.112 | 15.257 | 19.097 | 1.00 | 42.45 | C |
| ATOM | 1964 | OG1 | THR | C | 9 | 39.108 | 16.701 | 19.180 | 1.00 | 45.56 | O |
| ATOM | 1965 | CG2 | THR | C | 9 | 40.515 | 14.757 | 18.961 | 1.00 | 40.73 | C |
| ATOM | 1966 | C | THR | C | 9 | 36.847 | 15.389 | 18.127 | 1.00 | 41.08 | C |
| ATOM | 1967 | O | THR | C | 9 | 36.648 | 16.543 | 17.778 | 1.00 | 42.09 | O |
| ATOM | 1968 | N | ALA | C | 10 | 35.932 | 14.635 | 18.707 | 1.00 | 40.39 | N |
| ATOM | 1969 | CA | ALA | C | 10 | 34.587 | 15.110 | 19.081 | 1.00 | 40.33 | C |
| ATOM | 1970 | CB | ALA | C | 10 | 33.522 | 14.620 | 18.072 | 1.00 | 38.32 | C |
| ATOM | 1971 | C | ALA | C | 10 | 34.259 | 14.568 | 20.473 | 1.00 | 41.20 | C |
| ATOM | 1972 | O | ALA | C | 10 | 34.525 | 13.384 | 20.784 | 1.00 | 40.94 | O |
| ATOM | 1973 | N | THR | C | 11 | 33.736 | 15.455 | 21.324 | 1.00 | 42.57 | N |
| ATOM | 1974 | CA | THR | C | 11 | 33.123 | 15.099 | 22.616 | 1.00 | 42.23 | C |
| ATOM | 1975 | CB | THR | C | 11 | 33.759 | 15.861 | 23.749 | 1.00 | 42.79 | C |
| ATOM | 1976 | OG1 | THR | C | 11 | 35.145 | 15.491 | 23.827 | 1.00 | 46.26 | O |
| ATOM | 1977 | CG2 | THR | C | 11 | 33.078 | 15.537 | 25.097 | 1.00 | 40.59 | C |
| ATOM | 1978 | C | THR | C | 11 | 31.633 | 15.460 | 22.493 | 1.00 | 42.65 | C |
| ATOM | 1979 | O | THR | C | 11 | 31.325 | 16.618 | 22.223 | 1.00 | 43.18 | O |
| ATOM | 1980 | N | LYS | C | 12 | 30.743 | 14.467 | 22.657 | 1.00 | 41.78 | N |
| ATOM | 1981 | CA | LYS | C | 12 | 29.339 | 14.597 | 22.369 | 1.00 | 41.37 | C |

APPENDIX I-continued

| ATOM | 1982 | CB | LYS | C | 12 | 28.928 | 13.733 | 21.191 | 1.00 | 41.59 | C |
|---|---|---|---|---|---|---|---|---|---|---|---|
| ATOM | 1983 | CG | LYS | C | 12 | 29.465 | 14.167 | 19.826 | 1.00 | 41.91 | C |
| ATOM | 1984 | CD | LYS | C | 12 | 29.346 | 15.654 | 19.576 | 1.00 | 43.02 | C |
| ATOM | 1985 | CE | LYS | C | 12 | 28.977 | 15.936 | 18.151 | 1.00 | 46.80 | C |
| ATOM | 1986 | NZ | LYS | C | 12 | 29.307 | 17.320 | 17.716 | 1.00 | 49.30 | N |
| ATOM | 1987 | C | LYS | C | 12 | 28.579 | 14.096 | 23.536 | 1.00 | 42.56 | C |
| ATOM | 1988 | O | LYS | C | 12 | 29.097 | 13.230 | 24.256 | 1.00 | 43.65 | O |
| ATOM | 1989 | N | GLU | C | 13 | 27.341 | 14.602 | 23.726 | 1.00 | 41.23 | N |
| ATOM | 1990 | CA | GLU | C | 13 | 26.474 | 14.080 | 24.762 | 1.00 | 41.54 | C |
| ATOM | 1991 | CB | GLU | C | 13 | 25.675 | 15.232 | 25.379 | 1.00 | 41.00 | C |
| ATOM | 1992 | CG | GLU | C | 13 | 26.562 | 16.359 | 25.900 | 1.00 | 42.17 | C |
| ATOM | 1993 | CD | GLU | C | 13 | 25.723 | 17.635 | 26.233 | 1.00 | 46.00 | C |
| ATOM | 1994 | OE1 | GLU | C | 13 | 26.311 | 18.695 | 26.591 | 1.00 | 47.15 | O |
| ATOM | 1995 | OE2 | GLU | C | 13 | 24.466 | 17.550 | 26.116 | 1.00 | 48.60 | O |
| ATOM | 1996 | C | GLU | C | 13 | 25.563 | 13.073 | 24.149 | 1.00 | 40.75 | C |
| ATOM | 1997 | O | GLU | C | 13 | 25.335 | 13.105 | 22.910 | 1.00 | 42.27 | O |
| ATOM | 1998 | N | THR | C | 14 | 25.002 | 12.167 | 24.938 | 1.00 | 40.94 | N |
| ATOM | 1999 | CA | THR | C | 14 | 24.042 | 11.239 | 24.328 | 1.00 | 42.25 | C |
| ATOM | 2000 | CB | THR | C | 14 | 23.544 | 10.101 | 25.272 | 1.00 | 42.73 | C |
| ATOM | 2001 | OG1 | THR | C | 14 | 22.715 | 10.665 | 26.243 | 1.00 | 48.01 | O |
| ATOM | 2002 | CG2 | THR | C | 14 | 24.705 | 9.386 | 25.975 | 1.00 | 42.04 | C |
| ATOM | 2003 | C | THR | C | 14 | 22.861 | 12.015 | 23.700 | 1.00 | 40.89 | C |
| ATOM | 2004 | O | THR | C | 14 | 22.487 | 13.053 | 24.202 | 1.00 | 41.70 | O |
| ATOM | 2005 | N | GLY | C | 15 | 22.308 | 11.538 | 22.591 | 1.00 | 39.88 | N |
| ATOM | 2006 | CA | GLY | C | 15 | 21.224 | 12.239 | 21.898 | 1.00 | 38.62 | C |
| ATOM | 2007 | C | GLY | C | 15 | 21.690 | 13.211 | 20.812 | 1.00 | 38.27 | C |
| ATOM | 2008 | O | GLY | C | 15 | 20.912 | 13.537 | 19.886 | 1.00 | 39.29 | O |
| ATOM | 2009 | N | GLU | C | 16 | 22.921 | 13.685 | 20.902 | 1.00 | 36.77 | N |
| ATOM | 2010 | CA | GLU | C | 16 | 23.522 | 14.515 | 19.858 | 1.00 | 38.21 | C |
| ATOM | 2011 | CB | GLU | C | 16 | 24.766 | 15.286 | 20.373 | 1.00 | 37.37 | C |
| ATOM | 2012 | CG | GLU | C | 16 | 24.448 | 16.420 | 21.495 | 1.00 | 38.40 | C |
| ATOM | 2013 | CD | GLU | C | 16 | 25.627 | 17.359 | 21.780 | 1.00 | 38.50 | C |
| ATOM | 2014 | OE1 | GLU | C | 16 | 26.733 | 16.846 | 21.984 | 1.00 | 40.44 | O |
| ATOM | 2015 | OE2 | GLU | C | 16 | 25.489 | 18.609 | 21.757 | 1.00 | 38.88 | O |
| ATOM | 2016 | C | GLU | C | 16 | 23.874 | 13.652 | 18.635 | 1.00 | 40.24 | C |
| ATOM | 2017 | O | GLU | C | 16 | 23.852 | 12.414 | 18.745 | 1.00 | 42.05 | O |
| ATOM | 2018 | N | SER | C | 17 | 24.137 | 14.306 | 17.494 | 1.00 | 39.57 | N |
| ATOM | 2019 | CA | SER | C | 17 | 24.621 | 13.722 | 16.264 | 1.00 | 40.14 | C |
| ATOM | 2020 | CB | SER | C | 17 | 23.844 | 14.317 | 15.073 | 1.00 | 39.97 | C |
| ATOM | 2021 | OG | SER | C | 17 | 22.451 | 13.972 | 15.174 | 1.00 | 42.60 | O |
| ATOM | 2022 | C | SER | C | 17 | 26.094 | 14.113 | 16.057 | 1.00 | 40.75 | C |
| ATOM | 2023 | O | SER | C | 17 | 26.547 | 15.102 | 16.557 | 1.00 | 40.20 | O |
| ATOM | 2024 | N | LEU | C | 18 | 26.823 | 13.314 | 15.288 | 1.00 | 40.85 | N |
| ATOM | 2025 | CA | LEU | C | 18 | 28.139 | 13.643 | 14.874 | 1.00 | 41.38 | C |
| ATOM | 2026 | CB | LEU | C | 18 | 29.061 | 12.561 | 15.427 | 1.00 | 41.14 | C |
| ATOM | 2027 | CG | LEU | C | 18 | 30.600 | 12.596 | 15.451 | 1.00 | 44.10 | C |
| ATOM | 2028 | CD1 | LEU | C | 18 | 31.251 | 11.259 | 14.907 | 1.00 | 38.99 | C |
| ATOM | 2029 | CD2 | LEU | C | 18 | 31.291 | 13.933 | 15.015 | 1.00 | 41.87 | C |
| ATOM | 2030 | C | LEU | C | 18 | 28.102 | 13.544 | 13.321 | 1.00 | 41.20 | C |
| ATOM | 2031 | O | LEU | C | 18 | 27.616 | 12.564 | 12.803 | 1.00 | 39.57 | O |
| ATOM | 2032 | N | THR | C | 19 | 28.624 | 14.567 | 12.624 | 1.00 | 41.23 | N |
| ATOM | 2033 | CA | THR | C | 19 | 28.945 | 14.495 | 11.209 | 1.00 | 41.67 | C |
| ATOM | 2034 | CB | THR | C | 19 | 28.303 | 15.664 | 10.371 | 1.00 | 41.81 | C |
| ATOM | 2035 | OG1 | THR | C | 19 | 26.939 | 15.741 | 10.732 | 1.00 | 41.36 | O |
| ATOM | 2036 | CG2 | THR | C | 19 | 28.390 | 15.426 | 8.826 | 1.00 | 41.66 | C |
| ATOM | 2037 | C | THR | C | 19 | 30.442 | 14.493 | 11.061 | 1.00 | 41.89 | C |
| ATOM | 2038 | O | THR | C | 19 | 31.144 | 15.426 | 11.504 | 1.00 | 41.70 | O |
| ATOM | 2039 | N | ILE | C | 20 | 30.930 | 13.399 | 10.473 | 1.00 | 41.66 | N |
| ATOM | 2040 | CA | ILE | C | 20 | 32.321 | 13.291 | 10.062 | 1.00 | 42.12 | C |
| ATOM | 2041 | CB | ILE | C | 20 | 32.855 | 11.887 | 10.306 | 1.00 | 41.88 | C |
| ATOM | 2042 | CG1 | ILE | C | 20 | 32.758 | 11.550 | 11.820 | 1.00 | 41.13 | C |
| ATOM | 2043 | CD1 | ILE | C | 20 | 32.960 | 10.088 | 12.166 | 1.00 | 40.95 | C |
| ATOM | 2044 | CG2 | ILE | C | 20 | 34.363 | 11.820 | 9.859 | 1.00 | 42.36 | C |
| ATOM | 2045 | C | ILE | C | 20 | 32.348 | 13.605 | 8.568 | 1.00 | 42.26 | C |
| ATOM | 2046 | O | ILE | C | 20 | 31.661 | 12.949 | 7.823 | 1.00 | 41.71 | O |
| ATOM | 2047 | N | ASN | C | 21 | 33.104 | 14.624 | 8.159 | 1.00 | 43.04 | N |
| ATOM | 2048 | CA | ASN | C | 21 | 33.313 | 14.925 | 6.762 | 1.00 | 45.16 | C |
| ATOM | 2049 | CB | ASN | C | 21 | 33.189 | 16.438 | 6.512 | 1.00 | 46.62 | C |
| ATOM | 2050 | CG | ASN | C | 21 | 31.762 | 16.957 | 6.721 | 1.00 | 49.24 | C |
| ATOM | 2051 | OD1 | ASN | C | 21 | 30.831 | 16.593 | 5.972 | 1.00 | 56.70 | O |
| ATOM | 2052 | ND2 | ASN | C | 21 | 31.582 | 17.830 | 7.730 | 1.00 | 49.52 | N |
| ATOM | 2053 | C | ASN | C | 21 | 34.686 | 14.471 | 6.266 | 1.00 | 45.75 | C |
| ATOM | 2054 | O | ASN | C | 21 | 35.684 | 14.670 | 6.944 | 1.00 | 46.28 | O |
| ATOM | 2055 | N | CYS | C | 22 | 34.723 | 13.897 | 5.073 | 1.00 | 46.82 | N |
| ATOM | 2056 | CA | CYS | C | 22 | 35.959 | 13.487 | 4.390 | 1.00 | 48.35 | C |
| ATOM | 2057 | CB | CYS | C | 22 | 36.085 | 11.967 | 4.403 | 1.00 | 49.01 | C |
| ATOM | 2058 | SG | CYS | C | 22 | 36.404 | 11.250 | 6.007 | 1.00 | 54.40 | S |
| ATOM | 2059 | C | CYS | C | 22 | 35.984 | 13.967 | 2.918 | 1.00 | 47.56 | C |
| ATOM | 2060 | O | CYS | C | 22 | 34.978 | 13.866 | 2.185 | 1.00 | 47.67 | O |
| ATOM | 2061 | N | VAL | C | 23 | 37.123 | 14.505 | 2.496 | 1.00 | 46.77 | N |

APPENDIX I-continued

| | | | | | | | | | | | |
|---|---|---|---|---|---|---|---|---|---|---|---|
| ATOM | 2062 | CA | VAL | C | 23 | 37.304 | 14.992 | 1.118 | 1.00 | 44.55 | C |
| ATOM | 2063 | CB | VAL | C | 23 | 37.150 | 16.531 | 1.002 | 1.00 | 44.60 | C |
| ATOM | 2064 | CG1 | VAL | C | 23 | 37.928 | 17.212 | 2.000 | 1.00 | 46.21 | C |
| ATOM | 2065 | CG2 | VAL | C | 23 | 37.482 | 17.046 | −0.374 | 1.00 | 41.80 | C |
| ATOM | 2066 | C | VAL | C | 23 | 38.626 | 14.498 | 0.625 | 1.00 | 44.64 | C |
| ATOM | 2067 | O | VAL | C | 23 | 39.675 | 14.683 | 1.266 | 1.00 | 43.95 | O |
| ATOM | 2068 | N | LEU | C | 24 | 38.574 | 13.824 | −0.512 | 1.00 | 44.47 | N |
| ATOM | 2069 | CA | LEU | C | 24 | 39.784 | 13.393 | −1.220 | 1.00 | 44.52 | C |
| ATOM | 2070 | CB | LEU | C | 24 | 39.348 | 12.419 | −2.293 | 1.00 | 44.25 | C |
| ATOM | 2071 | CG | LEU | C | 24 | 40.109 | 11.175 | −2.724 | 1.00 | 44.73 | C |
| ATOM | 2072 | CD1 | LEU | C | 24 | 39.957 | 11.047 | −4.204 | 1.00 | 40.23 | C |
| ATOM | 2073 | CD2 | LEU | C | 24 | 41.538 | 11.066 | −2.237 | 1.00 | 39.12 | C |
| ATOM | 2074 | C | LEU | C | 24 | 40.400 | 14.631 | −1.912 | 1.00 | 44.53 | C |
| ATOM | 2075 | O | LEU | C | 24 | 39.900 | 15.064 | −2.955 | 1.00 | 44.70 | O |
| ATOM | 2076 | N | ARG | C | 25 | 41.478 | 15.178 | −1.362 | 1.00 | 44.03 | N |
| ATOM | 2077 | CA | ARG | C | 25 | 42.084 | 16.424 | −1.857 | 1.00 | 44.69 | C |
| ATOM | 2078 | CB | ARG | C | 25 | 42.553 | 17.314 | −0.692 | 1.00 | 44.52 | C |
| ATOM | 2079 | CG | ARG | C | 25 | 41.525 | 17.578 | 0.303 | 1.00 | 48.32 | C |
| ATOM | 2080 | CD | ARG | C | 25 | 41.769 | 18.944 | 0.893 | 1.00 | 55.19 | C |
| ATOM | 2081 | NE | ARG | C | 25 | 40.566 | 19.723 | 0.675 | 1.00 | 61.48 | N |
| ATOM | 2082 | CZ | ARG | C | 25 | 39.708 | 19.984 | 1.631 | 1.00 | 63.06 | C |
| ATOM | 2083 | NH1 | ARG | C | 25 | 39.998 | 19.570 | 2.840 | 1.00 | 64.66 | N |
| ATOM | 2084 | NH2 | ARG | C | 25 | 38.597 | 20.665 | 1.395 | 1.00 | 64.06 | N |
| ATOM | 2085 | C | ARG | C | 25 | 43.299 | 16.116 | −2.694 | 1.00 | 44.89 | C |
| ATOM | 2086 | O | ARG | C | 25 | 43.971 | 15.093 | −2.441 | 1.00 | 45.00 | O |
| ATOM | 2087 | N | ASP | C | 26 | 43.593 | 17.013 | −3.647 | 1.00 | 44.78 | N |
| ATOM | 2088 | CA | ASP | C | 26 | 44.661 | 16.859 | −4.650 | 1.00 | 45.57 | C |
| ATOM | 2089 | CB | ASP | C | 26 | 46.044 | 17.275 | −4.103 | 1.00 | 46.72 | C |
| ATOM | 2090 | CG | ASP | C | 26 | 45.991 | 18.501 | −3.221 | 1.00 | 50.19 | C |
| ATOM | 2091 | OD1 | ASP | C | 26 | 45.405 | 19.537 | −3.629 | 1.00 | 53.01 | O |
| ATOM | 2092 | OD2 | ASP | C | 26 | 46.552 | 18.429 | −2.099 | 1.00 | 56.34 | O |
| ATOM | 2093 | C | ASP | C | 26 | 44.784 | 15.464 | −5.185 | 1.00 | 44.38 | C |
| ATOM | 2094 | O | ASP | C | 26 | 45.871 | 14.927 | −5.215 | 1.00 | 43.71 | O |
| ATOM | 2095 | N | ALA | C | 27 | 43.679 | 14.845 | −5.567 | 1.00 | 44.56 | N |
| ATOM | 2096 | CA | ALA | C | 27 | 43.757 | 13.530 | −6.180 | 1.00 | 44.95 | C |
| ATOM | 2097 | CB | ALA | C | 27 | 42.740 | 12.552 | −5.573 | 1.00 | 43.12 | C |
| ATOM | 2098 | C | ALA | C | 27 | 43.581 | 13.633 | −7.690 | 1.00 | 46.25 | C |
| ATOM | 2099 | O | ALA | C | 27 | 42.797 | 14.464 | −8.174 | 1.00 | 46.95 | O |
| ATOM | 2100 | N | SER | C | 28 | 44.294 | 12.777 | −8.432 | 1.00 | 46.99 | N |
| ATOM | 2101 | CA | SER | C | 28 | 44.153 | 12.779 | −9.869 | 1.00 | 48.62 | C |
| ATOM | 2102 | CB | SER | C | 28 | 45.480 | 12.479 | −10.560 | 1.00 | 48.58 | C |
| ATOM | 2103 | OG | SER | C | 28 | 46.044 | 11.353 | −9.990 | 1.00 | 52.33 | O |
| ATOM | 2104 | C | SER | C | 28 | 43.026 | 11.836 | −10.303 | 1.00 | 48.24 | C |
| ATOM | 2105 | O | SER | C | 28 | 42.716 | 11.733 | −11.473 | 1.00 | 49.15 | O |
| ATOM | 2106 | N | PHE | C | 29 | 42.370 | 11.220 | −9.334 | 1.00 | 47.44 | N |
| ATOM | 2107 | CA | PHE | C | 29 | 41.340 | 10.221 | −9.612 | 1.00 | 46.65 | C |
| ATOM | 2108 | CB | PHE | C | 29 | 41.726 | 8.894 | −8.920 | 1.00 | 45.70 | C |
| ATOM | 2109 | CG | PHE | C | 29 | 43.158 | 8.502 | −9.180 | 1.00 | 42.81 | C |
| ATOM | 2110 | CD1 | PHE | C | 29 | 43.538 | 8.066 | −10.448 | 1.00 | 36.25 | C |
| ATOM | 2111 | CE1 | PHE | C | 29 | 44.850 | 7.768 | −10.742 | 1.00 | 40.99 | C |
| ATOM | 2112 | CZ | PHE | C | 29 | 45.820 | 7.884 | −9.731 | 1.00 | 43.75 | C |
| ATOM | 2113 | CE2 | PHE | C | 29 | 45.441 | 8.337 | −8.441 | 1.00 | 40.55 | C |
| ATOM | 2114 | CD2 | PHE | C | 29 | 44.116 | 8.649 | −8.189 | 1.00 | 40.78 | C |
| ATOM | 2115 | C | PHE | C | 29 | 39.958 | 10.697 | −9.171 | 1.00 | 46.58 | C |
| ATOM | 2116 | O | PHE | C | 29 | 39.831 | 11.601 | −8.317 | 1.00 | 46.70 | O |
| ATOM | 2117 | N | GLU | C | 30 | 38.942 | 10.067 | −9.750 | 1.00 | 45.81 | N |
| ATOM | 2118 | CA | GLU | C | 30 | 37.563 | 10.269 | −9.351 | 1.00 | 46.83 | C |
| ATOM | 2119 | CB | GLU | C | 30 | 36.632 | 9.980 | −10.536 | 1.00 | 47.06 | C |
| ATOM | 2120 | CG | GLU | C | 30 | 36.882 | 10.950 | −11.687 | 1.00 | 49.84 | C |
| ATOM | 2121 | CD | GLU | C | 30 | 36.469 | 12.382 | −11.319 | 1.00 | 57.62 | C |
| ATOM | 2122 | OE1 | GLU | C | 30 | 37.291 | 13.328 | −11.489 | 1.00 | 60.20 | O |
| ATOM | 2123 | OE2 | GLU | C | 30 | 35.322 | 12.553 | −10.835 | 1.00 | 58.67 | O |
| ATOM | 2124 | C | GLU | C | 30 | 37.257 | 9.401 | −8.127 | 1.00 | 46.19 | C |
| ATOM | 2125 | O | GLU | C | 30 | 37.833 | 8.321 | −7.956 | 1.00 | 47.70 | O |
| ATOM | 2126 | N | LEU | C | 31 | 36.387 | 9.880 | −7.259 | 1.00 | 45.21 | N |
| ATOM | 2127 | CA | LEU | C | 31 | 35.899 | 9.053 | −6.142 | 1.00 | 44.93 | C |
| ATOM | 2128 | CB | LEU | C | 31 | 35.102 | 9.934 | −5.217 | 1.00 | 43.15 | C |
| ATOM | 2129 | CG | LEU | C | 31 | 35.111 | 9.885 | −3.699 | 1.00 | 44.69 | C |
| ATOM | 2130 | CD1 | LEU | C | 31 | 33.683 | 10.296 | −3.177 | 1.00 | 36.97 | C |
| ATOM | 2131 | CD2 | LEU | C | 31 | 35.711 | 8.615 | −3.022 | 1.00 | 38.29 | C |
| ATOM | 2132 | C | LEU | C | 31 | 34.937 | 7.956 | −6.652 | 1.00 | 45.16 | C |
| ATOM | 2133 | O | LEU | C | 31 | 33.860 | 8.246 | −7.196 | 1.00 | 44.80 | O |
| ATOM | 2134 | N | LYS | C | 32 | 35.286 | 6.701 | −6.434 | 1.00 | 46.15 | N |
| ATOM | 2135 | CA | LYS | C | 32 | 34.505 | 5.608 | −6.991 | 1.00 | 46.54 | C |
| ATOM | 2136 | CB | LYS | C | 32 | 35.461 | 4.506 | −7.478 | 1.00 | 46.96 | C |
| ATOM | 2137 | CG | LYS | C | 32 | 34.801 | 3.264 | −8.090 | 1.00 | 50.13 | C |
| ATOM | 2138 | CD | LYS | C | 32 | 33.911 | 3.610 | −9.290 | 1.00 | 57.71 | C |
| ATOM | 2139 | CE | LYS | C | 32 | 33.263 | 2.363 | −9.882 | 1.00 | 61.56 | C |
| ATOM | 2140 | NZ | LYS | C | 32 | 33.432 | 1.172 | −8.953 | 1.00 | 64.12 | N |
| ATOM | 2141 | C | LYS | C | 32 | 33.606 | 5.063 | −5.905 | 1.00 | 46.00 | C |

APPENDIX I-continued

| | | | | | | | | | | | |
|---|---|---|---|---|---|---|---|---|---|---|---|
| ATOM | 2142 | O | LYS | C | 32 | 32.462 | 4.730 | −6.158 | 1.00 | 46.13 | O |
| ATOM | 2143 | N | ASP | C | 33 | 34.149 | 4.969 | −4.698 | 1.00 | 44.66 | N |
| ATOM | 2144 | CA | ASP | C | 33 | 33.519 | 4.229 | −3.609 | 1.00 | 44.59 | C |
| ATOM | 2145 | CB | ASP | C | 33 | 33.969 | 2.787 | −3.714 | 1.00 | 45.73 | C |
| ATOM | 2146 | CG | ASP | C | 33 | 32.854 | 1.826 | −3.570 | 1.00 | 53.17 | C |
| ATOM | 2147 | OD1 | ASP | C | 33 | 32.322 | 1.737 | −2.442 | 1.00 | 60.90 | O |
| ATOM | 2148 | OD2 | ASP | C | 33 | 32.510 | 1.158 | −4.597 | 1.00 | 61.93 | O |
| ATOM | 2149 | C | ASP | C | 33 | 34.007 | 4.777 | −2.272 | 1.00 | 42.39 | C |
| ATOM | 2150 | O | ASP | C | 33 | 35.028 | 5.440 | −2.230 | 1.00 | 39.76 | O |
| ATOM | 2151 | N | THR | C | 34 | 33.338 | 4.398 | −1.181 | 1.00 | 42.58 | N |
| ATOM | 2152 | CA | THR | C | 34 | 33.698 | 4.850 | 0.198 | 1.00 | 43.04 | C |
| ATOM | 2153 | CB | THR | C | 34 | 32.810 | 6.031 | 0.681 | 1.00 | 43.33 | C |
| ATOM | 2154 | OG1 | THR | C | 34 | 31.451 | 5.618 | 0.749 | 1.00 | 45.15 | O |
| ATOM | 2155 | CG2 | THR | C | 34 | 32.867 | 7.227 | −0.263 | 1.00 | 43.17 | C |
| ATOM | 2156 | C | THR | C | 34 | 33.529 | 3.715 | 1.235 | 1.00 | 43.65 | C |
| ATOM | 2157 | O | THR | C | 34 | 32.668 | 2.867 | 1.082 | 1.00 | 44.87 | O |
| ATOM | 2158 | N | GLY | C | 35 | 34.384 | 3.686 | 2.256 | 1.00 | 43.02 | N |
| ATOM | 2159 | CA | GLY | C | 35 | 34.214 | 2.825 | 3.400 | 1.00 | 40.60 | C |
| ATOM | 2160 | C | GLY | C | 35 | 34.387 | 3.562 | 4.711 | 1.00 | 40.55 | C |
| ATOM | 2161 | O | GLY | C | 35 | 35.086 | 4.603 | 4.784 | 1.00 | 40.16 | O |
| ATOM | 2162 | N | TRP | C | 36 | 33.817 | 2.969 | 5.766 | 1.00 | 39.56 | N |
| ATOM | 2163 | CA | TRP | C | 36 | 33.800 | 3.546 | 7.094 | 1.00 | 39.04 | C |
| ATOM | 2164 | CB | TRP | C | 36 | 32.434 | 4.191 | 7.420 | 1.00 | 37.69 | C |
| ATOM | 2165 | CG | TRP | C | 36 | 32.204 | 5.462 | 6.649 | 1.00 | 36.88 | C |
| ATOM | 2166 | CD1 | TRP | C | 36 | 31.534 | 5.601 | 5.445 | 1.00 | 37.03 | C |
| ATOM | 2167 | NE1 | TRP | C | 36 | 31.582 | 6.905 | 5.028 | 1.00 | 39.08 | N |
| ATOM | 2168 | CE2 | TRP | C | 36 | 32.299 | 7.641 | 5.951 | 1.00 | 36.41 | C |
| ATOM | 2169 | CD2 | TRP | C | 36 | 32.682 | 6.771 | 6.993 | 1.00 | 35.39 | C |
| ATOM | 2170 | CE3 | TRP | C | 36 | 33.372 | 7.289 | 8.105 | 1.00 | 39.61 | C |
| ATOM | 2171 | CZ3 | TRP | C | 36 | 33.629 | 8.658 | 8.149 | 1.00 | 41.57 | C |
| ATOM | 2172 | CH2 | TRP | C | 36 | 33.200 | 9.514 | 7.090 | 1.00 | 39.46 | C |
| ATOM | 2173 | CZ2 | TRP | C | 36 | 32.533 | 9.007 | 5.998 | 1.00 | 38.02 | C |
| ATOM | 2174 | C | TRP | C | 36 | 34.152 | 2.464 | 8.081 | 1.00 | 39.80 | C |
| ATOM | 2175 | O | TRP | C | 36 | 33.630 | 1.365 | 7.971 | 1.00 | 39.62 | O |
| ATOM | 2176 | N | TYR | C | 37 | 35.047 | 2.780 | 9.028 | 1.00 | 39.72 | N |
| ATOM | 2177 | CA | TYR | C | 37 | 35.586 | 1.769 | 9.988 | 1.00 | 42.18 | C |
| ATOM | 2178 | CB | TYR | C | 37 | 37.003 | 1.298 | 9.614 | 1.00 | 42.50 | C |
| ATOM | 2179 | CG | TYR | C | 37 | 37.114 | 0.995 | 8.128 | 1.00 | 46.10 | C |
| ATOM | 2180 | CD1 | TYR | C | 37 | 36.832 | −0.275 | 7.647 | 1.00 | 46.08 | C |
| ATOM | 2181 | CE1 | TYR | C | 37 | 36.869 | −0.558 | 6.267 | 1.00 | 49.05 | C |
| ATOM | 2182 | CZ | TYR | C | 37 | 37.246 | 0.447 | 5.381 | 1.00 | 48.62 | C |
| ATOM | 2183 | OH | TYR | C | 37 | 37.305 | 0.146 | 4.032 | 1.00 | 51.96 | O |
| ATOM | 2184 | CE2 | TYR | C | 37 | 37.562 | 1.732 | 5.836 | 1.00 | 48.05 | C |
| ATOM | 2185 | CD2 | TYR | C | 37 | 37.495 | 2.009 | 7.191 | 1.00 | 46.46 | C |
| ATOM | 2186 | C | TYR | C | 37 | 35.599 | 2.413 | 11.358 | 1.00 | 41.82 | C |
| ATOM | 2187 | O | TYR | C | 37 | 35.694 | 3.624 | 11.464 | 1.00 | 41.95 | O |
| ATOM | 2188 | N | ARG | C | 38 | 35.544 | 1.586 | 12.381 | 1.00 | 42.36 | N |
| ATOM | 2189 | CA | ARG | C | 38 | 35.573 | 2.021 | 13.729 | 1.00 | 44.49 | C |
| ATOM | 2190 | CB | ARG | C | 38 | 34.144 | 2.242 | 14.237 | 1.00 | 43.43 | C |
| ATOM | 2191 | CG | ARG | C | 38 | 34.110 | 2.406 | 15.718 | 1.00 | 47.74 | C |
| ATOM | 2192 | CD | ARG | C | 38 | 32.742 | 2.530 | 16.225 | 1.00 | 51.14 | C |
| ATOM | 2193 | NE | ARG | C | 38 | 31.885 | 1.427 | 15.821 | 1.00 | 52.19 | N |
| ATOM | 2194 | CZ | ARG | C | 38 | 30.571 | 1.409 | 16.035 | 1.00 | 57.68 | C |
| ATOM | 2195 | NH1 | ARG | C | 38 | 29.942 | 2.452 | 16.614 | 1.00 | 59.02 | N |
| ATOM | 2196 | NH2 | ARG | C | 38 | 29.868 | 0.353 | 15.673 | 1.00 | 59.82 | N |
| ATOM | 2197 | C | ARG | C | 38 | 36.288 | 0.991 | 14.613 | 1.00 | 45.46 | C |
| ATOM | 2198 | O | ARG | C | 38 | 36.115 | −0.222 | 14.456 | 1.00 | 46.19 | O |
| ATOM | 2199 | N | THR | C | 39 | 37.083 | 1.516 | 15.543 | 1.00 | 46.20 | N |
| ATOM | 2200 | CA | THR | C | 39 | 37.717 | 0.800 | 16.641 | 1.00 | 46.40 | C |
| ATOM | 2201 | CB | THR | C | 39 | 39.209 | 1.155 | 16.699 | 1.00 | 45.51 | C |
| ATOM | 2202 | OG1 | THR | C | 39 | 39.825 | 0.817 | 15.455 | 1.00 | 49.49 | O |
| ATOM | 2203 | CG2 | THR | C | 39 | 39.937 | 0.406 | 17.866 | 1.00 | 48.80 | C |
| ATOM | 2204 | C | THR | C | 39 | 36.992 | 1.338 | 17.885 | 1.00 | 47.15 | C |
| ATOM | 2205 | O | THR | C | 39 | 37.109 | 2.523 | 18.232 | 1.00 | 45.10 | O |
| ATOM | 2206 | N | LYS | C | 40 | 36.167 | 0.482 | 18.484 | 1.00 | 49.20 | N |
| ATOM | 2207 | CA | LYS | C | 40 | 35.389 | 0.844 | 19.650 | 1.00 | 51.33 | C |
| ATOM | 2208 | CB | LYS | C | 40 | 34.355 | −0.221 | 19.990 | 1.00 | 51.30 | C |
| ATOM | 2209 | CG | LYS | C | 40 | 32.952 | 0.226 | 19.595 | 1.00 | 55.88 | C |
| ATOM | 2210 | CD | LYS | C | 40 | 31.926 | −0.887 | 19.626 | 1.00 | 59.21 | C |
| ATOM | 2211 | CE | LYS | C | 40 | 31.099 | −0.803 | 20.895 | 1.00 | 63.11 | C |
| ATOM | 2212 | NZ | LYS | C | 40 | 31.075 | −2.176 | 21.526 | 1.00 | 61.59 | N |
| ATOM | 2213 | C | LYS | C | 40 | 36.333 | 1.157 | 20.816 | 1.00 | 52.57 | C |
| ATOM | 2214 | O | LYS | C | 40 | 37.423 | 0.611 | 20.886 | 1.00 | 50.99 | O |
| ATOM | 2215 | N | LEU | C | 41 | 35.938 | 2.114 | 21.659 | 1.00 | 54.39 | N |
| ATOM | 2216 | CA | LEU | C | 41 | 36.802 | 2.622 | 22.737 | 1.00 | 57.08 | C |
| ATOM | 2217 | CB | LEU | C | 41 | 36.066 | 3.736 | 23.533 | 1.00 | 57.10 | C |
| ATOM | 2218 | CG | LEU | C | 41 | 36.543 | 4.136 | 24.933 | 1.00 | 59.84 | C |
| ATOM | 2219 | CD1 | LEU | C | 41 | 35.549 | 5.096 | 25.662 | 1.00 | 61.21 | C |
| ATOM | 2220 | CD2 | LEU | C | 41 | 37.964 | 4.735 | 24.863 | 1.00 | 62.80 | C |
| ATOM | 2221 | C | LEU | C | 41 | 37.302 | 1.465 | 23.642 | 1.00 | 58.11 | C |

APPENDIX I-continued

| ATOM | 2222 | O | LEU | C | 41 | 36.505 | 0.742 | 24.266 | 1.00 | 58.05 | O |
|---|---|---|---|---|---|---|---|---|---|---|---|
| ATOM | 2223 | N | GLY | C | 42 | 38.616 | 1.264 | 23.669 | 1.00 | 59.71 | N |
| ATOM | 2224 | CA | GLY | C | 42 | 39.187 | 0.174 | 24.457 | 1.00 | 61.51 | C |
| ATOM | 2225 | C | GLY | C | 42 | 39.653 | −1.023 | 23.643 | 1.00 | 62.72 | C |
| ATOM | 2226 | O | GLY | C | 42 | 40.460 | −1.830 | 24.139 | 1.00 | 63.71 | O |
| ATOM | 2227 | N | SER | C | 43 | 39.164 | −1.138 | 22.404 | 1.00 | 62.76 | N |
| ATOM | 2228 | CA | SER | C | 43 | 39.511 | −2.239 | 21.519 | 1.00 | 62.79 | C |
| ATOM | 2229 | CB | SER | C | 43 | 38.328 | −2.559 | 20.602 | 1.00 | 62.63 | C |
| ATOM | 2230 | OG | SER | C | 43 | 38.301 | −3.927 | 20.271 | 1.00 | 61.87 | O |
| ATOM | 2231 | C | SER | C | 43 | 40.742 | −1.897 | 20.689 | 1.00 | 63.37 | C |
| ATOM | 2232 | O | SER | C | 43 | 41.116 | −0.728 | 20.557 | 1.00 | 63.84 | O |
| ATOM | 2233 | N | THR | C | 44 | 41.394 | −2.912 | 20.139 | 1.00 | 63.50 | N |
| ATOM | 2234 | CA | THR | C | 44 | 42.377 | −2.657 | 19.070 | 1.00 | 64.33 | C |
| ATOM | 2235 | CB | THR | C | 44 | 43.793 | −3.127 | 19.469 | 1.00 | 64.45 | C |
| ATOM | 2236 | OG1 | THR | C | 44 | 43.781 | −4.544 | 19.687 | 1.00 | 66.10 | O |
| ATOM | 2237 | CG2 | THR | C | 44 | 44.238 | −2.424 | 20.769 | 1.00 | 63.59 | C |
| ATOM | 2238 | C | THR | C | 44 | 41.890 | −3.251 | 17.729 | 1.00 | 63.70 | C |
| ATOM | 2239 | O | THR | C | 44 | 42.568 | −3.185 | 16.695 | 1.00 | 64.39 | O |
| ATOM | 2240 | N | ASN | C | 45 | 40.675 | −3.793 | 17.782 | 1.00 | 63.29 | N |
| ATOM | 2241 | CA | ASN | C | 45 | 39.968 | −4.421 | 16.665 | 1.00 | 63.06 | C |
| ATOM | 2242 | CB | ASN | C | 45 | 38.963 | −5.407 | 17.285 | 1.00 | 63.41 | C |
| ATOM | 2243 | CG | ASN | C | 45 | 38.299 | −6.286 | 16.258 | 1.00 | 64.24 | C |
| ATOM | 2244 | OD1 | ASN | C | 45 | 38.944 | −6.744 | 15.312 | 1.00 | 64.63 | O |
| ATOM | 2245 | ND2 | ASN | C | 45 | 36.996 | −6.530 | 16.436 | 1.00 | 64.01 | N |
| ATOM | 2246 | C | ASN | C | 45 | 39.202 | −3.426 | 15.744 | 1.00 | 62.52 | C |
| ATOM | 2247 | O | ASN | C | 45 | 38.108 | −2.951 | 16.115 | 1.00 | 62.14 | O |
| ATOM | 2248 | N | GLU | C | 46 | 39.763 | −3.111 | 14.573 | 1.00 | 61.57 | N |
| ATOM | 2249 | CA | GLU | C | 46 | 39.080 | −2.251 | 13.572 | 1.00 | 61.38 | C |
| ATOM | 2250 | CB | GLU | C | 46 | 40.062 | −1.708 | 12.530 | 1.00 | 61.16 | C |
| ATOM | 2251 | CG | GLU | C | 46 | 39.403 | −1.084 | 11.308 | 1.00 | 63.74 | C |
| ATOM | 2252 | CD | GLU | C | 46 | 40.014 | 0.267 | 10.932 | 1.00 | 66.98 | C |
| ATOM | 2253 | OE1 | GLU | C | 46 | 39.729 | 1.274 | 11.635 | 1.00 | 69.02 | O |
| ATOM | 2254 | OE2 | GLU | C | 46 | 40.770 | 0.320 | 9.935 | 1.00 | 67.74 | O |
| ATOM | 2255 | C | GLU | C | 46 | 37.917 | −2.948 | 12.868 | 1.00 | 60.84 | C |
| ATOM | 2256 | O | GLU | C | 46 | 38.086 | −4.018 | 12.322 | 1.00 | 61.63 | O |
| ATOM | 2257 | N | GLN | C | 47 | 36.748 | −2.322 | 12.856 | 1.00 | 60.18 | N |
| ATOM | 2258 | CA | GLN | C | 47 | 35.542 | −2.929 | 12.279 | 1.00 | 59.69 | C |
| ATOM | 2259 | CB | GLN | C | 47 | 34.492 | −3.142 | 13.364 | 1.00 | 60.04 | C |
| ATOM | 2260 | CG | GLN | C | 47 | 34.685 | −4.423 | 14.153 | 1.00 | 63.45 | C |
| ATOM | 2261 | CD | GLN | C | 47 | 33.988 | −4.364 | 15.502 | 1.00 | 67.03 | C |
| ATOM | 2262 | OE1 | GLN | C | 47 | 33.722 | −5.409 | 16.101 | 1.00 | 69.04 | O |
| ATOM | 2263 | NE2 | GLN | C | 47 | 33.687 | −3.134 | 15.992 | 1.00 | 65.48 | N |
| ATOM | 2264 | C | GLN | C | 47 | 34.882 | −2.103 | 11.188 | 1.00 | 57.90 | C |
| ATOM | 2265 | O | GLN | C | 47 | 34.807 | −0.893 | 11.276 | 1.00 | 56.91 | O |
| ATOM | 2266 | N | SER | C | 48 | 34.333 | −2.792 | 10.205 | 1.00 | 57.17 | N |
| ATOM | 2267 | CA | SER | C | 48 | 33.545 | −2.155 | 9.151 | 1.00 | 57.02 | C |
| ATOM | 2268 | CB | SER | C | 48 | 33.367 | −3.095 | 7.949 | 1.00 | 57.30 | C |
| ATOM | 2269 | OG | SER | C | 48 | 33.469 | −2.341 | 6.749 | 1.00 | 59.39 | O |
| ATOM | 2270 | C | SER | C | 48 | 32.203 | −1.664 | 9.682 | 1.00 | 55.73 | C |
| ATOM | 2271 | O | SER | C | 48 | 31.564 | −2.325 | 10.497 | 1.00 | 55.50 | O |
| ATOM | 2272 | N | ILE | C | 49 | 31.823 | −0.460 | 9.257 | 1.00 | 55.13 | N |
| ATOM | 2273 | CA | ILE | C | 49 | 30.555 | 0.176 | 9.651 | 1.00 | 54.08 | C |
| ATOM | 2274 | CB | ILE | C | 49 | 30.701 | 1.702 | 9.867 | 1.00 | 53.11 | C |
| ATOM | 2275 | CG1 | ILE | C | 49 | 31.364 | 2.013 | 11.191 | 1.00 | 54.19 | C |
| ATOM | 2276 | CD1 | ILE | C | 49 | 31.747 | 3.486 | 11.251 | 1.00 | 50.86 | C |
| ATOM | 2277 | CG2 | ILE | C | 49 | 29.335 | 2.437 | 9.866 | 1.00 | 53.88 | C |
| ATOM | 2278 | C | ILE | C | 49 | 29.495 | −0.094 | 8.577 | 1.00 | 53.70 | C |
| ATOM | 2279 | O | ILE | C | 49 | 29.695 | 0.176 | 7.389 | 1.00 | 54.09 | O |
| ATOM | 2280 | N | SER | C | 50 | 28.372 | −0.637 | 9.027 | 1.00 | 53.80 | N |
| ATOM | 2281 | CA | SER | C | 50 | 27.170 | −0.832 | 8.215 | 1.00 | 53.15 | C |
| ATOM | 2282 | CB | SER | C | 50 | 26.378 | −2.049 | 8.731 | 1.00 | 53.47 | C |
| ATOM | 2283 | OG | SER | C | 50 | 27.216 | −3.191 | 8.674 | 1.00 | 55.46 | O |
| ATOM | 2284 | C | SER | C | 50 | 26.299 | 0.421 | 8.248 | 1.00 | 51.25 | C |
| ATOM | 2285 | O | SER | C | 50 | 25.876 | 0.861 | 9.314 | 1.00 | 50.95 | O |
| ATOM | 2286 | N | ILE | C | 51 | 26.055 | 0.964 | 7.058 | 1.00 | 49.62 | N |
| ATOM | 2287 | CA | ILE | C | 51 | 25.252 | 2.177 | 6.854 | 1.00 | 47.96 | C |
| ATOM | 2288 | CB | ILE | C | 51 | 25.704 | 2.918 | 5.527 | 1.00 | 47.87 | C |
| ATOM | 2289 | CG1 | ILE | C | 51 | 27.198 | 3.362 | 5.611 | 1.00 | 47.14 | C |
| ATOM | 2290 | CD1 | ILE | C | 51 | 27.596 | 4.066 | 6.953 | 1.00 | 42.36 | C |
| ATOM | 2291 | CG2 | ILE | C | 51 | 24.764 | 4.088 | 5.185 | 1.00 | 47.30 | C |
| ATOM | 2292 | C | ILE | C | 51 | 23.750 | 1.837 | 6.844 | 1.00 | 46.21 | C |
| ATOM | 2293 | O | ILE | C | 51 | 23.318 | 0.974 | 6.084 | 1.00 | 47.08 | O |
| ATOM | 2294 | N | GLY | C | 52 | 22.958 | 2.488 | 7.697 | 1.00 | 44.14 | N |
| ATOM | 2295 | CA | GLY | C | 52 | 21.505 | 2.239 | 7.784 | 1.00 | 41.65 | C |
| ATOM | 2296 | C | GLY | C | 52 | 21.099 | 2.653 | 9.184 | 1.00 | 40.74 | C |
| ATOM | 2297 | O | GLY | C | 52 | 21.943 | 2.713 | 10.069 | 1.00 | 40.48 | O |
| ATOM | 2298 | N | GLY | C | 53 | 19.822 | 2.961 | 9.391 | 1.00 | 38.99 | N |
| ATOM | 2299 | CA | GLY | C | 53 | 19.345 | 3.387 | 10.677 | 1.00 | 37.19 | C |
| ATOM | 2300 | C | GLY | C | 53 | 19.888 | 4.738 | 11.055 | 1.00 | 37.85 | C |
| ATOM | 2301 | O | GLY | C | 53 | 19.829 | 5.692 | 10.269 | 1.00 | 37.66 | O |

APPENDIX I-continued

| ATOM | 2302 | N | ARG | C | 54 | 20.424 | 4.812 | 12.277 | 1.00 | 38.16 | N |
|---|---|---|---|---|---|---|---|---|---|---|---|
| ATOM | 2303 | CA | ARG | C | 54 | 21.107 | 5.990 | 12.806 | 1.00 | 36.67 | C |
| ATOM | 2304 | CB | ARG | C | 54 | 21.487 | 5.783 | 14.286 | 1.00 | 37.09 | C |
| ATOM | 2305 | CG | ARG | C | 54 | 20.294 | 5.610 | 15.167 | 1.00 | 36.01 | C |
| ATOM | 2306 | CD | ARG | C | 54 | 20.611 | 5.607 | 16.667 | 1.00 | 37.36 | C |
| ATOM | 2307 | NE | ARG | C | 54 | 21.596 | 4.563 | 16.963 | 1.00 | 39.11 | N |
| ATOM | 2308 | CZ | ARG | C | 54 | 22.885 | 4.774 | 17.227 | 1.00 | 39.90 | C |
| ATOM | 2309 | NH1 | ARG | C | 54 | 23.418 | 6.002 | 17.263 | 1.00 | 35.96 | N |
| ATOM | 2310 | NH2 | ARG | C | 54 | 23.645 | 3.734 | 17.490 | 1.00 | 38.73 | N |
| ATOM | 2311 | C | ARG | C | 54 | 22.310 | 6.430 | 12.016 | 1.00 | 37.64 | C |
| ATOM | 2312 | O | ARG | C | 54 | 22.696 | 7.611 | 12.105 | 1.00 | 38.33 | O |
| ATOM | 2313 | N | TYR | C | 55 | 22.927 | 5.527 | 11.242 | 1.00 | 38.47 | N |
| ATOM | 2314 | CA | TYR | C | 55 | 24.111 | 5.852 | 10.435 | 1.00 | 38.95 | C |
| ATOM | 2315 | CB | TYR | C | 55 | 25.104 | 4.647 | 10.444 | 1.00 | 41.10 | C |
| ATOM | 2316 | CG | TYR | C | 55 | 25.676 | 4.328 | 11.842 | 1.00 | 43.73 | C |
| ATOM | 2317 | CD1 | TYR | C | 55 | 24.897 | 3.737 | 12.850 | 1.00 | 45.50 | C |
| ATOM | 2318 | CE1 | TYR | C | 55 | 25.432 | 3.473 | 14.108 | 1.00 | 47.29 | C |
| ATOM | 2319 | CZ | TYR | C | 55 | 26.778 | 3.788 | 14.349 | 1.00 | 47.61 | C |
| ATOM | 2320 | OH | TYR | C | 55 | 27.392 | 3.558 | 15.581 | 1.00 | 49.34 | O |
| ATOM | 2321 | CE2 | TYR | C | 55 | 27.541 | 4.359 | 13.367 | 1.00 | 44.66 | C |
| ATOM | 2322 | CD2 | TYR | C | 55 | 27.001 | 4.622 | 12.141 | 1.00 | 44.65 | C |
| ATOM | 2323 | C | TYR | C | 55 | 23.703 | 6.228 | 8.973 | 1.00 | 38.22 | C |
| ATOM | 2324 | O | TYR | C | 55 | 23.137 | 5.426 | 8.270 | 1.00 | 38.89 | O |
| ATOM | 2325 | N | VAL | C | 56 | 24.009 | 7.436 | 8.522 | 1.00 | 37.84 | N |
| ATOM | 2326 | CA | VAL | C | 56 | 23.618 | 7.965 | 7.202 | 1.00 | 37.02 | C |
| ATOM | 2327 | CB | VAL | C | 56 | 22.603 | 9.173 | 7.358 | 1.00 | 37.86 | C |
| ATOM | 2328 | CG1 | VAL | C | 56 | 22.116 | 9.728 | 5.981 | 1.00 | 36.06 | C |
| ATOM | 2329 | CG2 | VAL | C | 56 | 21.430 | 8.757 | 8.169 | 1.00 | 36.23 | C |
| ATOM | 2330 | C | VAL | C | 56 | 24.901 | 8.476 | 6.531 | 1.00 | 38.69 | C |
| ATOM | 2331 | O | VAL | C | 56 | 25.605 | 9.334 | 7.094 | 1.00 | 37.27 | O |
| ATOM | 2332 | N | GLU | C | 57 | 25.230 | 7.898 | 5.369 | 1.00 | 39.95 | N |
| ATOM | 2333 | CA | GLU | C | 57 | 26.318 | 8.383 | 4.518 | 1.00 | 41.91 | C |
| ATOM | 2334 | CB | GLU | C | 57 | 27.001 | 7.223 | 3.793 | 1.00 | 42.73 | C |
| ATOM | 2335 | CG | GLU | C | 57 | 28.243 | 7.712 | 3.058 | 1.00 | 44.86 | C |
| ATOM | 2336 | CD | GLU | C | 57 | 29.213 | 6.641 | 2.626 | 1.00 | 46.27 | C |
| ATOM | 2337 | OE1 | GLU | C | 57 | 30.406 | 6.928 | 2.665 | 1.00 | 51.32 | O |
| ATOM | 2338 | OE2 | GLU | C | 57 | 28.819 | 5.529 | 2.281 | 1.00 | 45.88 | O |
| ATOM | 2339 | C | GLU | C | 57 | 25.772 | 9.321 | 3.461 | 1.00 | 42.24 | C |
| ATOM | 2340 | O | GLU | C | 57 | 24.679 | 9.095 | 2.933 | 1.00 | 42.46 | O |
| ATOM | 2341 | N | THR | C | 58 | 26.505 | 10.370 | 3.128 | 1.00 | 42.56 | N |
| ATOM | 2342 | CA | THR | C | 58 | 26.114 | 11.189 | 1.984 | 1.00 | 44.27 | C |
| ATOM | 2343 | CB | THR | C | 58 | 25.754 | 12.622 | 2.431 | 1.00 | 45.63 | C |
| ATOM | 2344 | OG1 | THR | C | 58 | 24.690 | 12.556 | 3.388 | 1.00 | 44.93 | O |
| ATOM | 2345 | CG2 | THR | C | 58 | 25.232 | 13.504 | 1.208 | 1.00 | 46.97 | C |
| ATOM | 2346 | C | THR | C | 58 | 27.348 | 11.189 | 1.130 | 1.00 | 44.50 | C |
| ATOM | 2347 | O | THR | C | 58 | 28.413 | 11.350 | 1.666 | 1.00 | 43.33 | O |
| ATOM | 2348 | N | VAL | C | 59 | 27.230 | 10.942 | −0.176 | 1.00 | 45.04 | N |
| ATOM | 2349 | CA | VAL | C | 59 | 28.406 | 10.977 | −1.063 | 1.00 | 45.53 | C |
| ATOM | 2350 | CB | VAL | C | 59 | 28.708 | 9.588 | −1.708 | 1.00 | 46.05 | C |
| ATOM | 2351 | CG1 | VAL | C | 59 | 29.915 | 9.649 | −2.706 | 1.00 | 47.53 | C |
| ATOM | 2352 | CG2 | VAL | C | 59 | 29.006 | 8.579 | −0.643 | 1.00 | 45.51 | C |
| ATOM | 2353 | C | VAL | C | 59 | 28.206 | 12.053 | −2.134 | 1.00 | 45.35 | C |
| ATOM | 2354 | O | VAL | C | 59 | 27.147 | 12.120 | −2.743 | 1.00 | 44.02 | O |
| ATOM | 2355 | N | ASN | C | 60 | 29.203 | 12.919 | −2.317 | 1.00 | 44.36 | N |
| ATOM | 2356 | CA | ASN | C | 60 | 29.194 | 13.869 | −3.435 | 1.00 | 44.75 | C |
| ATOM | 2357 | CB | ASN | C | 60 | 29.177 | 15.316 | −2.912 | 1.00 | 45.64 | C |
| ATOM | 2358 | CG | ASN | C | 60 | 28.884 | 16.325 | −4.015 | 1.00 | 47.39 | C |
| ATOM | 2359 | OD1 | ASN | C | 60 | 29.294 | 16.141 | −5.154 | 1.00 | 49.89 | O |
| ATOM | 2360 | ND2 | ASN | C | 60 | 28.148 | 17.385 | −3.681 | 1.00 | 49.11 | N |
| ATOM | 2361 | C | ASN | C | 60 | 30.404 | 13.658 | −4.329 | 1.00 | 44.46 | C |
| ATOM | 2362 | O | ASN | C | 60 | 31.482 | 14.175 | −4.051 | 1.00 | 44.94 | O |
| ATOM | 2363 | N | LYS | C | 61 | 30.277 | 12.837 | −5.357 | 1.00 | 43.78 | N |
| ATOM | 2364 | CA | LYS | C | 61 | 31.416 | 12.530 | −6.207 | 1.00 | 43.85 | C |
| ATOM | 2365 | CB | LYS | C | 61 | 31.024 | 11.439 | −7.200 | 1.00 | 45.23 | C |
| ATOM | 2366 | CG | LYS | C | 61 | 30.890 | 10.014 | −6.579 | 1.00 | 46.82 | C |
| ATOM | 2367 | CD | LYS | C | 61 | 30.106 | 9.171 | −7.582 | 1.00 | 50.75 | C |
| ATOM | 2368 | CE | LYS | C | 61 | 29.705 | 7.801 | −7.064 | 1.00 | 54.46 | C |
| ATOM | 2369 | NZ | LYS | C | 61 | 30.794 | 6.802 | −7.151 | 1.00 | 54.88 | N |
| ATOM | 2370 | C | LYS | C | 61 | 31.910 | 13.801 | −6.932 | 1.00 | 43.81 | C |
| ATOM | 2371 | O | LYS | C | 61 | 33.080 | 13.971 | −7.175 | 1.00 | 42.45 | O |
| ATOM | 2372 | N | GLY | C | 62 | 31.000 | 14.714 | −7.249 | 1.00 | 44.61 | N |
| ATOM | 2373 | CA | GLY | C | 62 | 31.383 | 15.991 | −7.859 | 1.00 | 45.46 | C |
| ATOM | 2374 | C | GLY | C | 62 | 32.487 | 16.728 | −7.119 | 1.00 | 45.37 | C |
| ATOM | 2375 | O | GLY | C | 62 | 33.376 | 17.295 | −7.727 | 1.00 | 45.73 | O |
| ATOM | 2376 | N | SER | C | 63 | 32.450 | 16.704 | −5.792 | 1.00 | 45.46 | N |
| ATOM | 2377 | CA | SER | C | 63 | 33.420 | 17.441 | −5.008 | 1.00 | 44.70 | C |
| ATOM | 2378 | CB | SER | C | 63 | 32.688 | 18.416 | −4.091 | 1.00 | 45.19 | C |
| ATOM | 2379 | OG | SER | C | 63 | 31.893 | 17.677 | −3.181 | 1.00 | 47.62 | O |
| ATOM | 2380 | C | SER | C | 63 | 34.264 | 16.451 | −4.232 | 1.00 | 44.60 | C |
| ATOM | 2381 | O | SER | C | 63 | 34.979 | 16.823 | −3.314 | 1.00 | 45.58 | O |

APPENDIX I-continued

| ATOM | 2382 | N | LYS | C | 64 | 34.200 | 15.185 | −4.631 | 1.00 | 43.31 | N |
|---|---|---|---|---|---|---|---|---|---|---|---|
| ATOM | 2383 | CA | LYS | C | 64 | 34.998 | 14.106 | −4.028 | 1.00 | 42.72 | C |
| ATOM | 2384 | CB | LYS | C | 64 | 36.477 | 14.180 | −4.442 | 1.00 | 43.43 | C |
| ATOM | 2385 | CG | LYS | C | 64 | 36.775 | 14.385 | −5.937 | 1.00 | 42.33 | C |
| ATOM | 2386 | CD | LYS | C | 64 | 38.280 | 14.079 | −6.230 | 1.00 | 41.50 | C |
| ATOM | 2387 | CE | LYS | C | 64 | 38.590 | 14.577 | −7.695 | 1.00 | 39.78 | C |
| ATOM | 2388 | NZ | LYS | C | 64 | 39.915 | 14.109 | −8.180 | 1.00 | 42.69 | N |
| ATOM | 2389 | C | LYS | C | 64 | 34.886 | 14.092 | −2.496 | 1.00 | 43.21 | C |
| ATOM | 2390 | O | LYS | C | 64 | 35.878 | 13.779 | −1.795 | 1.00 | 42.92 | O |
| ATOM | 2391 | N | SER | C | 65 | 33.699 | 14.441 | −1.992 | 1.00 | 41.43 | N |
| ATOM | 2392 | CA | SER | C | 65 | 33.469 | 14.458 | −0.580 | 1.00 | 42.62 | C |
| ATOM | 2393 | CB | SER | C | 65 | 33.231 | 15.866 | −0.083 | 1.00 | 43.83 | C |
| ATOM | 2394 | OG | SER | C | 65 | 32.354 | 16.529 | −0.959 | 1.00 | 45.50 | O |
| ATOM | 2395 | C | SER | C | 65 | 32.347 | 13.565 | −0.135 | 1.00 | 42.45 | C |
| ATOM | 2396 | O | SER | C | 65 | 31.421 | 13.224 | −0.874 | 1.00 | 40.59 | O |
| ATOM | 2397 | N | PHE | C | 66 | 32.466 | 13.139 | 1.103 | 1.00 | 42.45 | N |
| ATOM | 2398 | CA | PHE | C | 66 | 31.473 | 12.198 | 1.636 | 1.00 | 43.16 | C |
| ATOM | 2399 | CB | PHE | C | 66 | 31.730 | 10.756 | 1.181 | 1.00 | 42.27 | C |
| ATOM | 2400 | CG | PHE | C | 66 | 33.099 | 10.222 | 1.510 | 1.00 | 44.09 | C |
| ATOM | 2401 | CD1 | PHE | C | 66 | 34.242 | 10.716 | 0.857 | 1.00 | 42.19 | C |
| ATOM | 2402 | CE1 | PHE | C | 66 | 35.517 | 10.219 | 1.123 | 1.00 | 44.28 | C |
| ATOM | 2403 | CZ | PHE | C | 66 | 35.670 | 9.175 | 2.052 | 1.00 | 45.40 | C |
| ATOM | 2404 | CE2 | PHE | C | 66 | 34.513 | 8.620 | 2.721 | 1.00 | 43.80 | C |
| ATOM | 2405 | CD2 | PHE | C | 66 | 33.244 | 9.152 | 2.449 | 1.00 | 46.12 | C |
| ATOM | 2406 | C | PHE | C | 66 | 31.421 | 12.354 | 3.123 | 1.00 | 43.16 | C |
| ATOM | 2407 | O | PHE | C | 66 | 32.351 | 12.914 | 3.730 | 1.00 | 43.47 | O |
| ATOM | 2408 | N | SER | C | 67 | 30.295 | 12.004 | 3.716 | 1.00 | 43.08 | N |
| ATOM | 2409 | CA | SER | C | 67 | 30.192 | 12.283 | 5.145 | 1.00 | 43.78 | C |
| ATOM | 2410 | CB | SER | C | 67 | 29.498 | 13.599 | 5.348 | 1.00 | 42.88 | C |
| ATOM | 2411 | OG | SER | C | 67 | 28.148 | 13.307 | 5.122 | 1.00 | 50.83 | O |
| ATOM | 2412 | C | SER | C | 67 | 29.420 | 11.172 | 5.783 | 1.00 | 42.30 | C |
| ATOM | 2413 | O | SER | C | 67 | 28.653 | 10.502 | 5.119 | 1.00 | 42.27 | O |
| ATOM | 2414 | N | LEU | C | 68 | 29.704 | 10.935 | 7.050 | 1.00 | 40.76 | N |
| ATOM | 2415 | CA | LEU | C | 68 | 28.938 | 10.035 | 7.877 | 1.00 | 39.22 | C |
| ATOM | 2416 | CB | LEU | C | 68 | 29.870 | 9.117 | 8.675 | 1.00 | 39.26 | C |
| ATOM | 2417 | CG | LEU | C | 68 | 29.519 | 7.673 | 9.067 | 1.00 | 39.79 | C |
| ATOM | 2418 | CD1 | LEU | C | 68 | 30.187 | 7.273 | 10.332 | 1.00 | 36.92 | C |
| ATOM | 2419 | CD2 | LEU | C | 68 | 28.064 | 7.184 | 8.998 | 1.00 | 41.23 | C |
| ATOM | 2420 | C | LEU | C | 68 | 28.281 | 10.919 | 8.932 | 1.00 | 38.92 | C |
| ATOM | 2421 | O | LEU | C | 68 | 28.962 | 11.636 | 9.668 | 1.00 | 36.62 | O |
| ATOM | 2422 | N | ARG | C | 69 | 26.988 | 10.734 | 9.088 | 1.00 | 38.05 | N |
| ATOM | 2423 | CA | ARG | C | 69 | 26.216 | 11.297 | 10.182 | 1.00 | 38.81 | C |
| ATOM | 2424 | CB | ARG | C | 69 | 24.957 | 12.018 | 9.603 | 1.00 | 37.83 | C |
| ATOM | 2425 | CG | ARG | C | 69 | 24.394 | 12.996 | 10.666 | 1.00 | 42.79 | C |
| ATOM | 2426 | CD | ARG | C | 69 | 23.175 | 13.730 | 10.200 | 1.00 | 53.15 | C |
| ATOM | 2427 | NE | ARG | C | 69 | 23.050 | 14.889 | 11.076 | 1.00 | 60.64 | N |
| ATOM | 2428 | CZ | ARG | C | 69 | 22.234 | 14.973 | 12.136 | 1.00 | 64.79 | C |
| ATOM | 2429 | NH1 | ARG | C | 69 | 21.415 | 13.954 | 12.452 | 1.00 | 64.71 | N |
| ATOM | 2430 | NH2 | ARG | C | 69 | 22.227 | 16.089 | 12.882 | 1.00 | 64.93 | N |
| ATOM | 2431 | C | ARG | C | 69 | 25.714 | 10.174 | 11.063 | 1.00 | 38.49 | C |
| ATOM | 2432 | O | ARG | C | 69 | 25.016 | 9.296 | 10.576 | 1.00 | 38.05 | O |
| ATOM | 2433 | N | ILE | C | 70 | 26.036 | 10.204 | 12.355 | 1.00 | 38.71 | N |
| ATOM | 2434 | CA | ILE | C | 70 | 25.420 | 9.290 | 13.321 | 1.00 | 38.97 | C |
| ATOM | 2435 | CB | ILE | C | 70 | 26.478 | 8.582 | 14.218 | 1.00 | 39.33 | C |
| ATOM | 2436 | CG1 | ILE | C | 70 | 27.623 | 8.001 | 13.370 | 1.00 | 41.07 | C |
| ATOM | 2437 | CD1 | ILE | C | 70 | 28.826 | 7.749 | 14.203 | 1.00 | 42.56 | C |
| ATOM | 2438 | CG2 | ILE | C | 70 | 25.853 | 7.519 | 15.050 | 1.00 | 36.50 | C |
| ATOM | 2439 | C | ILE | C | 70 | 24.425 | 10.106 | 14.188 | 1.00 | 38.51 | C |
| ATOM | 2440 | O | ILE | C | 70 | 24.863 | 10.970 | 14.928 | 1.00 | 38.32 | O |
| ATOM | 2441 | N | SER | C | 71 | 23.124 | 9.833 | 14.069 | 1.00 | 36.88 | N |
| ATOM | 2442 | CA | SER | C | 71 | 22.084 | 10.437 | 14.955 | 1.00 | 38.63 | C |
| ATOM | 2443 | CB | SER | C | 71 | 20.691 | 10.355 | 14.353 | 1.00 | 36.29 | C |
| ATOM | 2444 | OG | SER | C | 71 | 20.721 | 10.830 | 13.058 | 1.00 | 42.47 | O |
| ATOM | 2445 | C | SER | C | 71 | 21.938 | 9.783 | 16.308 | 1.00 | 37.24 | C |
| ATOM | 2446 | O | SER | C | 71 | 22.280 | 8.640 | 16.509 | 1.00 | 39.57 | O |
| ATOM | 2447 | N | ASP | C | 72 | 21.394 | 10.530 | 17.218 | 1.00 | 37.94 | N |
| ATOM | 2448 | CA | ASP | C | 72 | 21.064 | 10.056 | 18.525 | 1.00 | 38.88 | C |
| ATOM | 2449 | CB | ASP | C | 72 | 19.761 | 9.261 | 18.465 | 1.00 | 38.48 | C |
| ATOM | 2450 | CG | ASP | C | 72 | 19.127 | 9.150 | 19.805 | 1.00 | 40.88 | C |
| ATOM | 2451 | OD1 | ASP | C | 72 | 19.397 | 10.036 | 20.649 | 1.00 | 41.95 | O |
| ATOM | 2452 | OD2 | ASP | C | 72 | 18.355 | 8.204 | 20.029 | 1.00 | 46.35 | O |
| ATOM | 2453 | C | ASP | C | 72 | 22.192 | 9.248 | 19.194 | 1.00 | 39.02 | C |
| ATOM | 2454 | O | ASP | C | 72 | 21.996 | 8.088 | 19.548 | 1.00 | 40.28 | O |
| ATOM | 2455 | N | LEU | C | 73 | 23.354 | 9.857 | 19.369 | 1.00 | 38.81 | N |
| ATOM | 2456 | CA | LEU | C | 73 | 24.525 | 9.137 | 19.900 | 1.00 | 39.26 | C |
| ATOM | 2457 | CB | LEU | C | 73 | 25.754 | 10.076 | 20.004 | 1.00 | 38.40 | C |
| ATOM | 2458 | CG | LEU | C | 73 | 26.271 | 10.505 | 18.635 | 1.00 | 37.52 | C |
| ATOM | 2459 | CD1 | LEU | C | 73 | 27.086 | 11.766 | 18.820 | 1.00 | 36.13 | C |
| ATOM | 2460 | CD2 | LEU | C | 73 | 27.118 | 9.367 | 18.077 | 1.00 | 35.66 | C |
| ATOM | 2461 | C | LEU | C | 73 | 24.290 | 8.464 | 21.258 | 1.00 | 38.78 | C |

APPENDIX I-continued

| ATOM | 2462 | O   | LEU | C | 73 | 23.600 | 9.018 | 22.132 | 1.00 | 38.58 | O |
|------|------|-----|-----|---|----|--------|-------|--------|------|-------|---|
| ATOM | 2463 | N   | ARG | C | 74 | 24.851 | 7.275 | 21.430 | 1.00 | 38.74 | N |
| ATOM | 2464 | CA  | ARG | C | 74 | 24.881 | 6.575 | 22.744 | 1.00 | 40.73 | C |
| ATOM | 2465 | CB  | ARG | C | 74 | 24.123 | 5.247 | 22.684 | 1.00 | 40.63 | C |
| ATOM | 2466 | CG  | ARG | C | 74 | 23.674 | 4.750 | 21.330 | 1.00 | 44.45 | C |
| ATOM | 2467 | CD  | ARG | C | 74 | 22.291 | 5.411 | 21.028 | 1.00 | 52.00 | C |
| ATOM | 2468 | NE  | ARG | C | 74 | 21.296 | 4.424 | 20.582 | 1.00 | 57.73 | N |
| ATOM | 2469 | CZ  | ARG | C | 74 | 20.034 | 4.701 | 20.272 | 1.00 | 54.39 | C |
| ATOM | 2470 | NH1 | ARG | C | 74 | 19.236 | 3.719 | 19.917 | 1.00 | 55.75 | N |
| ATOM | 2471 | NH2 | ARG | C | 74 | 19.588 | 5.942 | 20.292 | 1.00 | 49.28 | N |
| ATOM | 2472 | C   | ARG | C | 74 | 26.351 | 6.305 | 23.159 | 1.00 | 41.08 | C |
| ATOM | 2473 | O   | ARG | C | 74 | 27.223 | 6.297 | 22.283 | 1.00 | 39.54 | O |
| ATOM | 2474 | N   | VAL | C | 75 | 26.629 | 6.061 | 24.453 | 1.00 | 41.83 | N |
| ATOM | 2475 | CA  | VAL | C | 75 | 28.019 | 5.793 | 24.874 | 1.00 | 42.82 | C |
| ATOM | 2476 | CB  | VAL | C | 75 | 28.167 | 5.434 | 26.383 | 1.00 | 42.84 | C |
| ATOM | 2477 | CG1 | VAL | C | 75 | 27.517 | 6.484 | 27.263 | 1.00 | 42.05 | C |
| ATOM | 2478 | CG2 | VAL | C | 75 | 27.552 | 4.094 | 26.683 | 1.00 | 44.76 | C |
| ATOM | 2479 | C   | VAL | C | 75 | 28.658 | 4.705 | 24.017 | 1.00 | 43.85 | C |
| ATOM | 2480 | O   | VAL | C | 75 | 29.833 | 4.797 | 23.665 | 1.00 | 44.32 | O |
| ATOM | 2481 | N   | GLU | C | 76 | 27.888 | 3.668 | 23.662 | 1.00 | 44.43 | N |
| ATOM | 2482 | CA  | GLU | C | 76 | 28.437 | 2.562 | 22.865 | 1.00 | 45.15 | C |
| ATOM | 2483 | CB  | GLU | C | 76 | 27.474 | 1.346 | 22.799 | 1.00 | 46.21 | C |
| ATOM | 2484 | CG  | GLU | C | 76 | 25.983 | 1.699 | 22.474 | 1.00 | 51.67 | C |
| ATOM | 2485 | CD  | GLU | C | 76 | 25.070 | 1.966 | 23.696 | 1.00 | 56.22 | C |
| ATOM | 2486 | OE1 | GLU | C | 76 | 23.911 | 1.494 | 23.654 | 1.00 | 60.97 | O |
| ATOM | 2487 | OE2 | GLU | C | 76 | 25.456 | 2.651 | 24.684 | 1.00 | 58.26 | O |
| ATOM | 2488 | C   | GLU | C | 76 | 28.927 | 3.022 | 21.474 | 1.00 | 44.53 | C |
| ATOM | 2489 | O   | GLU | C | 76 | 29.708 | 2.291 | 20.812 | 1.00 | 43.93 | O |
| ATOM | 2490 | N   | ASP | C | 77 | 28.535 | 4.236 | 21.040 | 1.00 | 42.84 | N |
| ATOM | 2491 | CA  | ASP | C | 77 | 29.055 | 4.766 | 19.743 | 1.00 | 41.95 | C |
| ATOM | 2492 | CB  | ASP | C | 77 | 28.118 | 5.832 | 19.168 | 1.00 | 42.62 | C |
| ATOM | 2493 | CG  | ASP | C | 77 | 26.752 | 5.282 | 18.781 | 1.00 | 45.69 | C |
| ATOM | 2494 | OD1 | ASP | C | 77 | 26.657 | 4.110 | 18.318 | 1.00 | 43.73 | O |
| ATOM | 2495 | OD2 | ASP | C | 77 | 25.773 | 6.049 | 18.913 | 1.00 | 44.99 | O |
| ATOM | 2496 | C   | ASP | C | 77 | 30.508 | 5.313 | 19.846 | 1.00 | 40.76 | C |
| ATOM | 2497 | O   | ASP | C | 77 | 31.127 | 5.640 | 18.846 | 1.00 | 40.30 | O |
| ATOM | 2498 | N   | SER | C | 78 | 31.024 | 5.464 | 21.061 | 1.00 | 40.14 | N |
| ATOM | 2499 | CA  | SER | C | 78 | 32.383 | 5.978 | 21.240 | 1.00 | 40.43 | C |
| ATOM | 2500 | CB  | SER | C | 78 | 32.751 | 6.039 | 22.716 | 1.00 | 38.77 | C |
| ATOM | 2501 | OG  | SER | C | 78 | 31.800 | 6.795 | 23.385 | 1.00 | 40.31 | O |
| ATOM | 2502 | C   | SER | C | 78 | 33.411 | 5.118 | 20.519 | 1.00 | 40.44 | C |
| ATOM | 2503 | O   | SER | C | 78 | 33.259 | 3.898 | 20.413 | 1.00 | 41.58 | O |
| ATOM | 2504 | N   | GLY | C | 79 | 34.456 | 5.763 | 20.014 | 1.00 | 39.91 | N |
| ATOM | 2505 | CA  | GLY | C | 79 | 35.569 | 5.065 | 19.403 | 1.00 | 39.20 | C |
| ATOM | 2506 | C   | GLY | C | 79 | 36.243 | 5.931 | 18.378 | 1.00 | 39.12 | C |
| ATOM | 2507 | O   | GLY | C | 79 | 35.911 | 7.103 | 18.272 | 1.00 | 38.52 | O |
| ATOM | 2508 | N   | THR | C | 80 | 37.125 | 5.335 | 17.584 | 1.00 | 39.32 | N |
| ATOM | 2509 | CA  | THR | C | 80 | 37.814 | 6.062 | 16.539 | 1.00 | 40.74 | C |
| ATOM | 2510 | CB  | THR | C | 80 | 39.345 | 5.858 | 16.627 | 1.00 | 40.22 | C |
| ATOM | 2511 | OG1 | THR | C | 80 | 39.806 | 6.345 | 17.896 | 1.00 | 41.93 | O |
| ATOM | 2512 | CG2 | THR | C | 80 | 40.088 | 6.585 | 15.475 | 1.00 | 39.67 | C |
| ATOM | 2513 | C   | THR | C | 80 | 37.331 | 5.592 | 15.192 | 1.00 | 41.67 | C |
| ATOM | 2514 | O   | THR | C | 80 | 37.464 | 4.406 | 14.867 | 1.00 | 42.93 | O |
| ATOM | 2515 | N   | TYR | C | 81 | 36.797 | 6.532 | 14.413 | 1.00 | 41.16 | N |
| ATOM | 2516 | CA  | TYR | C | 81 | 36.235 | 6.302 | 13.098 | 1.00 | 41.38 | C |
| ATOM | 2517 | CB  | TYR | C | 81 | 34.934 | 7.118 | 12.928 | 1.00 | 41.71 | C |
| ATOM | 2518 | CG  | TYR | C | 81 | 33.832 | 6.627 | 13.831 | 1.00 | 41.50 | C |
| ATOM | 2519 | CD1 | TYR | C | 81 | 32.840 | 5.753 | 13.343 | 1.00 | 42.16 | C |
| ATOM | 2520 | CE1 | TYR | C | 81 | 31.777 | 5.275 | 14.208 | 1.00 | 37.37 | C |
| ATOM | 2521 | CZ  | TYR | C | 81 | 31.752 | 5.716 | 15.516 | 1.00 | 42.71 | C |
| ATOM | 2522 | OH  | TYR | C | 81 | 30.763 | 5.238 | 16.353 | 1.00 | 44.53 | O |
| ATOM | 2523 | CE2 | TYR | C | 81 | 32.747 | 6.575 | 16.023 | 1.00 | 41.06 | C |
| ATOM | 2524 | CD2 | TYR | C | 81 | 33.763 | 7.031 | 15.181 | 1.00 | 40.89 | C |
| ATOM | 2525 | C   | TYR | C | 81 | 37.221 | 6.760 | 12.031 | 1.00 | 41.95 | C |
| ATOM | 2526 | O   | TYR | C | 81 | 37.878 | 7.771 | 12.247 | 1.00 | 42.20 | O |
| ATOM | 2527 | N   | LYS | C | 82 | 37.373 | 5.968 | 10.947 | 1.00 | 41.37 | N |
| ATOM | 2528 | CA  | LYS | C | 82 | 38.121 | 6.382 | 9.764  | 1.00 | 42.18 | C |
| ATOM | 2529 | CB  | LYS | C | 82 | 39.448 | 5.632 | 9.579  | 1.00 | 41.37 | C |
| ATOM | 2530 | CG  | LYS | C | 82 | 40.368 | 5.886 | 10.712 | 1.00 | 46.60 | C |
| ATOM | 2531 | CD  | LYS | C | 82 | 41.821 | 5.742 | 10.339 | 1.00 | 52.93 | C |
| ATOM | 2532 | CE  | LYS | C | 82 | 42.613 | 5.556 | 11.625 | 1.00 | 55.71 | C |
| ATOM | 2533 | NZ  | LYS | C | 82 | 44.075 | 5.483 | 11.354 | 1.00 | 61.02 | N |
| ATOM | 2534 | C   | LYS | C | 82 | 37.281 | 6.164 | 8.540  | 1.00 | 41.18 | C |
| ATOM | 2535 | O   | LYS | C | 82 | 36.568 | 5.188 | 8.473  | 1.00 | 40.69 | O |
| ATOM | 2536 | N   | CYS | C | 83 | 37.420 | 7.065 | 7.587  | 1.00 | 40.93 | N |
| ATOM | 2537 | CA  | CYS | C | 83 | 36.864 | 6.904 | 6.294  | 1.00 | 44.17 | C |
| ATOM | 2538 | CB  | CYS | C | 83 | 36.274 | 8.199 | 5.799  | 1.00 | 43.61 | C |
| ATOM | 2539 | SG  | CYS | C | 83 | 37.465 | 9.490 | 5.676  | 1.00 | 48.89 | S |
| ATOM | 2540 | C   | CYS | C | 83 | 37.964 | 6.491 | 5.319  | 1.00 | 45.48 | C |
| ATOM | 2541 | O   | CYS | C | 83 | 39.145 | 6.776 | 5.525  | 1.00 | 46.68 | O |

APPENDIX I-continued

| ATOM | 2542 | N | GLN | C | 84 | 37.567 | 5.801 | 4.258 | 1.00 | 45.72 | N |
|---|---|---|---|---|---|---|---|---|---|---|---|
| ATOM | 2543 | CA | GLN | C | 84 | 38.485 | 5.529 | 3.193 | 1.00 | 44.76 | C |
| ATOM | 2544 | CB | GLN | C | 84 | 38.975 | 4.074 | 3.282 | 1.00 | 44.52 | C |
| ATOM | 2545 | CG | GLN | C | 84 | 39.885 | 3.726 | 2.122 | 1.00 | 45.70 | C |
| ATOM | 2546 | CD | GLN | C | 84 | 40.912 | 2.652 | 2.388 | 1.00 | 49.09 | C |
| ATOM | 2547 | OE1 | GLN | C | 84 | 42.083 | 2.752 | 1.918 | 1.00 | 52.22 | O |
| ATOM | 2548 | NE2 | GLN | C | 84 | 40.512 | 1.628 | 3.106 | 1.00 | 43.81 | N |
| ATOM | 2549 | C | GLN | C | 84 | 37.809 | 5.818 | 1.886 | 1.00 | 44.70 | C |
| ATOM | 2550 | O | GLN | C | 84 | 36.677 | 5.362 | 1.628 | 1.00 | 45.18 | O |
| ATOM | 2551 | N | ALA | C | 85 | 38.503 | 6.588 | 1.058 | 1.00 | 44.54 | N |
| ATOM | 2552 | CA | ALA | C | 85 | 38.073 | 6.857 | −0.324 | 1.00 | 43.12 | C |
| ATOM | 2553 | CB | ALA | C | 85 | 38.450 | 8.228 | −0.717 | 1.00 | 41.23 | C |
| ATOM | 2554 | C | ALA | C | 85 | 38.750 | 5.826 | −1.261 | 1.00 | 43.54 | C |
| ATOM | 2555 | O | ALA | C | 85 | 40.001 | 5.667 | −1.262 | 1.00 | 42.69 | O |
| ATOM | 2556 | N | PHE | C | 86 | 37.919 | 5.123 | −2.014 | 1.00 | 42.31 | N |
| ATOM | 2557 | CA | PHE | C | 86 | 38.354 | 4.226 | −3.079 | 1.00 | 42.97 | C |
| ATOM | 2558 | CB | PHE | C | 86 | 37.549 | 2.932 | −3.061 | 1.00 | 43.29 | C |
| ATOM | 2559 | CG | PHE | C | 86 | 37.713 | 2.185 | −1.762 | 1.00 | 45.80 | C |
| ATOM | 2560 | CD1 | PHE | C | 86 | 36.695 | 2.201 | −0.782 | 1.00 | 42.22 | C |
| ATOM | 2561 | CE1 | PHE | C | 86 | 36.905 | 1.563 | 0.421 | 1.00 | 42.36 | C |
| ATOM | 2562 | CZ | PHE | C | 86 | 38.101 | 0.899 | 0.668 | 1.00 | 42.36 | C |
| ATOM | 2563 | CE2 | PHE | C | 86 | 39.105 | 0.869 | −0.301 | 1.00 | 42.11 | C |
| ATOM | 2564 | CD2 | PHE | C | 86 | 38.913 | 1.529 | −1.489 | 1.00 | 43.32 | C |
| ATOM | 2565 | C | PHE | C | 86 | 38.206 | 4.860 | −4.425 | 1.00 | 42.06 | C |
| ATOM | 2566 | O | PHE | C | 86 | 37.274 | 5.618 | −4.692 | 1.00 | 41.81 | O |
| ATOM | 2567 | N | TYR | C | 87 | 39.169 | 4.558 | −5.277 | 1.00 | 42.72 | N |
| ATOM | 2568 | CA | TYR | C | 87 | 39.184 | 5.052 | −6.646 | 1.00 | 42.08 | C |
| ATOM | 2569 | CB | TYR | C | 87 | 39.938 | 6.398 | −6.719 | 1.00 | 43.64 | C |
| ATOM | 2570 | CG | TYR | C | 87 | 41.182 | 6.458 | −5.859 | 1.00 | 44.34 | C |
| ATOM | 2571 | CD1 | TYR | C | 87 | 41.161 | 7.043 | −4.589 | 1.00 | 46.58 | C |
| ATOM | 2572 | CE1 | TYR | C | 87 | 42.332 | 7.098 | −3.787 | 1.00 | 46.11 | C |
| ATOM | 2573 | CZ | TYR | C | 87 | 43.502 | 6.541 | −4.268 | 1.00 | 47.59 | C |
| ATOM | 2574 | OH | TYR | C | 87 | 44.668 | 6.553 | −3.504 | 1.00 | 48.00 | O |
| ATOM | 2575 | CE2 | TYR | C | 87 | 43.538 | 5.961 | −5.531 | 1.00 | 47.66 | C |
| ATOM | 2576 | CD2 | TYR | C | 87 | 42.385 | 5.926 | −6.320 | 1.00 | 48.34 | C |
| ATOM | 2577 | C | TYR | C | 87 | 39.850 | 3.971 | −7.494 | 1.00 | 41.63 | C |
| ATOM | 2578 | O | TYR | C | 87 | 40.505 | 3.080 | −6.962 | 1.00 | 40.18 | O |
| ATOM | 2579 | N | VAL | C | 88 | 39.649 | 4.060 | −8.807 | 1.00 | 40.58 | N |
| ATOM | 2580 | CA | VAL | C | 88 | 40.190 | 3.116 | −9.791 | 1.00 | 38.74 | C |
| ATOM | 2581 | CB | VAL | C | 88 | 39.090 | 2.177 | −10.417 | 1.00 | 38.40 | C |
| ATOM | 2582 | CG1 | VAL | C | 88 | 38.522 | 1.217 | −9.367 | 1.00 | 35.07 | C |
| ATOM | 2583 | CG2 | VAL | C | 88 | 37.906 | 2.991 | −11.012 | 1.00 | 37.81 | C |
| ATOM | 2584 | C | VAL | C | 88 | 40.912 | 3.876 | −10.888 | 1.00 | 38.92 | C |
| ATOM | 2585 | O | VAL | C | 88 | 40.597 | 5.063 | −11.145 | 1.00 | 38.50 | O |
| ATOM | 2586 | N | PHE | C | 89 | 41.883 | 3.200 | −11.534 | 1.00 | 37.31 | N |
| ATOM | 2587 | CA | PHE | C | 89 | 42.656 | 3.790 | −12.610 | 1.00 | 36.15 | C |
| ATOM | 2588 | CB | PHE | C | 89 | 43.787 | 4.711 | −12.062 | 1.00 | 36.75 | C |
| ATOM | 2589 | CG | PHE | C | 89 | 44.555 | 4.132 | −10.846 | 1.00 | 36.77 | C |
| ATOM | 2590 | CD1 | PHE | C | 89 | 44.066 | 4.284 | −9.550 | 1.00 | 38.64 | C |
| ATOM | 2591 | CE1 | PHE | C | 89 | 44.743 | 3.751 | −8.429 | 1.00 | 36.48 | C |
| ATOM | 2592 | CZ | PHE | C | 89 | 45.932 | 3.067 | −8.631 | 1.00 | 39.07 | C |
| ATOM | 2593 | CE2 | PHE | C | 89 | 46.401 | 2.894 | −9.914 | 1.00 | 37.47 | C |
| ATOM | 2594 | CD2 | PHE | C | 89 | 45.720 | 3.431 | −11.009 | 1.00 | 35.24 | C |
| ATOM | 2595 | C | PHE | C | 89 | 43.291 | 2.637 | −13.345 | 1.00 | 37.04 | C |
| ATOM | 2596 | O | PHE | C | 89 | 43.464 | 1.544 | −12.808 | 1.00 | 34.79 | O |
| ATOM | 2597 | N | PHE | C | 90 | 43.645 | 2.885 | −14.591 | 1.00 | 36.52 | N |
| ATOM | 2598 | CA | PHE | C | 90 | 44.378 | 1.903 | −15.331 | 1.00 | 37.25 | C |
| ATOM | 2599 | CB | PHE | C | 90 | 44.357 | 2.209 | −16.812 | 1.00 | 36.55 | C |
| ATOM | 2600 | CG | PHE | C | 90 | 43.017 | 1.968 | −17.458 | 1.00 | 35.98 | C |
| ATOM | 2601 | CD1 | PHE | C | 90 | 42.555 | 0.662 | −17.653 | 1.00 | 37.27 | C |
| ATOM | 2602 | CE1 | PHE | C | 90 | 41.365 | 0.403 | −18.313 | 1.00 | 35.06 | C |
| ATOM | 2603 | CZ | PHE | C | 90 | 40.588 | 1.508 | −18.772 | 1.00 | 40.72 | C |
| ATOM | 2604 | CE2 | PHE | C | 90 | 41.050 | 2.842 | −18.572 | 1.00 | 35.96 | C |
| ATOM | 2605 | CD2 | PHE | C | 90 | 42.266 | 3.045 | −17.941 | 1.00 | 30.26 | C |
| ATOM | 2606 | C | PHE | C | 90 | 45.793 | 1.765 | −14.824 | 1.00 | 38.44 | C |
| ATOM | 2607 | O | PHE | C | 90 | 46.373 | 2.754 | −14.304 | 1.00 | 37.09 | O |
| ATOM | 2608 | N | ALA | C | 91 | 46.305 | 0.523 | −14.949 | 1.00 | 38.72 | N |
| ATOM | 2609 | CA | ALA | C | 91 | 47.654 | 0.146 | −14.505 | 1.00 | 40.42 | C |
| ATOM | 2610 | CB | ALA | C | 91 | 47.942 | −1.248 | −14.918 | 1.00 | 39.03 | C |
| ATOM | 2611 | C | ALA | C | 91 | 48.790 | 1.067 | −14.986 | 1.00 | 41.68 | C |
| ATOM | 2612 | O | ALA | C | 91 | 49.730 | 1.312 | −14.221 | 1.00 | 42.62 | O |
| ATOM | 2613 | N | GLU | C | 92 | 48.683 | 1.578 | −16.211 | 1.00 | 42.40 | N |
| ATOM | 2614 | CA | GLU | C | 92 | 49.667 | 2.488 | −16.825 | 1.00 | 45.96 | C |
| ATOM | 2615 | CB | GLU | C | 92 | 49.609 | 2.365 | −18.350 | 1.00 | 46.83 | C |
| ATOM | 2616 | CG | GLU | C | 92 | 49.960 | 0.958 | −18.882 | 1.00 | 54.78 | C |
| ATOM | 2617 | CD | GLU | C | 92 | 51.461 | 0.705 | −19.228 | 1.00 | 65.73 | C |
| ATOM | 2618 | OE1 | GLU | C | 92 | 51.753 | 0.838 | −20.455 | 1.00 | 68.70 | O |
| ATOM | 2619 | OE2 | GLU | C | 92 | 52.324 | 0.333 | −18.328 | 1.00 | 67.00 | O |
| ATOM | 2620 | C | GLU | C | 92 | 49.561 | 3.991 | −16.450 | 1.00 | 46.75 | C |
| ATOM | 2621 | O | GLU | C | 92 | 50.310 | 4.807 | −16.965 | 1.00 | 47.85 | O |

APPENDIX I-continued

| ATOM | 2622 | N   | ASP | C | 93  | 48.622 | 4.360  | -15.586 | 1.00 | 46.84 | N |
|------|------|-----|-----|---|-----|--------|--------|---------|------|-------|---|
| ATOM | 2623 | CA  | ASP | C | 93  | 48.578 | 5.692  | -14.997 | 1.00 | 47.98 | C |
| ATOM | 2624 | CB  | ASP | C | 93  | 47.402 | 5.780  | -14.024 | 1.00 | 48.91 | C |
| ATOM | 2625 | CG  | ASP | C | 93  | 47.048 | 7.201  | -13.702 | 1.00 | 53.37 | C |
| ATOM | 2626 | OD1 | ASP | C | 93  | 47.669 | 7.763  | -12.756 | 1.00 | 59.02 | O |
| ATOM | 2627 | OD2 | ASP | C | 93  | 46.171 | 7.745  | -14.411 | 1.00 | 52.66 | O |
| ATOM | 2628 | C   | ASP | C | 93  | 49.855 | 5.869  | -14.185 | 1.00 | 46.99 | C |
| ATOM | 2629 | O   | ASP | C | 93  | 50.113 | 5.046  | -13.293 | 1.00 | 48.62 | O |
| ATOM | 2630 | N   | VAL | C | 94  | 50.638 | 6.908  | -14.499 | 1.00 | 43.77 | N |
| ATOM | 2631 | CA  | VAL | C | 94  | 51.934 | 7.192  | -13.906 | 1.00 | 40.69 | C |
| ATOM | 2632 | CB  | VAL | C | 94  | 53.120 | 6.915  | -14.893 | 1.00 | 40.79 | C |
| ATOM | 2633 | CG1 | VAL | C | 94  | 52.921 | 7.686  | -16.247 | 1.00 | 38.04 | C |
| ATOM | 2634 | CG2 | VAL | C | 94  | 53.260 | 5.446  | -15.184 | 1.00 | 38.24 | C |
| ATOM | 2635 | C   | VAL | C | 94  | 51.966 | 8.674  | -13.471 | 1.00 | 40.53 | C |
| ATOM | 2636 | O   | VAL | C | 94  | 51.209 | 9.479  | -13.973 | 1.00 | 39.56 | O |
| ATOM | 2637 | N   | GLY | C | 95  | 52.867 | 9.022  | -12.553 | 1.00 | 40.49 | N |
| ATOM | 2638 | CA  | GLY | C | 95  | 53.050 | 10.415 | -12.093 | 1.00 | 38.78 | C |
| ATOM | 2639 | C   | GLY | C | 95  | 52.272 | 10.847 | -10.852 | 1.00 | 38.81 | C |
| ATOM | 2640 | O   | GLY | C | 95  | 52.535 | 11.890 | -10.335 | 1.00 | 40.05 | O |
| ATOM | 2641 | N   | SER | C | 96  | 51.312 | 10.069 | -10.362 | 1.00 | 37.58 | N |
| ATOM | 2642 | CA  | SER | C | 96  | 50.546 | 10.497 | -9.227  | 1.00 | 39.65 | C |
| ATOM | 2643 | CB  | SER | C | 96  | 49.053 | 10.780 | -9.608  | 1.00 | 39.56 | C |
| ATOM | 2644 | OG  | SER | C | 96  | 49.035 | 11.894 | -10.504 | 1.00 | 43.48 | O |
| ATOM | 2645 | C   | SER | C | 96  | 50.567 | 9.465  | -8.136  | 1.00 | 39.35 | C |
| ATOM | 2646 | O   | SER | C | 96  | 50.517 | 8.279  | -8.401  | 1.00 | 39.38 | O |
| ATOM | 2647 | N   | ASN | C | 97  | 50.640 | 9.963  | -6.915  | 1.00 | 39.49 | N |
| ATOM | 2648 | CA  | ASN | C | 97  | 50.421 | 9.178  | -5.740  | 1.00 | 40.25 | C |
| ATOM | 2649 | CB  | ASN | C | 97  | 50.339 | 10.076 | -4.528  | 1.00 | 38.65 | C |
| ATOM | 2650 | CG  | ASN | C | 97  | 50.340 | 9.274  | -3.160  | 1.00 | 44.04 | C |
| ATOM | 2651 | OD1 | ASN | C | 97  | 50.540 | 9.865  | -2.086  | 1.00 | 43.90 | O |
| ATOM | 2652 | ND2 | ASN | C | 97  | 50.135 | 7.962  | -3.221  | 1.00 | 43.78 | N |
| ATOM | 2653 | C   | ASN | C | 97  | 49.107 | 8.442  | -5.898  | 1.00 | 38.81 | C |
| ATOM | 2654 | O   | ASN | C | 97  | 48.018 | 9.028  | -5.895  | 1.00 | 39.38 | O |
| ATOM | 2655 | N   | LYS | C | 98  | 49.235 | 7.141  | -5.999  | 1.00 | 38.34 | N |
| ATOM | 2656 | CA  | LYS | C | 98  | 48.109 | 6.210  | -6.077  | 1.00 | 37.85 | C |
| ATOM | 2657 | CB  | LYS | C | 98  | 48.641 | 4.910  | -6.704  | 1.00 | 37.89 | C |
| ATOM | 2658 | CG  | LYS | C | 98  | 49.077 | 5.156  | -8.197  | 1.00 | 34.79 | C |
| ATOM | 2659 | CD  | LYS | C | 98  | 49.488 | 3.865  | -8.838  | 1.00 | 40.63 | C |
| ATOM | 2660 | CE  | LYS | C | 98  | 49.867 | 4.054  | -10.316 | 1.00 | 40.81 | C |
| ATOM | 2661 | NZ  | LYS | C | 98  | 51.073 | 4.918  | -10.448 | 1.00 | 38.45 | N |
| ATOM | 2662 | C   | LYS | C | 98  | 47.375 | 5.892  | -4.755  | 1.00 | 39.19 | C |
| ATOM | 2663 | O   | LYS | C | 98  | 46.408 | 5.154  | -4.777  | 1.00 | 38.96 | O |
| ATOM | 2664 | N   | GLY | C | 99  | 47.858 | 6.420  | -3.636  | 1.00 | 38.59 | N |
| ATOM | 2665 | CA  | GLY | C | 99  | 47.449 | 5.964  | -2.296  | 1.00 | 40.76 | C |
| ATOM | 2666 | C   | GLY | C | 99  | 47.880 | 4.530  | -2.081  | 1.00 | 41.30 | C |
| ATOM | 2667 | O   | GLY | C | 99  | 48.795 | 4.036  | -2.767  | 1.00 | 43.80 | O |
| ATOM | 2668 | N   | ALA | C | 100 | 47.248 | 3.856  | -1.143  | 1.00 | 40.11 | N |
| ATOM | 2669 | CA  | ALA | C | 100 | 47.560 | 2.475  | -0.883  | 1.00 | 39.38 | C |
| ATOM | 2670 | CB  | ALA | C | 100 | 46.860 | 2.024  | 0.434   | 1.00 | 39.23 | C |
| ATOM | 2671 | C   | ALA | C | 100 | 46.989 | 1.713  | -2.025  | 1.00 | 39.51 | C |
| ATOM | 2672 | O   | ALA | C | 100 | 45.893 | 2.022  | -2.468  | 1.00 | 39.92 | O |
| ATOM | 2673 | N   | ILE | C | 101 | 47.710 | 0.705  | -2.490  | 1.00 | 39.69 | N |
| ATOM | 2674 | CA  | ILE | C | 101 | 47.214 | -0.164 | -3.542  | 1.00 | 39.24 | C |
| ATOM | 2675 | CB  | ILE | C | 101 | 48.382 | -0.869 | -4.334  | 1.00 | 39.71 | C |
| ATOM | 2676 | CG1 | ILE | C | 101 | 49.331 | 0.190  | -5.017  | 1.00 | 39.84 | C |
| ATOM | 2677 | CD1 | ILE | C | 101 | 48.627 | 1.159  | -5.924  | 1.00 | 36.72 | C |
| ATOM | 2678 | CG2 | ILE | C | 101 | 47.804 | -1.860 | -5.378  | 1.00 | 35.43 | C |
| ATOM | 2679 | C   | ILE | C | 101 | 46.322 | -1.192 | -2.832  | 1.00 | 40.48 | C |
| ATOM | 2680 | O   | ILE | C | 101 | 46.747 | -1.835 | -1.875  | 1.00 | 39.46 | O |
| ATOM | 2681 | N   | ILE | C | 102 | 45.077 | -1.290 | -3.277  | 1.00 | 41.20 | N |
| ATOM | 2682 | CA  | ILE | C | 102 | 44.077 | -2.062 | -2.594  | 1.00 | 42.13 | C |
| ATOM | 2683 | CB  | ILE | C | 102 | 42.722 | -1.275 | -2.453  | 1.00 | 42.58 | C |
| ATOM | 2684 | CG1 | ILE | C | 102 | 42.912 | -0.020 | -1.630  | 1.00 | 42.57 | C |
| ATOM | 2685 | CD1 | ILE | C | 102 | 43.084 | -0.204 | -0.096  | 1.00 | 41.89 | C |
| ATOM | 2686 | CG2 | ILE | C | 102 | 41.542 | -2.148 | -1.947  | 1.00 | 42.41 | C |
| ATOM | 2687 | C   | ILE | C | 102 | 43.887 | -3.331 | -3.396  | 1.00 | 41.41 | C |
| ATOM | 2688 | O   | ILE | C | 102 | 43.698 | -4.376 | -2.821  | 1.00 | 42.57 | O |
| ATOM | 2689 | N   | GLY | C | 103 | 43.942 | -3.261 | -4.715  | 1.00 | 40.57 | N |
| ATOM | 2690 | CA  | GLY | C | 103 | 43.742 | -4.479 | -5.498  | 1.00 | 38.60 | C |
| ATOM | 2691 | C   | GLY | C | 103 | 44.033 | -4.305 | -6.974  | 1.00 | 37.22 | C |
| ATOM | 2692 | O   | GLY | C | 103 | 44.253 | -3.238 | -7.441  | 1.00 | 37.08 | O |
| ATOM | 2693 | N   | LEU | C | 104 | 44.060 | -5.393 | -7.704  | 1.00 | 38.36 | N |
| ATOM | 2694 | CA  | LEU | C | 104 | 44.255 | -5.381 | -9.148  | 1.00 | 39.71 | C |
| ATOM | 2695 | CB  | LEU | C | 104 | 45.653 | -5.917 | -9.493  | 1.00 | 39.02 | C |
| ATOM | 2696 | CG  | LEU | C | 104 | 46.002 | -6.069 | -10.973 | 1.00 | 40.16 | C |
| ATOM | 2697 | CD1 | LEU | C | 104 | 45.968 | -4.664 | -11.690 | 1.00 | 34.76 | C |
| ATOM | 2698 | CD2 | LEU | C | 104 | 47.334 | -6.727 | -11.161 | 1.00 | 38.01 | C |
| ATOM | 2699 | C   | LEU | C | 104 | 43.142 | -6.283 | -9.728  | 1.00 | 41.24 | C |
| ATOM | 2700 | O   | LEU | C | 104 | 42.985 | -7.408 | -9.276  | 1.00 | 38.88 | O |
| ATOM | 2701 | N   | MET | C | 105 | 42.368 | -5.743 | -10.678 | 1.00 | 43.67 | N |

APPENDIX I-continued

| ATOM | 2702 | CA | MET | C | 105 | 41.297 | −6.447 | −11.366 | 1.00 | 47.58 | C |
|---|---|---|---|---|---|---|---|---|---|---|---|
| ATOM | 2703 | CB | MET | C | 105 | 40.101 | −5.568 | −11.687 | 1.00 | 47.39 | C |
| ATOM | 2704 | CG | MET | C | 105 | 39.496 | −4.652 | −10.666 | 1.00 | 50.10 | C |
| ATOM | 2705 | SD | MET | C | 105 | 37.752 | −4.217 | −11.239 | 1.00 | 57.87 | S |
| ATOM | 2706 | CE | MET | C | 105 | 37.532 | −4.959 | −12.846 | 1.00 | 54.27 | C |
| ATOM | 2707 | C | MET | C | 105 | 41.835 | −6.794 | −12.704 | 1.00 | 47.26 | C |
| ATOM | 2708 | O | MET | C | 105 | 42.684 | −6.094 | −13.231 | 1.00 | 47.11 | O |
| ATOM | 2709 | N | VAL | C | 106 | 41.329 | −7.879 | −13.266 | 1.00 | 48.20 | N |
| ATOM | 2710 | CA | VAL | C | 106 | 41.630 | −8.250 | −14.630 | 1.00 | 49.68 | C |
| ATOM | 2711 | CB | VAL | C | 106 | 41.031 | −9.665 | −14.914 | 1.00 | 50.52 | C |
| ATOM | 2712 | CG1 | VAL | C | 106 | 41.298 | −10.144 | −16.355 | 1.00 | 51.88 | C |
| ATOM | 2713 | CG2 | VAL | C | 106 | 41.664 | −10.679 | −13.916 | 1.00 | 51.57 | C |
| ATOM | 2714 | C | VAL | C | 106 | 41.214 | −7.095 | −15.602 | 1.00 | 48.70 | C |
| ATOM | 2715 | O | VAL | C | 106 | 40.269 | −6.361 | −15.355 | 1.00 | 49.46 | O |
| ATOM | 2716 | N | GLY | C | 107 | 42.012 | −6.859 | −16.629 | 1.00 | 48.36 | N |
| ATOM | 2717 | CA | GLY | C | 107 | 41.763 | −5.713 | −17.516 | 1.00 | 47.26 | C |
| ATOM | 2718 | C | GLY | C | 107 | 42.676 | −4.536 | −17.234 | 1.00 | 45.75 | C |
| ATOM | 2719 | O | GLY | C | 107 | 42.501 | −3.459 | −17.799 | 1.00 | 46.81 | O |
| ATOM | 2720 | N | GLY | C | 108 | 43.627 | −4.736 | −16.328 | 1.00 | 43.80 | N |
| ATOM | 2721 | CA | GLY | C | 108 | 44.597 | −3.735 | −15.974 | 1.00 | 42.42 | C |
| ATOM | 2722 | C | GLY | C | 108 | 44.050 | −2.585 | −15.171 | 1.00 | 41.50 | C |
| ATOM | 2723 | O | GLY | C | 108 | 44.487 | −1.448 | −15.371 | 1.00 | 43.12 | O |
| ATOM | 2724 | N | VAL | C | 109 | 43.083 | −2.852 | −14.304 | 1.00 | 39.69 | N |
| ATOM | 2725 | CA | VAL | C | 109 | 42.387 | −1.806 | −13.556 | 1.00 | 37.50 | C |
| ATOM | 2726 | CB | VAL | C | 109 | 40.845 | −1.962 | −13.644 | 1.00 | 37.78 | C |
| ATOM | 2727 | CG1 | VAL | C | 109 | 40.292 | −1.715 | −15.041 | 1.00 | 32.98 | C |
| ATOM | 2728 | CG2 | VAL | C | 109 | 40.105 | −1.033 | −12.610 | 1.00 | 35.07 | C |
| ATOM | 2729 | C | VAL | C | 109 | 42.802 | −1.942 | −12.103 | 1.00 | 38.36 | C |
| ATOM | 2730 | O | VAL | C | 109 | 42.639 | −3.027 | −11.512 | 1.00 | 36.60 | O |
| ATOM | 2731 | N | VAL | C | 110 | 43.336 | −0.870 | −11.513 | 1.00 | 37.27 | N |
| ATOM | 2732 | CA | VAL | C | 110 | 43.845 | −0.955 | −10.160 | 1.00 | 37.80 | C |
| ATOM | 2733 | CB | VAL | C | 110 | 45.245 | −0.371 | −10.070 | 1.00 | 38.39 | C |
| ATOM | 2734 | CG1 | VAL | C | 110 | 46.115 | −1.019 | −11.123 | 1.00 | 35.91 | C |
| ATOM | 2735 | CG2 | VAL | C | 110 | 45.851 | −0.565 | −8.672 | 1.00 | 34.68 | C |
| ATOM | 2736 | C | VAL | C | 110 | 42.897 | −0.237 | −9.248 | 1.00 | 39.02 | C |
| ATOM | 2737 | O | VAL | C | 110 | 42.247 | 0.697 | −9.695 | 1.00 | 38.55 | O |
| ATOM | 2738 | N | ILE | C | 111 | 42.743 | −0.718 | −8.010 | 1.00 | 39.64 | N |
| ATOM | 2739 | CA | ILE | C | 111 | 41.985 | −0.007 | −6.976 | 1.00 | 40.38 | C |
| ATOM | 2740 | CB | ILE | C | 111 | 41.039 | −0.966 | −6.233 | 1.00 | 40.84 | C |
| ATOM | 2741 | CG1 | ILE | C | 111 | 40.202 | −1.806 | −7.257 | 1.00 | 43.74 | C |
| ATOM | 2742 | CD1 | ILE | C | 111 | 39.645 | −3.116 | −6.586 | 1.00 | 44.34 | C |
| ATOM | 2743 | CG2 | ILE | C | 111 | 40.111 | −0.240 | −5.264 | 1.00 | 40.12 | C |
| ATOM | 2744 | C | ILE | C | 111 | 42.995 | 0.553 | −6.005 | 1.00 | 40.90 | C |
| ATOM | 2745 | O | ILE | C | 111 | 43.911 | −0.155 | −5.522 | 1.00 | 40.15 | O |
| ATOM | 2746 | N | GLY | C | 112 | 42.870 | 1.839 | −5.722 | 1.00 | 41.79 | N |
| ATOM | 2747 | CA | GLY | C | 112 | 43.727 | 2.465 | −4.695 | 1.00 | 41.67 | C |
| ATOM | 2748 | C | GLY | C | 112 | 42.804 | 3.024 | −3.631 | 1.00 | 42.53 | C |
| ATOM | 2749 | O | GLY | C | 112 | 41.599 | 3.097 | −3.837 | 1.00 | 42.69 | O |
| ATOM | 2750 | N | GLY | C | 113 | 43.352 | 3.378 | −2.479 | 1.00 | 42.32 | N |
| ATOM | 2751 | CA | GLY | C | 113 | 42.544 | 3.983 | −1.444 | 1.00 | 42.68 | C |
| ATOM | 2752 | C | GLY | C | 113 | 43.431 | 4.872 | −0.602 | 1.00 | 43.14 | C |
| ATOM | 2753 | O | GLY | C | 113 | 44.645 | 4.595 | −0.482 | 1.00 | 42.77 | O |
| ATOM | 2754 | N | GLU | C | 114 | 42.829 | 5.961 | −0.105 | 1.00 | 43.84 | N |
| ATOM | 2755 | CA | GLU | C | 114 | 43.389 | 6.874 | 0.895 | 1.00 | 45.57 | C |
| ATOM | 2756 | CB | GLU | C | 114 | 43.530 | 8.314 | 0.328 | 1.00 | 46.12 | C |
| ATOM | 2757 | CG | GLU | C | 114 | 44.677 | 8.540 | −0.659 | 1.00 | 48.41 | C |
| ATOM | 2758 | CD | GLU | C | 114 | 46.012 | 8.648 | 0.104 | 1.00 | 53.32 | C |
| ATOM | 2759 | OE1 | GLU | C | 114 | 45.961 | 8.894 | 1.318 | 1.00 | 54.08 | O |
| ATOM | 2760 | OE2 | GLU | C | 114 | 47.105 | 8.460 | −0.484 | 1.00 | 53.74 | O |
| ATOM | 2761 | C | GLU | C | 114 | 42.434 | 6.922 | 2.110 | 1.00 | 45.53 | C |
| ATOM | 2762 | O | GLU | C | 114 | 41.258 | 7.185 | 1.933 | 1.00 | 44.18 | O |
| ATOM | 2763 | N | LYS | C | 115 | 42.973 | 6.750 | 3.330 | 1.00 | 45.32 | N |
| ATOM | 2764 | CA | LYS | C | 115 | 42.202 | 6.844 | 4.591 | 1.00 | 44.84 | C |
| ATOM | 2765 | CB | LYS | C | 115 | 42.676 | 5.771 | 5.567 | 1.00 | 46.12 | C |
| ATOM | 2766 | CG | LYS | C | 115 | 42.435 | 4.362 | 5.125 | 1.00 | 51.00 | C |
| ATOM | 2767 | CD | LYS | C | 115 | 42.795 | 3.392 | 6.277 | 1.00 | 58.28 | C |
| ATOM | 2768 | CE | LYS | C | 115 | 41.567 | 2.885 | 7.055 | 1.00 | 57.90 | C |
| ATOM | 2769 | NZ | LYS | C | 115 | 41.949 | 1.742 | 8.016 | 1.00 | 54.76 | N |
| ATOM | 2770 | C | LYS | C | 115 | 42.365 | 8.197 | 5.290 | 1.00 | 44.22 | C |
| ATOM | 2771 | O | LYS | C | 115 | 43.431 | 8.823 | 5.252 | 1.00 | 43.62 | O |
| ATOM | 2772 | N | GLY | C | 116 | 41.305 | 8.645 | 5.954 | 1.00 | 43.05 | N |
| ATOM | 2773 | CA | GLY | C | 116 | 41.356 | 9.864 | 6.689 | 1.00 | 42.05 | C |
| ATOM | 2774 | C | GLY | C | 116 | 42.174 | 9.631 | 7.930 | 1.00 | 42.35 | C |
| ATOM | 2775 | O | GLY | C | 116 | 42.452 | 8.484 | 8.287 | 1.00 | 42.05 | O |
| ATOM | 2776 | N | ALA | C | 117 | 42.571 | 10.708 | 8.596 | 1.00 | 42.37 | N |
| ATOM | 2777 | CA | ALA | C | 117 | 43.399 | 10.550 | 9.757 | 1.00 | 43.05 | C |
| ATOM | 2778 | CB | ALA | C | 117 | 44.260 | 11.829 | 10.014 | 1.00 | 42.67 | C |
| ATOM | 2779 | C | ALA | C | 117 | 42.634 | 10.084 | 11.023 | 1.00 | 43.56 | C |
| ATOM | 2780 | O | ALA | C | 117 | 43.246 | 9.826 | 12.055 | 1.00 | 43.65 | O |
| ATOM | 2781 | N | GLY | C | 118 | 41.314 | 9.951 | 10.965 | 1.00 | 43.66 | N |

APPENDIX I-continued

| | | | | | | | | | | | |
|---|---|---|---|---|---|---|---|---|---|---|---|
| ATOM | 2782 | CA | GLY | C | 118 | 40.611 | 9.472 | 12.152 | 1.00 | 42.79 | C |
| ATOM | 2783 | C | GLY | C | 118 | 39.896 | 10.562 | 12.934 | 1.00 | 41.73 | C |
| ATOM | 2784 | O | GLY | C | 118 | 40.354 | 11.701 | 12.976 | 1.00 | 40.92 | O |
| ATOM | 2785 | N | THR | C | 119 | 38.743 | 10.194 | 13.496 | 1.00 | 39.98 | N |
| ATOM | 2786 | CA | THR | C | 119 | 37.946 | 11.020 | 14.384 | 1.00 | 38.58 | C |
| ATOM | 2787 | CB | THR | C | 119 | 36.488 | 11.253 | 13.783 | 1.00 | 39.57 | C |
| ATOM | 2788 | OG1 | THR | C | 119 | 36.588 | 12.076 | 12.602 | 1.00 | 38.54 | O |
| ATOM | 2789 | CG2 | THR | C | 119 | 35.520 | 11.976 | 14.801 | 1.00 | 36.85 | C |
| ATOM | 2790 | C | THR | C | 119 | 37.848 | 10.245 | 15.679 | 1.00 | 38.20 | C |
| ATOM | 2791 | O | THR | C | 119 | 37.235 | 9.181 | 15.707 | 1.00 | 38.00 | O |
| ATOM | 2792 | N | ALA | C | 120 | 38.444 | 10.762 | 16.760 | 1.00 | 39.02 | N |
| ATOM | 2793 | CA | ALA | C | 120 | 38.267 | 10.190 | 18.104 | 1.00 | 38.01 | C |
| ATOM | 2794 | CB | ALA | C | 120 | 39.460 | 10.554 | 19.000 | 1.00 | 37.67 | C |
| ATOM | 2795 | C | ALA | C | 120 | 36.956 | 10.710 | 18.698 | 1.00 | 38.14 | C |
| ATOM | 2796 | O | ALA | C | 120 | 36.900 | 11.849 | 19.022 | 1.00 | 38.99 | O |
| ATOM | 2797 | N | LEU | C | 121 | 35.904 | 9.888 | 18.786 | 1.00 | 37.88 | N |
| ATOM | 2798 | CA | LEU | C | 121 | 34.606 | 10.267 | 19.338 | 1.00 | 37.54 | C |
| ATOM | 2799 | CB | LEU | C | 121 | 33.405 | 9.771 | 18.456 | 1.00 | 37.32 | C |
| ATOM | 2800 | CG | LEU | C | 121 | 32.005 | 9.892 | 19.096 | 1.00 | 36.95 | C |
| ATOM | 2801 | CD1 | LEU | C | 121 | 31.645 | 11.412 | 19.345 | 1.00 | 30.48 | C |
| ATOM | 2802 | CD2 | LEU | C | 121 | 30.953 | 9.178 | 18.323 | 1.00 | 36.88 | C |
| ATOM | 2803 | C | LEU | C | 121 | 34.449 | 9.684 | 20.736 | 1.00 | 39.77 | C |
| ATOM | 2804 | O | LEU | C | 121 | 34.550 | 8.474 | 20.921 | 1.00 | 39.94 | O |
| ATOM | 2805 | N | THR | C | 122 | 34.231 | 10.558 | 21.715 | 1.00 | 39.58 | N |
| ATOM | 2806 | CA | THR | C | 122 | 33.743 | 10.128 | 23.012 | 1.00 | 42.41 | C |
| ATOM | 2807 | CB | THR | C | 122 | 34.744 | 10.283 | 24.221 | 1.00 | 42.49 | C |
| ATOM | 2808 | OG1 | THR | C | 122 | 34.066 | 10.807 | 25.351 | 1.00 | 47.39 | O |
| ATOM | 2809 | CG2 | THR | C | 122 | 35.975 | 11.103 | 23.923 | 1.00 | 44.50 | C |
| ATOM | 2810 | C | THR | C | 122 | 32.368 | 10.695 | 23.269 | 1.00 | 41.60 | C |
| ATOM | 2811 | O | THR | C | 122 | 32.115 | 11.879 | 22.992 | 1.00 | 40.70 | O |
| ATOM | 2812 | N | VAL | C | 123 | 31.465 | 9.800 | 23.664 | 1.00 | 41.20 | N |
| ATOM | 2813 | CA | VAL | C | 123 | 30.065 | 10.141 | 23.928 | 1.00 | 41.97 | C |
| ATOM | 2814 | CB | VAL | C | 123 | 29.040 | 9.174 | 23.218 | 1.00 | 41.64 | C |
| ATOM | 2815 | CG1 | VAL | C | 123 | 27.572 | 9.521 | 23.597 | 1.00 | 38.86 | C |
| ATOM | 2816 | CG2 | VAL | C | 123 | 29.222 | 9.177 | 21.701 | 1.00 | 36.97 | C |
| ATOM | 2817 | C | VAL | C | 123 | 29.901 | 10.060 | 25.442 | 1.00 | 43.60 | C |
| ATOM | 2818 | O | VAL | C | 123 | 30.189 | 9.036 | 26.029 | 1.00 | 43.27 | O |
| ATOM | 2819 | N | LYS | C | 124 | 29.459 | 11.137 | 26.070 | 1.00 | 46.27 | N |
| ATOM | 2820 | CA | LYS | C | 124 | 29.335 | 11.162 | 27.519 | 1.00 | 50.07 | C |
| ATOM | 2821 | CB | LYS | C | 124 | 29.566 | 12.574 | 28.019 | 1.00 | 51.04 | C |
| ATOM | 2822 | CG | LYS | C | 124 | 30.992 | 13.088 | 27.721 | 1.00 | 55.46 | C |
| ATOM | 2823 | CD | LYS | C | 124 | 31.184 | 14.509 | 28.264 | 1.00 | 62.63 | C |
| ATOM | 2824 | CE | LYS | C | 124 | 30.287 | 15.512 | 27.491 | 1.00 | 64.83 | C |
| ATOM | 2825 | NZ | LYS | C | 124 | 30.202 | 16.850 | 28.169 | 1.00 | 67.51 | N |
| ATOM | 2826 | C | LYS | C | 124 | 27.960 | 10.729 | 27.900 | 1.00 | 51.41 | C |
| ATOM | 2827 | O | LYS | C | 124 | 27.006 | 11.094 | 27.223 | 1.00 | 53.12 | O |
| ATOM | 2828 | N | ALA | C | 125 | 27.857 | 9.965 | 28.982 | 1.00 | 53.39 | N |
| ATOM | 2829 | CA | ALA | C | 125 | 26.584 | 9.427 | 29.504 | 1.00 | 55.35 | C |
| ATOM | 2830 | CB | ALA | C | 125 | 26.828 | 8.627 | 30.778 | 1.00 | 54.28 | C |
| ATOM | 2831 | C | ALA | C | 125 | 25.485 | 10.460 | 29.739 | 1.00 | 57.36 | C |
| ATOM | 2832 | O | ALA | C | 125 | 25.745 | 11.656 | 29.989 | 1.00 | 56.29 | O |
| ATOM | 2833 | N | ALA | C | 126 | 24.240 | 9.987 | 29.654 | 1.00 | 60.08 | N |
| ATOM | 2834 | CA | ALA | C | 126 | 23.084 | 10.865 | 29.877 | 1.00 | 62.33 | C |
| ATOM | 2835 | CB | ALA | C | 126 | 21.766 | 10.076 | 29.780 | 1.00 | 62.64 | C |
| ATOM | 2836 | C | ALA | C | 126 | 23.246 | 11.540 | 31.244 | 1.00 | 63.68 | C |
| ATOM | 2837 | O | ALA | C | 126 | 23.436 | 10.871 | 32.272 | 1.00 | 64.15 | O |
| ATOM | 2838 | OXT | ALA | C | 126 | 23.253 | 12.783 | 31.350 | 1.00 | 65.04 | O |
| ATOM | 2839 | N | ALA | D | 1 | 46.173 | −30.720 | −12.181 | 1.00 | 52.41 | N |
| ATOM | 2840 | CA | ALA | D | 1 | 47.352 | −29.997 | −11.635 | 1.00 | 52.38 | C |
| ATOM | 2841 | CB | ALA | D | 1 | 47.073 | −28.463 | −11.586 | 1.00 | 52.73 | C |
| ATOM | 2842 | C | ALA | D | 1 | 47.756 | −30.484 | −10.247 | 1.00 | 52.06 | C |
| ATOM | 2843 | O | ALA | D | 1 | 47.324 | −29.889 | −9.245 | 1.00 | 52.92 | O |
| ATOM | 2844 | N | TRP | D | 2 | 48.618 | −31.503 | −10.174 | 1.00 | 50.77 | N |
| ATOM | 2845 | CA | TRP | D | 2 | 49.207 | −31.901 | −8.886 | 1.00 | 49.15 | C |
| ATOM | 2846 | CB | TRP | D | 2 | 48.379 | −33.027 | −8.243 | 1.00 | 49.04 | C |
| ATOM | 2847 | CG | TRP | D | 2 | 48.455 | −34.342 | −8.948 | 1.00 | 48.39 | C |
| ATOM | 2848 | CD1 | TRP | D | 2 | 47.909 | −34.665 | −10.162 | 1.00 | 48.80 | C |
| ATOM | 2849 | NE1 | TRP | D | 2 | 48.181 | −35.993 | −10.473 | 1.00 | 47.88 | N |
| ATOM | 2850 | CE2 | TRP | D | 2 | 48.915 | −36.540 | −9.456 | 1.00 | 48.78 | C |
| ATOM | 2851 | CD2 | TRP | D | 2 | 49.105 | −35.532 | −8.474 | 1.00 | 48.50 | C |
| ATOM | 2852 | CE3 | TRP | D | 2 | 49.816 | −35.851 | −7.312 | 1.00 | 49.44 | C |
| ATOM | 2853 | CZ3 | TRP | D | 2 | 50.318 | −37.152 | −7.169 | 1.00 | 48.14 | C |
| ATOM | 2854 | CH2 | TRP | D | 2 | 50.130 | −38.111 | −8.167 | 1.00 | 48.46 | C |
| ATOM | 2855 | CZ2 | TRP | D | 2 | 49.430 | −37.833 | −9.311 | 1.00 | 48.68 | C |
| ATOM | 2856 | C | TRP | D | 2 | 50.692 | −32.283 | −8.969 | 1.00 | 48.37 | C |
| ATOM | 2857 | O | TRP | D | 2 | 51.129 | −32.808 | −9.982 | 1.00 | 47.97 | O |
| ATOM | 2858 | N | VAL | D | 3 | 51.447 | −32.014 | −7.892 | 1.00 | 47.21 | N |
| ATOM | 2859 | CA | VAL | D | 3 | 52.880 | −32.359 | −7.783 | 1.00 | 46.09 | C |
| ATOM | 2860 | CB | VAL | D | 3 | 53.713 | −31.248 | −7.051 | 1.00 | 45.63 | C |
| ATOM | 2861 | CG1 | VAL | D | 3 | 55.086 | −31.739 | −6.681 | 1.00 | 45.70 | C |

APPENDIX I-continued

| | | | | | | | | | | |
|---|---|---|---|---|---|---|---|---|---|---|
| ATOM | 2862 | CG2 | VAL | D | 3 | 53.857 | −30.036 | −7.931 | 1.00 | 45.94 C |
| ATOM | 2863 | C | VAL | D | 3 | 53.042 | −33.724 | −7.090 | 1.00 | 45.51 C |
| ATOM | 2864 | O | VAL | D | 3 | 52.541 | −33.953 | −5.995 | 1.00 | 45.34 O |
| ATOM | 2865 | N | ASP | D | 4 | 53.726 | −34.629 | −7.766 | 1.00 | 44.30 N |
| ATOM | 2866 | CA | ASP | D | 4 | 53.861 | −36.002 | −7.344 | 1.00 | 43.85 C |
| ATOM | 2867 | CB | ASP | D | 4 | 53.638 | −36.897 | −8.574 | 1.00 | 43.56 C |
| ATOM | 2868 | CG | ASP | D | 4 | 53.731 | −38.385 | −8.283 | 1.00 | 46.38 C |
| ATOM | 2869 | OD1 | ASP | D | 4 | 53.456 | −39.152 | −9.224 | 1.00 | 48.84 O |
| ATOM | 2870 | OD2 | ASP | D | 4 | 54.085 | −38.824 | −7.165 | 1.00 | 49.73 O |
| ATOM | 2871 | C | ASP | D | 4 | 55.282 | −36.096 | −6.773 | 1.00 | 42.85 C |
| ATOM | 2872 | O | ASP | D | 4 | 56.260 | −36.173 | −7.527 | 1.00 | 43.36 O |
| ATOM | 2873 | N | GLN | D | 5 | 55.399 | −36.044 | −5.450 | 1.00 | 40.53 N |
| ATOM | 2874 | CA | GLN | D | 5 | 56.695 | −36.068 | −4.816 | 1.00 | 39.40 C |
| ATOM | 2875 | CB | GLN | D | 5 | 56.769 | −34.988 | −3.723 | 1.00 | 38.84 C |
| ATOM | 2876 | CG | GLN | D | 5 | 58.080 | −34.973 | −2.919 | 1.00 | 37.60 C |
| ATOM | 2877 | CD | GLN | D | 5 | 58.067 | −33.903 | −1.836 | 1.00 | 40.37 C |
| ATOM | 2878 | OE1 | GLN | D | 5 | 57.169 | −33.053 | −1.805 | 1.00 | 39.68 O |
| ATOM | 2879 | NE2 | GLN | D | 5 | 59.067 | −33.928 | −0.944 | 1.00 | 37.57 N |
| ATOM | 2880 | C | GLN | D | 5 | 56.978 | −37.445 | −4.208 | 1.00 | 39.58 C |
| ATOM | 2881 | O | GLN | D | 5 | 56.165 | −37.959 | −3.443 | 1.00 | 39.26 O |
| ATOM | 2882 | N | THR | D | 6 | 58.153 | −37.997 | −4.531 | 1.00 | 39.50 N |
| ATOM | 2883 | CA | THR | D | 6 | 58.650 | −39.281 | −4.032 | 1.00 | 39.81 C |
| ATOM | 2884 | CB | THR | D | 6 | 58.637 | −40.379 | −5.152 | 1.00 | 39.82 C |
| ATOM | 2885 | OG1 | THR | D | 6 | 59.280 | −39.861 | −6.318 | 1.00 | 41.35 O |
| ATOM | 2886 | CG2 | THR | D | 6 | 57.202 | −40.812 | −5.536 | 1.00 | 41.10 C |
| ATOM | 2887 | C | THR | D | 6 | 60.103 | −39.129 | −3.536 | 1.00 | 39.11 C |
| ATOM | 2888 | O | THR | D | 6 | 60.846 | −38.306 | −4.047 | 1.00 | 38.91 O |
| ATOM | 2889 | N | PRO | D | 7 | 60.509 | −39.925 | −2.532 | 1.00 | 38.82 N |
| ATOM | 2890 | CA | PRO | D | 7 | 59.674 | −40.854 | −1.771 | 1.00 | 38.84 C |
| ATOM | 2891 | CB | PRO | D | 7 | 60.708 | −41.859 | −1.250 | 1.00 | 39.29 C |
| ATOM | 2892 | CG | PRO | D | 7 | 61.982 | −40.990 | −1.047 | 1.00 | 38.10 C |
| ATOM | 2893 | CD | PRO | D | 7 | 61.918 | −39.932 | −2.080 | 1.00 | 38.51 C |
| ATOM | 2894 | C | PRO | D | 7 | 58.938 | −40.128 | −0.616 | 1.00 | 38.96 C |
| ATOM | 2895 | O | PRO | D | 7 | 59.364 | −39.093 | −0.218 | 1.00 | 38.31 O |
| ATOM | 2896 | N | ARG | D | 8 | 57.835 | −40.664 | −0.098 | 1.00 | 40.27 N |
| ATOM | 2897 | CA | ARG | D | 8 | 57.128 | −40.039 | 1.046 | 1.00 | 40.80 C |
| ATOM | 2898 | CB | ARG | D | 8 | 55.743 | −40.686 | 1.236 | 1.00 | 40.70 C |
| ATOM | 2899 | CG | ARG | D | 8 | 54.775 | −40.011 | 2.223 | 1.00 | 45.33 C |
| ATOM | 2900 | CD | ARG | D | 8 | 54.283 | −38.614 | 1.746 | 1.00 | 52.07 C |
| ATOM | 2901 | NE | ARG | D | 8 | 54.080 | −38.557 | 0.289 | 1.00 | 54.98 N |
| ATOM | 2902 | CZ | ARG | D | 8 | 52.900 | −38.616 | −0.330 | 1.00 | 57.24 C |
| ATOM | 2903 | NH1 | ARG | D | 8 | 51.758 | −38.714 | 0.359 | 1.00 | 56.56 N |
| ATOM | 2904 | NH2 | ARG | D | 8 | 52.862 | −38.549 | −1.658 | 1.00 | 58.04 N |
| ATOM | 2905 | C | ARG | D | 8 | 57.977 | −40.100 | 2.331 | 1.00 | 40.53 C |
| ATOM | 2906 | O | ARG | D | 8 | 57.929 | −39.207 | 3.158 | 1.00 | 40.81 O |
| ATOM | 2907 | N | THR | D | 9 | 58.770 | −41.153 | 2.475 | 1.00 | 40.47 N |
| ATOM | 2908 | CA | THR | D | 9 | 59.629 | −41.350 | 3.634 | 1.00 | 40.91 C |
| ATOM | 2909 | CB | THR | D | 9 | 58.994 | −42.340 | 4.695 | 1.00 | 41.45 C |
| ATOM | 2910 | OG1 | THR | D | 9 | 58.726 | −43.600 | 4.084 | 1.00 | 41.04 O |
| ATOM | 2911 | CG2 | THR | D | 9 | 57.639 | −41.805 | 5.351 | 1.00 | 41.38 C |
| ATOM | 2912 | C | THR | D | 9 | 60.999 | −41.914 | 3.169 | 1.00 | 41.67 C |
| ATOM | 2913 | O | THR | D | 9 | 61.083 | −42.696 | 2.225 | 1.00 | 40.23 O |
| ATOM | 2914 | N | ALA | D | 10 | 62.064 | −41.522 | 3.868 | 1.00 | 42.06 N |
| ATOM | 2915 | CA | ALA | D | 10 | 63.392 | −42.065 | 3.635 | 1.00 | 41.77 C |
| ATOM | 2916 | CB | ALA | D | 10 | 64.160 | −41.142 | 2.735 | 1.00 | 42.21 C |
| ATOM | 2917 | C | ALA | D | 10 | 64.086 | −42.181 | 4.998 | 1.00 | 42.56 C |
| ATOM | 2918 | O | ALA | D | 10 | 63.811 | −41.387 | 5.903 | 1.00 | 40.53 O |
| ATOM | 2919 | N | THR | D | 11 | 64.914 | −43.211 | 5.161 | 1.00 | 43.58 N |
| ATOM | 2920 | CA | THR | D | 11 | 65.800 | −43.354 | 6.320 | 1.00 | 45.06 C |
| ATOM | 2921 | CB | THR | D | 11 | 65.427 | −44.561 | 7.235 | 1.00 | 45.98 C |
| ATOM | 2922 | OG1 | THR | D | 11 | 64.100 | −44.386 | 7.754 | 1.00 | 48.35 O |
| ATOM | 2923 | CG2 | THR | D | 11 | 66.423 | −44.712 | 8.442 | 1.00 | 45.10 C |
| ATOM | 2924 | C | THR | D | 11 | 67.177 | −43.562 | 5.723 | 1.00 | 46.01 C |
| ATOM | 2925 | O | THR | D | 11 | 67.379 | −44.392 | 4.825 | 1.00 | 46.79 O |
| ATOM | 2926 | N | LYS | D | 12 | 68.118 | −42.766 | 6.193 | 1.00 | 46.59 N |
| ATOM | 2927 | CA | LYS | D | 12 | 69.488 | −42.806 | 5.725 | 1.00 | 46.11 C |
| ATOM | 2928 | CB | LYS | D | 12 | 69.766 | −41.586 | 4.863 | 1.00 | 45.49 C |
| ATOM | 2929 | CG | LYS | D | 12 | 68.877 | −41.544 | 3.598 | 1.00 | 44.78 C |
| ATOM | 2930 | CD | LYS | D | 12 | 69.231 | −42.666 | 2.588 | 1.00 | 40.67 C |
| ATOM | 2931 | CE | LYS | D | 12 | 68.264 | −42.658 | 1.445 | 1.00 | 42.32 C |
| ATOM | 2932 | NZ | LYS | D | 12 | 68.712 | −43.565 | 0.374 | 1.00 | 41.82 N |
| ATOM | 2933 | C | LYS | D | 12 | 70.441 | −42.847 | 6.903 | 1.00 | 47.39 C |
| ATOM | 2934 | O | LYS | D | 12 | 70.080 | −42.564 | 8.065 | 1.00 | 46.27 O |
| ATOM | 2935 | N | GLU | D | 13 | 71.669 | −43.213 | 6.583 | 1.00 | 48.57 N |
| ATOM | 2936 | CA | GLU | D | 13 | 72.742 | −43.190 | 7.538 | 1.00 | 49.48 C |
| ATOM | 2937 | CB | GLU | D | 13 | 73.578 | −44.461 | 7.335 | 1.00 | 50.69 C |
| ATOM | 2938 | CG | GLU | D | 13 | 73.899 | −45.243 | 8.610 | 1.00 | 53.61 C |
| ATOM | 2939 | CD | GLU | D | 13 | 75.339 | −45.752 | 8.601 | 1.00 | 59.15 C |
| ATOM | 2940 | OE1 | GLU | D | 13 | 75.609 | −46.771 | 9.288 | 1.00 | 59.36 O |
| ATOM | 2941 | OE2 | GLU | D | 13 | 76.200 | −45.139 | 7.892 | 1.00 | 59.86 O |

APPENDIX I-continued

| | | | | | | | | | | |
|---|---|---|---|---|---|---|---|---|---|---|
| ATOM | 2942 | C | GLU | D | 13 | 73.534 | −41.911 | 7.193 | 1.00 | 48.81 C |
| ATOM | 2943 | O | GLU | D | 13 | 73.480 | −41.453 | 6.043 | 1.00 | 48.11 O |
| ATOM | 2944 | N | THR | D | 14 | 74.259 | −41.324 | 8.155 | 1.00 | 48.09 N |
| ATOM | 2945 | CA | THR | D | 14 | 75.143 | −40.192 | 7.810 | 1.00 | 47.65 C |
| ATOM | 2946 | CB | THR | D | 14 | 75.925 | −39.621 | 9.031 | 1.00 | 47.59 C |
| ATOM | 2947 | OG1 | THR | D | 14 | 76.628 | −40.678 | 9.687 | 1.00 | 48.03 O |
| ATOM | 2948 | CG2 | THR | D | 14 | 74.987 | −38.998 | 10.048 | 1.00 | 47.29 C |
| ATOM | 2949 | C | THR | D | 14 | 76.117 | −40.593 | 6.681 | 1.00 | 47.56 C |
| ATOM | 2950 | O | THR | D | 14 | 76.583 | −41.748 | 6.620 | 1.00 | 47.03 O |
| ATOM | 2951 | N | GLY | D | 15 | 76.414 | −39.648 | 5.793 | 1.00 | 46.77 N |
| ATOM | 2952 | CA | GLY | D | 15 | 77.304 | −39.915 | 4.667 | 1.00 | 46.69 C |
| ATOM | 2953 | C | GLY | D | 15 | 76.607 | −40.296 | 3.367 | 1.00 | 46.34 C |
| ATOM | 2954 | O | GLY | D | 15 | 77.083 | −39.969 | 2.293 | 1.00 | 46.24 O |
| ATOM | 2955 | N | GLU | D | 16 | 75.484 | −40.998 | 3.474 | 1.00 | 46.52 N |
| ATOM | 2956 | CA | GLU | D | 16 | 74.670 | −41.389 | 2.327 | 1.00 | 46.87 C |
| ATOM | 2957 | CB | GLU | D | 16 | 73.574 | −42.384 | 2.757 | 1.00 | 46.63 C |
| ATOM | 2958 | CG | GLU | D | 16 | 74.023 | −43.586 | 3.578 | 1.00 | 46.69 C |
| ATOM | 2959 | CD | GLU | D | 16 | 72.979 | −44.733 | 3.575 | 1.00 | 48.35 C |
| ATOM | 2960 | OE1 | GLU | D | 16 | 73.193 | −45.693 | 2.807 | 1.00 | 53.70 O |
| ATOM | 2961 | OE2 | GLU | D | 16 | 71.954 | −44.705 | 4.299 | 1.00 | 48.55 O |
| ATOM | 2962 | C | GLU | D | 16 | 74.003 | −40.187 | 1.632 | 1.00 | 46.94 C |
| ATOM | 2963 | O | GLU | D | 16 | 74.209 | −39.019 | 1.977 | 1.00 | 46.67 O |
| ATOM | 2964 | N | SER | D | 17 | 73.174 | −40.471 | 0.637 | 1.00 | 47.38 N |
| ATOM | 2965 | CA | SER | D | 17 | 72.518 | −39.376 | −0.056 | 1.00 | 47.46 C |
| ATOM | 2966 | CB | SER | D | 17 | 73.184 | −39.131 | −1.410 | 1.00 | 48.28 C |
| ATOM | 2967 | OG | SER | D | 17 | 72.749 | −40.047 | −2.416 | 1.00 | 52.49 O |
| ATOM | 2968 | C | SER | D | 17 | 71.029 | −39.642 | −0.196 | 1.00 | 46.61 C |
| ATOM | 2969 | O | SER | D | 17 | 70.588 | −40.785 | 0.001 | 1.00 | 46.62 O |
| ATOM | 2970 | N | LEU | D | 18 | 70.263 | −38.583 | −0.477 | 1.00 | 44.97 N |
| ATOM | 2971 | CA | LEU | D | 18 | 68.829 | −38.674 | −0.742 | 1.00 | 43.88 C |
| ATOM | 2972 | CB | LEU | D | 18 | 68.010 | −37.924 | 0.319 | 1.00 | 44.17 C |
| ATOM | 2973 | CG | LEU | D | 18 | 66.612 | −38.336 | 0.802 | 1.00 | 44.22 C |
| ATOM | 2974 | CD1 | LEU | D | 18 | 65.730 | −37.114 | 0.965 | 1.00 | 44.33 C |
| ATOM | 2975 | CD2 | LEU | D | 18 | 65.950 | −39.375 | −0.033 | 1.00 | 43.22 C |
| ATOM | 2976 | C | LEU | D | 18 | 68.614 | −37.943 | −2.049 | 1.00 | 43.24 C |
| ATOM | 2977 | O | LEU | D | 18 | 69.159 | −36.865 | −2.231 | 1.00 | 42.98 O |
| ATOM | 2978 | N | THR | D | 19 | 67.817 | −38.528 | −2.936 | 1.00 | 42.05 N |
| ATOM | 2979 | CA | THR | D | 19 | 67.259 | −37.821 | −4.062 | 1.00 | 41.13 C |
| ATOM | 2980 | CB | THR | D | 19 | 67.673 | −38.509 | −5.373 | 1.00 | 41.27 C |
| ATOM | 2981 | OG1 | THR | D | 19 | 68.982 | −39.032 | −5.185 | 1.00 | 42.63 O |
| ATOM | 2982 | CG2 | THR | D | 19 | 67.703 | −37.531 | −6.542 | 1.00 | 39.59 C |
| ATOM | 2983 | C | THR | D | 19 | 65.731 | −37.751 | −3.892 | 1.00 | 40.45 C |
| ATOM | 2984 | O | THR | D | 19 | 65.055 | −38.763 | −3.753 | 1.00 | 40.58 O |
| ATOM | 2985 | N | ILE | D | 20 | 65.207 | −36.542 | −3.859 | 1.00 | 39.89 N |
| ATOM | 2986 | CA | ILE | D | 20 | 63.766 | −36.329 | −3.894 | 1.00 | 40.16 C |
| ATOM | 2987 | CB | ILE | D | 20 | 63.326 | −35.181 | −2.940 | 1.00 | 40.54 C |
| ATOM | 2988 | CG1 | ILE | D | 20 | 63.757 | −35.493 | −1.505 | 1.00 | 41.28 C |
| ATOM | 2989 | CD1 | ILE | D | 20 | 63.883 | −34.280 | −0.649 | 1.00 | 41.55 C |
| ATOM | 2990 | CG2 | ILE | D | 20 | 61.799 | −34.926 | −3.043 | 1.00 | 39.20 C |
| ATOM | 2991 | C | ILE | D | 20 | 63.383 | −35.979 | −5.323 | 1.00 | 39.22 C |
| ATOM | 2992 | O | ILE | D | 20 | 64.012 | −35.141 | −5.904 | 1.00 | 38.55 O |
| ATOM | 2993 | N | ASN | D | 21 | 62.358 | −36.632 | −5.859 | 1.00 | 39.57 N |
| ATOM | 2994 | CA | ASN | D | 21 | 61.852 | −36.370 | −7.213 | 1.00 | 41.08 C |
| ATOM | 2995 | CB | ASN | D | 21 | 61.773 | −37.676 | −7.967 | 1.00 | 41.24 C |
| ATOM | 2996 | CG | ASN | D | 21 | 63.008 | −37.956 | −8.759 | 1.00 | 43.85 C |
| ATOM | 2997 | OD1 | ASN | D | 21 | 63.215 | −37.323 | −9.793 | 1.00 | 48.63 O |
| ATOM | 2998 | ND2 | ASN | D | 21 | 63.814 | −38.942 | −8.325 | 1.00 | 43.95 N |
| ATOM | 2999 | C | ASN | D | 21 | 60.453 | −35.779 | −7.184 | 1.00 | 41.77 C |
| ATOM | 3000 | O | ASN | D | 21 | 59.636 | −36.200 | −6.375 | 1.00 | 41.70 O |
| ATOM | 3001 | N | CYS | D | 22 | 60.180 | −34.794 | −8.039 | 1.00 | 42.41 N |
| ATOM | 3002 | CA | CYS | D | 22 | 58.840 | −34.207 | −8.137 | 1.00 | 43.48 C |
| ATOM | 3003 | CB | CYS | D | 22 | 58.774 | −32.833 | −7.476 | 1.00 | 42.75 C |
| ATOM | 3004 | SG | CYS | D | 22 | 59.105 | −32.836 | −5.677 | 1.00 | 49.46 S |
| ATOM | 3005 | C | CYS | D | 22 | 58.428 | −34.062 | −9.580 | 1.00 | 43.16 C |
| ATOM | 3006 | O | CYS | D | 22 | 59.168 | −33.495 | −10.359 | 1.00 | 43.59 O |
| ATOM | 3007 | N | VAL | D | 23 | 57.228 | −34.523 | −9.918 | 1.00 | 43.81 N |
| ATOM | 3008 | CA | VAL | D | 23 | 56.647 | −34.300 | −11.241 | 1.00 | 44.50 C |
| ATOM | 3009 | CB | VAL | D | 23 | 56.382 | −35.665 | −11.979 | 1.00 | 44.28 C |
| ATOM | 3010 | CG1 | VAL | D | 23 | 55.931 | −35.444 | −13.468 | 1.00 | 44.41 C |
| ATOM | 3011 | CG2 | VAL | D | 23 | 57.614 | −36.588 | −11.902 | 1.00 | 42.56 C |
| ATOM | 3012 | C | VAL | D | 23 | 55.358 | −33.477 | −11.211 | 1.00 | 45.73 C |
| ATOM | 3013 | O | VAL | D | 23 | 54.510 | −33.746 | −10.265 | 1.00 | 45.32 O |
| ATOM | 3014 | N | LEU | D | 24 | 55.224 | −32.460 | −11.986 | 1.00 | 47.64 N |
| ATOM | 3015 | CA | LEU | D | 24 | 53.951 | −31.724 | −12.179 | 1.00 | 48.97 C |
| ATOM | 3016 | CB | LEU | D | 24 | 54.214 | −30.344 | −12.795 | 1.00 | 48.56 C |
| ATOM | 3017 | CG | LEU | D | 24 | 53.466 | −29.079 | −12.328 | 1.00 | 49.30 C |
| ATOM | 3018 | CD1 | LEU | D | 24 | 53.669 | −27.924 | −13.368 | 1.00 | 46.03 C |
| ATOM | 3019 | CD2 | LEU | D | 24 | 51.974 | −29.319 | −11.999 | 1.00 | 48.04 C |
| ATOM | 3020 | C | LEU | D | 24 | 52.983 | −32.521 | −13.083 | 1.00 | 49.95 C |
| ATOM | 3021 | O | LEU | D | 24 | 53.134 | −32.529 | −14.313 | 1.00 | 50.57 O |

APPENDIX I-continued

| | | | | | | | | | | | |
|---|---|---|---|---|---|---|---|---|---|---|---|
| ATOM | 3022 | N | ARG | D | 25 | 52.001 | −33.195 | −12.471 | 1.00 | 51.10 | N |
| ATOM | 3023 | CA | ARG | D | 25 | 51.019 | −34.050 | −13.192 | 1.00 | 51.64 | C |
| ATOM | 3024 | CB | ARG | D | 25 | 50.696 | −35.313 | −12.386 | 1.00 | 51.32 | C |
| ATOM | 3025 | CG | ARG | D | 25 | 51.863 | −36.063 | −11.871 | 1.00 | 49.97 | C |
| ATOM | 3026 | CD | ARG | D | 25 | 52.204 | −37.166 | −12.794 | 1.00 | 47.93 | C |
| ATOM | 3027 | NE | ARG | D | 25 | 53.274 | −37.967 | −12.225 | 1.00 | 47.52 | N |
| ATOM | 3028 | CZ | ARG | D | 25 | 53.981 | −38.861 | −12.909 | 1.00 | 47.68 | C |
| ATOM | 3029 | NH1 | ARG | D | 25 | 53.741 | −39.083 | −14.202 | 1.00 | 46.46 | N |
| ATOM | 3030 | NH2 | ARG | D | 25 | 54.941 | −39.536 | −12.298 | 1.00 | 48.61 | N |
| ATOM | 3031 | C | ARG | D | 25 | 49.699 | −33.318 | −13.473 | 1.00 | 52.55 | C |
| ATOM | 3032 | O | ARG | D | 25 | 49.412 | −32.286 | −12.847 | 1.00 | 52.60 | O |
| ATOM | 3033 | N | ASP | D | 26 | 48.891 | −33.884 | −14.386 | 1.00 | 53.55 | N |
| ATOM | 3034 | CA | ASP | D | 26 | 47.619 | −33.276 | −14.857 | 1.00 | 54.33 | C |
| ATOM | 3035 | CB | ASP | D | 26 | 46.477 | −33.475 | −13.843 | 1.00 | 54.58 | C |
| ATOM | 3036 | CG | ASP | D | 26 | 45.374 | −34.384 | −14.368 | 1.00 | 55.93 | C |
| ATOM | 3037 | OD1 | ASP | D | 26 | 44.789 | −34.090 | −15.443 | 1.00 | 57.14 | O |
| ATOM | 3038 | OD2 | ASP | D | 26 | 45.089 | −35.398 | −13.694 | 1.00 | 57.19 | O |
| ATOM | 3039 | C | ASP | D | 26 | 47.694 | −31.801 | −15.233 | 1.00 | 54.37 | C |
| ATOM | 3040 | O | ASP | D | 26 | 46.708 | −31.085 | −15.092 | 1.00 | 54.79 | O |
| ATOM | 3041 | N | ALA | D | 27 | 48.845 | −31.346 | −15.719 | 1.00 | 54.73 | N |
| ATOM | 3042 | CA | ALA | D | 27 | 49.050 | −29.918 | −15.985 | 1.00 | 54.79 | C |
| ATOM | 3043 | CB | ALA | D | 27 | 50.415 | −29.475 | −15.472 | 1.00 | 54.57 | C |
| ATOM | 3044 | C | ALA | D | 27 | 48.897 | −29.583 | −17.469 | 1.00 | 54.93 | C |
| ATOM | 3045 | O | ALA | D | 27 | 49.543 | −30.202 | −18.321 | 1.00 | 55.09 | O |
| ATOM | 3046 | N | SER | D | 28 | 48.038 | −28.617 | −17.781 | 1.00 | 54.75 | N |
| ATOM | 3047 | CA | SER | D | 28 | 47.935 | −28.133 | −19.152 | 1.00 | 54.93 | C |
| ATOM | 3048 | CB | SER | D | 28 | 46.488 | −27.753 | −19.510 | 1.00 | 55.22 | C |
| ATOM | 3049 | OG | SER | D | 28 | 46.074 | −26.557 | −18.862 | 1.00 | 55.13 | O |
| ATOM | 3050 | C | SER | D | 28 | 48.892 | −26.952 | −19.338 | 1.00 | 54.84 | C |
| ATOM | 3051 | O | SER | D | 28 | 49.138 | −26.492 | −20.463 | 1.00 | 54.36 | O |
| ATOM | 3052 | N | PHE | D | 29 | 49.413 | −26.472 | −18.209 | 1.00 | 54.77 | N |
| ATOM | 3053 | CA | PHE | D | 29 | 50.460 | −25.448 | −18.167 | 1.00 | 54.65 | C |
| ATOM | 3054 | CB | PHE | D | 29 | 50.152 | −24.392 | −17.096 | 1.00 | 55.22 | C |
| ATOM | 3055 | CG | PHE | D | 29 | 49.499 | −24.951 | −15.847 | 1.00 | 56.31 | C |
| ATOM | 3056 | CD1 | PHE | D | 29 | 50.206 | −25.806 | −14.988 | 1.00 | 56.26 | C |
| ATOM | 3057 | CE1 | PHE | D | 29 | 49.596 | −26.332 | −13.834 | 1.00 | 57.52 | C |
| ATOM | 3058 | CZ | PHE | D | 29 | 48.269 | −25.993 | −13.528 | 1.00 | 57.03 | C |
| ATOM | 3059 | CE2 | PHE | D | 29 | 47.554 | −25.124 | −14.385 | 1.00 | 58.39 | C |
| ATOM | 3060 | CD2 | PHE | D | 29 | 48.174 | −24.614 | −15.534 | 1.00 | 56.93 | C |
| ATOM | 3061 | C | PHE | D | 29 | 51.867 | −26.058 | −17.966 | 1.00 | 54.11 | C |
| ATOM | 3062 | O | PHE | D | 29 | 52.019 | −27.269 | −17.723 | 1.00 | 53.85 | O |
| ATOM | 3063 | N | GLU | D | 30 | 52.884 | −25.210 | −18.091 | 1.00 | 53.36 | N |
| ATOM | 3064 | CA | GLU | D | 30 | 54.270 | −25.660 | −18.088 | 1.00 | 52.94 | C |
| ATOM | 3065 | CB | GLU | D | 30 | 55.046 | −25.061 | −19.275 | 1.00 | 53.22 | C |
| ATOM | 3066 | CG | GLU | D | 30 | 54.424 | −25.259 | −20.663 | 1.00 | 54.41 | C |
| ATOM | 3067 | CD | GLU | D | 30 | 54.848 | −26.554 | −21.333 | 1.00 | 56.12 | C |
| ATOM | 3068 | OE1 | GLU | D | 30 | 55.997 | −27.002 | −21.121 | 1.00 | 57.05 | O |
| ATOM | 3069 | OE2 | GLU | D | 30 | 54.028 | −27.124 | −22.079 | 1.00 | 56.87 | O |
| ATOM | 3070 | C | GLU | D | 30 | 54.947 | −25.262 | −16.778 | 1.00 | 51.85 | C |
| ATOM | 3071 | O | GLU | D | 30 | 54.501 | −24.352 | −16.081 | 1.00 | 51.46 | O |
| ATOM | 3072 | N | LEU | D | 31 | 56.045 | −25.942 | −16.474 | 1.00 | 51.22 | N |
| ATOM | 3073 | CA | LEU | D | 31 | 56.825 | −25.688 | −15.275 | 1.00 | 49.86 | C |
| ATOM | 3074 | CB | LEU | D | 31 | 57.710 | −26.901 | −14.991 | 1.00 | 49.53 | C |
| ATOM | 3075 | CG | LEU | D | 31 | 58.340 | −26.964 | −13.595 | 1.00 | 48.63 | C |
| ATOM | 3076 | CD1 | LEU | D | 31 | 57.315 | −26.642 | −12.490 | 1.00 | 43.48 | C |
| ATOM | 3077 | CD2 | LEU | D | 31 | 58.957 | −28.337 | −13.398 | 1.00 | 46.35 | C |
| ATOM | 3078 | C | LEU | D | 31 | 57.695 | −24.468 | −15.489 | 1.00 | 49.34 | C |
| ATOM | 3079 | O | LEU | D | 31 | 58.652 | −24.527 | −16.250 | 1.00 | 49.11 | O |
| ATOM | 3080 | N | LYS | D | 32 | 57.362 | −23.366 | −14.838 | 1.00 | 49.24 | N |
| ATOM | 3081 | CA | LYS | D | 32 | 58.155 | −22.156 | −14.986 | 1.00 | 49.60 | C |
| ATOM | 3082 | CB | LYS | D | 32 | 57.325 | −20.901 | −14.692 | 1.00 | 49.77 | C |
| ATOM | 3083 | CG | LYS | D | 32 | 56.343 | −20.516 | −15.862 | 1.00 | 51.34 | C |
| ATOM | 3084 | CD | LYS | D | 32 | 56.909 | −20.827 | −17.265 | 1.00 | 50.23 | C |
| ATOM | 3085 | CE | LYS | D | 32 | 55.918 | −20.497 | −18.363 | 1.00 | 51.66 | C |
| ATOM | 3086 | NZ | LYS | D | 32 | 55.711 | −21.653 | −19.277 | 1.00 | 51.95 | N |
| ATOM | 3087 | C | LYS | D | 32 | 59.398 | −22.205 | −14.111 | 1.00 | 50.13 | C |
| ATOM | 3088 | O | LYS | D | 32 | 60.530 | −22.068 | −14.608 | 1.00 | 50.59 | O |
| ATOM | 3089 | N | ASP | D | 33 | 59.174 | −22.422 | −12.820 | 1.00 | 48.97 | N |
| ATOM | 3090 | CA | ASP | D | 33 | 60.207 | −22.327 | −11.799 | 1.00 | 49.30 | C |
| ATOM | 3091 | CB | ASP | D | 33 | 60.268 | −20.869 | −11.293 | 1.00 | 49.60 | C |
| ATOM | 3092 | CG | ASP | D | 33 | 61.514 | −20.592 | −10.464 | 1.00 | 54.11 | C |
| ATOM | 3093 | OD1 | ASP | D | 33 | 62.644 | −21.000 | −10.869 | 1.00 | 55.49 | O |
| ATOM | 3094 | OD2 | ASP | D | 33 | 61.356 | −19.998 | −9.367 | 1.00 | 59.32 | O |
| ATOM | 3095 | C | ASP | D | 33 | 59.965 | −23.362 | −10.629 | 1.00 | 47.92 | C |
| ATOM | 3096 | O | ASP | D | 33 | 58.887 | −23.942 | −10.506 | 1.00 | 47.18 | O |
| ATOM | 3097 | N | THR | D | 34 | 60.964 | −23.576 | −9.782 | 1.00 | 47.12 | N |
| ATOM | 3098 | CA | THR | D | 34 | 60.882 | −24.571 | −8.714 | 1.00 | 45.90 | C |
| ATOM | 3099 | CB | THR | D | 34 | 61.701 | −25.848 | −9.054 | 1.00 | 46.44 | C |
| ATOM | 3100 | OG1 | THR | D | 34 | 63.095 | −25.523 | −9.217 | 1.00 | 43.45 | O |
| ATOM | 3101 | CG2 | THR | D | 34 | 61.172 | −26.526 | −10.312 | 1.00 | 46.59 | C |

APPENDIX I-continued

| ATOM | 3102 | C | THR | D | 34 | 61.449 | −24.004 | −7.427 | 1.00 | 46.20 | C |
| --- | --- | --- | --- | --- | --- | --- | --- | --- | --- | --- | --- |
| ATOM | 3103 | O | THR | D | 34 | 62.340 | −23.122 | −7.464 | 1.00 | 46.30 | O |
| ATOM | 3104 | N | GLY | D | 35 | 60.944 | −24.509 | −6.290 | 1.00 | 45.15 | N |
| ATOM | 3105 | CA | GLY | D | 35 | 61.530 | −24.211 | −4.995 | 1.00 | 44.20 | C |
| ATOM | 3106 | C | GLY | D | 35 | 61.560 | −25.447 | −4.130 | 1.00 | 44.10 | C |
| ATOM | 3107 | O | GLY | D | 35 | 60.734 | −26.358 | −4.309 | 1.00 | 43.01 | O |
| ATOM | 3108 | N | TRP | D | 36 | 62.497 | −25.440 | −3.172 | 1.00 | 43.91 | N |
| ATOM | 3109 | CA | TRP | D | 36 | 62.680 | −26.524 | −2.222 | 1.00 | 43.17 | C |
| ATOM | 3110 | CB | TRP | D | 36 | 63.989 | −27.274 | −2.505 | 1.00 | 42.16 | C |
| ATOM | 3111 | CG | TRP | D | 36 | 63.897 | −28.084 | −3.748 | 1.00 | 42.33 | C |
| ATOM | 3112 | CD1 | TRP | D | 36 | 64.287 | −27.709 | −4.990 | 1.00 | 41.86 | C |
| ATOM | 3113 | NE1 | TRP | D | 36 | 64.020 | −28.710 | −5.901 | 1.00 | 41.80 | N |
| ATOM | 3114 | CE2 | TRP | D | 36 | 63.440 | −29.761 | −5.246 | 1.00 | 39.28 | C |
| ATOM | 3115 | CD2 | TRP | D | 36 | 63.339 | −29.404 | −3.881 | 1.00 | 41.23 | C |
| ATOM | 3116 | CE3 | TRP | D | 36 | 62.771 | −30.315 | −2.975 | 1.00 | 40.97 | C |
| ATOM | 3117 | CZ3 | TRP | D | 36 | 62.320 | −31.538 | −3.462 | 1.00 | 41.67 | C |
| ATOM | 3118 | CH2 | TRP | D | 36 | 62.442 | −31.859 | −4.835 | 1.00 | 42.09 | C |
| ATOM | 3119 | CZ2 | TRP | D | 36 | 63.008 | −30.988 | −5.737 | 1.00 | 39.64 | C |
| ATOM | 3120 | C | TRP | D | 36 | 62.666 | −25.949 | −0.848 | 1.00 | 43.26 | C |
| ATOM | 3121 | O | TRP | D | 36 | 63.284 | −24.931 | −0.618 | 1.00 | 42.62 | O |
| ATOM | 3122 | N | TYR | D | 37 | 61.921 | −26.603 | 0.042 | 1.00 | 43.77 | N |
| ATOM | 3123 | CA | TYR | D | 37 | 61.774 | −26.215 | 1.445 | 1.00 | 44.44 | C |
| ATOM | 3124 | CB | TYR | D | 37 | 60.384 | −25.667 | 1.724 | 1.00 | 45.80 | C |
| ATOM | 3125 | CG | TYR | D | 37 | 59.912 | −24.825 | 0.615 | 1.00 | 50.24 | C |
| ATOM | 3126 | CD1 | TYR | D | 37 | 60.243 | −23.457 | 0.557 | 1.00 | 52.74 | C |
| ATOM | 3127 | CE1 | TYR | D | 37 | 59.827 | −22.661 | −0.510 | 1.00 | 53.61 | C |
| ATOM | 3128 | CZ | TYR | D | 37 | 59.078 | −23.238 | −1.534 | 1.00 | 53.15 | C |
| ATOM | 3129 | OH | TYR | D | 37 | 58.677 | −22.491 | −2.597 | 1.00 | 53.11 | O |
| ATOM | 3130 | CE2 | TYR | D | 37 | 58.744 | −24.592 | −1.499 | 1.00 | 53.55 | C |
| ATOM | 3131 | CD2 | TYR | D | 37 | 59.167 | −25.382 | −0.419 | 1.00 | 51.12 | C |
| ATOM | 3132 | C | TYR | D | 37 | 61.987 | −27.398 | 2.367 | 1.00 | 43.19 | C |
| ATOM | 3133 | O | TYR | D | 37 | 61.769 | −28.539 | 1.964 | 1.00 | 41.62 | O |
| ATOM | 3134 | N | ARG | D | 38 | 62.305 | −27.064 | 3.620 | 1.00 | 42.47 | N |
| ATOM | 3135 | CA | ARG | D | 38 | 62.552 | −28.009 | 4.705 | 1.00 | 43.75 | C |
| ATOM | 3136 | CB | ARG | D | 38 | 64.045 | −28.379 | 4.717 | 1.00 | 43.86 | C |
| ATOM | 3137 | CG | ARG | D | 38 | 64.576 | −28.648 | 6.062 | 1.00 | 48.19 | C |
| ATOM | 3138 | CD | ARG | D | 38 | 65.373 | −29.910 | 6.170 | 1.00 | 53.19 | C |
| ATOM | 3139 | NE | ARG | D | 38 | 66.808 | −29.728 | 5.932 | 1.00 | 58.72 | N |
| ATOM | 3140 | CZ | ARG | D | 38 | 67.438 | −28.558 | 5.839 | 1.00 | 57.26 | C |
| ATOM | 3141 | NH1 | ARG | D | 38 | 66.768 | −27.415 | 5.974 | 1.00 | 56.27 | N |
| ATOM | 3142 | NH2 | ARG | D | 38 | 68.751 | −28.546 | 5.624 | 1.00 | 57.23 | N |
| ATOM | 3143 | C | ARG | D | 38 | 62.090 | −27.458 | 6.088 | 1.00 | 42.91 | C |
| ATOM | 3144 | O | ARG | D | 38 | 62.281 | −26.267 | 6.405 | 1.00 | 42.55 | O |
| ATOM | 3145 | N | THR | D | 39 | 61.471 | −28.341 | 6.874 | 1.00 | 42.58 | N |
| ATOM | 3146 | CA | THR | D | 39 | 61.179 | −28.177 | 8.299 | 1.00 | 41.28 | C |
| ATOM | 3147 | CB | THR | D | 39 | 59.656 | −28.312 | 8.600 | 1.00 | 41.27 | C |
| ATOM | 3148 | OG1 | THR | D | 39 | 58.892 | −27.440 | 7.743 | 1.00 | 43.39 | O |
| ATOM | 3149 | CG2 | THR | D | 39 | 59.344 | −27.965 | 10.027 | 1.00 | 42.59 | C |
| ATOM | 3150 | C | THR | D | 39 | 61.989 | −29.229 | 9.060 | 1.00 | 41.19 | C |
| ATOM | 3151 | O | THR | D | 39 | 61.748 | −30.449 | 8.968 | 1.00 | 40.45 | O |
| ATOM | 3152 | N | LYS | D | 40 | 62.968 | −28.750 | 9.804 | 1.00 | 40.73 | N |
| ATOM | 3153 | CA | LYS | D | 40 | 63.868 | −29.605 | 10.541 | 1.00 | 41.06 | C |
| ATOM | 3154 | CB | LYS | D | 40 | 64.893 | −28.753 | 11.289 | 1.00 | 41.28 | C |
| ATOM | 3155 | CG | LYS | D | 40 | 66.298 | −29.293 | 11.229 | 1.00 | 45.60 | C |
| ATOM | 3156 | CD | LYS | D | 40 | 67.141 | −28.840 | 12.503 | 1.00 | 49.44 | C |
| ATOM | 3157 | CE | LYS | D | 40 | 68.173 | −29.941 | 12.917 | 1.00 | 47.27 | C |
| ATOM | 3158 | NZ | LYS | D | 40 | 68.965 | −29.678 | 14.177 | 1.00 | 50.09 | N |
| ATOM | 3159 | C | LYS | D | 40 | 63.075 | −30.457 | 11.539 | 1.00 | 41.44 | C |
| ATOM | 3160 | O | LYS | D | 40 | 62.069 | −30.038 | 12.073 | 1.00 | 40.57 | O |
| ATOM | 3161 | N | LEU | D | 41 | 63.524 | −31.676 | 11.782 | 1.00 | 41.67 | N |
| ATOM | 3162 | CA | LEU | D | 41 | 62.755 | −32.533 | 12.643 | 1.00 | 42.41 | C |
| ATOM | 3163 | CB | LEU | D | 41 | 63.321 | −33.947 | 12.570 | 1.00 | 41.48 | C |
| ATOM | 3164 | CG | LEU | D | 41 | 62.834 | −34.954 | 13.562 | 1.00 | 42.23 | C |
| ATOM | 3165 | CD1 | LEU | D | 41 | 63.555 | −36.244 | 13.284 | 1.00 | 38.77 | C |
| ATOM | 3166 | CD2 | LEU | D | 41 | 61.360 | −35.124 | 13.379 | 1.00 | 42.31 | C |
| ATOM | 3167 | C | LEU | D | 41 | 62.723 | −31.942 | 14.067 | 1.00 | 42.92 | C |
| ATOM | 3168 | O | LEU | D | 41 | 63.747 | −31.819 | 14.744 | 1.00 | 42.91 | O |
| ATOM | 3169 | N | GLY | D | 42 | 61.531 | −31.532 | 14.484 | 1.00 | 43.29 | N |
| ATOM | 3170 | CA | GLY | D | 42 | 61.306 | −31.127 | 15.848 | 1.00 | 44.22 | C |
| ATOM | 3171 | C | GLY | D | 42 | 61.080 | −29.639 | 15.878 | 1.00 | 45.23 | C |
| ATOM | 3172 | O | GLY | D | 42 | 60.854 | −29.079 | 16.923 | 1.00 | 45.24 | O |
| ATOM | 3173 | N | SER | D | 43 | 61.155 | −29.018 | 14.704 | 1.00 | 46.01 | N |
| ATOM | 3174 | CA | SER | D | 43 | 60.973 | −27.595 | 14.531 | 1.00 | 47.24 | C |
| ATOM | 3175 | CB | SER | D | 43 | 62.214 | −27.065 | 13.803 | 1.00 | 46.38 | C |
| ATOM | 3176 | OG | SER | D | 43 | 61.967 | −25.912 | 13.064 | 1.00 | 48.60 | O |
| ATOM | 3177 | C | SER | D | 43 | 59.635 | −27.315 | 13.798 | 1.00 | 48.54 | C |
| ATOM | 3178 | O | SER | D | 43 | 59.126 | −28.181 | 13.090 | 1.00 | 48.74 | O |
| ATOM | 3179 | N | THR | D | 44 | 59.057 | −26.130 | 13.995 | 1.00 | 50.34 | N |
| ATOM | 3180 | CA | THR | D | 44 | 57.829 | −25.713 | 13.289 | 1.00 | 52.56 | C |
| ATOM | 3181 | CB | THR | D | 44 | 56.759 | −25.084 | 14.274 | 1.00 | 53.48 | C |

APPENDIX I-continued

| | | | | | | | | | | | |
|---|---|---|---|---|---|---|---|---|---|---|---|
| ATOM | 3182 | OG1 | THR | D | 44 | 56.875 | −25.640 | 15.613 | 1.00 | 52.17 | O |
| ATOM | 3183 | CG2 | THR | D | 44 | 55.331 | −25.334 | 13.742 | 1.00 | 54.43 | C |
| ATOM | 3184 | C | THR | D | 44 | 58.044 | −24.766 | 12.057 | 1.00 | 54.01 | C |
| ATOM | 3185 | O | THR | D | 44 | 57.128 | −24.557 | 11.228 | 1.00 | 54.29 | O |
| ATOM | 3186 | N | ASN | D | 45 | 59.246 | −24.208 | 11.908 | 1.00 | 54.74 | N |
| ATOM | 3187 | CA | ASN | D | 45 | 59.508 | −23.303 | 10.784 | 1.00 | 55.53 | C |
| ATOM | 3188 | CB | ASN | D | 45 | 60.529 | −22.227 | 11.169 | 1.00 | 56.24 | C |
| ATOM | 3189 | CG | ASN | D | 45 | 61.816 | −22.827 | 11.744 | 1.00 | 59.18 | C |
| ATOM | 3190 | OD1 | ASN | D | 45 | 62.441 | −23.684 | 11.108 | 1.00 | 63.33 | O |
| ATOM | 3191 | ND2 | ASN | D | 45 | 62.210 | −22.391 | 12.954 | 1.00 | 59.01 | N |
| ATOM | 3192 | C | ASN | D | 45 | 59.965 | −24.043 | 9.524 | 1.00 | 55.48 | C |
| ATOM | 3193 | O | ASN | D | 45 | 60.900 | −24.875 | 9.572 | 1.00 | 55.04 | O |
| ATOM | 3194 | N | GLU | D | 46 | 59.292 | −23.739 | 8.413 | 1.00 | 55.16 | N |
| ATOM | 3195 | CA | GLU | D | 46 | 59.654 | −24.237 | 7.120 | 1.00 | 55.65 | C |
| ATOM | 3196 | CB | GLU | D | 46 | 58.413 | −24.405 | 6.238 | 1.00 | 56.04 | C |
| ATOM | 3197 | CG | GLU | D | 46 | 58.708 | −25.157 | 4.911 | 1.00 | 56.84 | C |
| ATOM | 3198 | CD | GLU | D | 46 | 57.527 | −25.197 | 3.937 | 1.00 | 58.64 | C |
| ATOM | 3199 | OE1 | GLU | D | 46 | 57.030 | −26.309 | 3.624 | 1.00 | 64.99 | O |
| ATOM | 3200 | OE2 | GLU | D | 46 | 57.106 | −24.115 | 3.448 | 1.00 | 64.43 | O |
| ATOM | 3201 | C | GLU | D | 46 | 60.613 | −23.246 | 6.494 | 1.00 | 54.79 | C |
| ATOM | 3202 | O | GLU | D | 46 | 60.260 | −22.103 | 6.253 | 1.00 | 55.34 | O |
| ATOM | 3203 | N | GLN | D | 47 | 61.827 | −23.695 | 6.233 | 1.00 | 53.79 | N |
| ATOM | 3204 | CA | GLN | D | 47 | 62.853 | −22.868 | 5.641 | 1.00 | 52.99 | C |
| ATOM | 3205 | CB | GLN | D | 47 | 64.145 | −23.017 | 6.442 | 1.00 | 53.28 | C |
| ATOM | 3206 | CG | GLN | D | 47 | 64.900 | −21.697 | 6.634 | 1.00 | 57.45 | C |
| ATOM | 3207 | CD | GLN | D | 47 | 64.465 | −20.874 | 7.888 | 1.00 | 59.69 | C |
| ATOM | 3208 | OE1 | GLN | D | 47 | 65.207 | −19.989 | 8.343 | 1.00 | 58.09 | O |
| ATOM | 3209 | NE2 | GLN | D | 47 | 63.291 | −21.193 | 8.452 | 1.00 | 61.05 | N |
| ATOM | 3210 | C | GLN | D | 47 | 63.105 | −23.262 | 4.184 | 1.00 | 51.77 | C |
| ATOM | 3211 | O | GLN | D | 47 | 63.009 | −24.438 | 3.832 | 1.00 | 50.62 | O |
| ATOM | 3212 | N | SER | D | 48 | 63.439 | −22.274 | 3.341 | 1.00 | 50.27 | N |
| ATOM | 3213 | CA | SER | D | 48 | 63.767 | −22.526 | 1.941 | 1.00 | 49.06 | C |
| ATOM | 3214 | CB | SER | D | 48 | 63.715 | −21.209 | 1.153 | 1.00 | 50.37 | C |
| ATOM | 3215 | OG | SER | D | 48 | 62.799 | −20.303 | 1.782 | 1.00 | 54.39 | O |
| ATOM | 3216 | C | SER | D | 48 | 65.158 | −23.135 | 1.844 | 1.00 | 46.80 | C |
| ATOM | 3217 | O | SER | D | 48 | 66.000 | −22.874 | 2.670 | 1.00 | 46.24 | O |
| ATOM | 3218 | N | ILE | D | 49 | 65.401 | −23.952 | 0.838 | 1.00 | 46.02 | N |
| ATOM | 3219 | CA | ILE | D | 49 | 66.723 | −24.566 | 0.630 | 1.00 | 45.76 | C |
| ATOM | 3220 | CB | ILE | D | 49 | 66.583 | −26.054 | 0.296 | 1.00 | 45.49 | C |
| ATOM | 3221 | CG1 | ILE | D | 49 | 66.175 | −26.853 | 1.553 | 1.00 | 44.65 | C |
| ATOM | 3222 | CD1 | ILE | D | 49 | 65.438 | −28.191 | 1.239 | 1.00 | 45.72 | C |
| ATOM | 3223 | CG2 | ILE | D | 49 | 67.837 | −26.618 | −0.311 | 1.00 | 45.66 | C |
| ATOM | 3224 | C | ILE | D | 49 | 67.497 | −23.813 | −0.475 | 1.00 | 46.86 | C |
| ATOM | 3225 | O | ILE | D | 49 | 66.993 | −23.579 | −1.580 | 1.00 | 46.20 | O |
| ATOM | 3226 | N | SER | D | 50 | 68.714 | −23.400 | −0.154 | 1.00 | 48.31 | N |
| ATOM | 3227 | CA | SER | D | 50 | 69.582 | −22.795 | −1.161 | 1.00 | 50.07 | C |
| ATOM | 3228 | CB | SER | D | 50 | 70.610 | −21.875 | −0.521 | 1.00 | 49.69 | C |
| ATOM | 3229 | OG | SER | D | 50 | 69.966 | −20.656 | −0.222 | 1.00 | 51.30 | O |
| ATOM | 3230 | C | SER | D | 50 | 70.259 | −23.905 | −1.918 | 1.00 | 50.54 | C |
| ATOM | 3231 | O | SER | D | 50 | 70.853 | −24.804 | −1.304 | 1.00 | 50.91 | O |
| ATOM | 3232 | N | ILE | D | 51 | 70.136 | −23.854 | −3.247 | 1.00 | 51.03 | N |
| ATOM | 3233 | CA | ILE | D | 51 | 70.803 | −24.826 | −4.120 | 1.00 | 50.47 | C |
| ATOM | 3234 | CB | ILE | D | 51 | 70.134 | −24.926 | −5.529 | 1.00 | 50.18 | C |
| ATOM | 3235 | CG1 | ILE | D | 51 | 68.659 | −25.348 | −5.394 | 1.00 | 49.97 | C |
| ATOM | 3236 | CD1 | ILE | D | 51 | 68.424 | −26.692 | −4.703 | 1.00 | 47.26 | C |
| ATOM | 3237 | CG2 | ILE | D | 51 | 70.886 | −25.890 | −6.438 | 1.00 | 50.01 | C |
| ATOM | 3238 | C | ILE | D | 51 | 72.267 | −24.464 | −4.162 | 1.00 | 50.13 | C |
| ATOM | 3239 | O | ILE | D | 51 | 72.621 | −23.304 | −4.390 | 1.00 | 51.21 | O |
| ATOM | 3240 | N | GLY | D | 52 | 73.112 | −25.450 | −3.903 | 1.00 | 49.83 | N |
| ATOM | 3241 | CA | GLY | D | 52 | 74.537 | −25.220 | −3.804 | 1.00 | 49.62 | C |
| ATOM | 3242 | C | GLY | D | 52 | 75.198 | −26.276 | −2.957 | 1.00 | 49.66 | C |
| ATOM | 3243 | O | GLY | D | 52 | 74.639 | −26.711 | −1.948 | 1.00 | 50.36 | O |
| ATOM | 3244 | N | GLY | D | 53 | 76.371 | −26.698 | −3.407 | 1.00 | 49.38 | N |
| ATOM | 3245 | CA | GLY | D | 53 | 77.253 | −27.612 | −2.696 | 1.00 | 49.23 | C |
| ATOM | 3246 | C | GLY | D | 53 | 76.697 | −29.008 | −2.480 | 1.00 | 49.36 | C |
| ATOM | 3247 | O | GLY | D | 53 | 76.756 | −29.935 | −3.362 | 1.00 | 49.29 | O |
| ATOM | 3248 | N | ARG | D | 54 | 76.120 | −29.151 | −1.269 | 1.00 | 49.43 | N |
| ATOM | 3249 | CA | ARG | D | 54 | 75.465 | −30.394 | −0.907 | 1.00 | 49.74 | C |
| ATOM | 3250 | CB | ARG | D | 54 | 75.282 | −30.480 | 0.624 | 1.00 | 49.32 | C |
| ATOM | 3251 | CG | ARG | D | 54 | 76.280 | −31.418 | 1.274 | 1.00 | 50.69 | C |
| ATOM | 3252 | CD | ARG | D | 54 | 76.661 | −31.101 | 2.722 | 1.00 | 50.07 | C |
| ATOM | 3253 | NE | ARG | D | 54 | 75.585 | −30.643 | 3.597 | 1.00 | 48.37 | N |
| ATOM | 3254 | CZ | ARG | D | 54 | 74.591 | −31.392 | 4.086 | 1.00 | 49.71 | C |
| ATOM | 3255 | NH1 | ARG | D | 54 | 74.447 | −32.683 | 3.773 | 1.00 | 49.71 | N |
| ATOM | 3256 | NH2 | ARG | D | 54 | 73.710 | −30.832 | 4.899 | 1.00 | 47.05 | N |
| ATOM | 3257 | C | ARG | D | 54 | 74.141 | −30.581 | −1.660 | 1.00 | 49.58 | C |
| ATOM | 3258 | O | ARG | D | 54 | 73.723 | −31.708 | −1.911 | 1.00 | 50.26 | O |
| ATOM | 3259 | N | TYR | D | 55 | 73.485 | −29.486 | −2.017 | 1.00 | 49.51 | N |
| ATOM | 3260 | CA | TYR | D | 55 | 72.126 | −29.555 | −2.579 | 1.00 | 49.79 | C |
| ATOM | 3261 | CB | TYR | D | 55 | 71.193 | −28.546 | −1.877 | 1.00 | 49.87 | C |

APPENDIX I-continued

| ATOM | 3262 | CG | TYR | D | 55 | 71.207 | −28.685 | −0.366 | 1.00 | 50.16 | C |
|---|---|---|---|---|---|---|---|---|---|---|---|
| ATOM | 3263 | CD1 | TYR | D | 55 | 72.286 | −28.218 | 0.368 | 1.00 | 50.07 | C |
| ATOM | 3264 | CE1 | TYR | D | 55 | 72.336 | −28.353 | 1.725 | 1.00 | 51.90 | C |
| ATOM | 3265 | CZ | TYR | D | 55 | 71.290 | −28.965 | 2.417 | 1.00 | 52.02 | C |
| ATOM | 3266 | OH | TYR | D | 55 | 71.409 | −29.070 | 3.799 | 1.00 | 51.10 | O |
| ATOM | 3267 | CE2 | TYR | D | 55 | 70.183 | −29.449 | 1.720 | 1.00 | 50.23 | C |
| ATOM | 3268 | CD2 | TYR | D | 55 | 70.158 | −29.306 | 0.317 | 1.00 | 48.86 | C |
| ATOM | 3269 | C | TYR | D | 55 | 72.155 | −29.335 | −4.089 | 1.00 | 49.96 | C |
| ATOM | 3270 | O | TYR | D | 55 | 72.233 | −28.193 | −4.549 | 1.00 | 49.02 | O |
| ATOM | 3271 | N | VAL | D | 56 | 72.139 | −30.445 | −4.840 | 1.00 | 50.10 | N |
| ATOM | 3272 | CA | VAL | D | 56 | 72.158 | −30.378 | −6.319 | 1.00 | 50.02 | C |
| ATOM | 3273 | CB | VAL | D | 56 | 73.128 | −31.484 | −6.945 | 1.00 | 49.66 | C |
| ATOM | 3274 | CG1 | VAL | D | 56 | 72.672 | −31.803 | −8.492 | 1.00 | 49.55 | C |
| ATOM | 3275 | CG2 | VAL | D | 56 | 74.716 | −31.073 | −6.641 | 1.00 | 50.23 | C |
| ATOM | 3276 | C | VAL | D | 56 | 70.703 | −30.509 | −6.834 | 1.00 | 50.01 | C |
| ATOM | 3277 | O | VAL | D | 56 | 69.996 | −31.474 | −6.542 | 1.00 | 50.57 | O |
| ATOM | 3278 | N | GLU | D | 57 | 70.240 | −29.514 | −7.565 | 1.00 | 50.47 | N |
| ATOM | 3279 | CA | GLU | D | 57 | 68.959 | −29.637 | −8.261 | 1.00 | 50.96 | C |
| ATOM | 3280 | CB | GLU | D | 57 | 68.069 | −28.432 | −8.002 | 1.00 | 49.91 | C |
| ATOM | 3281 | CG | GLU | D | 57 | 66.785 | −28.464 | −8.792 | 1.00 | 48.91 | C |
| ATOM | 3282 | CD | GLU | D | 57 | 65.896 | −27.281 | −8.499 | 1.00 | 46.98 | C |
| ATOM | 3283 | OE1 | GLU | D | 57 | 66.400 | −26.213 | −8.111 | 1.00 | 46.14 | O |
| ATOM | 3284 | OE2 | GLU | D | 57 | 64.670 | −27.425 | −8.644 | 1.00 | 49.35 | O |
| ATOM | 3285 | C | GLU | D | 57 | 69.192 | −29.777 | −9.755 | 1.00 | 51.88 | C |
| ATOM | 3286 | O | GLU | D | 57 | 70.071 | −29.125 | −10.302 | 1.00 | 52.11 | O |
| ATOM | 3287 | N | THR | D | 58 | 68.414 | −30.645 | −10.396 | 1.00 | 53.11 | N |
| ATOM | 3288 | CA | THR | D | 58 | 68.383 | −30.727 | −11.854 | 1.00 | 54.42 | C |
| ATOM | 3289 | CB | THR | D | 58 | 69.137 | −31.978 | −12.403 | 1.00 | 54.38 | C |
| ATOM | 3290 | OG1 | THR | D | 58 | 68.449 | −33.205 | −11.829 | 1.00 | 56.17 | O |
| ATOM | 3291 | CG2 | THR | D | 58 | 70.734 | −31.924 | −12.037 | 1.00 | 55.32 | C |
| ATOM | 3292 | C | THR | D | 58 | 66.896 | −30.691 | −12.250 | 1.00 | 55.02 | C |
| ATOM | 3293 | O | THR | D | 58 | 66.072 | −31.406 | −11.670 | 1.00 | 55.11 | O |
| ATOM | 3294 | N | VAL | D | 59 | 66.577 | −29.813 | −13.219 | 1.00 | 55.68 | N |
| ATOM | 3295 | CA | VAL | D | 59 | 65.203 | −29.468 | −13.615 | 1.00 | 55.90 | C |
| ATOM | 3296 | CB | VAL | D | 59 | 64.926 | −27.955 | −13.378 | 1.00 | 55.61 | C |
| ATOM | 3297 | CG1 | VAL | D | 59 | 64.629 | −27.687 | −11.961 | 1.00 | 55.58 | C |
| ATOM | 3298 | CG2 | VAL | D | 59 | 66.144 | −27.115 | −13.745 | 1.00 | 57.13 | C |
| ATOM | 3299 | C | VAL | D | 59 | 64.991 | −29.817 | −15.100 | 1.00 | 56.39 | C |
| ATOM | 3300 | O | VAL | D | 59 | 65.863 | −29.553 | −15.950 | 1.00 | 55.93 | O |
| ATOM | 3301 | N | ASN | D | 60 | 63.840 | −30.415 | −15.410 | 1.00 | 56.80 | N |
| ATOM | 3302 | CA | ASN | D | 60 | 63.549 | −30.882 | −16.774 | 1.00 | 56.63 | C |
| ATOM | 3303 | CB | ASN | D | 60 | 63.691 | −32.413 | −16.873 | 1.00 | 56.38 | C |
| ATOM | 3304 | CG | ASN | D | 60 | 64.099 | −32.854 | −18.348 | 1.00 | 57.37 | C |
| ATOM | 3305 | OD1 | ASN | D | 60 | 65.090 | −33.646 | −18.466 | 1.00 | 56.92 | O |
| ATOM | 3306 | ND2 | ASN | D | 60 | 63.351 | −32.354 | −19.408 | 1.00 | 55.67 | N |
| ATOM | 3307 | C | ASN | D | 60 | 62.172 | −30.461 | −17.310 | 1.00 | 56.88 | C |
| ATOM | 3308 | O | ASN | D | 60 | 61.252 | −31.423 | −17.192 | 1.00 | 56.87 | O |
| ATOM | 3309 | N | LYS | D | 61 | 62.032 | −28.997 | −17.392 | 1.00 | 57.33 | N |
| ATOM | 3310 | CA | LYS | D | 61 | 60.747 | −28.473 | −17.883 | 1.00 | 57.81 | C |
| ATOM | 3311 | CB | LYS | D | 61 | 60.891 | −26.968 | −18.145 | 1.00 | 58.40 | C |
| ATOM | 3312 | CG | LYS | D | 61 | 59.597 | −26.259 | −18.597 | 1.00 | 59.54 | C |
| ATOM | 3313 | CD | LYS | D | 61 | 59.929 | −25.060 | −19.492 | 1.00 | 61.86 | C |
| ATOM | 3314 | CE | LYS | D | 61 | 58.690 | −24.361 | −20.096 | 1.00 | 61.96 | C |
| ATOM | 3315 | NZ | LYS | D | 61 | 58.446 | −23.001 | −19.525 | 1.00 | 62.65 | N |
| ATOM | 3316 | C | LYS | D | 61 | 60.212 | −29.215 | −19.141 | 1.00 | 57.89 | C |
| ATOM | 3317 | O | LYS | D | 61 | 58.997 | −29.366 | −19.309 | 1.00 | 58.21 | O |
| ATOM | 3318 | N | GLY | D | 62 | 61.122 | −29.693 | −20.002 | 1.00 | 57.58 | N |
| ATOM | 3319 | CA | GLY | D | 62 | 60.761 | −30.486 | −21.186 | 1.00 | 57.06 | C |
| ATOM | 3320 | C | GLY | D | 62 | 60.000 | −31.791 | −20.907 | 1.00 | 56.82 | C |
| ATOM | 3321 | O | GLY | D | 62 | 59.381 | −32.386 | −21.864 | 1.00 | 57.25 | O |
| ATOM | 3322 | N | SER | D | 63 | 60.060 | −32.244 | −19.594 | 1.00 | 55.97 | N |
| ATOM | 3323 | CA | SER | D | 63 | 59.302 | −33.409 | −19.125 | 1.00 | 54.90 | C |
| ATOM | 3324 | CB | SER | D | 63 | 60.272 | −34.621 | −18.908 | 1.00 | 55.09 | C |
| ATOM | 3325 | OG | SER | D | 63 | 60.645 | −34.692 | −17.338 | 1.00 | 54.74 | O |
| ATOM | 3326 | C | SER | D | 63 | 58.474 | −33.104 | −17.762 | 1.00 | 53.75 | C |
| ATOM | 3327 | O | SER | D | 63 | 57.786 | −34.003 | −17.034 | 1.00 | 53.64 | O |
| ATOM | 3328 | N | LYS | D | 64 | 58.533 | −31.834 | −17.394 | 1.00 | 52.95 | N |
| ATOM | 3329 | CA | LYS | D | 64 | 57.857 | −31.310 | −16.167 | 1.00 | 52.47 | C |
| ATOM | 3330 | CB | LYS | D | 64 | 56.344 | −31.240 | −16.372 | 1.00 | 52.40 | C |
| ATOM | 3331 | CG | LYS | D | 64 | 55.971 | −29.890 | −17.112 | 1.00 | 53.07 | C |
| ATOM | 3332 | CD | LYS | D | 64 | 54.977 | −30.113 | −18.294 | 1.00 | 53.84 | C |
| ATOM | 3333 | CE | LYS | D | 64 | 53.558 | −30.322 | −17.603 | 1.00 | 53.96 | C |
| ATOM | 3334 | NZ | LYS | D | 64 | 52.517 | −30.001 | −18.618 | 1.00 | 51.87 | N |
| ATOM | 3335 | C | LYS | D | 64 | 58.301 | −31.907 | −14.795 | 1.00 | 51.17 | C |
| ATOM | 3336 | O | LYS | D | 64 | 57.603 | −31.826 | −13.761 | 1.00 | 51.55 | O |
| ATOM | 3337 | N | SER | D | 65 | 59.517 | −32.439 | −14.827 | 1.00 | 49.79 | N |
| ATOM | 3338 | CA | SER | D | 65 | 60.167 | −33.103 | −13.708 | 1.00 | 49.92 | C |
| ATOM | 3339 | CB | SER | D | 65 | 60.834 | −34.407 | −14.213 | 1.00 | 49.55 | C |
| ATOM | 3340 | OG | SER | D | 65 | 61.759 | −34.932 | −13.248 | 1.00 | 53.24 | O |
| ATOM | 3341 | C | SER | D | 65 | 61.234 | −32.168 | −13.120 | 1.00 | 49.16 | C |

APPENDIX I-continued

| | | | | | | | | | | | |
|---|---|---|---|---|---|---|---|---|---|---|---|
| ATOM | 3342 | O | SER | D | 65 | 61.838 | −31.333 | −13.866 | 1.00 | 48.96 | O |
| ATOM | 3343 | N | PHE | D | 66 | 61.437 | −32.304 | −11.802 | 1.00 | 47.24 | N |
| ATOM | 3344 | CA | PHE | D | 66 | 62.543 | −31.670 | −11.066 | 1.00 | 46.15 | C |
| ATOM | 3345 | CB | PHE | D | 66 | 62.277 | −30.171 | −10.826 | 1.00 | 44.90 | C |
| ATOM | 3346 | CG | PHE | D | 66 | 61.128 | −29.867 | −9.891 | 1.00 | 44.59 | C |
| ATOM | 3347 | CD1 | PHE | D | 66 | 59.801 | −29.989 | −10.317 | 1.00 | 42.09 | C |
| ATOM | 3348 | CE1 | PHE | D | 66 | 58.738 | −29.686 | −9.470 | 1.00 | 41.74 | C |
| ATOM | 3349 | CZ | PHE | D | 66 | 58.997 | −29.224 | −8.170 | 1.00 | 42.61 | C |
| ATOM | 3350 | CE2 | PHE | D | 66 | 60.315 | −29.087 | −7.722 | 1.00 | 43.21 | C |
| ATOM | 3351 | CD2 | PHE | D | 66 | 61.376 | −29.410 | −8.586 | 1.00 | 44.86 | C |
| ATOM | 3352 | C | PHE | D | 66 | 62.988 | −32.439 | −9.769 | 1.00 | 45.82 | C |
| ATOM | 3353 | O | PHE | D | 66 | 62.222 | −33.197 | −9.181 | 1.00 | 46.26 | O |
| ATOM | 3354 | N | SER | D | 67 | 64.238 | −32.257 | −9.351 | 1.00 | 45.70 | N |
| ATOM | 3355 | CA | SER | D | 67 | 64.862 | −33.149 | −8.367 | 1.00 | 45.45 | C |
| ATOM | 3356 | CB | SER | D | 67 | 65.603 | −34.242 | −9.113 | 1.00 | 45.90 | C |
| ATOM | 3357 | OG | SER | D | 67 | 64.734 | −35.335 | −9.256 | 1.00 | 47.19 | O |
| ATOM | 3358 | C | SER | D | 67 | 65.871 | −32.497 | −7.455 | 1.00 | 45.20 | C |
| ATOM | 3359 | O | SER | D | 67 | 66.655 | −31.642 | −7.902 | 1.00 | 46.01 | O |
| ATOM | 3360 | N | LEU | D | 68 | 65.872 | −32.930 | −6.196 | 1.00 | 44.54 | N |
| ATOM | 3361 | CA | LEU | D | 68 | 66.855 | −32.507 | −5.212 | 1.00 | 44.12 | C |
| ATOM | 3362 | CB | LEU | D | 68 | 66.203 | −31.902 | −3.968 | 1.00 | 43.76 | C |
| ATOM | 3363 | CG | LEU | D | 68 | 66.799 | −30.640 | −3.315 | 1.00 | 44.66 | C |
| ATOM | 3364 | CD1 | LEU | D | 68 | 66.693 | −30.684 | −1.812 | 1.00 | 45.00 | C |
| ATOM | 3365 | CD2 | LEU | D | 68 | 68.213 | −30.336 | −3.739 | 1.00 | 41.15 | C |
| ATOM | 3366 | C | LEU | D | 68 | 67.653 | −33.717 | −4.766 | 1.00 | 43.76 | C |
| ATOM | 3367 | O | LEU | D | 68 | 67.095 | −34.701 | −4.302 | 1.00 | 41.85 | O |
| ATOM | 3368 | N | ARG | D | 69 | 68.966 | −33.629 | −4.920 | 1.00 | 44.26 | N |
| ATOM | 3369 | CA | ARG | D | 69 | 69.873 | −34.621 | −4.383 | 1.00 | 45.51 | C |
| ATOM | 3370 | CB | ARG | D | 69 | 70.817 | −35.147 | −5.493 | 1.00 | 44.78 | C |
| ATOM | 3371 | CG | ARG | D | 69 | 71.578 | −36.356 | −5.011 | 1.00 | 47.38 | C |
| ATOM | 3372 | CD | ARG | D | 69 | 72.519 | −36.978 | −6.039 | 1.00 | 50.01 | C |
| ATOM | 3373 | NE | ARG | D | 69 | 73.038 | −38.236 | −5.447 | 1.00 | 64.56 | N |
| ATOM | 3374 | CZ | ARG | D | 69 | 74.278 | −38.371 | −4.916 | 1.00 | 70.54 | C |
| ATOM | 3375 | NH1 | ARG | D | 69 | 75.200 | −37.308 | −4.958 | 1.00 | 70.65 | N |
| ATOM | 3376 | NH2 | ARG | D | 69 | 74.628 | −39.585 | −4.368 | 1.00 | 70.40 | N |
| ATOM | 3377 | C | ARG | D | 69 | 70.647 | −33.877 | −3.316 | 1.00 | 44.18 | C |
| ATOM | 3378 | O | ARG | D | 69 | 71.228 | −32.821 | −3.583 | 1.00 | 45.88 | O |
| ATOM | 3379 | N | ILE | D | 70 | 70.611 | −34.393 | −2.100 | 1.00 | 44.15 | N |
| ATOM | 3380 | CA | ILE | D | 70 | 71.400 | −33.865 | −1.004 | 1.00 | 43.11 | C |
| ATOM | 3381 | CB | ILE | D | 70 | 70.560 | −33.577 | 0.247 | 1.00 | 43.37 | C |
| ATOM | 3382 | CG1 | ILE | D | 70 | 69.343 | −32.713 | −0.092 | 1.00 | 40.96 | C |
| ATOM | 3383 | CD1 | ILE | D | 70 | 68.184 | −33.028 | 0.730 | 1.00 | 43.95 | C |
| ATOM | 3384 | CG2 | ILE | D | 70 | 71.443 | −32.879 | 1.306 | 1.00 | 43.28 | C |
| ATOM | 3385 | C | ILE | D | 70 | 72.431 | −34.947 | −0.699 | 1.00 | 43.35 | C |
| ATOM | 3386 | O | ILE | D | 70 | 72.072 | −36.079 | −0.404 | 1.00 | 42.77 | O |
| ATOM | 3387 | N | SER | D | 71 | 73.707 | −34.619 | −0.851 | 1.00 | 43.10 | N |
| ATOM | 3388 | CA | SER | D | 71 | 74.735 | −35.597 | −0.571 | 1.00 | 43.65 | C |
| ATOM | 3389 | CB | SER | D | 71 | 75.794 | −35.590 | −1.669 | 1.00 | 43.42 | C |
| ATOM | 3390 | OG | SER | D | 71 | 76.168 | −34.259 | −1.929 | 1.00 | 44.36 | O |
| ATOM | 3391 | C | SER | D | 71 | 75.306 | −35.317 | 0.817 | 1.00 | 43.63 | C |
| ATOM | 3392 | O | SER | D | 71 | 74.923 | −34.309 | 1.447 | 1.00 | 44.14 | O |
| ATOM | 3393 | N | ASP | D | 72 | 76.156 | −36.232 | 1.309 | 1.00 | 43.29 | N |
| ATOM | 3394 | CA | ASP | D | 72 | 76.858 | −36.065 | 2.582 | 1.00 | 42.35 | C |
| ATOM | 3395 | CB | ASP | D | 72 | 77.912 | −34.951 | 2.458 | 1.00 | 42.24 | C |
| ATOM | 3396 | CG | ASP | D | 72 | 78.973 | −35.012 | 3.572 | 1.00 | 44.75 | C |
| ATOM | 3397 | OD1 | ASP | D | 72 | 78.995 | −36.012 | 4.344 | 1.00 | 42.13 | O |
| ATOM | 3398 | OD2 | ASP | D | 72 | 79.800 | −34.057 | 3.659 | 1.00 | 47.88 | O |
| ATOM | 3399 | C | ASP | D | 72 | 75.880 | −35.777 | 3.746 | 1.00 | 41.01 | C |
| ATOM | 3400 | O | ASP | D | 72 | 75.935 | −34.731 | 4.394 | 1.00 | 40.46 | O |
| ATOM | 3401 | N | LEU | D | 73 | 74.982 | −36.713 | 4.003 | 1.00 | 40.43 | N |
| ATOM | 3402 | CA | LEU | D | 73 | 73.915 | −36.470 | 4.965 | 1.00 | 39.98 | C |
| ATOM | 3403 | CB | LEU | D | 73 | 72.761 | −37.447 | 4.752 | 1.00 | 40.03 | C |
| ATOM | 3404 | CG | LEU | D | 73 | 71.891 | −37.260 | 3.493 | 1.00 | 38.61 | C |
| ATOM | 3405 | CD1 | LEU | D | 73 | 70.971 | −38.462 | 3.446 | 1.00 | 37.16 | C |
| ATOM | 3406 | CD2 | LEU | D | 73 | 71.094 | −36.006 | 3.576 | 1.00 | 38.44 | C |
| ATOM | 3407 | C | LEU | D | 73 | 74.409 | −36.458 | 6.424 | 1.00 | 39.77 | C |
| ATOM | 3408 | O | LEU | D | 73 | 75.344 | −37.149 | 6.802 | 1.00 | 38.86 | O |
| ATOM | 3409 | N | ARG | D | 74 | 73.784 | −35.600 | 7.214 | 1.00 | 40.34 | N |
| ATOM | 3410 | CA | ARG | D | 74 | 74.125 | −35.418 | 8.616 | 1.00 | 40.91 | C |
| ATOM | 3411 | CB | ARG | D | 74 | 74.711 | −34.024 | 8.803 | 1.00 | 41.22 | C |
| ATOM | 3412 | CG | ARG | D | 74 | 75.561 | −33.574 | 7.623 | 1.00 | 44.83 | C |
| ATOM | 3413 | CD | ARG | D | 74 | 76.259 | −32.276 | 7.888 | 1.00 | 51.37 | C |
| ATOM | 3414 | NE | ARG | D | 74 | 75.309 | −31.193 | 8.146 | 1.00 | 55.28 | N |
| ATOM | 3415 | CZ | ARG | D | 74 | 75.645 | −30.008 | 8.662 | 1.00 | 56.79 | C |
| ATOM | 3416 | NH1 | ARG | D | 74 | 76.913 | −29.758 | 8.987 | 1.00 | 55.96 | N |
| ATOM | 3417 | NH2 | ARG | D | 74 | 74.711 | −29.079 | 8.868 | 1.00 | 56.56 | N |
| ATOM | 3418 | C | ARG | D | 74 | 72.820 | −35.563 | 9.406 | 1.00 | 40.45 | C |
| ATOM | 3419 | O | ARG | D | 74 | 71.735 | −35.292 | 8.851 | 1.00 | 40.13 | O |
| ATOM | 3420 | N | VAL | D | 75 | 72.901 | −36.003 | 10.663 | 1.00 | 39.63 | N |
| ATOM | 3421 | CA | VAL | D | 75 | 71.700 | −36.030 | 11.512 | 1.00 | 40.06 | C |

APPENDIX I-continued

| ATOM | 3422 | CB  | VAL | D | 75 | 71.970 | −36.527 | 12.963 | 1.00 | 39.68 | C |
| ATOM | 3423 | CG1 | VAL | D | 75 | 72.504 | −37.923 | 12.939 | 1.00 | 37.56 | C |
| ATOM | 3424 | CG2 | VAL | D | 75 | 72.893 | −35.615 | 13.685 | 1.00 | 41.38 | C |
| ATOM | 3425 | C   | VAL | D | 75 | 70.872 | −34.702 | 11.509 | 1.00 | 40.03 | C |
| ATOM | 3426 | O   | VAL | D | 75 | 69.652 | −34.750 | 11.502 | 1.00 | 40.31 | O |
| ATOM | 3427 | N   | GLU | D | 76 | 71.516 | −33.534 | 11.474 | 1.00 | 39.38 | N |
| ATOM | 3428 | CA  | GLU | D | 76 | 70.783 | −32.267 | 11.413 | 1.00 | 38.58 | C |
| ATOM | 3429 | CB  | GLU | D | 76 | 71.704 | −31.072 | 11.643 | 1.00 | 39.43 | C |
| ATOM | 3430 | CG  | GLU | D | 76 | 73.155 | −31.300 | 11.253 | 1.00 | 43.81 | C |
| ATOM | 3431 | CD  | GLU | D | 76 | 73.899 | −32.091 | 12.300 | 1.00 | 49.07 | C |
| ATOM | 3432 | OE1 | GLU | D | 76 | 74.410 | −33.201 | 12.002 | 1.00 | 50.38 | O |
| ATOM | 3433 | OE2 | GLU | D | 76 | 73.963 | −31.604 | 13.445 | 1.00 | 53.73 | O |
| ATOM | 3434 | C   | GLU | D | 76 | 70.012 | −32.038 | 10.113 | 1.00 | 37.13 | C |
| ATOM | 3435 | O   | GLU | D | 76 | 69.328 | −31.018 | 9.981  | 1.00 | 36.46 | O |
| ATOM | 3436 | N   | ASP | D | 77 | 70.139 | −32.955 | 9.156  | 1.00 | 35.88 | N |
| ATOM | 3437 | CA  | ASP | D | 77 | 69.302 | −32.934 | 7.896  | 1.00 | 35.98 | C |
| ATOM | 3438 | CB  | ASP | D | 77 | 69.995 | −33.640 | 6.719  | 1.00 | 35.29 | C |
| ATOM | 3439 | CG  | ASP | D | 77 | 71.259 | −32.944 | 6.258  | 1.00 | 36.12 | C |
| ATOM | 3440 | OD1 | ASP | D | 77 | 71.314 | −31.707 | 6.247  | 1.00 | 34.87 | O |
| ATOM | 3441 | OD2 | ASP | D | 77 | 72.200 | −33.674 | 5.890  | 1.00 | 39.60 | O |
| ATOM | 3442 | C   | ASP | D | 77 | 67.933 | −33.626 | 8.022  | 1.00 | 35.40 | C |
| ATOM | 3443 | O   | ASP | D | 77 | 67.106 | −33.451 | 7.146  | 1.00 | 35.70 | O |
| ATOM | 3444 | N   | SER | D | 78 | 67.740 | −34.480 | 9.027  | 1.00 | 34.77 | N |
| ATOM | 3445 | CA  | SER | D | 78 | 66.422 | −34.981 | 9.345  | 1.00 | 35.45 | C |
| ATOM | 3446 | CB  | SER | D | 78 | 66.473 | −35.750 | 10.659 | 1.00 | 35.78 | C |
| ATOM | 3447 | OG  | SER | D | 78 | 67.436 | −36.770 | 10.546 | 1.00 | 36.74 | O |
| ATOM | 3448 | C   | SER | D | 78 | 65.321 | −33.899 | 9.393  | 1.00 | 35.23 | C |
| ATOM | 3449 | O   | SER | D | 78 | 65.471 | −32.828 | 10.038 | 1.00 | 35.34 | O |
| ATOM | 3450 | N   | GLY | D | 79 | 64.210 | −34.192 | 8.716  | 1.00 | 33.82 | N |
| ATOM | 3451 | CA  | GLY | D | 79 | 63.078 | −33.271 | 8.649  | 1.00 | 34.33 | C |
| ATOM | 3452 | C   | GLY | D | 79 | 62.191 | −33.603 | 7.481  | 1.00 | 35.45 | C |
| ATOM | 3453 | O   | GLY | D | 79 | 62.404 | −34.627 | 6.767  | 1.00 | 36.59 | O |
| ATOM | 3454 | N   | THR | D | 80 | 61.239 | −32.707 | 7.242  | 1.00 | 36.95 | N |
| ATOM | 3455 | CA  | THR | D | 80 | 60.265 | −32.773 | 6.142  | 1.00 | 37.81 | C |
| ATOM | 3456 | CB  | THR | D | 80 | 58.812 | −32.455 | 6.589  | 1.00 | 37.21 | C |
| ATOM | 3457 | OG1 | THR | D | 80 | 58.540 | −33.092 | 7.845  | 1.00 | 42.51 | O |
| ATOM | 3458 | CG2 | THR | D | 80 | 57.794 | −32.957 | 5.599  | 1.00 | 36.93 | C |
| ATOM | 3459 | C   | THR | D | 80 | 60.658 | −31.822 | 5.030  | 1.00 | 39.38 | C |
| ATOM | 3460 | O   | THR | D | 80 | 60.734 | −30.616 | 5.253  | 1.00 | 39.45 | O |
| ATOM | 3461 | N   | TYR | D | 81 | 60.882 | −32.394 | 3.835  | 1.00 | 39.69 | N |
| ATOM | 3462 | CA  | TYR | D | 81 | 61.244 | −31.683 | 2.641  | 1.00 | 40.11 | C |
| ATOM | 3463 | CB  | TYR | D | 81 | 62.433 | −32.367 | 1.967  | 1.00 | 40.22 | C |
| ATOM | 3464 | CG  | TYR | D | 81 | 63.719 | −32.354 | 2.802  | 1.00 | 39.55 | C |
| ATOM | 3465 | CD1 | TYR | D | 81 | 64.755 | −31.515 | 2.468  | 1.00 | 39.29 | C |
| ATOM | 3466 | CE1 | TYR | D | 81 | 65.935 | −31.489 | 3.213  | 1.00 | 39.91 | C |
| ATOM | 3467 | CZ  | TYR | D | 81 | 66.087 | −32.315 | 4.305  | 1.00 | 40.52 | C |
| ATOM | 3468 | OH  | TYR | D | 81 | 67.291 | −32.242 | 5.010  | 1.00 | 39.06 | O |
| ATOM | 3469 | CE2 | TYR | D | 81 | 65.066 | −33.175 | 4.655  | 1.00 | 37.99 | C |
| ATOM | 3470 | CD2 | TYR | D | 81 | 63.892 | −33.194 | 3.897  | 1.00 | 38.47 | C |
| ATOM | 3471 | C   | TYR | D | 81 | 60.064 | −31.621 | 1.693  | 1.00 | 40.88 | C |
| ATOM | 3472 | O   | TYR | D | 81 | 59.242 | −32.572 | 1.577  | 1.00 | 42.06 | O |
| ATOM | 3473 | N   | LYS | D | 82 | 59.925 | −30.469 | 1.063  | 1.00 | 41.23 | N |
| ATOM | 3474 | CA  | LYS | D | 82 | 58.819 | −30.189 | 0.172  | 1.00 | 41.95 | C |
| ATOM | 3475 | CB  | LYS | D | 82 | 57.779 | −29.315 | 0.863  | 1.00 | 42.23 | C |
| ATOM | 3476 | CG  | LYS | D | 82 | 56.447 | −30.008 | 1.156  | 1.00 | 46.06 | C |
| ATOM | 3477 | CD  | LYS | D | 82 | 55.949 | −29.607 | 2.549  | 1.00 | 53.37 | C |
| ATOM | 3478 | CE  | LYS | D | 82 | 54.875 | −30.528 | 3.091  | 1.00 | 51.30 | C |
| ATOM | 3479 | NZ  | LYS | D | 82 | 53.540 | −30.122 | 2.613  | 1.00 | 50.40 | N |
| ATOM | 3480 | C   | LYS | D | 82 | 59.381 | −29.472 | −1.028 | 1.00 | 42.24 | C |
| ATOM | 3481 | O   | LYS | D | 82 | 60.236 | −28.607 | −0.899 | 1.00 | 41.51 | O |
| ATOM | 3482 | N   | CYS | D | 83 | 58.912 | −29.863 | −2.207 | 1.00 | 43.47 | N |
| ATOM | 3483 | CA  | CYS | D | 83 | 59.163 | −29.117 | −3.400 | 1.00 | 44.82 | C |
| ATOM | 3484 | CB  | CYS | D | 83 | 59.474 | −30.038 | −4.564 | 1.00 | 45.49 | C |
| ATOM | 3485 | SG  | CYS | D | 83 | 58.161 | −31.141 | −4.953 | 1.00 | 44.99 | S |
| ATOM | 3486 | C   | CYS | D | 83 | 57.923 | −28.295 | −3.711 | 1.00 | 45.88 | C |
| ATOM | 3487 | O   | CYS | D | 83 | 56.827 | −28.610 | −3.259 | 1.00 | 46.33 | O |
| ATOM | 3488 | N   | GLN | D | 84 | 58.132 | −27.220 | −4.465 | 1.00 | 46.29 | N |
| ATOM | 3489 | CA  | GLN | D | 84 | 57.058 | −26.400 | −5.007 | 1.00 | 45.80 | C |
| ATOM | 3490 | CB  | GLN | D | 84 | 56.949 | −25.084 | −4.280 | 1.00 | 46.07 | C |
| ATOM | 3491 | CG  | GLN | D | 84 | 55.811 | −24.290 | −4.826 | 1.00 | 47.89 | C |
| ATOM | 3492 | CD  | GLN | D | 84 | 55.202 | −23.369 | −3.835 | 1.00 | 50.52 | C |
| ATOM | 3493 | OE1 | GLN | D | 84 | 54.030 | −23.056 | −3.953 | 1.00 | 54.26 | O |
| ATOM | 3494 | NE2 | GLN | D | 84 | 55.991 | −22.898 | −2.861 | 1.00 | 50.71 | N |
| ATOM | 3495 | C   | GLN | D | 84 | 57.352 | −26.107 | −6.466 | 1.00 | 44.92 | C |
| ATOM | 3496 | O   | GLN | D | 84 | 58.466 | −25.756 | −6.822 | 1.00 | 44.76 | O |
| ATOM | 3497 | N   | ALA | D | 85 | 56.328 | −26.309 | −7.271 | 1.00 | 44.45 | N |
| ATOM | 3498 | CA  | ALA | D | 85 | 56.287 | −26.074 | −8.693 | 1.00 | 44.03 | C |
| ATOM | 3499 | CB  | ALA | D | 85 | 55.513 | −27.178 | −9.330 | 1.00 | 43.73 | C |
| ATOM | 3500 | C   | ALA | D | 85 | 55.581 | −24.740 | −8.953 | 1.00 | 44.64 | C |
| ATOM | 3501 | O   | ALA | D | 85 | 54.506 | −24.480 | −8.398 | 1.00 | 45.56 | O |

APPENDIX I-continued

| | | | | | | | | | | | |
|---|---|---|---|---|---|---|---|---|---|---|---|
| ATOM | 3502 | N | PHE | D | 86 | 56.179 | −23.900 | −9.797 | 1.00 | 44.70 | N |
| ATOM | 3503 | CA | PHE | D | 86 | 55.646 | −22.570 | −10.110 | 1.00 | 43.77 | C |
| ATOM | 3504 | CB | PHE | D | 86 | 56.662 | −21.505 | −9.755 | 1.00 | 43.68 | C |
| ATOM | 3505 | CG | PHE | D | 86 | 56.899 | −21.325 | −8.234 | 1.00 | 43.64 | C |
| ATOM | 3506 | CD1 | PHE | D | 86 | 58.108 | −21.734 | −7.644 | 1.00 | 39.50 | C |
| ATOM | 3507 | CE1 | PHE | D | 86 | 58.352 | −21.536 | −6.258 | 1.00 | 41.98 | C |
| ATOM | 3508 | CZ | PHE | D | 86 | 57.392 | −20.906 | −5.466 | 1.00 | 43.10 | C |
| ATOM | 3509 | CE2 | PHE | D | 86 | 56.164 | −20.469 | −6.060 | 1.00 | 42.82 | C |
| ATOM | 3510 | CD2 | PHE | D | 86 | 55.936 | −20.693 | −7.427 | 1.00 | 42.57 | C |
| ATOM | 3511 | C | PHE | D | 86 | 55.284 | −22.518 | −11.581 | 1.00 | 43.35 | C |
| ATOM | 3512 | O | PHE | D | 86 | 56.047 | −22.948 | −12.451 | 1.00 | 43.61 | O |
| ATOM | 3513 | N | TYR | D | 87 | 54.071 | −22.067 | −11.860 | 1.00 | 43.20 | N |
| ATOM | 3514 | CA | TYR | D | 87 | 53.528 | −22.118 | −13.225 | 1.00 | 42.85 | C |
| ATOM | 3515 | CB | TYR | D | 87 | 52.706 | −23.392 | −13.419 | 1.00 | 42.88 | C |
| ATOM | 3516 | CG | TYR | D | 87 | 51.616 | −23.570 | −12.381 | 1.00 | 43.24 | C |
| ATOM | 3517 | CD1 | TYR | D | 87 | 50.361 | −23.023 | −12.574 | 1.00 | 41.66 | C |
| ATOM | 3518 | CE1 | TYR | D | 87 | 49.378 | −23.166 | −11.626 | 1.00 | 43.81 | C |
| ATOM | 3519 | CZ | TYR | D | 87 | 49.645 | −23.855 | −10.456 | 1.00 | 42.83 | C |
| ATOM | 3520 | OH | TYR | D | 87 | 48.635 | −23.981 | −9.495 | 1.00 | 45.90 | O |
| ATOM | 3521 | CE2 | TYR | D | 87 | 50.879 | −24.412 | −10.260 | 1.00 | 40.71 | C |
| ATOM | 3522 | CD2 | TYR | D | 87 | 51.849 | −24.270 | −11.203 | 1.00 | 41.31 | C |
| ATOM | 3523 | C | TYR | D | 87 | 52.678 | −20.887 | −13.442 | 1.00 | 42.38 | C |
| ATOM | 3524 | O | TYR | D | 87 | 52.341 | −20.184 | −12.479 | 1.00 | 41.90 | O |
| ATOM | 3525 | N | VAL | D | 88 | 52.328 | −20.625 | −14.690 | 1.00 | 42.33 | N |
| ATOM | 3526 | CA | VAL | D | 88 | 51.484 | −19.482 | −15.014 | 1.00 | 42.91 | C |
| ATOM | 3527 | CB | VAL | D | 88 | 52.241 | −18.322 | −15.725 | 1.00 | 42.23 | C |
| ATOM | 3528 | CG1 | VAL | D | 88 | 52.648 | −18.693 | −17.134 | 1.00 | 42.89 | C |
| ATOM | 3529 | CG2 | VAL | D | 88 | 53.461 | −17.852 | −14.923 | 1.00 | 42.15 | C |
| ATOM | 3530 | C | VAL | D | 88 | 50.343 | −20.009 | −15.861 | 1.00 | 43.65 | C |
| ATOM | 3531 | O | VAL | D | 88 | 50.483 | −21.016 | −16.523 | 1.00 | 44.60 | O |
| ATOM | 3532 | N | PHE | D | 89 | 49.204 | −19.351 | −15.789 | 1.00 | 44.07 | N |
| ATOM | 3533 | CA | PHE | D | 89 | 48.019 | −19.716 | −16.558 | 1.00 | 44.21 | C |
| ATOM | 3534 | CB | PHE | D | 89 | 47.186 | −20.807 | −15.865 | 1.00 | 43.34 | C |
| ATOM | 3535 | CG | PHE | D | 89 | 46.719 | −20.466 | −14.459 | 1.00 | 42.59 | C |
| ATOM | 3536 | CD1 | PHE | D | 89 | 45.427 | −19.948 | −14.236 | 1.00 | 42.34 | C |
| ATOM | 3537 | CE1 | PHE | D | 89 | 44.978 | −19.651 | −12.942 | 1.00 | 41.00 | C |
| ATOM | 3538 | CZ | PHE | D | 89 | 45.828 | −19.873 | −11.839 | 1.00 | 41.21 | C |
| ATOM | 3539 | CE2 | PHE | D | 89 | 47.115 | −20.389 | −12.048 | 1.00 | 40.99 | C |
| ATOM | 3540 | CD2 | PHE | D | 89 | 47.547 | −20.683 | −13.358 | 1.00 | 39.83 | C |
| ATOM | 3541 | C | PHE | D | 89 | 47.258 | −18.419 | −16.699 | 1.00 | 45.29 | C |
| ATOM | 3542 | O | PHE | D | 89 | 47.586 | −17.446 | −16.012 | 1.00 | 44.92 | O |
| ATOM | 3543 | N | PHE | D | 90 | 46.278 | −18.379 | −17.594 | 1.00 | 46.60 | N |
| ATOM | 3544 | CA | PHE | D | 90 | 45.525 | −17.166 | −17.790 | 1.00 | 47.84 | C |
| ATOM | 3545 | CB | PHE | D | 90 | 45.113 | −17.033 | −19.229 | 1.00 | 49.12 | C |
| ATOM | 3546 | CG | PHE | D | 90 | 46.217 | −16.590 | −20.135 | 1.00 | 52.21 | C |
| ATOM | 3547 | CD1 | PHE | D | 90 | 46.291 | −15.259 | −20.561 | 1.00 | 55.64 | C |
| ATOM | 3548 | CE1 | PHE | D | 90 | 47.315 | −14.828 | −21.443 | 1.00 | 57.08 | C |
| ATOM | 3549 | CZ | PHE | D | 90 | 48.263 | −15.751 | −21.908 | 1.00 | 55.59 | C |
| ATOM | 3550 | CE2 | PHE | D | 90 | 48.194 | −17.095 | −21.480 | 1.00 | 57.82 | C |
| ATOM | 3551 | CD2 | PHE | D | 90 | 47.171 | −17.503 | −20.596 | 1.00 | 55.72 | C |
| ATOM | 3552 | C | PHE | D | 90 | 44.331 | −17.079 | −16.865 | 1.00 | 47.66 | C |
| ATOM | 3553 | O | PHE | D | 90 | 43.697 | −18.071 | −16.572 | 1.00 | 46.94 | O |
| ATOM | 3554 | N | ALA | D | 91 | 44.053 | −15.867 | −16.398 | 1.00 | 48.49 | N |
| ATOM | 3555 | CA | ALA | D | 91 | 42.982 | −15.599 | −15.447 | 1.00 | 49.73 | C |
| ATOM | 3556 | CB | ALA | D | 91 | 42.942 | −14.112 | −15.129 | 1.00 | 48.83 | C |
| ATOM | 3557 | C | ALA | D | 91 | 41.632 | −16.093 | −15.969 | 1.00 | 51.41 | C |
| ATOM | 3558 | O | ALA | D | 91 | 40.799 | −16.593 | −15.209 | 1.00 | 51.12 | O |
| ATOM | 3559 | N | GLU | D | 92 | 41.441 | −15.964 | −17.282 | 1.00 | 53.68 | N |
| ATOM | 3560 | CA | GLU | D | 92 | 40.229 | −16.427 | −17.962 | 1.00 | 56.07 | C |
| ATOM | 3561 | CB | GLU | D | 92 | 40.134 | −15.798 | −19.358 | 1.00 | 56.18 | C |
| ATOM | 3562 | CG | GLU | D | 92 | 40.983 | −16.517 | −20.403 | 1.00 | 57.25 | C |
| ATOM | 3563 | CD | GLU | D | 92 | 41.361 | −15.626 | −21.547 | 1.00 | 59.32 | C |
| ATOM | 3564 | OE1 | GLU | D | 92 | 42.579 | −15.479 | −21.797 | 1.00 | 59.13 | O |
| ATOM | 3565 | OE2 | GLU | D | 92 | 40.441 | −15.065 | −22.189 | 1.00 | 60.55 | O |
| ATOM | 3566 | C | GLU | D | 92 | 40.105 | −17.952 | −18.095 | 1.00 | 57.18 | C |
| ATOM | 3567 | O | GLU | D | 92 | 39.052 | −18.416 | −18.520 | 1.00 | 57.56 | O |
| ATOM | 3568 | N | ASP | D | 93 | 41.171 | −18.709 | −17.789 | 1.00 | 58.82 | N |
| ATOM | 3569 | CA | ASP | D | 93 | 41.110 | −20.181 | −17.684 | 1.00 | 60.41 | C |
| ATOM | 3570 | CB | ASP | D | 93 | 42.458 | −20.800 | −17.271 | 1.00 | 60.06 | C |
| ATOM | 3571 | CG | ASP | D | 93 | 42.370 | −22.306 | −16.993 | 1.00 | 62.32 | C |
| ATOM | 3572 | OD1 | ASP | D | 93 | 43.088 | −22.798 | −16.075 | 1.00 | 63.69 | O |
| ATOM | 3573 | OD2 | ASP | D | 93 | 41.580 | −23.010 | −17.680 | 1.00 | 63.08 | O |
| ATOM | 3574 | C | ASP | D | 93 | 39.992 | −20.523 | −16.698 | 1.00 | 61.55 | C |
| ATOM | 3575 | O | ASP | D | 93 | 40.234 | −20.746 | −15.495 | 1.00 | 61.84 | O |
| ATOM | 3576 | N | VAL | D | 94 | 38.775 | −20.549 | −17.266 | 1.00 | 62.79 | N |
| ATOM | 3577 | CA | VAL | D | 94 | 37.473 | −20.563 | −16.567 | 1.00 | 63.66 | C |
| ATOM | 3578 | CB | VAL | D | 94 | 36.302 | −20.047 | −17.526 | 1.00 | 63.67 | C |
| ATOM | 3579 | CG1 | VAL | D | 94 | 35.125 | −19.424 | −16.748 | 1.00 | 63.68 | C |
| ATOM | 3580 | CG2 | VAL | D | 94 | 35.843 | −21.115 | −18.522 | 1.00 | 63.79 | C |
| ATOM | 3581 | C | VAL | D | 94 | 37.238 | −21.948 | −15.970 | 1.00 | 64.13 | C |

APPENDIX I-continued

| | | | | | | | | | | | |
|---|---|---|---|---|---|---|---|---|---|---|---|
| ATOM | 3582 | O | VAL | D | 94 | 38.119 | −22.810 | −16.078 | 1.00 | 64.47 | O |
| ATOM | 3583 | N | GLY | D | 95 | 36.089 | −22.145 | −15.317 | 1.00 | 64.40 | N |
| ATOM | 3584 | CA | GLY | D | 95 | 35.774 | −23.376 | −14.568 | 1.00 | 64.71 | C |
| ATOM | 3585 | C | GLY | D | 95 | 36.866 | −24.412 | −14.294 | 1.00 | 65.01 | C |
| ATOM | 3586 | O | GLY | D | 95 | 36.569 | −25.624 | −14.258 | 1.00 | 65.10 | O |
| ATOM | 3587 | N | SER | D | 96 | 38.110 | −23.954 | −14.083 | 1.00 | 65.03 | N |
| ATOM | 3588 | CA | SER | D | 96 | 39.264 | −24.858 | −13.891 | 1.00 | 65.03 | C |
| ATOM | 3589 | CB | SER | D | 96 | 40.390 | −24.533 | −14.887 | 1.00 | 65.25 | C |
| ATOM | 3590 | OG | SER | D | 96 | 41.339 | −25.594 | −14.955 | 1.00 | 64.98 | O |
| ATOM | 3591 | C | SER | D | 96 | 39.806 | −24.852 | −12.454 | 1.00 | 64.82 | C |
| ATOM | 3592 | O | SER | D | 96 | 40.023 | −23.779 | −11.867 | 1.00 | 65.31 | O |
| ATOM | 3593 | N | ASN | D | 97 | 40.052 | −26.057 | −11.928 | 1.00 | 63.87 | N |
| ATOM | 3594 | CA | ASN | D | 97 | 40.392 | −26.313 | −10.521 | 1.00 | 62.98 | C |
| ATOM | 3595 | CB | ASN | D | 97 | 39.702 | −27.644 | −10.104 | 1.00 | 63.42 | C |
| ATOM | 3596 | CG | ASN | D | 97 | 39.953 | −28.045 | −8.633 | 1.00 | 65.04 | C |
| ATOM | 3597 | OD1 | ASN | D | 97 | 40.047 | −27.190 | −7.736 | 1.00 | 66.76 | O |
| ATOM | 3598 | ND2 | ASN | D | 97 | 40.030 | −29.363 | −8.387 | 1.00 | 63.43 | N |
| ATOM | 3599 | C | ASN | D | 97 | 41.921 | −26.317 | −10.231 | 1.00 | 61.78 | C |
| ATOM | 3600 | O | ASN | D | 97 | 42.552 | −27.385 | −10.142 | 1.00 | 61.83 | O |
| ATOM | 3601 | N | LYS | D | 98 | 42.507 | −25.129 | −10.063 | 1.00 | 59.84 | N |
| ATOM | 3602 | CA | LYS | D | 98 | 43.970 | −24.994 | −9.904 | 1.00 | 58.24 | C |
| ATOM | 3603 | CB | LYS | D | 98 | 44.446 | −23.620 | −10.431 | 1.00 | 58.64 | C |
| ATOM | 3604 | CG | LYS | D | 98 | 44.251 | −23.361 | −11.938 | 1.00 | 57.61 | C |
| ATOM | 3605 | CD | LYS | D | 98 | 42.829 | −22.926 | −12.285 | 1.00 | 57.73 | C |
| ATOM | 3606 | CE | LYS | D | 98 | 42.248 | −21.834 | −11.301 | 1.00 | 59.29 | C |
| ATOM | 3607 | NZ | LYS | D | 98 | 41.046 | −20.972 | −12.134 | 1.00 | 57.74 | N |
| ATOM | 3608 | C | LYS | D | 98 | 44.493 | −25.245 | −8.461 | 1.00 | 57.13 | C |
| ATOM | 3609 | O | LYS | D | 98 | 43.767 | −25.784 | −7.606 | 1.00 | 57.08 | O |
| ATOM | 3610 | N | GLY | D | 99 | 45.767 | −24.891 | −8.225 | 1.00 | 55.60 | N |
| ATOM | 3611 | CA | GLY | D | 99 | 46.378 | −24.754 | −6.872 | 1.00 | 52.95 | C |
| ATOM | 3612 | C | GLY | D | 99 | 46.501 | −23.279 | −6.415 | 1.00 | 50.67 | C |
| ATOM | 3613 | O | GLY | D | 99 | 45.678 | −22.440 | −6.801 | 1.00 | 51.24 | O |
| ATOM | 3614 | N | ALA | D | 100 | 47.510 | −22.956 | −5.601 | 1.00 | 47.56 | N |
| ATOM | 3615 | CA | ALA | D | 100 | 47.594 | −21.643 | −4.932 | 1.00 | 44.47 | C |
| ATOM | 3616 | CB | ALA | D | 100 | 48.583 | −21.700 | −3.781 | 1.00 | 44.23 | C |
| ATOM | 3617 | C | ALA | D | 100 | 47.948 | −20.493 | −5.881 | 1.00 | 42.73 | C |
| ATOM | 3618 | O | ALA | D | 100 | 48.733 | −20.692 | −6.805 | 1.00 | 41.87 | O |
| ATOM | 3619 | N | ILE | D | 101 | 47.368 | −19.313 | −5.635 | 1.00 | 40.81 | N |
| ATOM | 3620 | CA | ILE | D | 101 | 47.614 | −18.108 | −6.395 | 1.00 | 40.35 | C |
| ATOM | 3621 | CB | ILE | D | 101 | 46.370 | −17.176 | −6.453 | 1.00 | 40.67 | C |
| ATOM | 3622 | CG1 | ILE | D | 101 | 45.119 | −17.901 | −6.945 | 1.00 | 41.30 | C |
| ATOM | 3623 | CD1 | ILE | D | 101 | 45.229 | −18.533 | −8.316 | 1.00 | 44.91 | C |
| ATOM | 3624 | CG2 | ILE | D | 101 | 46.719 | −15.835 | −7.192 | 1.00 | 38.52 | C |
| ATOM | 3625 | C | ILE | D | 101 | 48.703 | −17.316 | −5.677 | 1.00 | 40.37 | C |
| ATOM | 3626 | O | ILE | D | 101 | 48.578 | −17.042 | −4.478 | 1.00 | 40.20 | O |
| ATOM | 3627 | N | ILE | D | 102 | 49.757 | −16.950 | −6.405 | 1.00 | 39.73 | N |
| ATOM | 3628 | CA | ILE | D | 102 | 50.891 | −16.245 | −5.850 | 1.00 | 38.51 | C |
| ATOM | 3629 | CB | ILE | D | 102 | 52.225 | −16.834 | −6.388 | 1.00 | 39.69 | C |
| ATOM | 3630 | CG1 | ILE | D | 102 | 52.294 | −18.341 | −6.159 | 1.00 | 40.45 | C |
| ATOM | 3631 | CD1 | ILE | D | 102 | 52.156 | −18.810 | −4.767 | 1.00 | 39.56 | C |
| ATOM | 3632 | CG2 | ILE | D | 102 | 53.461 | −16.084 | −5.804 | 1.00 | 40.43 | C |
| ATOM | 3633 | C | ILE | D | 102 | 50.816 | −14.788 | −6.296 | 1.00 | 37.28 | C |
| ATOM | 3634 | O | ILE | D | 102 | 51.315 | −13.893 | −5.613 | 1.00 | 38.01 | O |
| ATOM | 3635 | N | GLY | D | 103 | 50.181 | −14.539 | −7.424 | 1.00 | 35.03 | N |
| ATOM | 3636 | CA | GLY | D | 103 | 50.172 | −13.194 | −7.991 | 1.00 | 33.31 | C |
| ATOM | 3637 | C | GLY | D | 103 | 49.411 | −13.068 | −9.275 | 1.00 | 32.34 | C |
| ATOM | 3638 | O | GLY | D | 103 | 49.072 | −14.050 | −9.924 | 1.00 | 31.10 | O |
| ATOM | 3639 | N | LEU | D | 104 | 49.098 | −11.840 | −9.621 | 1.00 | 32.17 | N |
| ATOM | 3640 | CA | LEU | D | 104 | 48.403 | −11.557 | −10.841 | 1.00 | 32.15 | C |
| ATOM | 3641 | CB | LEU | D | 104 | 46.965 | −11.134 | −10.534 | 1.00 | 33.36 | C |
| ATOM | 3642 | CG | LEU | D | 104 | 46.100 | −10.577 | −11.696 | 1.00 | 35.07 | C |
| ATOM | 3643 | CD1 | LEU | D | 104 | 44.837 | −9.947 | −11.110 | 1.00 | 35.43 | C |
| ATOM | 3644 | CD2 | LEU | D | 104 | 45.772 | −11.706 | −12.740 | 1.00 | 34.01 | C |
| ATOM | 3645 | C | LEU | D | 104 | 49.131 | −10.472 | −11.532 | 1.00 | 32.05 | C |
| ATOM | 3646 | O | LEU | D | 104 | 49.436 | −9.462 | −10.903 | 1.00 | 31.50 | O |
| ATOM | 3647 | N | MET | D | 105 | 49.419 | −10.679 | −12.826 | 1.00 | 31.71 | N |
| ATOM | 3648 | CA | MET | D | 105 | 50.112 | −9.717 | −13.682 | 1.00 | 31.42 | C |
| ATOM | 3649 | CB | MET | D | 105 | 51.206 | −10.403 | −14.533 | 1.00 | 31.83 | C |
| ATOM | 3650 | CG | MET | D | 105 | 52.155 | −11.228 | −13.703 | 1.00 | 36.87 | C |
| ATOM | 3651 | SD | MET | D | 105 | 53.267 | −10.213 | −12.674 | 1.00 | 43.45 | S |
| ATOM | 3652 | CE | MET | D | 105 | 54.104 | −9.296 | −13.942 | 1.00 | 32.92 | C |
| ATOM | 3653 | C | MET | D | 105 | 49.131 | −9.055 | −14.624 | 1.00 | 30.41 | C |
| ATOM | 3654 | O | MET | D | 105 | 48.154 | −9.673 | −15.072 | 1.00 | 29.25 | O |
| ATOM | 3655 | N | VAL | D | 106 | 49.362 | −7.789 | −14.917 | 1.00 | 29.43 | N |
| ATOM | 3656 | CA | VAL | D | 106 | 48.394 | −7.148 | −15.760 | 1.00 | 30.76 | C |
| ATOM | 3657 | CB | VAL | D | 106 | 48.317 | −5.542 | −15.699 | 1.00 | 30.85 | C |
| ATOM | 3658 | CG1 | VAL | D | 106 | 48.876 | −4.946 | −14.421 | 1.00 | 28.68 | C |
| ATOM | 3659 | CG2 | VAL | D | 106 | 48.867 | −4.937 | −16.875 | 1.00 | 27.85 | C |
| ATOM | 3660 | C | VAL | D | 106 | 48.670 | −7.711 | −17.170 | 1.00 | 31.76 | C |
| ATOM | 3661 | O | VAL | D | 106 | 49.843 | −7.941 | −17.524 | 1.00 | 32.26 | O |

APPENDIX I-continued

| ATOM | 3662 | N | GLY | D | 107 | 47.590 | −7.909 | −17.944 | 1.00 | 31.86 | N |
|---|---|---|---|---|---|---|---|---|---|---|---|
| ATOM | 3663 | CA | GLY | D | 107 | 47.602 | −8.730 | −19.149 | 1.00 | 31.60 | C |
| ATOM | 3664 | C | GLY | D | 107 | 46.937 | −10.076 | −18.867 | 1.00 | 31.76 | C |
| ATOM | 3665 | O | GLY | D | 107 | 46.782 | −10.884 | −19.774 | 1.00 | 32.48 | O |
| ATOM | 3666 | N | GLY | D | 108 | 46.594 | −10.347 | −17.602 | 1.00 | 31.73 | N |
| ATOM | 3667 | CA | GLY | D | 108 | 45.845 | −11.561 | −17.219 | 1.00 | 30.76 | C |
| ATOM | 3668 | C | GLY | D | 108 | 46.575 | −12.837 | −16.858 | 1.00 | 30.68 | C |
| ATOM | 3669 | O | GLY | D | 108 | 45.940 | −13.868 | −16.709 | 1.00 | 31.60 | O |
| ATOM | 3670 | N | VAL | D | 109 | 47.894 | −12.799 | −16.705 | 1.00 | 31.23 | N |
| ATOM | 3671 | CA | VAL | D | 109 | 48.659 | −14.009 | −16.355 | 1.00 | 31.01 | C |
| ATOM | 3672 | CB | VAL | D | 109 | 50.115 | −13.935 | −16.919 | 1.00 | 31.60 | C |
| ATOM | 3673 | CG1 | VAL | D | 109 | 50.128 | −14.044 | −18.453 | 1.00 | 30.53 | C |
| ATOM | 3674 | CG2 | VAL | D | 109 | 50.988 | −14.970 | −16.332 | 1.00 | 28.81 | C |
| ATOM | 3675 | C | VAL | D | 109 | 48.653 | −14.172 | −14.835 | 1.00 | 32.20 | C |
| ATOM | 3676 | O | VAL | D | 109 | 48.994 | −13.258 | −14.125 | 1.00 | 32.24 | O |
| ATOM | 3677 | N | VAL | D | 110 | 48.207 | −15.323 | −14.332 | 1.00 | 33.52 | N |
| ATOM | 3678 | CA | VAL | D | 110 | 48.274 | −15.592 | −12.911 | 1.00 | 34.03 | C |
| ATOM | 3679 | CB | VAL | D | 110 | 46.863 | −15.796 | −12.233 | 1.00 | 34.35 | C |
| ATOM | 3680 | CG1 | VAL | D | 110 | 46.831 | −16.818 | −11.135 | 1.00 | 33.72 | C |
| ATOM | 3681 | CG2 | VAL | D | 110 | 45.754 | −15.985 | −13.234 | 1.00 | 34.18 | C |
| ATOM | 3682 | C | VAL | D | 110 | 49.389 | −16.575 | −12.582 | 1.00 | 35.97 | C |
| ATOM | 3683 | O | VAL | D | 110 | 49.627 | −17.552 | −13.306 | 1.00 | 35.08 | O |
| ATOM | 3684 | N | ILE | D | 111 | 50.130 | −16.253 | −11.526 | 1.00 | 38.15 | N |
| ATOM | 3685 | CA | ILE | D | 111 | 51.201 | −17.117 | −11.055 | 1.00 | 40.04 | C |
| ATOM | 3686 | CB | ILE | D | 111 | 52.441 | −16.328 | −10.556 | 1.00 | 39.96 | C |
| ATOM | 3687 | CG1 | ILE | D | 111 | 53.021 | −15.546 | −11.706 | 1.00 | 40.77 | C |
| ATOM | 3688 | CD1 | ILE | D | 111 | 52.827 | −14.083 | −11.586 | 1.00 | 42.20 | C |
| ATOM | 3689 | CG2 | ILE | D | 111 | 53.550 | −17.273 | −10.029 | 1.00 | 40.87 | C |
| ATOM | 3690 | C | ILE | D | 111 | 50.628 | −18.015 | −10.003 | 1.00 | 40.99 | C |
| ATOM | 3691 | O | ILE | D | 111 | 50.059 | −17.563 | −8.987 | 1.00 | 41.58 | O |
| ATOM | 3692 | N | GLY | D | 112 | 50.722 | −19.313 | −10.257 | 1.00 | 42.26 | N |
| ATOM | 3693 | CA | GLY | D | 112 | 50.331 | −20.269 | −9.235 | 1.00 | 41.93 | C |
| ATOM | 3694 | C | GLY | D | 112 | 51.500 | −21.086 | −8.715 | 1.00 | 43.09 | C |
| ATOM | 3695 | O | GLY | D | 112 | 52.575 | −21.142 | −9.325 | 1.00 | 42.76 | O |
| ATOM | 3696 | N | GLY | D | 113 | 51.266 | −21.778 | −7.598 | 1.00 | 44.33 | N |
| ATOM | 3697 | CA | GLY | D | 113 | 52.260 | −22.648 | −7.011 | 1.00 | 45.49 | C |
| ATOM | 3698 | C | GLY | D | 113 | 51.626 | −23.882 | −6.435 | 1.00 | 47.03 | C |
| ATOM | 3699 | O | GLY | D | 113 | 50.533 | −23.830 | −5.852 | 1.00 | 47.41 | O |
| ATOM | 3700 | N | GLU | D | 114 | 52.319 | −25.001 | −6.599 | 1.00 | 47.97 | N |
| ATOM | 3701 | CA | GLU | D | 114 | 51.835 | −26.273 | −6.122 | 1.00 | 48.98 | C |
| ATOM | 3702 | CB | GLU | D | 114 | 51.275 | −27.062 | −7.304 | 1.00 | 49.06 | C |
| ATOM | 3703 | CG | GLU | D | 114 | 50.539 | −28.280 | −6.942 | 1.00 | 52.21 | C |
| ATOM | 3704 | CD | GLU | D | 114 | 49.046 | −28.083 | −6.856 | 1.00 | 56.29 | C |
| ATOM | 3705 | OE1 | GLU | D | 114 | 48.457 | −28.646 | −5.897 | 1.00 | 58.05 | O |
| ATOM | 3706 | OE2 | GLU | D | 114 | 48.462 | −27.412 | −7.753 | 1.00 | 57.66 | O |
| ATOM | 3707 | C | GLU | D | 114 | 52.968 | −27.042 | −5.375 | 1.00 | 49.12 | C |
| ATOM | 3708 | O | GLU | D | 114 | 54.066 | −27.250 | −5.899 | 1.00 | 48.87 | O |
| ATOM | 3709 | N | LYS | D | 115 | 52.678 | −27.446 | −4.147 | 1.00 | 48.78 | N |
| ATOM | 3710 | CA | LYS | D | 115 | 53.615 | −28.192 | −3.317 | 1.00 | 48.72 | C |
| ATOM | 3711 | CB | LYS | D | 115 | 53.481 | −27.719 | −1.866 | 1.00 | 49.82 | C |
| ATOM | 3712 | CG | LYS | D | 115 | 54.298 | −26.510 | −1.509 | 1.00 | 51.17 | C |
| ATOM | 3713 | CD | LYS | D | 115 | 54.010 | −26.041 | −0.090 | 1.00 | 56.06 | C |
| ATOM | 3714 | CE | LYS | D | 115 | 55.030 | −24.958 | 0.334 | 1.00 | 62.44 | C |
| ATOM | 3715 | NZ | LYS | D | 115 | 54.544 | −24.084 | 1.479 | 1.00 | 66.54 | N |
| ATOM | 3716 | C | LYS | D | 115 | 53.450 | −29.733 | −3.408 | 1.00 | 47.04 | C |
| ATOM | 3717 | O | LYS | D | 115 | 52.334 | −30.258 | −3.557 | 1.00 | 46.88 | O |
| ATOM | 3718 | N | GLY | D | 116 | 54.576 | −30.441 | −3.346 | 1.00 | 46.00 | N |
| ATOM | 3719 | CA | GLY | D | 116 | 54.576 | −31.909 | −3.157 | 1.00 | 44.67 | C |
| ATOM | 3720 | C | GLY | D | 116 | 54.109 | −32.255 | −1.746 | 1.00 | 44.37 | C |
| ATOM | 3721 | O | GLY | D | 116 | 54.088 | −31.386 | −0.850 | 1.00 | 44.53 | O |
| ATOM | 3722 | N | ALA | D | 117 | 53.718 | −33.515 | −1.544 | 1.00 | 43.07 | N |
| ATOM | 3723 | CA | ALA | D | 117 | 53.148 | −33.918 | −0.289 | 1.00 | 41.97 | C |
| ATOM | 3724 | CB | ALA | D | 117 | 52.397 | −35.199 | −0.448 | 1.00 | 41.67 | C |
| ATOM | 3725 | C | ALA | D | 117 | 54.208 | −34.037 | 0.806 | 1.00 | 41.59 | C |
| ATOM | 3726 | O | ALA | D | 117 | 53.855 | −34.218 | 1.958 | 1.00 | 42.73 | O |
| ATOM | 3727 | N | GLY | D | 118 | 55.487 | −33.984 | 0.449 | 1.00 | 40.27 | N |
| ATOM | 3728 | CA | GLY | D | 118 | 56.542 | −33.997 | 1.430 | 1.00 | 39.78 | C |
| ATOM | 3729 | C | GLY | D | 118 | 57.349 | −35.274 | 1.452 | 1.00 | 41.03 | C |
| ATOM | 3730 | O | GLY | D | 118 | 56.891 | −36.346 | 1.032 | 1.00 | 41.30 | O |
| ATOM | 3731 | N | THR | D | 119 | 58.575 | −35.170 | 1.943 | 1.00 | 41.33 | N |
| ATOM | 3732 | CA | THR | D | 119 | 59.336 | −36.361 | 2.271 | 1.00 | 41.15 | C |
| ATOM | 3733 | CB | THR | D | 119 | 60.404 | −36.914 | 1.152 | 1.00 | 41.78 | C |
| ATOM | 3734 | OG1 | THR | D | 119 | 61.763 | −36.991 | 1.623 | 1.00 | 46.65 | O |
| ATOM | 3735 | CG2 | THR | D | 119 | 60.283 | −36.324 | −0.201 | 1.00 | 36.84 | C |
| ATOM | 3736 | C | THR | D | 119 | 59.867 | −36.263 | 3.698 | 1.00 | 40.96 | C |
| ATOM | 3737 | O | THR | D | 119 | 60.532 | −35.282 | 4.053 | 1.00 | 40.91 | O |
| ATOM | 3738 | N | ALA | D | 120 | 59.514 | −37.258 | 4.517 | 1.00 | 38.25 | N |
| ATOM | 3739 | CA | ALA | D | 120 | 60.005 | −37.311 | 5.887 | 1.00 | 37.80 | C |
| ATOM | 3740 | CB | ALA | D | 120 | 58.969 | −38.040 | 6.791 | 1.00 | 35.79 | C |
| ATOM | 3741 | C | ALA | D | 120 | 61.369 | −38.034 | 5.933 | 1.00 | 37.39 | C |

APPENDIX I-continued

| ATOM | 3742 | O | ALA | D | 120 | 61.421 | −39.245 | 5.827 | 1.00 | 37.29 | O |
|---|---|---|---|---|---|---|---|---|---|---|---|
| ATOM | 3743 | N | LEU | D | 121 | 62.471 | −37.298 | 6.048 | 1.00 | 37.88 | N |
| ATOM | 3744 | CA | LEU | D | 121 | 63.791 | −37.950 | 6.023 | 1.00 | 37.30 | C |
| ATOM | 3745 | CB | LEU | D | 121 | 64.792 | −37.133 | 5.216 | 1.00 | 37.16 | C |
| ATOM | 3746 | CG | LEU | D | 121 | 66.302 | −37.438 | 5.387 | 1.00 | 36.66 | C |
| ATOM | 3747 | CD1 | LEU | D | 121 | 66.766 | −38.702 | 4.727 | 1.00 | 34.65 | C |
| ATOM | 3748 | CD2 | LEU | D | 121 | 67.118 | −36.308 | 4.863 | 1.00 | 34.00 | C |
| ATOM | 3749 | C | LEU | D | 121 | 64.286 | −38.098 | 7.456 | 1.00 | 38.21 | C |
| ATOM | 3750 | O | LEU | D | 121 | 64.305 | −37.112 | 8.182 | 1.00 | 37.52 | O |
| ATOM | 3751 | N | THR | D | 122 | 64.672 | −39.322 | 7.853 | 1.00 | 39.39 | N |
| ATOM | 3752 | CA | THR | D | 122 | 65.420 | −39.553 | 9.093 | 1.00 | 40.36 | C |
| ATOM | 3753 | CB | THR | D | 122 | 64.764 | −40.661 | 9.897 | 1.00 | 41.03 | C |
| ATOM | 3754 | OG1 | THR | D | 122 | 63.433 | −40.254 | 10.264 | 1.00 | 40.03 | O |
| ATOM | 3755 | CG2 | THR | D | 122 | 65.574 | −41.056 | 11.168 | 1.00 | 41.88 | C |
| ATOM | 3756 | C | THR | D | 122 | 66.850 | −39.909 | 8.706 | 1.00 | 41.03 | C |
| ATOM | 3757 | O | THR | D | 122 | 67.056 | −40.848 | 7.985 | 1.00 | 40.84 | O |
| ATOM | 3758 | N | VAL | D | 123 | 67.835 | −39.101 | 9.103 | 1.00 | 42.99 | N |
| ATOM | 3759 | CA | VAL | D | 123 | 69.234 | −39.583 | 9.052 | 1.00 | 44.79 | C |
| ATOM | 3760 | CB | VAL | D | 123 | 70.202 | −38.754 | 8.099 | 1.00 | 45.22 | C |
| ATOM | 3761 | CG1 | VAL | D | 123 | 71.523 | −38.462 | 8.713 | 1.00 | 44.87 | C |
| ATOM | 3762 | CG2 | VAL | D | 123 | 69.528 | −37.548 | 7.456 | 1.00 | 43.50 | C |
| ATOM | 3763 | C | VAL | D | 123 | 69.796 | −40.080 | 10.409 | 1.00 | 46.99 | C |
| ATOM | 3764 | O | VAL | D | 123 | 69.848 | −39.349 | 11.408 | 1.00 | 46.54 | O |
| ATOM | 3765 | N | LYS | D | 124 | 70.123 | −41.378 | 10.437 | 1.00 | 49.38 | N |
| ATOM | 3766 | CA | LYS | D | 124 | 70.636 | −42.039 | 11.647 | 1.00 | 50.47 | C |
| ATOM | 3767 | CB | LYS | D | 124 | 70.156 | −43.525 | 11.743 | 1.00 | 49.98 | C |
| ATOM | 3768 | CG | LYS | D | 124 | 68.619 | −43.748 | 12.007 | 1.00 | 50.05 | C |
| ATOM | 3769 | CD | LYS | D | 124 | 68.052 | −43.043 | 13.279 | 1.00 | 49.05 | C |
| ATOM | 3770 | CE | LYS | D | 124 | 66.688 | −43.609 | 13.767 | 1.00 | 48.44 | C |
| ATOM | 3771 | NZ | LYS | D | 124 | 65.834 | −42.572 | 14.515 | 1.00 | 47.51 | N |
| ATOM | 3772 | C | LYS | D | 124 | 72.171 | −41.904 | 11.655 | 1.00 | 50.68 | C |
| ATOM | 3773 | O | LYS | D | 124 | 72.808 | −42.063 | 10.610 | 1.00 | 51.52 | O |
| ATOM | 3774 | N | ALA | D | 125 | 72.722 | −41.535 | 12.816 | 1.00 | 51.34 | N |
| ATOM | 3775 | CA | ALA | D | 125 | 74.161 | −41.416 | 13.055 | 1.00 | 52.01 | C |
| ATOM | 3776 | CB | ALA | D | 125 | 74.443 | −41.064 | 14.528 | 1.00 | 51.75 | C |
| ATOM | 3777 | C | ALA | D | 125 | 74.834 | −42.715 | 12.711 | 1.00 | 52.46 | C |
| ATOM | 3778 | O | ALA | D | 125 | 74.540 | −43.751 | 13.329 | 1.00 | 52.80 | O |
| ATOM | 3779 | OXT | ALA | D | 125 | 75.650 | −42.744 | 11.792 | 1.00 | 52.94 | O |
| ATOM | 3780 | O | HOH | W | 1 | 27.537 | −6.895 | −25.418 | 1.00 | 49.96 | O |
| ATOM | 3781 | O | HOH | W | 2 | 16.484 | −15.501 | −2.860 | 1.00 | 51.92 | O |
| ATOM | 3782 | O | HOH | W | 3 | 64.994 | −13.128 | −29.648 | 1.00 | 61.47 | O |
| ATOM | 3783 | O | HOH | W | 4 | 58.640 | −8.263 | −15.036 | 1.00 | 51.01 | O |
| ATOM | 3784 | O | HOH | W | 5 | 49.811 | −21.870 | −19.181 | 1.00 | 53.77 | O |
| ATOM | 3785 | O | HOH | W | 6 | 47.451 | 15.219 | 8.922 | 1.00 | 53.13 | O |
| ATOM | 3786 | O | HOH | W | 7 | 57.241 | 6.450 | −33.199 | 1.00 | 67.49 | O |
| ATOM | 3787 | O | HOH | W | 8 | 55.602 | −37.210 | 4.291 | 1.00 | 45.54 | O |
| ATOM | 3788 | O | HOH | W | 9 | 71.793 | −8.853 | −14.510 | 1.00 | 53.04 | O |
| ATOM | 3789 | O | HOH | W | 10 | 28.959 | 18.294 | 23.084 | 1.00 | 44.15 | O |
| ATOM | 3790 | O | HOH | W | 11 | 51.211 | −1.996 | −16.782 | 1.00 | 34.13 | O |
| ATOM | 3791 | O | HOH | W | 12 | 20.537 | 2.113 | 13.747 | 1.00 | 37.57 | O |
| ATOM | 3792 | O | HOH | W | 13 | 63.618 | −7.963 | −22.008 | 1.00 | 48.46 | O |
| ATOM | 3793 | O | HOH | W | 14 | 15.973 | −5.480 | −1.302 | 1.00 | 58.45 | O |
| ATOM | 3794 | O | HOH | W | 15 | 47.026 | 19.336 | −8.349 | 1.00 | 45.60 | O |
| ATOM | 3795 | O | HOH | W | 16 | 38.870 | 18.600 | 16.145 | 1.00 | 48.41 | O |
| ATOM | 3796 | O | HOH | W | 17 | 55.643 | −13.712 | −15.385 | 1.00 | 53.69 | O |
| ATOM | 3797 | O | HOH | W | 18 | 29.523 | 17.221 | 14.352 | 1.00 | 33.22 | O |
| ATOM | 3798 | O | HOH | W | 19 | 74.183 | −13.852 | −32.153 | 1.00 | 45.21 | O |
| ATOM | 3799 | O | HOH | W | 20 | 51.603 | 5.048 | −41.486 | 1.00 | 67.11 | O |
| ATOM | 3800 | O | HOH | W | 21 | 75.638 | −22.627 | 9.738 | 1.00 | 66.50 | O |
| ATOM | 3801 | O | HOH | W | 22 | 16.178 | 1.770 | −16.784 | 1.00 | 63.18 | O |
| ATOM | 3802 | O | HOH | W | 23 | 72.855 | −27.072 | 5.746 | 1.00 | 46.62 | O |
| ATOM | 3803 | O | HOH | W | 24 | 28.469 | 17.946 | −7.226 | 1.00 | 50.63 | O |
| ATOM | 3804 | O | HOH | W | 25 | 52.814 | 15.053 | −42.546 | 1.00 | 68.81 | O |
| ATOM | 3805 | O | HOH | W | 26 | 54.094 | 10.191 | −35.541 | 1.00 | 68.73 | O |
| ATOM | 3806 | O | HOH | W | 27 | 28.221 | 15.502 | −7.510 | 1.00 | 61.71 | O |
| ATOM | 3807 | O | HOH | W | 28 | 29.651 | −7.408 | −0.031 | 1.00 | 77.42 | O |
| ATOM | 3808 | O | HOH | W | 29 | 55.208 | −11.816 | −1.694 | 1.00 | 65.92 | O |
| ATOM | 3809 | O | HOH | W | 30 | 65.842 | −14.431 | −7.424 | 1.00 | 62.18 | O |
| ATOM | 3810 | O | HOH | W | 31 | 86.092 | −37.988 | 19.084 | 1.00 | 62.21 | O |
| ATOM | 3811 | O | HOH | W | 32 | 57.547 | −17.020 | −8.281 | 1.00 | 54.14 | O |
| ATOM | 3812 | O | HOH | W | 33 | 15.238 | −25.319 | −14.960 | 1.00 | 48.17 | O |
| ATOM | 3813 | O | HOH | W | 34 | 32.868 | −10.730 | −16.000 | 1.00 | 60.24 | O |
| ATOM | 3814 | O | HOH | W | 35 | 27.383 | −23.747 | −14.732 | 1.00 | 54.01 | O |
| ATOM | 3815 | O | HOH | W | 36 | 45.466 | −36.429 | −7.768 | 1.00 | 61.01 | O |
| ATOM | 3816 | O | HOH | W | 37 | 85.751 | 6.805 | −23.803 | 1.00 | 63.72 | O |
| ATOM | 3817 | O | HOH | W | 38 | 64.003 | −17.550 | −25.097 | 1.00 | 52.50 | O |
| ATOM | 3818 | O | HOH | W | 39 | 18.054 | 10.470 | 11.460 | 1.00 | 31.24 | O |
| ATOM | 3819 | O | HOH | W | 40 | 3.495 | −9.168 | −13.711 | 1.00 | 46.96 | O |
| ATOM | 3820 | O | HOH | W | 41 | 41.882 | −5.080 | 13.345 | 1.00 | 59.64 | O |
| ATOM | 3821 | O | HOH | W | 42 | 53.605 | −40.677 | −18.373 | 1.00 | 65.41 | O |

APPENDIX I-continued

| | | | | | | | | | | | |
|---|---|---|---|---|---|---|---|---|---|---|---|
| ATOM | 3822 | O | HOH | W | 43 | 36.386 | −1.428 | −3.036 | 1.00 | 50.71 | O |
| ATOM | 3823 | O | HOH | W | 44 | 73.455 | −43.317 | −0.552 | 1.00 | 59.07 | O |
| ATOM | 3824 | O | HOH | W | 45 | 78.144 | −43.753 | 12.847 | 1.00 | 65.80 | O |
| ATOM | 3825 | O | HOH | W | 46 | 57.888 | −11.778 | −11.462 | 1.00 | 57.52 | O |
| ATOM | 3826 | O | HOH | W | 47 | 45.202 | −5.340 | 3.650 | 1.00 | 48.23 | O |
| ATOM | 3827 | O | HOH | W | 48 | 63.611 | −10.382 | −24.415 | 1.00 | 50.05 | O |
| ATOM | 3828 | O | HOH | W | 49 | 57.536 | 6.456 | −7.141 | 1.00 | 28.46 | O |
| ATOM | 3829 | O | HOH | W | 50 | 58.272 | −0.505 | −0.424 | 1.00 | 30.38 | O |
| ATOM | 3830 | O | HOH | W | 51 | 46.690 | −1.769 | 0.708 | 1.00 | 25.84 | O |
| ATOM | 3831 | O | HOH | W | 52 | 43.295 | 5.650 | −15.284 | 1.00 | 31.89 | O |
| ATOM | 3832 | O | HOH | W | 53 | 64.526 | 9.634 | −19.506 | 1.00 | 29.96 | O |
| ATOM | 3833 | O | HOH | W | 54 | 23.155 | −22.622 | −14.253 | 1.00 | 34.18 | O |
| ATOM | 3834 | O | HOH | W | 55 | 64.074 | −2.755 | −3.506 | 1.00 | 32.46 | O |
| ATOM | 3835 | O | HOH | W | 56 | 65.733 | −39.979 | 14.780 | 1.00 | 50.48 | O |
| ATOM | 3836 | O | HOH | W | 57 | 25.603 | 12.096 | 6.016 | 1.00 | 29.23 | O |
| ATOM | 3837 | O | HOH | W | 58 | 16.263 | −22.766 | −25.732 | 1.00 | 37.53 | O |
| ATOM | 3838 | O | HOH | W | 59 | 51.239 | 2.681 | −2.880 | 1.00 | 34.06 | O |
| ATOM | 3839 | O | HOH | W | 60 | 54.458 | −2.187 | −19.524 | 1.00 | 40.20 | O |
| ATOM | 3840 | O | HOH | W | 61 | 71.361 | 7.864 | −19.372 | 1.00 | 37.66 | O |
| ATOM | 3841 | O | HOH | W | 62 | 56.520 | 7.752 | −18.350 | 1.00 | 37.39 | O |
| ATOM | 3842 | O | HOH | W | 63 | 13.694 | −9.946 | −29.896 | 1.00 | 38.42 | O |
| ATOM | 3843 | O | HOH | W | 64 | 61.439 | −41.245 | 8.021 | 1.00 | 41.37 | O |
| ATOM | 3844 | O | HOH | W | 65 | 39.971 | 3.043 | 13.470 | 1.00 | 51.30 | O |
| ATOM | 3845 | O | HOH | W | 66 | 28.958 | 15.268 | 1.059 | 1.00 | 43.67 | O |
| ATOM | 3846 | O | HOH | W | 67 | 30.104 | 2.750 | 2.608 | 1.00 | 40.29 | O |
| ATOM | 3847 | O | HOH | W | 68 | 69.821 | −2.267 | −8.072 | 1.00 | 33.11 | O |
| ATOM | 3848 | O | HOH | W | 69 | 52.286 | −7.121 | −16.541 | 1.00 | 38.11 | O |
| ATOM | 3849 | O | HOH | W | 70 | 58.487 | −28.442 | 5.036 | 1.00 | 37.01 | O |
| ATOM | 3850 | O | HOH | W | 71 | 25.719 | 16.565 | 13.085 | 1.00 | 44.30 | O |
| ATOM | 3851 | O | HOH | W | 72 | 52.822 | −11.013 | −17.837 | 1.00 | 45.81 | O |
| ATOM | 3852 | O | HOH | W | 73 | 22.805 | −12.848 | −21.485 | 1.00 | 48.51 | O |
| ATOM | 3853 | O | HOH | W | 74 | 36.702 | 17.554 | 5.981 | 1.00 | 37.50 | O |
| ATOM | 3854 | O | HOH | W | 75 | 71.895 | −9.443 | −24.558 | 1.00 | 45.80 | O |
| ATOM | 3855 | O | HOH | W | 76 | 41.108 | 15.717 | −5.487 | 1.00 | 39.02 | O |
| ATOM | 3856 | O | HOH | W | 77 | 18.799 | 8.481 | 10.303 | 1.00 | 46.57 | O |
| ATOM | 3857 | O | HOH | W | 78 | 61.610 | 7.007 | −4.915 | 1.00 | 50.08 | O |
| ATOM | 3858 | O | HOH | W | 79 | 60.439 | −0.706 | −2.323 | 1.00 | 33.12 | O |
| ATOM | 3859 | O | HOH | W | 80 | 58.416 | 5.614 | −9.104 | 1.00 | 39.99 | O |
| ATOM | 3860 | O | HOH | W | 81 | 55.764 | −3.255 | −35.605 | 1.00 | 54.28 | O |
| ATOM | 3861 | O | HOH | W | 82 | 42.688 | 13.409 | 7.580 | 1.00 | 32.60 | O |
| ATOM | 3862 | O | HOH | W | 83 | 56.203 | 7.504 | −13.473 | 1.00 | 53.50 | O |
| ATOM | 3863 | O | HOH | W | 84 | 49.392 | −17.628 | −1.745 | 1.00 | 48.43 | O |
| ATOM | 3864 | O | HOH | W | 85 | 38.478 | 17.991 | −4.303 | 1.00 | 51.79 | O |
| ATOM | 3865 | O | HOH | W | 86 | 27.380 | 11.533 | −6.035 | 1.00 | 43.44 | O |
| ATOM | 3866 | O | HOH | W | 87 | 17.419 | −2.527 | −17.186 | 1.00 | 46.81 | O |
| ATOM | 3867 | O | HOH | W | 88 | 65.605 | 11.412 | −34.743 | 1.00 | 39.99 | O |
| ATOM | 3868 | O | HOH | W | 89 | 22.567 | −9.323 | 0.874 | 1.00 | 67.08 | O |
| ATOM | 3869 | O | HOH | W | 90 | 60.466 | −7.608 | −10.787 | 1.00 | 44.79 | O |
| ATOM | 3870 | O | HOH | W | 91 | 70.029 | 13.354 | −25.195 | 1.00 | 48.65 | O |
| ATOM | 3871 | O | HOH | W | 92 | 27.738 | −0.724 | 12.598 | 1.00 | 46.67 | O |
| ATOM | 3872 | O | HOH | W | 93 | 67.709 | −9.736 | −34.668 | 1.00 | 44.52 | O |
| ATOM | 3873 | O | HOH | W | 94 | 66.469 | −42.220 | −2.677 | 1.00 | 50.32 | O |
| ATOM | 3874 | O | HOH | W | 95 | 39.659 | 4.264 | 19.635 | 1.00 | 47.26 | O |
| ATOM | 3875 | O | HOH | W | 96 | 33.798 | −0.629 | 0.634 | 1.00 | 57.82 | O |
| ATOM | 3876 | O | HOH | W | 97 | 68.516 | 5.533 | −7.794 | 1.00 | 38.76 | O |
| ATOM | 3877 | O | HOH | W | 98 | 57.378 | 4.251 | −27.603 | 1.00 | 49.36 | O |
| ATOM | 3878 | O | HOH | W | 99 | 45.738 | 12.067 | 6.077 | 1.00 | 40.86 | O |
| ATOM | 3879 | O | HOH | W | 100 | 72.260 | −27.692 | −8.666 | 1.00 | 69.19 | O |
| ATOM | 3880 | O | HOH | W | 101 | 74.870 | 5.332 | −30.099 | 1.00 | 41.86 | O |
| ATOM | 3881 | O | HOH | W | 102 | 19.884 | −13.568 | −28.826 | 1.00 | 38.32 | O |
| ATOM | 3882 | O | HOH | W | 103 | 3.023 | −14.597 | −13.318 | 1.00 | 47.56 | O |
| ATOM | 3883 | O | HOH | W | 104 | 44.498 | −8.083 | −17.403 | 1.00 | 48.70 | O |
| ATOM | 3884 | O | HOH | W | 105 | 75.836 | −5.431 | −10.641 | 1.00 | 58.00 | O |
| ATOM | 3885 | O | HOH | W | 106 | 60.710 | 7.924 | −15.560 | 1.00 | 30.19 | O |
| ATOM | 3886 | O | HOH | W | 107 | 40.439 | −9.476 | 15.038 | 1.00 | 60.28 | O |
| ATOM | 3887 | O | HOH | W | 108 | 56.235 | −30.734 | 8.744 | 1.00 | 53.65 | O |
| ATOM | 3888 | O | HOH | W | 109 | 63.101 | −1.697 | −1.511 | 1.00 | 31.65 | O |
| ATOM | 3889 | O | HOH | W | 110 | 56.808 | 5.705 | −16.251 | 1.00 | 33.23 | O |
| ATOM | 3890 | O | HOH | W | 111 | 38.263 | 8.376 | 22.049 | 1.00 | 55.72 | O |
| ATOM | 3891 | O | HOH | W | 112 | 64.897 | −23.439 | −3.286 | 1.00 | 46.93 | O |
| ATOM | 3892 | O | HOH | W | 113 | 30.449 | −20.129 | −16.647 | 1.00 | 51.12 | O |
| ATOM | 3893 | O | HOH | W | 114 | 24.716 | −6.274 | −13.423 | 1.00 | 48.87 | O |
| ATOM | 3894 | O | HOH | W | 115 | 69.646 | 14.058 | −27.887 | 1.00 | 43.33 | O |
| ATOM | 3895 | O | HOH | W | 116 | 74.378 | 8.019 | −23.439 | 1.00 | 42.12 | O |
| ATOM | 3896 | O | HOH | W | 117 | 74.411 | −6.755 | −12.312 | 1.00 | 46.21 | O |
| ATOM | 3897 | O | HOH | W | 118 | 80.776 | −40.223 | 6.131 | 1.00 | 51.98 | O |
| ATOM | 3898 | O | HOH | W | 119 | 16.271 | −26.835 | −20.387 | 1.00 | 53.48 | O |
| ATOM | 3899 | O | HOH | W | 120 | 45.888 | 8.444 | 12.000 | 1.00 | 56.59 | O |
| ATOM | 3900 | O | HOH | W | 121 | 69.004 | −39.355 | 13.718 | 1.00 | 48.52 | O |
| ATOM | 3901 | O | HOH | W | 122 | 44.628 | 1.826 | 3.253 | 1.00 | 55.53 | O |

APPENDIX I-continued

| ATOM | 3902 | O | HOH | W | 123 | 10.540 | −21.289 | −24.117 | 1.00 | 55.75 | O |
|---|---|---|---|---|---|---|---|---|---|---|---|
| ATOM | 3903 | O | HOH | W | 124 | 39.519 | 7.553 | −11.796 | 1.00 | 42.99 | O |
| ATOM | 3904 | O | HOH | W | 125 | 17.953 | 2.631 | 6.934 | 1.00 | 46.87 | O |
| ATOM | 3905 | O | HOH | W | 126 | 59.706 | −42.276 | 8.568 | 1.00 | 49.22 | O |
| ATOM | 3906 | O | HOH | W | 127 | 71.515 | 9.604 | −9.652 | 1.00 | 51.76 | O |
| ATOM | 3907 | O | HOH | W | 128 | 22.711 | −2.131 | 7.099 | 1.00 | 56.06 | O |
| ATOM | 3908 | O | HOH | W | 129 | 50.497 | 1.860 | −26.962 | 1.00 | 48.49 | O |
| ATOM | 3909 | O | HOH | W | 130 | 13.213 | −25.189 | −17.571 | 1.00 | 47.33 | O |
| ATOM | 3910 | O | HOH | W | 131 | 36.422 | −18.594 | 1.861 | 1.00 | 59.55 | O |
| ATOM | 3911 | O | HOH | W | 132 | 67.824 | −18.443 | 8.774 | 1.00 | 64.42 | O |
| ATOM | 3912 | O | HOH | W | 133 | 38.702 | 9.149 | 25.860 | 1.00 | 63.04 | O |
| ATOM | 3913 | O | HOH | W | 134 | 26.829 | −19.030 | −19.104 | 1.00 | 49.31 | O |
| ATOM | 3914 | O | HOH | W | 135 | 59.736 | −32.012 | 10.576 | 1.00 | 35.03 | O |
| ATOM | 3915 | O | HOH | W | 136 | 64.103 | 0.614 | −0.340 | 1.00 | 40.32 | O |
| ATOM | 3916 | O | HOH | W | 137 | 68.933 | −33.671 | −8.563 | 1.00 | 47.24 | O |
| ATOM | 3917 | O | HOH | W | 138 | 30.091 | −18.545 | 3.715 | 1.00 | 65.55 | O |
| ATOM | 3918 | O | HOH | W | 139 | 11.871 | −19.774 | −24.246 | 1.00 | 33.50 | O |
| ATOM | 3919 | O | HOH | W | 140 | 54.104 | −8.838 | −17.264 | 1.00 | 43.66 | O |
| ATOM | 3920 | O | HOH | W | 141 | 68.475 | −6.296 | −7.780 | 1.00 | 51.54 | O |
| ATOM | 3921 | O | HOH | W | 142 | 61.319 | 8.970 | −35.221 | 1.00 | 63.08 | O |
| ATOM | 3922 | O | HOH | W | 143 | 5.216 | −2.074 | −13.989 | 1.00 | 53.77 | O |
| ATOM | 3923 | O | HOH | W | 144 | 77.471 | −7.485 | −20.605 | 1.00 | 62.28 | O |
| ATOM | 3924 | O | HOH | W | 145 | 22.942 | −15.078 | −26.211 | 1.00 | 45.04 | O |
| ATOM | 3925 | O | HOH | W | 146 | 62.912 | −3.121 | −6.057 | 1.00 | 35.08 | O |
| ATOM | 3926 | O | HOH | W | 147 | 60.466 | −10.624 | −21.327 | 1.00 | 50.25 | O |
| ATOM | 3927 | O | HOH | W | 148 | 49.218 | 8.905 | −16.800 | 1.00 | 51.16 | O |
| ATOM | 3928 | O | HOH | W | 149 | 33.265 | 10.047 | −10.678 | 1.00 | 48.18 | O |
| ATOM | 3929 | O | HOH | W | 150 | 58.095 | 9.361 | −4.575 | 1.00 | 50.70 | O |
| ATOM | 3930 | O | HOH | W | 151 | 44.991 | −5.664 | −19.770 | 1.00 | 52.37 | O |
| ATOM | 3931 | O | HOH | W | 152 | 46.997 | −10.249 | −1.900 | 1.00 | 46.25 | O |
| ATOM | 3932 | O | HOH | W | 153 | 30.534 | 2.664 | −1.760 | 1.00 | 51.90 | O |
| ATOM | 3933 | O | HOH | W | 154 | 75.688 | −26.530 | 1.235 | 1.00 | 61.29 | O |
| ATOM | 3934 | O | HOH | W | 155 | 31.837 | 18.468 | 15.789 | 1.00 | 47.11 | O |
| ATOM | 3935 | O | HOH | W | 156 | 22.573 | −6.055 | −12.416 | 1.00 | 40.78 | O |
| ATOM | 3936 | O | HOH | W | 157 | 69.966 | −24.619 | 2.582 | 1.00 | 51.01 | O |
| ATOM | 3937 | O | HOH | W | 158 | 7.080 | −14.929 | −10.596 | 1.00 | 46.45 | O |
| ATOM | 3938 | O | HOH | W | 159 | 30.087 | 19.609 | −1.446 | 1.00 | 65.48 | O |
| ATOM | 3939 | O | HOH | W | 160 | 35.321 | 18.508 | 20.566 | 1.00 | 53.81 | O |
| ATOM | 3940 | O | HOH | W | 161 | 66.872 | −33.922 | 14.718 | 1.00 | 52.80 | O |
| ATOM | 3941 | O | HOH | W | 162 | 19.048 | −21.457 | −21.483 | 1.00 | 49.57 | O |
| ATOM | 3942 | O | HOH | W | 163 | 55.940 | 2.690 | −8.893 | 1.00 | 32.16 | O |
| ATOM | 3943 | O | HOH | W | 164 | 73.832 | −5.186 | −31.071 | 1.00 | 44.92 | O |
| ATOM | 3944 | O | HOH | W | 165 | 73.497 | 4.469 | −51.566 | 1.00 | 49.98 | O |
| ATOM | 3945 | O | HOH | W | 166 | 46.143 | −24.184 | 2.265 | 1.00 | 65.14 | O |
| ATOM | 3946 | O | HOH | W | 167 | 53.822 | −6.318 | −27.868 | 1.00 | 59.13 | O |
| ATOM | 3947 | O | HOH | W | 168 | 22.273 | −7.060 | −32.842 | 1.00 | 55.91 | O |
| ATOM | 3948 | O | HOH | W | 169 | 69.920 | 5.647 | −54.927 | 1.00 | 52.38 | O |
| ATOM | 3949 | O | HOH | W | 170 | 75.276 | −0.500 | −18.493 | 1.00 | 56.03 | O |
| ATOM | 3950 | O | HOH | W | 171 | 74.355 | −7.796 | −18.378 | 1.00 | 51.15 | O |
| ATOM | 3951 | O | HOH | W | 172 | 49.846 | 7.730 | −10.950 | 1.00 | 26.02 | O |
| ATOM | 3952 | O | HOH | W | 173 | 74.688 | 6.874 | −18.930 | 1.00 | 59.05 | O |
| ATOM | 3953 | O | HOH | W | 174 | 8.532 | −17.930 | −12.696 | 1.00 | 46.51 | O |
| ATOM | 3954 | O | HOH | W | 175 | 65.329 | 10.399 | −23.289 | 1.00 | 31.68 | O |
| ATOM | 3955 | O | HOH | W | 176 | 62.448 | −6.262 | −23.487 | 1.00 | 45.41 | O |
| ATOM | 3956 | O | HOH | W | 177 | 13.206 | −11.211 | −6.299 | 1.00 | 49.50 | O |
| ATOM | 3957 | O | HOH | W | 178 | 61.714 | 2.022 | −1.453 | 1.00 | 36.23 | O |
| ATOM | 3958 | O | HOH | W | 179 | 46.778 | 11.434 | −6.992 | 1.00 | 35.69 | O |
| ATOM | 3959 | O | HOH | W | 180 | 27.754 | 6.719 | −4.382 | 1.00 | 58.45 | O |
| ATOM | 3960 | O | HOH | W | 181 | 15.241 | −0.832 | −13.316 | 1.00 | 42.58 | O |
| ATOM | 3961 | O | HOH | W | 182 | 58.699 | 9.096 | −7.863 | 1.00 | 34.47 | O |
| ATOM | 3962 | O | HOH | W | 183 | 64.941 | −16.861 | 0.001 | 1.00 | 64.80 | O |
| ATOM | 3963 | O | HOH | W | 184 | 77.519 | −7.298 | −17.771 | 1.00 | 59.86 | O |
| ATOM | 3964 | O | HOH | W | 185 | 61.404 | −45.244 | 5.009 | 1.00 | 47.15 | O |
| ATOM | 3965 | O | HOH | W | 186 | 21.672 | −2.040 | −10.318 | 1.00 | 50.64 | O |
| ATOM | 3966 | O | HOH | W | 187 | 29.956 | −0.092 | −9.945 | 1.00 | 62.76 | O |
| ATOM | 3967 | O | HOH | W | 188 | 36.410 | 15.705 | −10.591 | 1.00 | 55.05 | O |
| ATOM | 3968 | O | HOH | W | 189 | 77.269 | −24.718 | −6.307 | 1.00 | 58.93 | O |
| ATOM | 3969 | O | HOH | W | 190 | 53.639 | −41.684 | 4.960 | 1.00 | 46.88 | O |
| ATOM | 3970 | O | HOH | W | 191 | 39.701 | −8.194 | −19.650 | 1.00 | 68.65 | O |
| ATOM | 3971 | O | HOH | W | 192 | 72.960 | 11.333 | −30.255 | 1.00 | 57.07 | O |
| ATOM | 3972 | O | HOH | W | 193 | 69.245 | −8.902 | −20.463 | 1.00 | 59.91 | O |
| ATOM | 3973 | O | HOH | W | 194 | 25.519 | 2.766 | −5.298 | 1.00 | 62.24 | O |
| ATOM | 3974 | O | HOH | W | 195 | 23.823 | −18.240 | −23.523 | 1.00 | 53.83 | O |
| ATOM | 3975 | O | HOH | W | 196 | 76.411 | −10.927 | −28.761 | 1.00 | 57.41 | O |
| ATOM | 3976 | O | HOH | W | 197 | 68.909 | 7.633 | −3.751 | 1.00 | 54.97 | O |
| ATOM | 3977 | O | HOH | W | 198 | 68.238 | 4.063 | −57.802 | 1.00 | 60.28 | O |
| ATOM | 3978 | O | HOH | W | 199 | 57.902 | −43.905 | 0.785 | 1.00 | 47.08 | O |
| ATOM | 3979 | O | HOH | W | 200 | 26.387 | 1.586 | 19.253 | 1.00 | 57.98 | O |
| ATOM | 3980 | O | HOH | W | 201 | 37.729 | 12.225 | 22.176 | 1.00 | 36.41 | O |
| ATOM | 3981 | O | HOH | W | 202 | 52.534 | 7.353 | −41.886 | 1.00 | 66.91 | O |

APPENDIX I-continued

| ATOM | 3982 | O | HOH | W | 203 | 27.054 | −0.735 | 4.862 | 1.00 | 51.36 | O |
| --- | --- | --- | --- | --- | --- | --- | --- | --- | --- | --- | --- |
| ATOM | 3983 | O | HOH | W | 204 | 42.236 | −8.736 | 1.239 | 1.00 | 49.54 | O |
| ATOM | 3984 | O | HOH | W | 205 | 72.453 | −49.755 | 2.535 | 1.00 | 57.88 | O |
| ATOM | 3985 | O | HOH | W | 206 | 21.715 | 13.751 | 27.357 | 1.00 | 63.70 | O |
| ATOM | 3986 | O | HOH | W | 207 | 72.850 | 11.054 | −33.545 | 1.00 | 48.23 | O |
| ATOM | 3987 | O | HOH | W | 208 | 72.490 | 9.599 | −53.823 | 1.00 | 63.34 | O |
| ATOM | 3988 | O | HOH | W | 209 | 62.543 | 16.639 | −24.176 | 1.00 | 32.72 | O |
| ATOM | 3989 | O | HOH | W | 210 | 45.124 | −6.604 | −14.457 | 1.00 | 40.86 | O |
| ATOM | 3990 | O | HOH | W | 211 | 67.128 | 11.703 | −20.217 | 1.00 | 33.12 | O |
| ATOM | 3991 | O | HOH | W | 212 | 71.826 | −45.136 | 14.739 | 1.00 | 57.74 | O |
| ATOM | 3992 | O | HOH | W | 213 | 57.710 | 7.585 | −21.003 | 1.00 | 45.04 | O |
| ATOM | 3993 | O | HOH | W | 214 | 38.961 | −13.213 | −15.679 | 1.00 | 47.33 | O |
| ATOM | 3994 | O | HOH | W | 215 | 44.800 | 6.821 | 8.691 | 1.00 | 43.90 | O |
| ATOM | 3995 | O | HOH | W | 216 | 52.098 | −22.105 | −2.209 | 1.00 | 58.29 | O |
| ATOM | 3996 | O | HOH | W | 217 | 59.838 | −5.952 | −22.966 | 1.00 | 42.78 | O |
| ATOM | 3997 | O | HOH | W | 218 | 18.495 | −22.454 | −8.937 | 1.00 | 43.08 | O |
| ATOM | 3998 | O | HOH | W | 219 | 41.438 | −0.960 | 2.947 | 1.00 | 47.12 | O |
| ATOM | 3999 | O | HOH | W | 220 | 28.357 | −12.574 | 2.320 | 1.00 | 67.42 | O |
| ATOM | 4000 | O | HOH | W | 221 | 31.534 | 1.142 | 5.187 | 1.00 | 52.28 | O |
| ATOM | 4001 | O | HOH | W | 222 | 52.061 | −0.982 | −33.448 | 1.00 | 66.10 | O |
| ATOM | 4002 | O | HOH | W | 223 | 70.684 | −25.967 | −10.607 | 1.00 | 59.78 | O |
| ATOM | 4003 | O | HOH | W | 224 | 24.630 | −22.237 | −21.050 | 1.00 | 62.09 | O |
| ATOM | 4004 | O | HOH | W | 225 | 42.829 | −4.753 | −0.058 | 1.00 | 47.47 | O |
| ATOM | 4005 | O | HOH | W | 226 | 70.534 | 13.938 | −33.309 | 1.00 | 57.59 | O |
| ATOM | 4006 | O | HOH | W | 227 | 37.629 | 6.169 | −9.632 | 1.00 | 35.87 | O |
| ATOM | 4007 | O | HOH | W | 228 | 39.050 | −3.195 | 8.473 | 1.00 | 56.47 | O |
| ATOM | 4008 | O | HOH | W | 229 | 50.163 | −25.989 | −2.653 | 1.00 | 57.19 | O |
| ATOM | 4009 | O | HOH | W | 230 | 66.728 | 8.298 | −2.609 | 1.00 | 53.22 | O |
| ATOM | 4010 | O | HOH | W | 231 | 46.144 | 4.981 | 2.915 | 1.00 | 49.44 | O |
| ATOM | 4011 | O | HOH | W | 232 | 64.030 | 15.931 | −27.869 | 1.00 | 50.25 | O |
| ATOM | 4012 | O | HOH | W | 233 | 78.237 | −11.718 | −16.675 | 1.00 | 66.40 | O |
| ATOM | 4013 | O | HOH | W | 234 | 3.812 | −6.905 | −25.561 | 1.00 | 46.71 | O |
| ATOM | 4014 | O | HOH | W | 235 | 64.296 | −9.563 | −18.956 | 1.00 | 55.82 | O |
| ATOM | 4015 | O | HOH | W | 236 | 57.040 | 10.985 | −10.979 | 1.00 | 33.38 | O |
| ATOM | 4016 | O | HOH | W | 237 | 68.114 | 0.724 | −44.435 | 1.00 | 47.88 | O |
| ATOM | 4017 | O | HOH | W | 238 | 77.812 | 2.986 | −35.556 | 1.00 | 54.12 | O |
| ATOM | 4018 | O | HOH | W | 239 | 68.542 | 13.125 | −10.000 | 1.00 | 42.93 | O |
| ATOM | 4019 | O | HOH | W | 240 | 70.815 | 11.906 | −8.762 | 1.00 | 61.18 | O |
| ATOM | 4020 | O | HOH | W | 241 | 59.743 | −4.943 | −32.625 | 1.00 | 68.83 | O |
| ATOM | 4021 | O | HOH | W | 242 | 53.599 | −2.593 | −24.738 | 1.00 | 57.17 | O |
| ATOM | 4022 | O | HOH | W | 243 | 28.804 | −22.157 | −13.530 | 1.00 | 66.00 | O |
| ATOM | 4023 | O | HOH | W | 244 | 12.528 | −20.034 | −9.931 | 1.00 | 54.81 | O |
| ATOM | 4024 | O | HOH | W | 245 | 18.999 | −13.928 | −26.454 | 1.00 | 37.34 | O |
| ATOM | 4025 | O | HOH | W | 246 | 9.399 | −7.555 | −10.236 | 1.00 | 51.74 | O |
| ATOM | 4026 | O | HOH | W | 247 | 9.422 | −23.577 | −21.883 | 1.00 | 51.71 | O |
| ATOM | 4027 | O | HOH | W | 248 | 48.989 | 16.285 | −2.427 | 1.00 | 52.11 | O |
| ATOM | 4028 | O | HOH | W | 249 | 25.370 | 13.160 | 27.839 | 1.00 | 51.67 | O |
| ATOM | 4029 | O | HOH | W | 250 | 34.924 | 12.483 | −8.217 | 1.00 | 36.25 | O |
| ATOM | 4030 | O | HOH | W | 251 | 55.418 | −37.562 | −1.079 | 1.00 | 39.90 | O |
| ATOM | 4031 | O | HOH | W | 252 | 65.053 | −34.377 | −13.229 | 1.00 | 61.20 | O |
| ATOM | 4032 | O | HOH | W | 253 | 65.103 | −23.855 | −7.015 | 1.00 | 61.09 | O |
| ATOM | 4033 | O | HOH | W | 254 | 59.191 | −30.854 | 12.930 | 1.00 | 31.05 | O |
| ATOM | 4034 | O | HOH | W | 255 | 74.576 | −21.281 | −5.297 | 1.00 | 62.37 | O |
| ATOM | 4035 | O | HOH | W | 256 | 77.566 | −33.129 | 5.274 | 1.00 | 55.66 | O |
| ATOM | 4036 | O | HOH | W | 257 | 53.903 | −22.288 | −17.014 | 1.00 | 50.27 | O |
| ATOM | 4037 | O | HOH | W | 258 | 45.037 | −8.754 | −15.227 | 1.00 | 49.48 | O |
| ATOM | 4038 | O | HOH | W | 259 | 22.148 | 10.033 | 10.947 | 1.00 | 39.41 | O |
| ATOM | 4039 | O | HOH | W | 260 | 65.185 | −7.017 | −20.794 | 1.00 | 45.24 | O |
| ATOM | 4040 | O | HOH | W | 261 | 35.881 | −2.206 | 17.490 | 1.00 | 44.28 | O |
| ATOM | 4041 | O | HOH | W | 262 | 51.882 | 0.389 | −39.836 | 1.00 | 67.72 | O |
| ATOM | 4042 | O | HOH | W | 263 | 31.840 | 18.088 | 10.972 | 1.00 | 46.55 | O |
| ATOM | 4043 | O | HOH | W | 264 | 0.515 | −17.290 | −27.161 | 1.00 | 54.35 | O |
| ATOM | 4044 | O | HOH | W | 265 | 69.618 | −46.411 | 15.204 | 1.00 | 62.11 | O |
| ATOM | 4045 | O | HOH | W | 266 | 30.859 | 7.314 | 28.270 | 1.00 | 50.41 | O |
| ATOM | 4046 | O | HOH | W | 267 | 18.081 | 11.850 | 9.552 | 1.00 | 53.90 | O |
| ATOM | 4047 | O | HOH | W | 268 | 59.391 | −23.586 | 16.532 | 1.00 | 66.97 | O |
| ATOM | 4048 | O | HOH | W | 269 | 35.395 | 5.989 | −11.309 | 1.00 | 48.68 | O |
| ATOM | 4049 | O | HOH | W | 270 | 16.271 | 1.278 | 9.498 | 1.00 | 66.12 | O |
| ATOM | 4050 | O | HOH | W | 271 | 46.429 | 19.602 | 7.510 | 1.00 | 50.45 | O |
| ATOM | 4051 | O | HOH | W | 272 | 41.687 | 0.016 | 6.150 | 1.00 | 48.74 | O |
| ATOM | 4052 | O | HOH | W | 273 | 55.497 | −10.087 | 2.040 | 1.00 | 52.80 | O |
| ATOM | 4053 | O | HOH | W | 274 | 11.272 | −9.479 | −30.539 | 1.00 | 38.85 | O |
| ATOM | 4054 | O | HOH | W | 275 | 54.397 | −1.130 | −21.031 | 1.00 | 54.26 | O |
| ATOM | 4055 | O | HOH | W | 276 | 12.883 | −21.707 | −24.390 | 1.00 | 53.71 | O |
| ATOM | 4056 | O | HOH | W | 277 | 18.287 | −21.975 | −25.586 | 1.00 | 45.47 | O |
| ATOM | 4057 | O | HOH | W | 278 | 46.785 | 0.418 | −18.533 | 1.00 | 32.22 | O |
| ATOM | 4058 | O | HOH | W | 279 | 45.873 | −0.317 | −20.312 | 1.00 | 58.31 | O |
| ATOM | 4059 | O | HOH | W | 280 | 46.094 | −1.639 | −18.715 | 1.00 | 40.18 | O |
| ATOM | 4060 | O | HOH | W | 281 | 42.337 | −11.592 | −18.551 | 1.00 | 65.25 | O |
| ATOM | 4061 | O | HOH | W | 282 | 39.890 | 13.264 | −12.839 | 1.00 | 51.77 | O |

APPENDIX I-continued

| | | | | | | | | | | | |
|---|---|---|---|---|---|---|---|---|---|---|---|
| ATOM | 4062 | O | HOH | W | 283 | 44.794 | 10.396 | 3.595 | 1.00 | 40.28 | O |
| ATOM | 4063 | O | HOH | W | 284 | 39.618 | 18.733 | 13.341 | 1.00 | 51.45 | O |
| ATOM | 4064 | O | HOH | W | 285 | 53.173 | −35.468 | −3.845 | 1.00 | 38.36 | O |
| ATOM | 4065 | O | HOH | W | 286 | 17.906 | −8.860 | −0.520 | 1.00 | 47.10 | O |
| ATOM | 4066 | O | HOH | W | 287 | 67.074 | −7.604 | −16.718 | 1.00 | 36.14 | O |
| ATOM | 4067 | O | HOH | W | 288 | 12.354 | −4.311 | −22.662 | 1.00 | 46.21 | O |
| ATOM | 4068 | O | HOH | W | 289 | 74.559 | −22.448 | −0.574 | 1.00 | 63.95 | O |
| ATOM | 4069 | O | HOH | W | 290 | 24.579 | 9.857 | −1.018 | 1.00 | 42.40 | O |
| ATOM | 4070 | O | HOH | W | 291 | 42.836 | −14.137 | −19.076 | 1.00 | 48.67 | O |
| ATOM | 4071 | O | HOH | W | 292 | 42.577 | −32.888 | −9.222 | 1.00 | 58.27 | O |
| ATOM | 4072 | O | HOH | W | 293 | 51.889 | −30.288 | 0.706 | 1.00 | 47.73 | O |
| ATOM | 4073 | O | HOH | W | 294 | 58.591 | 9.524 | −11.965 | 1.00 | 64.46 | O |
| ATOM | 4074 | O | HOH | W | 295 | 23.195 | 6.118 | 25.651 | 1.00 | 51.90 | O |
| ATOM | 4075 | O | HOH | W | 296 | 62.053 | −7.731 | −30.991 | 1.00 | 49.35 | O |
| ATOM | 4076 | O | HOH | W | 297 | 49.685 | −0.059 | −34.867 | 1.00 | 57.45 | O |
| ATOM | 4077 | O | HOH | W | 298 | 27.481 | 15.626 | 30.011 | 1.00 | 62.52 | O |
| ATOM | 4078 | O | HOH | W | 299 | 22.412 | 16.454 | 25.493 | 1.00 | 43.70 | O |
| ATOM | 4079 | O | HOH | W | 300 | 63.991 | −24.156 | −11.886 | 1.00 | 44.37 | O |
| ATOM | 4080 | O | HOH | W | 301 | 23.584 | −2.108 | −14.137 | 1.00 | 51.53 | O |
| ATOM | 4081 | O | HOH | W | 302 | 16.320 | −11.014 | 1.961 | 1.00 | 61.11 | O |
| ATOM | 4082 | O | HOH | W | 303 | 21.217 | −22.569 | −24.840 | 1.00 | 58.72 | O |
| ATOM | 4083 | O | HOH | W | 304 | 41.646 | 17.848 | −7.228 | 1.00 | 65.03 | O |
| ATOM | 4084 | O | HOH | W | 305 | 22.950 | 17.731 | 10.015 | 1.00 | 58.75 | O |
| ATOM | 4085 | O | HOH | W | 306 | 56.767 | 7.202 | 2.006 | 1.00 | 62.33 | O |
| ATOM | 4086 | O | HOH | W | 307 | 58.177 | −38.332 | −8.428 | 1.00 | 51.10 | O |
| ATOM | 4087 | O | HOH | W | 308 | 36.859 | 6.714 | 22.042 | 1.00 | 67.48 | O |
| ATOM | 4088 | O | HOH | W | 309 | 8.548 | −9.082 | −6.377 | 1.00 | 64.08 | O |
| ATOM | 4089 | O | HOH | W | 310 | 77.441 | 6.499 | −18.901 | 1.00 | 53.22 | O |
| ATOM | 4090 | O | HOH | W | 311 | 50.214 | −2.598 | −28.240 | 1.00 | 65.39 | O |
| ATOM | 4091 | O | HOH | W | 312 | 67.157 | −32.383 | 12.563 | 1.00 | 52.04 | O |
| ATOM | 4092 | O | HOH | W | 313 | 42.103 | 10.501 | 15.691 | 1.00 | 58.68 | O |
| ATOM | 4093 | O | HOH | W | 314 | 32.134 | −22.541 | −14.797 | 1.00 | 64.57 | O |
| ATOM | 4094 | O | HOH | W | 315 | 49.067 | 3.344 | −37.222 | 1.00 | 67.11 | O |
| ATOM | 4095 | O | HOH | W | 316 | 61.987 | −46.753 | 3.536 | 1.00 | 61.36 | O |
| ATOM | 4096 | O | HOH | W | 317 | 60.318 | −9.489 | −9.294 | 1.00 | 50.74 | O |
| ATOM | 4097 | O | HOH | W | 318 | 48.190 | −10.315 | 0.317 | 1.00 | 44.60 | O |
| ATOM | 4098 | O | HOH | W | 319 | 50.098 | −10.842 | −18.057 | 1.00 | 53.04 | O |
| ATOM | 4099 | O | HOH | W | 320 | 46.094 | 9.952 | 6.886 | 1.00 | 54.78 | O |
| ATOM | 4100 | O | HOH | W | 321 | 74.455 | 7.920 | −30.461 | 1.00 | 54.66 | O |
| ATOM | 4101 | O | HOH | W | 322 | 73.297 | −11.177 | −30.246 | 1.00 | 54.61 | O |
| ATOM | 4102 | O | HOH | W | 323 | 55.869 | 3.785 | −16.712 | 1.00 | 47.04 | O |
| ATOM | 4103 | O | HOH | W | 324 | 17.752 | −20.654 | −6.176 | 1.00 | 66.30 | O |
| ATOM | 4104 | O | HOH | W | 325 | 19.223 | −5.198 | −23.515 | 1.00 | 66.40 | O |
| ATOM | 4105 | O | HOH | W | 326 | 14.416 | −5.443 | −29.063 | 1.00 | 58.70 | O |
| ATOM | 4106 | O | HOH | W | 327 | 20.794 | −20.150 | −22.576 | 1.00 | 47.38 | O |
| ATOM | 4107 | O | HOH | W | 328 | 46.970 | 9.591 | −3.000 | 1.00 | 61.77 | O |
| ATOM | 4108 | O | HOH | W | 329 | 44.733 | 9.137 | −4.905 | 1.00 | 58.82 | O |
| ATOM | 4109 | O | HOH | W | 330 | 44.656 | 15.089 | 8.206 | 1.00 | 62.37 | O |
| ATOM | 4110 | O | HOH | W | 331 | 41.354 | 13.880 | 11.375 | 1.00 | 49.54 | O |
| ATOM | 4111 | O | HOH | W | 332 | 37.483 | 14.530 | 22.480 | 1.00 | 53.31 | O |
| ATOM | 4112 | O | HOH | W | 333 | 41.722 | 19.379 | −3.546 | 1.00 | 50.97 | O |
| ATOM | 4113 | O | HOH | W | 334 | 42.731 | 13.993 | −12.884 | 1.00 | 72.77 | O |
| ATOM | 4114 | O | HOH | W | 335 | 23.790 | 0.599 | 10.614 | 1.00 | 45.38 | O |
| ATOM | 4115 | O | HOH | W | 336 | 59.513 | −7.372 | −13.143 | 1.00 | 61.55 | O |
| ATOM | 4116 | O | HOH | W | 337 | 56.314 | 9.708 | −14.663 | 1.00 | 50.95 | O |
| ATOM | 4117 | O | HOH | W | 338 | 31.978 | −18.528 | −15.554 | 1.00 | 67.33 | O |
| ATOM | 4118 | O | HOH | W | 339 | 56.351 | −11.784 | −4.728 | 1.00 | 42.25 | O |
| ATOM | 4119 | O | HOH | W | 340 | 32.235 | −7.490 | −8.002 | 1.00 | 48.45 | O |
| ATOM | 4120 | O | HOH | W | 341 | 11.039 | −11.212 | −5.888 | 1.00 | 56.05 | O |
| ATOM | 4121 | O | HOH | W | 342 | 45.883 | 15.519 | −9.499 | 1.00 | 60.90 | O |
| ATOM | 4122 | O | HOH | W | 343 | 42.607 | 11.894 | 21.114 | 1.00 | 59.64 | O |
| ATOM | 4123 | O | HOH | W | 344 | 64.897 | −45.210 | 2.801 | 1.00 | 46.00 | O |
| ATOM | 4124 | O | HOH | W | 345 | 62.414 | −44.124 | 9.836 | 1.00 | 54.24 | O |
| ATOM | 4125 | O | HOH | W | 346 | 66.607 | −47.490 | 14.098 | 1.00 | 51.46 | O |
| ATOM | 4126 | O | HOH | W | 347 | 33.184 | 9.901 | 29.054 | 1.00 | 54.19 | O |
| ATOM | 4127 | O | HOH | W | 348 | 61.338 | −8.260 | −18.802 | 1.00 | 61.80 | O |
| ATOM | 4128 | O | HOH | W | 349 | 58.915 | 10.462 | −1.335 | 1.00 | 59.07 | O |
| ATOM | 4129 | O | HOH | W | 350 | 72.985 | 11.119 | −6.571 | 1.00 | 57.45 | O |
| ATOM | 4130 | O | HOH | W | 351 | 52.715 | −5.406 | −30.681 | 1.00 | 76.01 | O |
| ATOM | 4131 | O | HOH | W | 352 | 79.919 | −27.316 | −4.944 | 1.00 | 61.96 | O |
| ATOM | 4132 | O | HOH | W | 353 | 71.264 | 8.651 | −47.201 | 1.00 | 49.44 | O |
| ATOM | 4133 | O | HOH | W | 354 | 22.664 | 12.842 | 33.813 | 1.00 | 49.23 | O |
| ATOM | 4134 | O | HOH | W | 355 | 27.068 | 20.483 | 22.480 | 1.00 | 39.84 | O |
| ATOM | 4135 | O | HOH | W | 356 | 31.821 | −0.902 | 1.857 | 1.00 | 55.00 | O |
| ATOM | 4136 | O | HOH | W | 357 | 35.021 | −1.745 | 3.155 | 1.00 | 59.58 | O |
| ATOM | 4137 | O | HOH | W | 358 | 39.467 | 2.391 | 21.237 | 1.00 | 73.05 | O |
| ATOM | 4138 | O | HOH | W | 359 | 35.690 | −6.904 | −2.480 | 1.00 | 64.18 | O |
| ATOM | 4139 | O | HOH | W | 360 | 38.038 | −8.228 | −14.500 | 1.00 | 64.77 | O |
| ATOM | 4140 | O | HOH | W | 361 | 56.585 | −29.520 | 5.841 | 1.00 | 60.72 | O |
| ATOM | 4141 | O | HOH | W | 362 | 55.461 | −35.538 | 5.382 | 1.00 | 54.96 | O |

APPENDIX I-continued

| ATOM | 4142 | O | HOH | W | 363 | 62.048 | −20.002 | −5.479 | 1.00 | 55.47 | O |
|---|---|---|---|---|---|---|---|---|---|---|---|
| ATOM | 4143 | O | HOH | W | 364 | 65.219 | −29.258 | 15.468 | 1.00 | 67.43 | O |
| ATOM | 4144 | O | HOH | W | 365 | 15.338 | −5.304 | −5.505 | 1.00 | 54.06 | O |
| ATOM | 4145 | O | HOH | W | 366 | 28.667 | 17.880 | 30.849 | 1.00 | 58.81 | O |
| ATOM | 4146 | O | HOH | W | 367 | 7.490 | −4.018 | −9.949 | 1.00 | 49.82 | O |
| ATOM | 4147 | O | HOH | W | 368 | 41.902 | −0.891 | 15.421 | 1.00 | 58.16 | O |
| ATOM | 4148 | O | HOH | W | 369 | 23.205 | −24.145 | −0.987 | 1.00 | 49.15 | O |
| ATOM | 4149 | O | HOH | W | 370 | 46.687 | 7.432 | 6.640 | 1.00 | 58.62 | O |
| ATOM | 4150 | O | HOH | W | 371 | 47.413 | 16.850 | −8.082 | 1.00 | 59.32 | O |
| ATOM | 4151 | O | HOH | W | 372 | 6.503 | −2.107 | −24.879 | 1.00 | 52.47 | O |
| ATOM | 4152 | O | HOH | W | 373 | 47.592 | −16.616 | −26.050 | 1.00 | 54.23 | O |
| ATOM | 4153 | O | HOH | W | 374 | 32.148 | 2.927 | 25.177 | 1.00 | 51.95 | O |
| ATOM | 4154 | O | HOH | W | 375 | 70.869 | 13.479 | −15.671 | 1.00 | 61.78 | O |
| ATOM | 4155 | O | HOH | W | 376 | 32.233 | −9.491 | 0.706 | 1.00 | 64.72 | O |
| ATOM | 4156 | O | HOH | W | 377 | 43.162 | −20.025 | −20.830 | 1.00 | 61.56 | O |
| ATOM | 4157 | O | HOH | W | 378 | 7.447 | −21.877 | −18.708 | 1.00 | 54.28 | O |
| ATOM | 4158 | O | HOH | W | 379 | 64.478 | −20.926 | −14.628 | 1.00 | 56.28 | O |
| ATOM | 4159 | O | HOH | W | 380 | 70.262 | −45.646 | 1.731 | 1.00 | 65.26 | O |
| ATOM | 4160 | O | HOH | W | 381 | 20.516 | 12.524 | 8.760 | 1.00 | 43.73 | O |
| ATOM | 4161 | O | HOH | W | 382 | 74.928 | 8.949 | −8.247 | 1.00 | 54.24 | O |
| ATOM | 4162 | O | HOH | W | 383 | 18.257 | −25.208 | −7.910 | 1.00 | 50.96 | O |
| ATOM | 4163 | O | HOH | W | 384 | 34.170 | 18.737 | 17.233 | 1.00 | 47.03 | O |
| ATOM | 4164 | O | HOH | W | 385 | 21.137 | 2.084 | 3.808 | 1.00 | 65.70 | O |
| ATOM | 4165 | O | HOH | W | 386 | 38.186 | −4.444 | −15.698 | 1.00 | 66.07 | O |
| ATOM | 4166 | O | HOH | W | 387 | 38.985 | −6.466 | −8.831 | 1.00 | 51.93 | O |
| ATOM | 4167 | O | HOH | W | 388 | 3.906 | −16.558 | −13.958 | 1.00 | 54.64 | O |
| ATOM | 4168 | O | HOH | W | 389 | 33.087 | −21.326 | −9.095 | 1.00 | 66.75 | O |
| ATOM | 4169 | O | HOH | W | 390 | 27.295 | −14.177 | 5.542 | 1.00 | 58.06 | O |
| ATOM | 4170 | O | HOH | W | 391 | 41.013 | −5.818 | 20.816 | 1.00 | 60.46 | O |
| ATOM | 4171 | O | HOH | W | 392 | 22.713 | 1.185 | 14.363 | 1.00 | 64.09 | O |
| ATOM | 4172 | O | HOH | W | 393 | 48.064 | 6.165 | 1.998 | 1.00 | 61.05 | O |
| ATOM | 4173 | O | HOH | W | 394 | 46.193 | 7.105 | 3.046 | 1.00 | 37.46 | O |

The invention claimed is:

1. An amyloid β-peptide-immunoglobulin new antigen receptor fusion molecule (Aβ-IgNAR molecule) having the amino acid sequence of any one of SEQ ID NOs: 15 to 24.

2. The Aβ-IgNAR molecule of claim 1 having the amino acid sequence of SEQ ID NO: 15.

3. The Aβ-IgNAR molecule of claim 1 having the amino acid sequence of SEQ ID NO: 16.

4. The Aβ-IgNAR molecule of claim 1 having the amino acid sequence of SEQ ID NO: 17.

5. The Aβ-IgNAR molecule of claim 1 having the amino acid sequence of SEQ ID NO: 18.

6. The Aβ-IgNAR molecule of claim 1 having the amino acid sequence of SEQ ID NO: 19.

7. The Aβ-IgNAR molecule of claim 1 having the amino acid sequence of SEQ ID NO: 20.

8. The Aβ-IgNAR molecule of claim 1 having the amino acid sequence of SEQ ID NO: 21.

9. The Aβ-IgNAR molecule of claim 1 having the amino acid sequence of SEQ ID NO: 22.

10. The Aβ-IgNAR molecule of claim 1 having the amino acid sequence of SEQ ID NO: 23.

11. The Aβ-IgNAR molecule of claim 1 having the amino acid sequence of SEQ ID NO: 24.

12. A composition comprising a crystal having the coordinates set forth in Appendix I in space group $P3_2$ with cell parameters a=b=79.40, c=84.89 Å, which is produced from the Aβ-IgNAR molecule having the amino acid sequence of SEQ ID NO:2.

13. The composition of claim 12 in which the crystal comprises an Aβ-IgNAR molecule monomer.

14. The composition of claim 12 in which the crystal comprises an Aβ-IgNAR molecule dimer.

15. The composition of claim 12 in which the crystal comprises an Aβ-IgNAR molecule tetramer.

16. An amyloid β-peptide-immunoglobulin new antigen receptor fusion molecule (Aβ-IgNAR molecule) comprising amino acids in the sequence of residues 1-87 of the IgNAR set forth as SEQ ID NO:3 fused to amino acids in the sequence of residues 18-41 set forth as SEQ ID NO:1, the sequence of residues 88-111 set forth as SEQ ID NO:19, the sequence of residues 88-111 set forth as SEQ ID NO:20, the sequence of residues 88-111 set forth as SEQ ID NO:21, the sequence of residues 88-111 set forth as SEQ ID NO:22, the sequence of residues 88-110 set forth as SEQ ID NO:23, or the sequence of residues 88-111 set forth as SEQ ID NO:24.

17. The Aβ-IgNAR molecule of claim 16 comprising amino acids in the sequence of residues 1-87 of the IgNAR set forth as SEQ ID NO:3 fused to amino acids in the sequence of residues 18-41 set forth as SEQ ID NO:1.

18. The Aβ-IgNAR molecule of claim 16 comprising amino acids in the sequence of residues 1-87 of the IgNAR set forth as SEQ ID NO:3 fused to amino acids in the sequence of residues 88-111 set forth as SEQ ID NO:19.

19. The Aβ-IgNAR molecule of claim 16 comprising amino acids in the sequence of residues 1-87 of the IgNAR set forth as SEQ ID NO:3 fused to amino acids in the sequence of residues 88-111 set forth as SEQ ID NO:20.

20. The Aβ-IgNAR molecule of claim 16 comprising amino acids in the sequence of residues 1-87 of the IgNAR set forth as SEQ ID N0:3 fused to amino acids in the sequence of residues 88-111 set forth as SEQ ID NO:21.

21. The Aβ-IgNAR molecule of claim 16 comprising amino acids in the sequence of residues 1-87 of the IgNAR set forth as SEQ ID NO:3 fused to amino acids in, the sequence of residues 88-111 set forth as SEQ ID NO:22.

22. The Aβ-IgNAR molecule of claim 16 comprising amino acids in the sequence of residues 1-87 of the IgNAR set forth as SEQ ID NO:3 fused to amino acids in the sequence of residues 88-110 set forth as SEQ ID NO:23.

23. The Aβ-IgNAR molecule of claim 16 comprising amino acids in the sequence of residues 1-87 of the IgNAR set forth as SEQ ID NO:3 fused to amino acids in the sequence of residues 88-111 set forth as SEQ ID NO:24.

* * * * *